US012503507B2

(12) United States Patent
Jensen

(10) Patent No.: US 12,503,507 B2
(45) Date of Patent: Dec. 23, 2025

(54) DEFINED COMPOSITION GENE MODIFIED T-CELL PRODUCTS

(71) Applicant: Seattle Children's Hospital, Seattle, WA (US)

(72) Inventor: Michael C. Jensen, Bainbridge Island, WA (US)

(73) Assignee: Seattle Children's Hospital, Seattle, WA (US)

(*) Notice: Subject to any disclaimer, the term of this patent is extended or adjusted under 35 U.S.C. 154(b) by 840 days.

(21) Appl. No.: 17/660,114

(22) Filed: Apr. 21, 2022

(65) Prior Publication Data

US 2022/0372140 A1 Nov. 24, 2022

Related U.S. Application Data

(63) Continuation of application No. 15/302,426, filed as application No. PCT/US2015/024866 on Apr. 8, 2015, now abandoned.

(Continued)

(51) Int. Cl.

| | |
|---|---|
| ***A61K 35/17*** | (2025.01) |
| ***A61K 35/28*** | (2015.01) |
| ***A61K 38/17*** | (2006.01) |
| ***A61K 38/19*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 14/71*** | (2006.01) |
| ***C07K 14/715*** | (2006.01) |
| ***C07K 14/725*** | (2006.01) |
| ***C07K 16/28*** | (2006.01) |
| ***C07K 16/32*** | (2006.01) |
| ***C07K 19/00*** | (2006.01) |
| ***C12N 5/0783*** | (2010.01) |

(Continued)

(52) U.S. Cl.

CPC .......... *C07K 16/2803* (2013.01); *A61K 35/28* (2013.01); *A61K 38/1774* (2013.01); *A61K 38/179* (2013.01); *A61K 38/1793* (2013.01); *A61K 39/3955* (2013.01); *A61K 40/11* (2025.01); *A61K 40/31* (2025.01); *A61K 40/4211* (2025.01); *C07K 14/7051* (2013.01); *C07K 14/70517* (2013.01); *C07K 14/70521* (2013.01); *C07K 14/70578* (2013.01); *C07K 14/71* (2013.01); *C07K 14/7151* (2013.01); *C07K 16/2818* (2013.01); *C07K 16/32* (2013.01); *C12N 5/0636* (2013.01); *C12N 5/0638* (2013.01); *C12N 9/12* (2013.01); *C12N 15/85* (2013.01); *C12Y 207/10001* (2013.01); *A61K 2035/124* (2013.01); *A61K 2039/505* (2013.01); *A61K 2039/572* (2013.01); *C07K 2317/14* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 15/62* (2013.01); *C12N 2510/00* (2013.01); *C12N 2800/90* (2013.01); *G01N 33/68* (2013.01)

(58) Field of Classification Search

None

See application file for complete search history.

(56) References Cited

U.S. PATENT DOCUMENTS 5,783,186 A 7/1998 Arakawa et al.
6,040,177 A 3/2000 Riddell et al.

(Continued)

FOREIGN PATENT DOCUMENTS

CN 1809277 7/2006
DE 10 2011118018 4/2013

(Continued)

OTHER PUBLICATIONS

Sterner and Sterner, CAR-T cell therapy: current limitations and potential strategies, Blood Cancer Journal (2021) 11:69, pp. 1-11.*

(Continued)

*Primary Examiner* — Maria Marvich

(74) *Attorney, Agent, or Firm* — Knobbe, Martens, Olson & Bear LLP

(57) ABSTRACT

Aspects of the invention described herein, concern approaches to make genetically modified T-cells comprising a chimeric antigen receptor for human therapy. In some alternatives, the methods utilize a selection and/or isolation of CD4+ and/or CD8+ T-cells from a mixed T-cell population, such as, peripheral blood or apheresis derived mononuclear cells. Once selected/isolated, the CD4+ and/or CD8+ T-cells are then activated, genetically modified, and propagated, preferably, in separate or isolated cultures in the presence of one or more cytokines, which support survival, engraftment and/or proliferation of the cells, as well as, preferably promoting or inducing the retention of cell surface receptors, such as CD62L, CD28, and/or CD27. Included herein are also methods of treatment, inhibition, amelioration, or elimination of a cancer by administering to a subject in need thereof, one or more types of the genetically engineered T-cells or compositions that comprise the genetically engineered T-cell prepared as described herein.

20 Claims, 152 Drawing Sheets

Specification includes a Sequence Listing.

Related U.S. Application Data

(60) Provisional application No. 62/090,845, filed on Dec. 11, 2014, provisional application No. 62/089,730, filed on Dec. 9, 2014, provisional application No. 62/088,363, filed on Dec. 5, 2014, provisional application No. 62/058,973, filed on Oct. 2, 2014, provisional application No. 61/986,479, filed on Apr. 30, 2014, provisional application No. 61/977,751, filed on Apr. 10, 2014.

(51) Int. Cl.

| | |
|---|---|
| ***C12N 9/12*** | (2006.01) |
| ***C12N 15/85*** | (2006.01) |
| *A61K 35/12* | (2015.01) |
| *A61K 39/00* | (2006.01) |
| *C12N 15/62* | (2006.01) |
| *G01N 33/68* | (2006.01) |

(56) References Cited

U.S. PATENT DOCUMENTS

| | | | | |
|---|---|---|---|---|
| 6,133,027 | A | 10/2000 | Yee et al. | |
| 7,070,995 | B2 | 7/2006 | Jensen | |
| 7,446,179 | B2 | 11/2008 | Jensen et al. | |
| 7,709,253 | B2 | 5/2010 | Gambhir et al. | |
| 7,910,101 | B2 | 3/2011 | Cunningham et al. | |
| 8,066,994 | B2 | 11/2011 | Gillies et al. | |
| 8,802,374 | B2 | 8/2014 | Jensen | |
| 8,822,647 | B2 | 9/2014 | Jensen | |
| 8,916,381 | B1 | 12/2014 | June et al. | |
| 8,975,071 | B1 | 3/2015 | June et al. | |
| 9,328,156 | B2 | 5/2016 | June et al. | |
| 9,345,785 | B2 | 5/2016 | Law et al. | |
| 9,447,194 | B2 | 9/2016 | Jensen | |
| 9,481,728 | B2 | 11/2016 | June et al. | |
| 9,499,629 | B2 | 11/2016 | June et al. | |
| 9,518,123 | B2 | 12/2016 | June et al. | |
| 9,540,445 | B2 | 1/2017 | June et al. | |
| 9,629,877 | B2 | 4/2017 | Cooper et al. | |
| 9,701,758 | B2 | 7/2017 | Cooper et al. | |
| 9,856,322 | B2 | 1/2018 | Campana et al. | |
| 10,125,193 | B2 | 11/2018 | Cooper et al. | |
| 10,172,885 | B2 | 1/2019 | Pule | |
| 10,221,245 | B2 | 3/2019 | Brogdon et al. | |
| 10,266,592 | B2 | 4/2019 | Jensen et al. | |
| 10,287,350 | B2 | 5/2019 | Kochenderfer | |
| 10,358,474 | B2 | 7/2019 | Baeuerle et al. | |
| 10,457,730 | B2 | 10/2019 | Pule et al. | |
| 10,533,055 | B2 | 1/2020 | Chen et al. | |
| 10,604,740 | B2 | 3/2020 | Li et al. | |
| 10,611,837 | B2 | 4/2020 | Jensen et al. | |
| 10,626,187 | B2 | 4/2020 | Wiltzius et al. | |
| 10,639,329 | B2 | 5/2020 | Dropulic et al. | |
| 10,738,279 | B2 | 8/2020 | Lee | |
| 10,780,118 | B2 | 9/2020 | Jensen | |
| 10,800,833 | B2 | 10/2020 | Jantz et al. | |
| 10,828,352 | B2 | 11/2020 | Berger et al. | |
| 10,844,120 | B2 | 11/2020 | Wiltzius et al. | |
| 10,865,242 | B2 | 12/2020 | Jensen | |
| 10,869,888 | B2 | 12/2020 | Xiao et al. | |
| 10,927,184 | B2 | 2/2021 | Brogdon et al. | |
| 11,034,763 | B2 | 6/2021 | Wu et al. | |
| 11,104,732 | B2 | 8/2021 | Cao et al. | |
| 11,123,369 | B2 | 9/2021 | Jensen et al. | |
| 11,155,616 | B2 | 10/2021 | Jensen et al. | |
| 11,408,005 | B2 | 8/2022 | Jensen et al. | |
| 11,639,387 | B2 | 5/2023 | Jensen | |
| 2002/0111474 | A1 | 8/2002 | Capon et al. | |
| 2003/0143559 | A1 | 7/2003 | Bracken et al. | |
| 2003/0148982 | A1 | 8/2003 | Brenner et al. | |
| 2003/0215427 | A1 | 11/2003 | Jensen | |
| 2004/0037816 | A1 | 2/2004 | Boyd | |
| 2005/0060762 | A1 | 3/2005 | Bleck | |
| 2005/0129671 | A1 | 6/2005 | Cooper et al. | |
| 2006/0160090 | A1 | 7/2006 | Anzures et al. | |
| 2006/0160104 | A1 | 7/2006 | Johnson | |
| 2006/0246548 | A1 | 11/2006 | Jensen | |
| 2007/0020237 | A1 | 1/2007 | Yoon | |
| 2007/0087346 | A1 | 4/2007 | Ciliberto et al. | |
| 2007/0166318 | A1 | 7/2007 | Macina et al. | |
| 2008/0044413 | A1 | 2/2008 | Hammond | |
| 2008/0096813 | A1 | 4/2008 | Frankel et al. | |
| 2009/0098142 | A1 | 4/2009 | Kasalan et al. | |
| 2009/0098604 | A1 | 4/2009 | Gallo et al. | |
| 2010/0226901 | A1 | 9/2010 | Smolke | |
| 2011/0287020 | A1 | 11/2011 | Gruber et al. | |
| 2012/0046645 | A1 | 2/2012 | Cal | |
| 2012/0148552 | A1 | 6/2012 | Jensen | |
| 2012/0297493 | A1 | 11/2012 | Cooper et al. | |
| 2012/0301447 | A1 | 11/2012 | Jensen | |
| 2013/0011394 | A1 | 1/2013 | Knoetgen | |
| 2013/0071414 | A1 | 3/2013 | Dotti et al. | |
| 2013/0280220 | A1 | 10/2013 | Ahmed et al. | |
| 2013/0287748 | A1 | 10/2013 | June et al. | |
| 2014/0056868 | A1 | 2/2014 | Zechiedrich et al. | |
| 2014/0099309 | A1 | 4/2014 | Power | |
| 2014/0112956 | A1 | 4/2014 | Karlsson-Parra et al. | |
| 2014/0120622 | A1 | 5/2014 | Gregory | |
| 2014/0271635 | A1 | 9/2014 | Brogdon et al. | |
| 2014/0314795 | A1 | 10/2014 | Riddell et al. | |
| 2015/0038684 | A1 | 2/2015 | Jensen | |
| 2015/0038694 | A1 | 2/2015 | Nicotra | |
| 2015/0225480 | A1 * | 8/2015 | Powell, Jr. | A61K 40/31<br>435/325 |
| 2015/0299656 | A1 | 10/2015 | Gattinoni et al. | |
| 2015/0329640 | A1 | 11/2015 | Finer | |
| 2016/0017048 | A1 | 1/2016 | Dotti et al. | |
| 2016/0310575 | A1 | 10/2016 | Belli et al. | |
| 2017/0015746 | A1 | 1/2017 | Jensen | |
| 2017/0029774 | A1 | 2/2017 | Jensen et al. | |
| 2017/0037121 | A1 | 2/2017 | Schlothauer | |
| 2017/0209543 | A9 | 7/2017 | Jensen | |
| 2017/0224733 | A1 | 8/2017 | Badie et al. | |
| 2018/0028567 | A1 | 2/2018 | Li et al. | |
| 2020/0215108 | A1 | 7/2020 | Jensen et al. | |
| 2020/0354477 | A1 | 11/2020 | Jensen et al. | |
| 2021/0002364 | A1 | 1/2021 | Jensen et al. | |
| 2021/0139583 | A1 | 5/2021 | Jensen et al. | |
| 2021/0371517 | A1 | 12/2021 | Jensen | |
| 2022/0064292 | A1 | 3/2022 | Jensen | |
| 2022/0380461 | A1 | 12/2022 | Jensen | |
| 2022/0411805 | A1 | 12/2022 | Jensen | |
| 2023/0130938 | A1 | 4/2023 | Jensen | |
| 2023/0227551 | A1 | 7/2023 | Jensen | |

FOREIGN PATENT DOCUMENTS

| | | |
|---|---|---|
| JP | 2006-518753 | 8/2006 |
| RU | 2003 129 528 A | 4/2005 |
| WO | WO 92/08796 | 5/1992 |
| WO | WO 94/00143 | 1/1994 |
| WO | WO 98/18923 | 5/1998 |
| WO | WO 00/23573 | 4/2000 |
| WO | WO 01/098506 | 12/2001 |
| WO | WO 02/33101 | 4/2002 |
| WO | WO 02/072605 | 9/2002 |
| WO | WO 02/097099 | 12/2002 |
| WO | WO 03/025228 | 3/2003 |
| WO | WO 03/087338 | 10/2003 |
| WO | WO 05/017102 | 2/2005 |
| WO | WO 05/040212 | 5/2005 |
| WO | WO 05/108617 | 11/2005 |
| WO | WO 07/073499 | 6/2007 |
| WO | WO 07/137267 | 11/2007 |
| WO | WO 08/012237 | 1/2008 |
| WO | WO 09/013359 | 1/2009 |
| WO | WO 09/091826 | 7/2009 |
| WO | WO 10/036986 | 4/2010 |
| WO | WO 10/141543 | 12/2010 |
| WO | WO 11/041093 | 4/2011 |
| WO | WO 11/056894 | 5/2011 |
| WO | WO 12/031744 | 3/2012 |
| WO | WO 12/079000 | 6/2012 |

(56) References Cited

FOREIGN PATENT DOCUMENTS

| | | |
|---|---|---|
| WO | WO 12/099973 | 7/2012 |
| WO | WO 12/129514 | 9/2012 |
| WO | WO 12/140130 | 10/2012 |
| WO | WO 13/059593 | 4/2013 |
| WO | WO 13/074916 | 5/2013 |
| WO | WO 13/123061 | 8/2013 |
| WO | WO 13/126733 | 8/2013 |
| WO | WO 13/154760 | 10/2013 |
| WO | WO 13/177533 | 11/2013 |
| WO | WO 13/178635 | 12/2013 |
| WO | WO 14/031687 | 2/2014 |
| WO | WO 14/039044 | 3/2014 |
| WO | WO 14/055657 | 4/2014 |
| WO | WO 14/055668 | 4/2014 |
| WO | WO 14/153270 | 9/2014 |
| WO | WO 15/066551 | 5/2015 |
| WO | WO 15/075468 | 5/2015 |
| WO | WO 15/092024 | 6/2015 |
| WO | WO 15/105522 | 7/2015 |
| WO | WO 15/142675 | 9/2015 |
| WO | WO 15/157399 | 10/2015 |
| WO | WO 15/157432 | 10/2015 |
| WO | WO 20/033272 | 2/2020 |

OTHER PUBLICATIONS

Kochenderfer and Rosenberg, Treating B-cell cancer with T cells expressing anti-CD19 chimeric antigen receptors, Nat Rev Clin Oncol. May 2013 ; 10(5): 267-276.*

Badri et al., 2016, Optimization of radiation dosing schedules for proneural glioblastoma, J Math Bio, 72(5):1301-1336.

Baylot et al., 2017, TCTP Has a Crucial Role in the Different Stages of Prostate Cancer Malignant Progression, Results Probl Cell Differ, 64:255-261.

Dolgikh et al., 2013, Heterologous expression of the extracellular domain of the HER2 receptor in bacteria, Scientific notes of St. Petersburg State Medical University named after. I. P. Pavlova, 20(4):70-73.

Hu et al., 2004, Insufficient p65 phosphorylation at S536 specifically contributes to the lack of NF-kB activation and transmformation in resistant JB6 cells, Carcinogenesis, 25(10):1991-2003.

Jost et al., 2013, Structural basis for eliciting a cytotoxic effect in HER2-overexpressing cancer cells via binding to the extracellular domain of HER2, Structure, 21(11):1979-1991.

Jubala et al., 2005, CD20 Expression in normal canine B cells and in canine non-Hodgkin lymphoma, Vet Pathol 42:468-476.

Kim et al, 2007, Efficiency of the Elongation Factor-1alpha Promoter in Mammalian Embryonic Stem Cells Using Lentiviral Gene Delivery Systems, Stem Cells and Development, 16:537-545.

Majowicz et al., 2012, Murine CD4+ CD25-cells activated in vitro with PMA/ionomycin and anti-CD3 acquire regulatory function and ameliorate experimental colitis in vivo, BMC Gastroenterology, 12:1-9.

Markley, Apr. 2020, IL-7 and IL-21 are superior to IL-2 and IL-15 in promoting human T cell-mediated rejection of systemic lymphoma in immunodeficient mice, Blood, 115(17):3508-3519.

Olsen et al., Feb. 2013, Pitfalls in determining the cytokine profile of human T cells, Journal of Immunological Methods, 390:106-112.

Pan et al., 2022, CAR race to cancer immunotherapy: from CAR T, CAR NK to CAR macrophage therapy, J Exp Clin Cancer Res, 41(1):119.

Piche-Nicholas et al., 2018, Changes in complementarity-determining regions significantly alter IgG binding to the neonatal Fc receptor (FcRn)and pharmacokinetics, MABS 10(1):81-94.

Poosarla et al., 2017, Computational de novo design of antibodies binding to a peptide with high affinity, Biotechnology and Bioengineering, 114(6):1331-1342.

Rudikoff et al., Mar. 1982, Single amino acid substitution altering antigen-binding specificity, PNAS, 79:1979-1983.

Sentman, Aug. 1, 0213, Challenges of creating effective chimeric antigen receptors for cancer therapy, Immunotherapy 5(8):783-785.

Wu et al., 1999, Humanization of a murine monoclonal antibody by simultaneous optimization of framework and CDR residues, J. Mol. Biol. 294:151-162.

Yu et al., 2008, Interaction between bevacizumab and murine VEGF-A: a reassessment, Investigative Ophthalmology & Visual Science, 49(2):522-527.

Aalberse et al., "IgG4 breaking the rules," Immunology (2002) 105:9-19.

Aertgeerts et al., "Structural analysis of the mechanism of inhibition and allosteric activation of the kinase domain of HER2 protein," Journal of Biological Chemistry (2011) vol. 286, No. 21, p. 18756-18765, Becb Весь текст , c. 18759-18765.

Ahmed et al., "Regression of experimental medulloblastoma following transfer of HER2-specific T cells," Cancer Res. (Jun. 15, 2007) 67(12):5957-64.

Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.

Ahmed, Nabil, "Her2 Chimeric Antigen Receptor Expressing T Cells in Advanced Sarcoma," ClinicalTrials.gov Identifier: NCT00902044 (May 14, 2009) pp. 1-11.

Altschul et al., "Local Alignment Statistics, [27] Multiple Alignment and Phylogenetic Trees," Methods in Enzymology (1996) 266:460-480.

Bejcek et al. "Development and Characterization of Three Recombinant Single Chain Antibody Fragments (scFvs) Directed against the CD19 Antigen," Cancer Res (1995) 55:2346-2351.

Berglund et al., "The epitope space of the human proteome," Protein Science (2008) 17:606-613.

Brentjens et al: "CD19-targeted T cells rapidly induce molecular remissions in adults with chemotherapy-refractory acute lymphoblastic leukemia", Science Translational Medicine, 5(177), Mar. 20, 2013.

Budde et al., "Combining a CD20 Chimeric Antigen Receptor and an Inducible Caspase 9 Suicide Switch to Improve the Efficacy and Safety of T Cell Adoptive Immunotherapy for Lymphoma", PLOS ONE (2013) 8(12): e82742. https://doi.org/10.1371/journal.pone.0082742.

Cartellieri et al., "A Novel Ex Vivo Isolation and Expansion Procedure for Chimeric Antigen Receptor Engrafted Human T Cells," PLOS ONE (Apr. 3, 2014) vol. 9, No. 4, e93745, pp. 1-12.

Cha et al., "IL-7 + IL-15 are superior to IL-2 for the ex vivo expansion of 4T1 mammary carcinoma-specific T cells with greater efficacy against tumors in vivo," Breast Cancer Research and Treatment, Springer, NY, US (Oct. 14, 2009) vol. 122, No. 2, pp. 359-369.

Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.

Chen et al., "Minicircle DNA vectors devoid of bacterial DNA result in persistent and high-level transgene expression in vivo", Mol Ther. (2003) 8(3), 495-500.

Chen et al., 2013, Fusion protein linkers: property, design and functionality, Advanced Drug Delivery Reviews, 65(10):1357-1369.

Cho et al., "Structure of the extracellular region of HER2 alone and in complex with the Herceptin Fab", Nature (Feb. 13, 2003) 421(6924):756-760.

Circosta et al., "T Cell Receptor (TCR) Gene Transfer with Lentiviral Vectors Allows Efficient Redirection of Tumor Specificity in Naïve and Memory T Cells Without Prior Stimulation of Endogenous TCR," Human Gene Therapy (Nov. 18, 2009) vol. 20, No. 12, pp. 1576-1588.

Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.

(56) References Cited

OTHER PUBLICATIONS

Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen," Drug Metab Dispos (2002) 30(8): 869-874.
Database Geneseq [Online] May 5, 2005 (May 5, 2005), "Human splice variant protein expressed in ovary cells DEX0487 002.orf. 4.", XP002771301, retrieved from EBI accession No. GSP:ADY30515. Database accession No. ADY30515 ; & WO 2005/017102 A2 (Diadexus Inc [US]; Macina Roberto A [US]; Turner Leah R [US]; Sun Yong) Feb. 24, 2005 (Feb. 24, 2005).
Database UniProt [Online] Oct. 3, 2012 (Oct. 3, 2012), "SubName: Full=Receptor tyrosine-protein kinase erbB-2 {ECO: 00003131Ensembl:ENSP00000464252}; Flags: Fragment;", XP002771300, retrieved from EBI accession No. UNIPROT:J3QRJ7 Database accession No. J3QRJ7.
Dotti, Gianpietro, et al. "Design and development of therapies using chimeric antigen receptor-expressing T cells." Immunological reviews 257.1 (2014): 107-126.
Ercikan-Abali et al., "Active Site-Directed Double Mutants of Dihydrofolate Reductase," Cancer Res., (1996) vol. 56, No. 18, pp. 4142-4145.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-Independent Proliferation and Functional Differentiation of CD8+ T Lymphocytes," The Journal of Immunology (2008) 180:7958-7968.
Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.
Gargett et al., "Different cytokine and stimulation conditions influence the expansion and immune phenotype of third-generation chimeric antigen receptor T cells specific for tumor antigen GD2," Cytotherapy (2015) 17.4: 487-495.
Garrett et al., "Novel engineered trastuzumab conformational epitopes demonstrate in vitro and in vivo antitumor properties against HER-2/neu," The Journal of Immunology (Jun. 1, 2007) 178:7120-7131.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Giry-Laterriere et al. "Polyswitch lentivectors: 'all-in-one' lentiviral vectors for drug-inducible gene expression, live selection, and recombination cloning", *Human Gene Therapy,* Oct. 2011, 22:1255-1267.
Godiska et al., "Linear plasmid vector for cloning of repetitive or unstable sequences in *Exccherichia coli,*" (Dec. 29, 2009) Nuc Acids Res, vol. 38, No. 6, e88, pp. 1-9.
Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.
Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.
Han Weidong, "Treatment of Chemotherapy Refractory Human Epidermal growth Factor Receptor-2(HER-2) Positive Advanced Solid Tumors (CART-HER-2)", (Sep. 5, 2013) ClinicalTrials.gov Identifier: NCT01935843, pp. 1-7.
Holtkamp et al., "Modification of antigen-encoding RNA increases stability, translational efficacy, and T-cell stimulatory capacity of dendritic cells," Blood (Oct. 28, 2014), 2006/108:509-4017.
Hong et al., "Diverse solid tumors expressing a restricted epitope of L1-CAM can be targeted by chimeric antigen receptor redirected T lymphocytes," J Immunotherapy (2014) vol. 37, No. 2, pp. 93-104.
Hudecek et al. Receptor affinity and extracellular domain modifications affect tumor recognition by ROR1-specific chimeric antigen receptor T-cells. Clin Cancer Res. Jun. 15, 2013; 19(12): 3153-3164.
Hudecek et al., Nov. 16, 2012, The Non-Signaling Extracellular Spacer Domain of CD19-Specific Chimeric Antigen Receptors Is Decisive for in Vivo Anti-Tumor Activity, Blood, 120(21):951, 3 pp.
Hudecek et al., Sep. 11, 2014, "The Nonsignaling Extracellular Spacer Domain of Chimeric Antigen Receptors Is Decisive for In Vivo Antitumor Activity", Cancer Immunology Research, 3(2):125-135.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Designing chimeric antigen receptors to effectively and safely target tumors," Curr Opin Immunol. (Apr. 2015) 33:9-15.
Jensen et al: "Design and implementation of adoptive therapy with chimeric antigen receptor-modified T cells", Immunological Reviews., Special Issue, Dec. 13, 2013 vol. 257, No. 1; 127-144.
Johansen et al., "Evaluation of Tet-on system to avoid transgene down-regulation in ex vivo gene transfer to the CNS," Gene Therapy (2002) 9:1291-1301.
Johnston et al. "Regulated expression of erythropoietin from an AAV vector safely improves the anemia of beta-thalassemia in a mouse model," Mol Ther. Apr. 1, 2003, 7(4):493-497.
Jonnalagadda et al., "Efficient selection of genetically modified human T cells using methotrexate-resistant human dihydrofolate reductase," Gene Therapy, vol. 20, No. 8. Jan. 10, 2013, pp. 853-860.
Kacherovsky et al., "Combination of Sleeping Beauty transposition and chemically induced dimerization selection for robust production of engineered cells," Nucleic Acids Research (2012) 49(11):e85.
Kacherovsky et al., "Multiplexed 1-16 gene transfer to a human T-cell line by combining Sleeping Beauty transposon system with methotrexate selection", Biotechnology and Bioengineering (Jul. 23, 2015) vol. 112, No. 7, pp. 1429-1436.
Kay et al, "A robust system for production of minicircle DNA vectors", Nature Biotechnology, vol. 28, No. 12, Nov. 21, 2010, pp. 1287-1289.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Kunkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Lin et al., 2009, Optimization and validation of a robust human T-cell culture method for monitoring phenotypic and polyfunctional antigen-specific CD4 and CD8 T-cell responses, Cytotherapy, 11(7):912-922.
Littlewood et al., "A modified oestrogen receptor ligand-binding domain as an improved switch for the regulation of heterologous proteins," Nucleic Acids Res (May 25, 1995) 23(10):1686-1690.
Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) vol. 7, No. 6, pp. 539-544.
Liu et al., "IL-21 synergizes with IL-7 to augment expansion and anti-tumor function of cytotoxic T cells," International Immunology (2007) vol. 19, No. 10, pp. 1213-1221.

(56) References Cited

OTHER PUBLICATIONS

Loeken, Mary R., "Effects of mutation of the CREB binding site of the somatostatin promoter on cyclic AMP responsiveness in CV-1 cells", *Gene Expr.* (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, "Immunotherapy of Malignant Disease Using Chimeric Antigen Receptor Engrafted T Cells", *ISRN Oncology,* vol. 2012, pp. 1-23, Nov. 14, 2012.
Mátés et al., "Molecular evolution of a novel hyperactive Sleeping Beauty transposase enables robust stable gene transfer in vertebrates," Nature Genetics (Jun. 2009) vol. 41, No. 6, pp. 753-761.
Mcgehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.
Mckinlay et al., "Blood monocytes, myeloid dendritic cells and the cytokines interleukin (IL)-7 and IL-15 maintain human CD4+ T memory cells with mixed helper/regulatory function," Immunology (2006) vol. 120, pp. 392-403.
Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
O'Reilly et al., "Identification of an activating transcription factor (ATF) binding site in the human transforming growth factor-beta 2 promoter," J. Biol. Chem. (Oct. 5, 1992) 267:19938-19943.
Pakula et al., "Genetic analysis of protein stability and function," Annual review of genetics (1989) vol. 23, No. 1, p. 289-310, c.305-306.
Papapetrou et al. "Harnessing endogenous miR-181a to segregate transgenic antigen receptor expression in developing versus post-thymic T cells in murine hematopoietic chimeras", The Journal of clinical investigation. Jan. 5, 2009;119(1):157-68.
Park et al., "Adoptive Transfer of Chimeric Antigen Receptor Re-Directed Cytolytic T Lymphocyte Clones in Patients with Neuroblastoma," Mol. Ther. (Apr. 2007) vol. 15, No. 4; pp. 825-833.
Pelloquin et al., Dec. 1986, Human B lymphocytes immortalization by Epstein-Barr virus in the presence of cyclosporin A, In Vitro Cell Dev Biol, 22(12):689-694.
Pezutto et al., May 1, 1987, CD19 monoclonal antibody HD37 inhibits anti-immunoglobulin-induced B cell activation and proliferation, The Journal of Immunology, 138(9):2793-2799.
Pollock et al. "Delivery of a stringent dimerizer-regulated gene expression system in a single retroviral vector," Proc Natl Acad Sci. USA Nov. 21, 2000, 97(24):13221-1326.
Promega, "pSP64 Poly(A) Vector Sequence and Map," Technical Bulletin No. 052, Revised May 2000, pp. 1-8.
Riddell et al. "Adoptive therapy with chimeric antigen receptor modified T cells of defined subset composition." Cancer journal (Sudbury, Mass. ) 20.2 (2014): 141-144.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Robinsons et al., Jan. 1991, Metabolites, pharmacodynamics, and pharmacokinetics of tamoxifen in rats and mice compared to the breast cancer patient, Drug Metab Dispos, 19(1):36-43.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98. DOI: 10.1158/2159-8290.CD-12-0548.
Schmittgen et al. "Analyzing real-time PCR data by the comparative C(T) method", *Nat Protoc.* 2008:3(6):1101-8.
Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Sharma et al., "Efficient Sleeping Beauty DNA Transposition from DNA Minicircles," Mol Ther Nuc Acids (2013) 2:e74, 1-10.
Surh et al., "Homeostasis of memory T cells," Immunological Reviews (2006) vol. 211, pp. 154-163.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, R. "The SRE: a growth factor responsive transcriptional regulator. (PMID:2133110)", *Seminars in Cancer Biology,* Feb. 1, 1990, 1(1):47-58.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunistic fungal pathogen *Aspergillus fumigatus,*" BMC Microbiol. (2005) 5(1):11 pages.
Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.
Wang et. al., "A transgene-encoded cell surface polypeptide for selection, in vivo tracking, and ablation of engineered cells", Blood, vol. 118, No. 5, Aug. 4, 2011 (Aug. 4, 2011), pp. 1255-1263.
Weill et al., "Translational control by changes in poly(A) tail length: recycling mRNAs," Nature Structural & Molecular Biology (Jun. 2012) vol. 19, No. 6, pp. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.
Yant et al. "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.
Ye et al., "Characterization of a silencer regulatory element in the human interferon-gamma promoter," J. Biol. Chem., (Oct. 14, 1994) 269:25728-25734.
Zambon et al., "Increased Expression of the Pro-Apoptotic Protein Bim: A Mechanism for cAMP/PKA-Induced Apoptosis of Immature T Cells," J. Biol. Chem. (2011) 286(38):33260-33267.
Zeng et al., "Synergy of IL-21 and IL-15 in regulating CD8+ T cell expansion and function," JEM (Jan. 3, 2005) vol. 201, No. 1, pp. 139-148.
Zheng, Changyu et al., "All Human EF1" Promoters Are Not Equal: Markedly Affect Gene Expression in Constructs from Different Sources, International Journal of Medical Sciences (2014) 11(5):404-408.
Burns et al., 2010, A high molecular weight melanoma-associated antigen-specific chimeric antigen receptor redirects lymphocytes to target human melanomas, Cancer Research, 70(8):3027-3033.
Chen et al., Jan. 2007, Generation of a transgenic mouse model with chondrocyte-specific and tamoxifen-inducible expression of cre recombinase, Genesis, 45:44-50.
Chen et al., Sep. 15, 2005, NF-κ-B RelA phosphorylation regulates RelA acetylation, Molecular and Cellular Biology, 25(18):7966-7975.
Courtney et al., 2018, TCR signaling: mechanisms of initiation and propagation, Trends in Biochemical Sciences, 43(2):108-123.
Dolezal et al., 2000, ScFv multimers of the anti-neuraminidase antibody NC10: shortening of the linker in single-chain Fv fragment assembled in VL to VH orientation drives the formation of dimers, trimers, tetramers and higher molecular mass multimers, Protein Engineering, 13(8):565-574.
Edwards et al., 2003, The remarkable flexibility of the human antibody repertoire; isolation of over one thousand different antibodies to a single protein, BLyS, J. Mol. Biol., 334:103-118.

(56) References Cited

OTHER PUBLICATIONS

Guedan et al., 2018, Enhancing CAR T cell persistence through ICOS and 4-1BB costimulation, JCI Insight, 3(1):11-13.
Guha et al., 2017, Frontline science: functionally impaired geriatric CAR-T cells rescued by increased α5β1 integrin expression, Journal of Leukocyte Biology, 102(2):201-208.
Hege et al., 2017, Safety, tumor trafficking and immunogenicity of chimeric antigen receptor (CAR)-T cells specific for TAG-72 in colorectal cancer, Journal for Immunotherapy of Cancer, 5(1):1-14.
Kanamori et al., A human-tissue type whose host is a human cell expression of plasminogen activator, Tissue Culture Research, 8(2):31-39, 1990.
Kochenderfer et al., Accession No. ADM64594.1, FMC63-28Z receptor protein, Jun. 11, 2012, Genbank.
Lloyd et al., 2009, Modelling the human immune response: performance of a $10^{11}$ human antibody repertoire against a broad panel of therapeutically relevant antigens, Protein Engineering, Design & Selection 22(3):159-168.
Long et al., 2015, 4-1BB costimulation ameliorates T cell exhaustion induced by tonic signaling of chimeric antigen receptors, Nature Medicine, 21(6):581-590.
Maeda et al., 1997, Engineering of functional chimeric protein G—Vargula Luciferase, Analytical Biochemistry, 249(2):147-152.
Maus et al., 2013, T cells expressing chimeric antigen receptors can cause anaphylaxis in humans, Cancer Immunology Research, 1(1):26-31.
Nakazawa et al., May 2009, 231. Expression of multiple transgenes in human T cells from PiggyBac transposons, Molecular Therapy, 17(Suppl 1):S91.
Richman et al., 2018, High-affinity GD2-specific CAR T cells induce fatal encephalitis in a preclinical neuroblastoma model, Cancer Immunology Research, 6(1):36-46.
Sadelain et al., 2009, The promise and potential pitfalls of chimeric antigen receptors, Current Opinion in Immunology, 21:215-223.
Schamel et al., 2019, The TCR is an allosterically regulated macromolecular machinery changing its conformation while working, Immunological Reviews, 291(1):8-25.
Teplyakov et al., 2014, Antibody modeling assessment II. Structures and models, Proteins: Structure, Function, and Bioinformatics, 82(8):1563-1582.
Turtle et al., 2016, CD19 CAR-T cells of defined CD4+: CD8+ composition in adult B cell ALL patients, The Journal of Clinical Investigation, 126(6):2123-2138.
Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.
Yang et al., Feb. 16, 2010, Functional interplay between acetylation and methylation of the RelA subunit of NF-κ-B, Molecular and Cellular Biology, 30(9):2170-2180.
Andersch et al., 2019, CD171- and GD2-specific CAR-T cells potently target retinoblastoma cells in preclinical in vitro testing, BMC Cancer, 19:895.
Ang et al., May 1, 2009, 62. Conditional activation of T cells to specifically target c-Met under hypoxia, Cancer—Apoptosis & Suicide/Cancer Immunotherapy, Adoptive T Cell Therapy, 17(Suppl 1):S25-SA26.
Brunner et al., Jan. 1999, Cytotoxic T cells: Double-barreled shot guns, Nature Medicine, 5(1):20.
ClinicalTrials.gov Identifier: NCT02311621, first posted Dec. 9, 2014, 9 pp.
Cooper et al., Jul. 2004, Enhanced transgene expression in quiescent and activated human CD8+ T cells, Human Gene Therapy, 15:648-658.
Gardner et al., Nov. 29, 2018, Early clinical experience of CD19 x CD22 dual specific Car T cells for enhanced anti-leukemic targeting of acute lymphoblastic leukemia, Blood, 132(Supplement 1):278.
GenBank AH002596.2, Jul. 2016, *Homo sapiens* albumin (ALB) gene, partial cds, 2 pp.
Hoefnagel et al., Mar. 2001, A comparison of targeting of neuroblastoma with mIBG and anti L1-Cam antibody mAb chCE7: therapeutic efficacy in a neuroblastoma xenograft model and imaging of neuropblastoma patients, Eur J Nucl Med 28(3):359-368.
Hong et al., Jan. 13, 2016, L1 cell adhesion molecule-specific chimeric antigen receptor-redirected human T cells exhibit specific and efficient antitumor activity against human ovarian cancer in mice, PLOS One, 11(1):e0146885, 18 pp.
Jonnalagadda et al., Apr. 2015, Chimeric antigen receptors with mutated IgG4 Fc spacer avoid Fc receptor binding and improve T cell persistence and antitumor efficacy, Molecular Therapy, 23(4)L757-768.
Kunkele et al., Jan. 15, 2017, Preclinical assessment of CD171-directed CART-cell adoptive therapy for childhood neuroblastoma: CE7 epitope target safety and product manufacturing feasibility, Clin Cancer Res 23(2):466-477.
Makino et al., 2003, Hypoxia-inducible factor regulates survival of antigen receprot-driven T cells, J. Immunol. 171:6534-6540.
Muller et al., Dec. 2008, Spliceosomal peptide P140 for immunotherapy of systemic lupus erythematosus: results of an early phase II clinical trial, Arthritis & Rheumatism: Official Journal of the 8 American College of Rheumatology, 58(12):3873-3883.
Schonmann et al. 1986, Production and characterization of monoclonal antibodies against human neuropblastoma, Int J Cancer, 37:255-262.
Tey et al., 2007, Inducible caspase 9 suicide gene to improve the safety of allodepleted T cells after haploidentical stem cell transplantation, Biol. Blood & Marrow Transplantation, 13:913-924.

* cited by examiner

PATIENT CHARACTERISTICS

| ID | Age (y) | Relapse # | # of prior HSCT | Time from most recent HSCT (mo) | Prior CD19 directed therapy | Cytogenetics | % ALL in marrow Pre T cell | Lympho-depletion | Dose Level | Response |
|---|---|---|---|---|---|---|---|---|---|---|
| S01 | 21 | 2 | 1 | 6 | No | Ph-like | 59 | Cytoxan 3g/$m^2$ | 1 | MRD-CR |
| S02 | 22 | 2 | 1 | 16 | No | | 0.34 | Cytoxan/Etoposide | 1 | MRD-CR |
| S03 | 21 | 2 | 1 | 28 | No | | 96 | Cytoxan 3gm/$m^2$ | 1 | MRD-CR |
| S04 | 11 | 2 | 2 | 14 | No | | MRD neg | Cytoxan 3g/$m^2$ | 1 | MRD-CR |
| S05 | 19 | 2 | 1 | 36 | No | iAMP21, Monoso my 7 | MRD neg | Cytoxan 3g/$m^2$ | 1 | MRD-CR |
| S06 | 4 | 2 | 1 | 5 | BiTE | | 54 | Fludarabine | 1 | PD |
| S10 | 17 | 2 | 1 | 22 | BiTE | Hypo-diploid | 7.8 | Cytoxan 3g/$m^2$ | 1 | MRD-CR |
| S07 | 1 | 2 | 1 | 8 | BiTE | t(4;11) MLL | 77 | Cytoxan 1.5g/$m^2$ | 2 | MRD-CR |
| S08 | 23 | 1 | 1 | 33 | No | IKZF1 delection, Ph-like | 75 | Cytoxan 3g/$m^2$ | 2 | MRD-CR |
| S09 | 6 | 2 | 1 | 6 | No | iAMP21 | 92 | Cytoxan 3g/$m^2$ | 2 | PR |
| S15 | 13 | 1 | 1 | 18 | CD19 CAR pre-HSCT | Trisomy 10 | 1.39 | Cytoxan 3g/$m^2$ | 2 | MRD-CR |
| S11 | 15 | 2 | 1 | 59 | No | | 15 | Cytoxan 3g/$m^2$ | 3 | MRD-CR |
| S13 | 8 | 2 | 1 | 13 | No | Hypo-diploid | 8.3 | Cytoxan 3g/$m^2$ | 3 | MRD-CR |

HSCT hematopoietic stem cell transplant; BiTE blinatumomab; MPF multiparameter flow; Ph-like Philadelphia-like; iAMP21 internal amplification of chromosome 21; MRD minimal residual disease; CR complete remission; PR partial response; PD progressive disease

FIG. 5

Ig or TCR Rearrangements as a Marker of MRD

| ID | % of B cell reads BM pre T-cells | Day 21 BM | Day 63 BM | Later Time Point |
|---|---|---|---|---|
| S01 | 97.4 | Negative (<0.0025%) | Positive (0.0016%) | Negative (<0.0002%) |
| S03 | 98.9 | Positive (0.096%) | Negative (<0.0007%) | |
| S04 | 0.02 | Negative (<0.0002%) | Negative (<0.0002%) | |
| S07 | 44.4 | Positive (0.017%) | Positive (0.0018%) | Positive-3mo (0.0004%) |
| S08 | 88.5 | Negative*(<0.0002%) | Negative (<0.0002%) | |
| S10 | 62.7 | Negative (<0.0014%) | Pending | |
| S11 | 58.4/38.1 | Positive (0.0071%) | Pending | |

Assay performed by Adaptive Technologies. * day 42; < indicates upper bound of highest 95% confidence interval

FIG. 9

| Cohort | Patient ID | Age (y) | Relapse# | Amount of disease in BM at enrollment by MPF | Current progress in study / off study |
|---|---|---|---|---|---|
| 1A | 14602-S01 | 21 | 2 | 90 | In long term follow up |
| 1A | 14602-S02 | 22 | 2 | 0.4 | In long term follow up |
| 1A | 14602-S03 | 21 | 2 | 90 | In long term follow up |
| 1A | 14602-S04 | 11 | 2 | 0.04 | In long term follow up |
| 1A | 14602-S05 | 19 | 2 | 2 | In long term follow up |
| 1A | 14602-S06 | 4 | 2 | 54 | D+42 |
| 1B | 14602-S07 | 1 | 2 | 69 | D+21 |
| 1B | 14602-S08 | 23 | 1 | 98.6 | D+7 |
| 1B | 14602-S09 | 6 | 2 | 30 | Pre T cell infusion |
| TBD | 14602-S10 | 17 | 2 | 1.94 | Pre T cell infusion |
| TBD | 14602-S11 | 15 | 2 | 23 | Pre T cell infusion |
| TBD | 14602-S12 | 12 | 3 | 0.04 | Pre T cell infusion |

FIG. 10

Peripheral Blood Day +14:

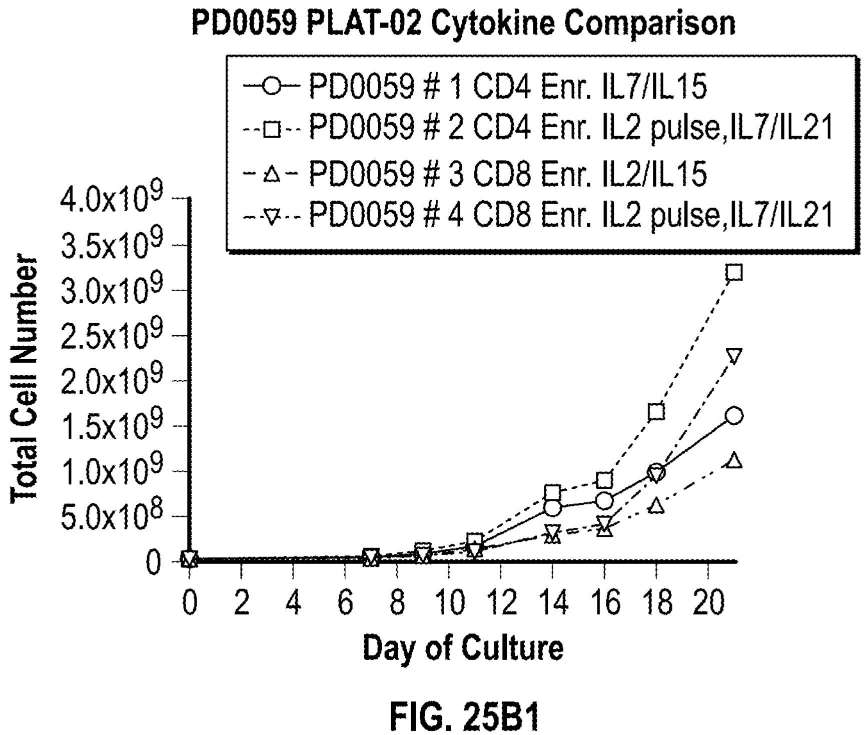
FIG. 25B1
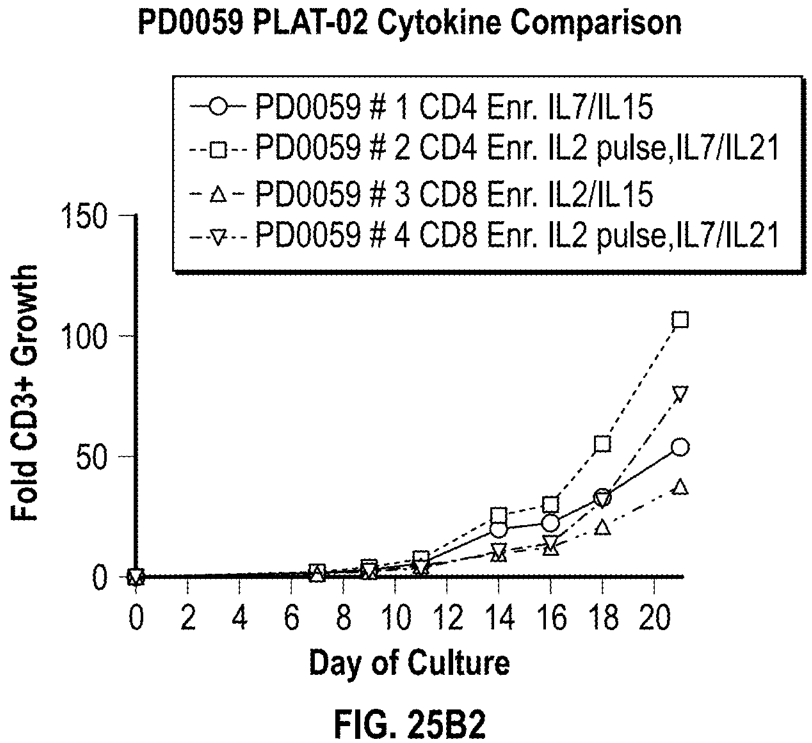
FIG. 25B2

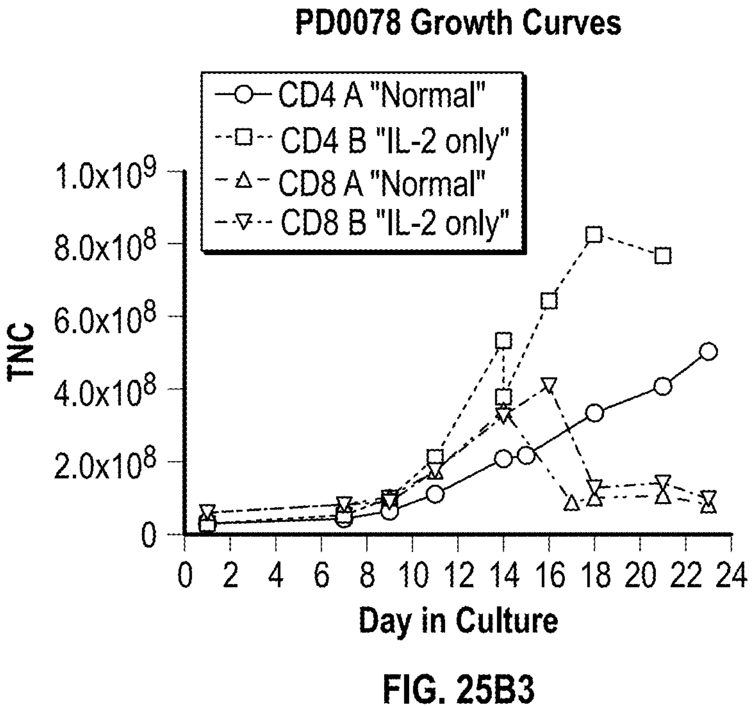
FIG. 25B3
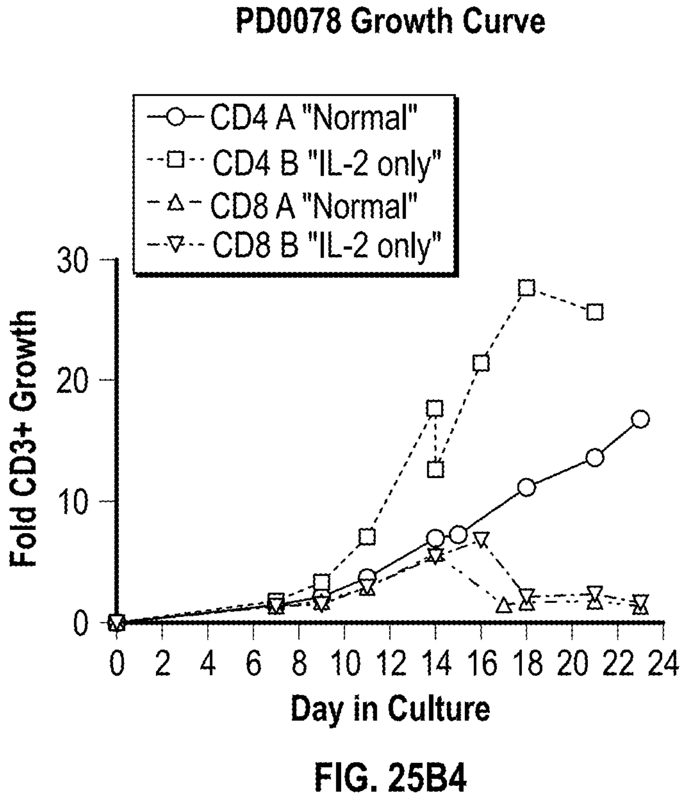
FIG. 25B4

| | |
|---|---|
| Starting Material: | PD0038 CD4/CD8 selected |
| Transduction: | D+1, ZRX-014 |
| Stim Reagent: | CTS 3/28 |
| Scale: | Full (pooled 50:50 product) |

| | |
|---|---|
| Starting Material: | Fresh,APH-NDPBMC-004 |
| Transduction: | D+1, ZRX-014 |
| Stim Reagent: | CTS 3/28 |
| Scale: | Full scale |

| | |
|---|---|
| Starting Material: | Fresh, APH - NDPBMC-007 |
| Transduction: | D+1, ZRX-014 |
| Stim Reagent: | CTS 3/28 |
| Scale: | Fullscale |

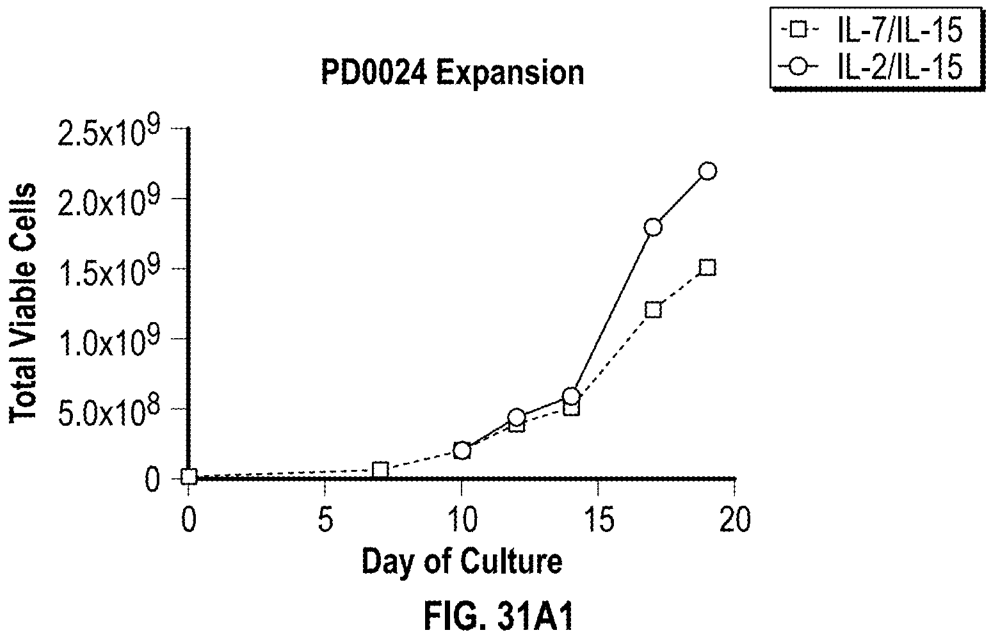
FIG. 31A1
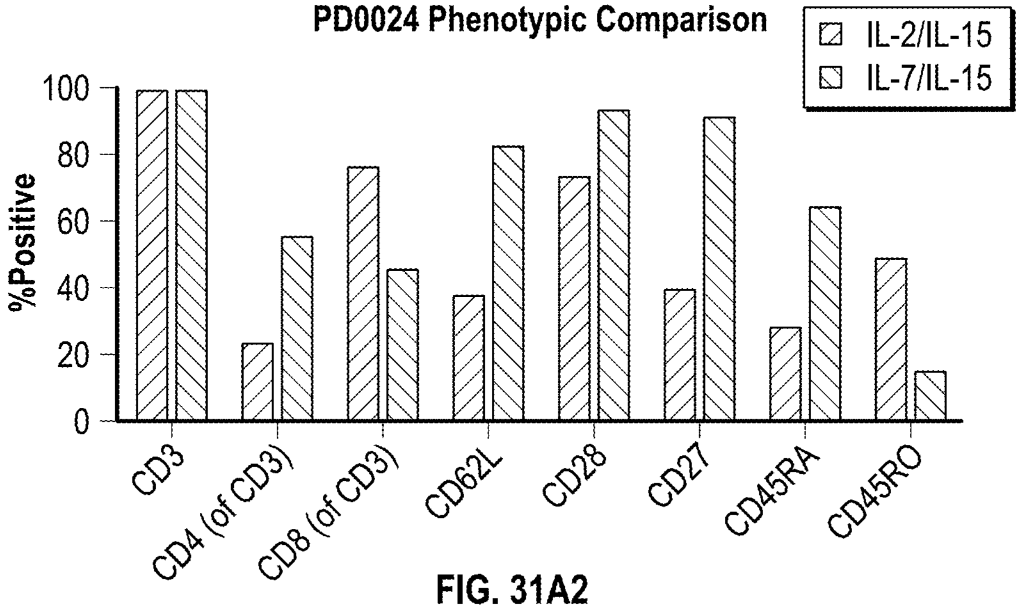
FIG. 31A2

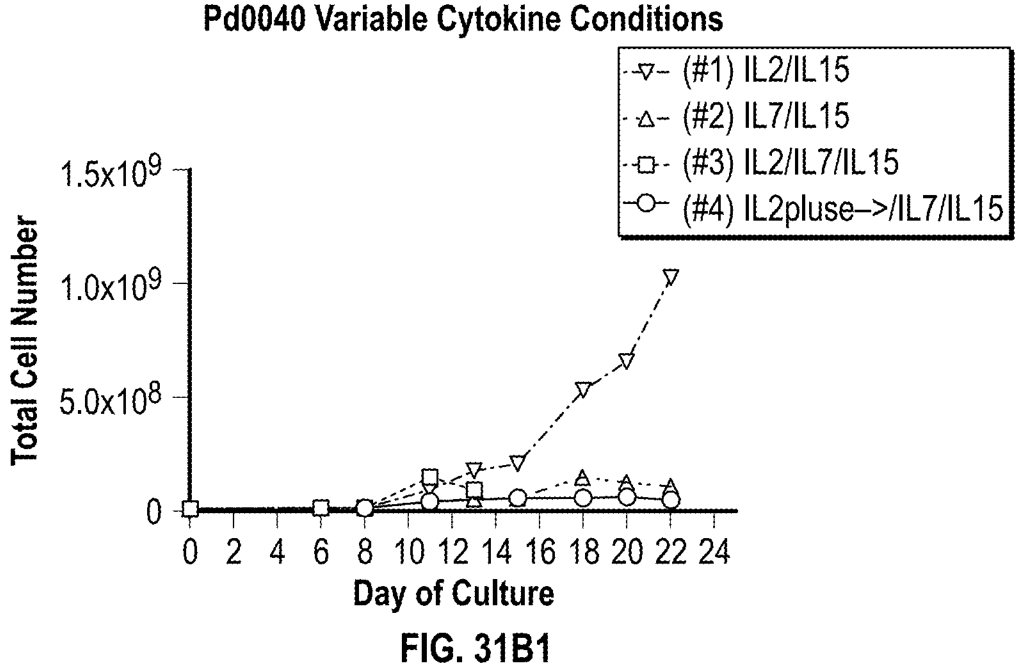
FIG. 31B1
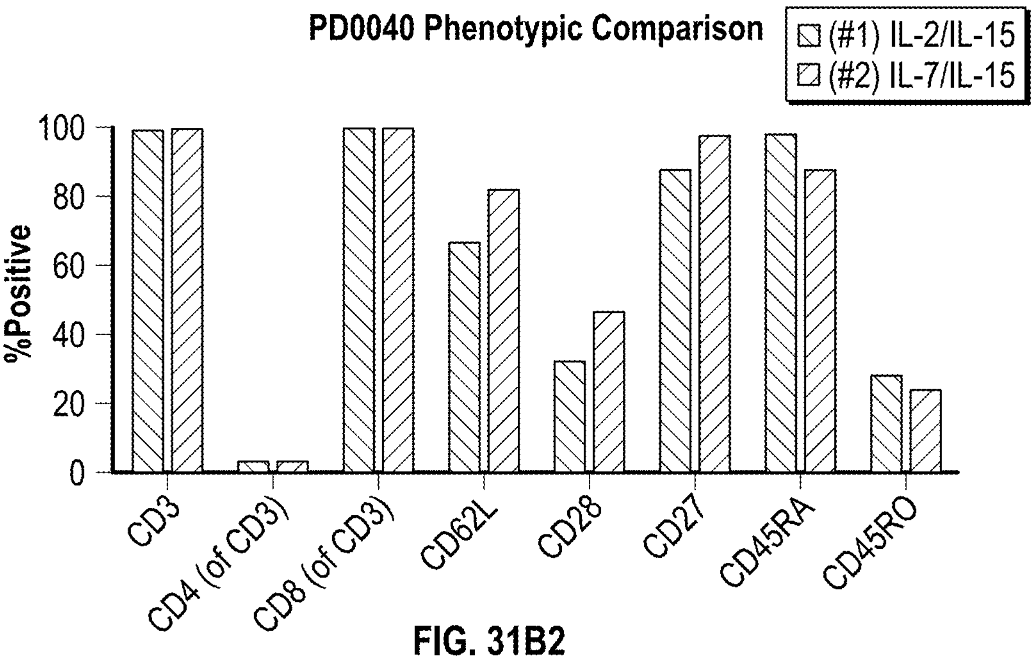
FIG. 31B2

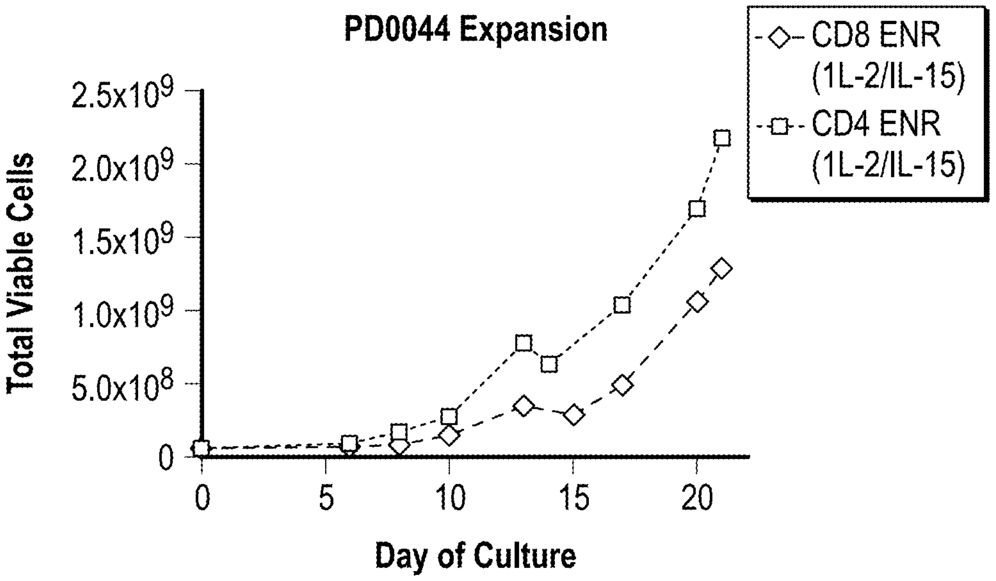
FIG. 32A1
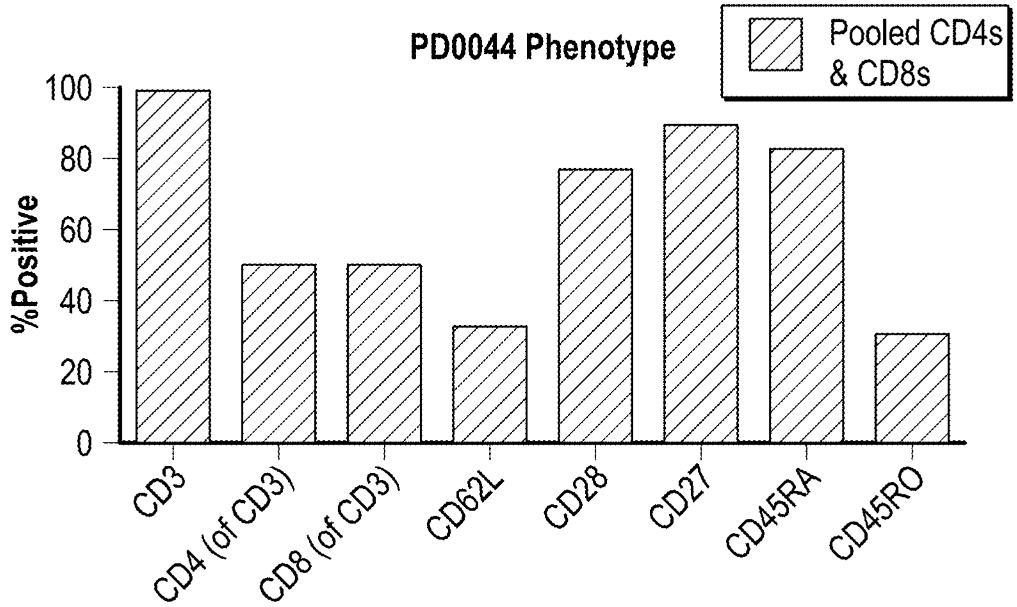
Growing CD8-enriched cultures in IL-2/IL-15 and CD4-enriched cultures in IL-7/IL-15 yields robust expansion of both cultures and strong expression of memory phenotype (representative data shown above)
FIG. 32A2

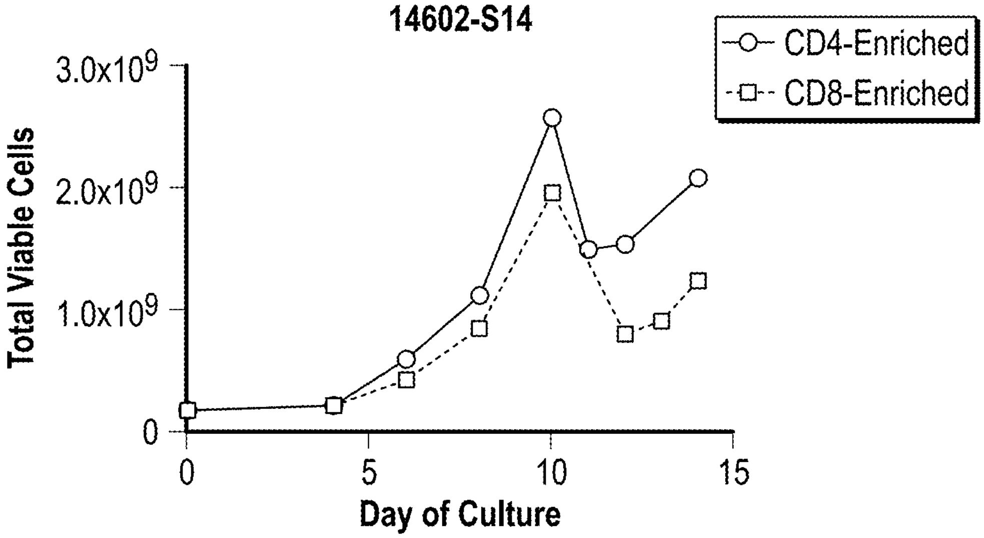
FIG. 32B1
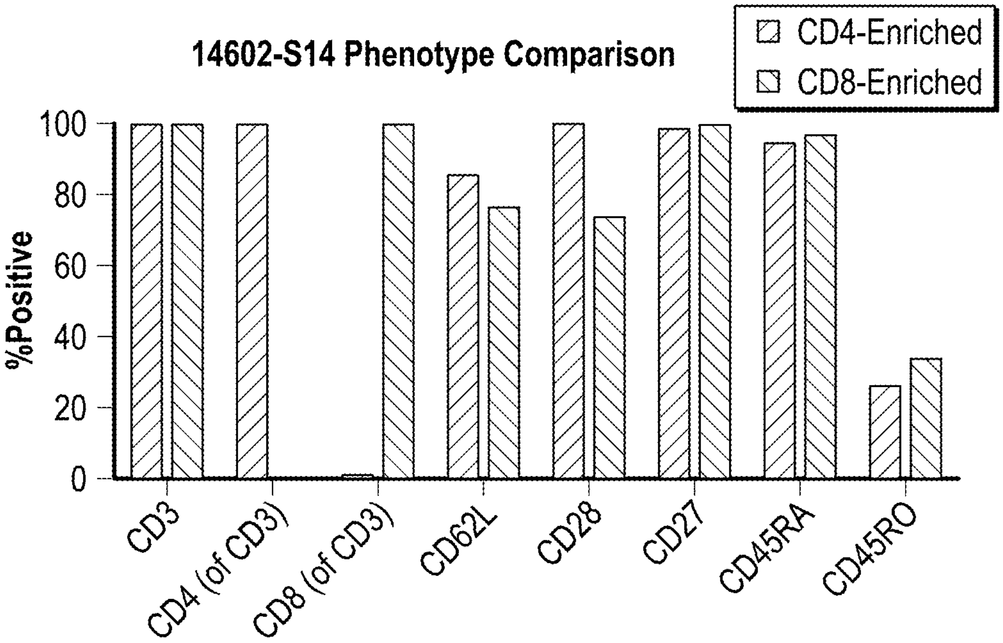
Growing CD8-enriched cultures in IL-2/IL-15 and CD4-enriched cultures in IL-7/IL-15 yields robust expansion of both cultures and strong expression of memory phenotype (representative data shown above)
FIG. 32B2

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S01 CD4 | 98.7 | 98.3 | | 96.6 |
| 14602-S01 CD8 | 98.1 | | 96.9 | 92.5 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S02 CD4 | 94.9 | 94.5 | | 95.5 |
| 14602-S02 CD8 | 98.5 | | 98.2 | 97.8 |

| Product ID | Total EGFRt+ (pre-cryo) | CD4+/EGFRt+ (pre-cryo) | CD8+/EGFRt+ (pre-cryo) | Total EGFRt+ (release testing) | CD3 | CD4+CD8- (of CD3) |
|---|---|---|---|---|---|---|
| 14602-S03 CD4 | 98.3 | 98.2 | | 97.2 | 98.5 | 97.7 |
| 14602-S03 CD8 | 93.6 | | 93.1 | 96.2 | | |
| 14602-S03-02 CD8 | 96.6 | | 95.9 | | | |

| CD4-CD8+ (of CD3) | CD62L | Total CD28 from CD28(CD3) | CD27 | CD127 | CD45RA+/CD45RO- | CD45RA+ |
|---|---|---|---|---|---|---|
| 0.2 | 60.9 | 97.4 | 98 | 23.7 | 66.2 | 84.9 |
| | | | | | | |
| | | | | | | |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S04 CD4 | 95.6 | 95.5 | | 94.2 |
| 14602-S04-02 CD8 | 99.4 | | 99.2 | 94.5 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S05 CD4 | 95.2 | 95.1 | | 97.7 |
| 14602-S05 CD8 | 97.5 | | 97.3 | 96.6 |

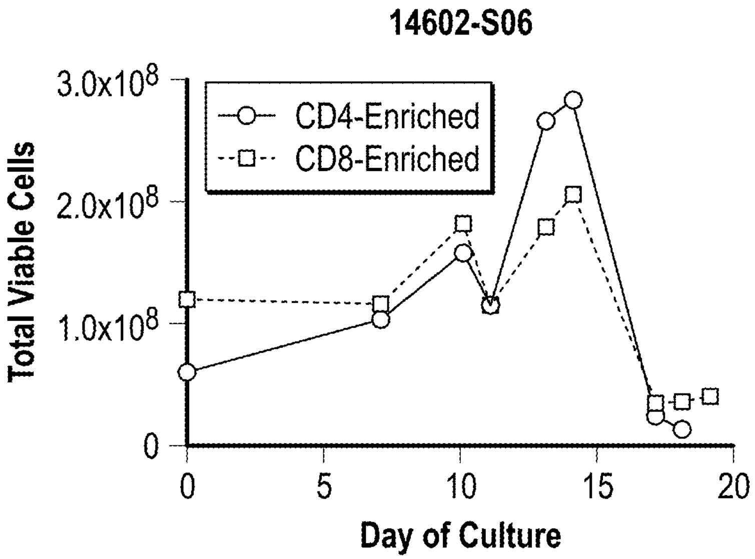
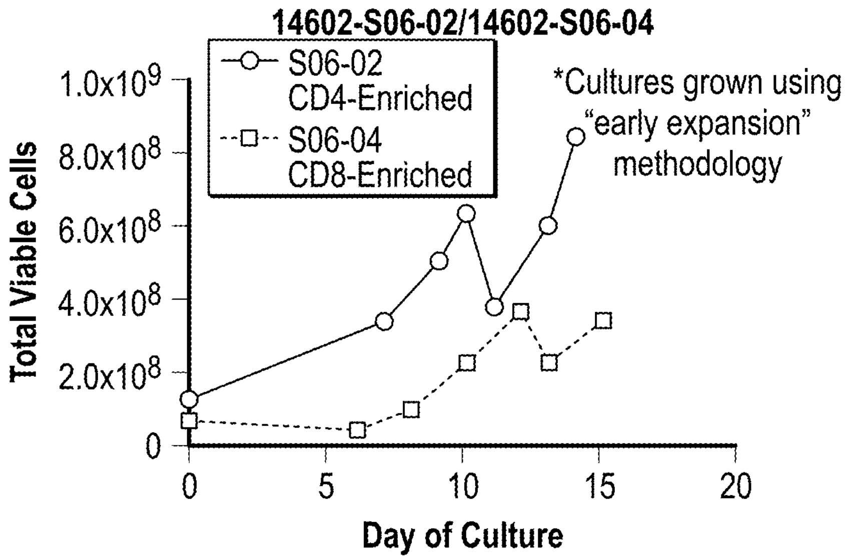
| Product ID | Total EGFRt+ (pre-cryo) | CD4+/EGFRt+ (pre-cryo) | CD8+/EGFRt+ (pre-cryo) | Total EGFRt+ (release testing) | CD3 | CD4+CD8- (of CD3) | CD4-CD8+ (of CD3) | CD62L | Total CD28 from CD28(CD3) | CD27 | CD127 | CD45RA+/CD45RO- | CD45RA+ |
|---|---|---|---|---|---|---|---|---|---|---|---|---|---|
| 14602-S06 CD8 | 99.8 | | 99.7 | 97 | | | | | | | | | |
| 14602-S06-02 CD4 | 98.1 | 98.1 | | 98.5 | | | | | | | | | |
| 14602-S06-04 CD8 | 99.4 | | 94.4 | 95.5 | 98.3 | 0.1 | 98.3 | 49.2 | 57.7 | 99.9 | 70.3 | 48.3 | 99.3 |
FIG. 34C

| Product ID | Total EGFRt+ (pre-cryo) | CD4+/EGFRt+ (pre-cryo) | CD8+/EGFRt+ (pre-cryo) | Total EGFRt+ (release testing) | CD3 | CD4+CD8- (of CD3) |
|---|---|---|---|---|---|---|
| 14602-S07 CD4 | 98.6 | 98.5 | | 94.1 | 84.3 | 98.7 |
| 14602-S07 CD8 | 99.3 | | 99 | 95.2 | 99.6 | 0.7 |

| CD4-CD8+ (of CD3) | CD62L | total CD28 (from CD28/CD3) | CD27 | CD127 | CD45RA+/ CD45RO- | CD45RA+ |
|---|---|---|---|---|---|---|
| 0 | 57 | 98.8 | 99.4 | 37 | 51.4 | 65.5 |
| 97.3 | 66.1 | 51.2 | 99.8 | 55.6 | 52.8 | 94 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S08 CD4 | 97.4 | 97.3 | | 96.1 |
| 14602-S08 CD8 | 97.8 | | 97.6 | 95.6 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S09 CD4 | 99.4 | 99.4 | | 95.2 |
| 14602-S09 CD8 | 99.3 | | 99 | 92.5 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S10 CD4 | 98.6 | 98.4 | | 97.7 |
| 14602-S10 CD8 | 97.6 | | 93.4 | 96.1 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S11 CD4 | 99.2 | 99.1 | | 98.1 |
| 14602-S11 CD8 | 97.1 | | 97.1 | 93.7 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S12 CD4 | 98.7 | 98.7 | | 97.3 |
| 14602-S12 CD8 | 99.8 | | 99.8 | 94 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S13 CD4 | 99.8 | 99.8 | | 95.9 |
| 14602-S14 CD8 | 99.8 | | 99.8 | 97 |

| Product ID | Total EGFRt+ (pre-cryo) | CD4+/EGFRt+ (pre-cryo) | CD8+/EGFRt+ (pre-cryo) | Total EGFRt+ (release testing) | CD3 | CD4+CD8- (of CD3) |
|---|---|---|---|---|---|---|
| 14602-S14 CD4 | 99.4 | 99.4 | | 98.4 | 99.8 | 99.5 |
| 14602-S14 CD8 | 99.4 | | 99.2 | 95.1 | 99.8 | 0 |

| CD4-CD8+ (of CD3) | CD62L | total CD28 (from CD28/CD3) | CD27 | CD127 | CD45RA+/ CD45RO- | CD45RA+ |
|---|---|---|---|---|---|---|
| 0 | 85.3 | 99.4 | 98.3 | 82.5 | 71.3 | 94.1 |
| 99.5 | 76.1 | 73.6 | 99.4 | 67 | 63.6 | 96.8 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S15 CD4 | 98.1 | 98 | | 97.7 |
| 14602-S15 CD8 | 98.4 | | 97.9 | 96.2 |

| Product ID | Total EGFRt+ (pre-cryo) | CD4+/EGFRt+ (pre-cryo) | CD8+/EGFRt+ (pre-cryo) | Total EGFRt+ (release testing) |
|---|---|---|---|---|
| 14602-S16 CD4 | 96.9 | 96.9 | | 96.3 |
| 14602-S16 CD8 | 96.2 | | 95.8 | 94.9 |

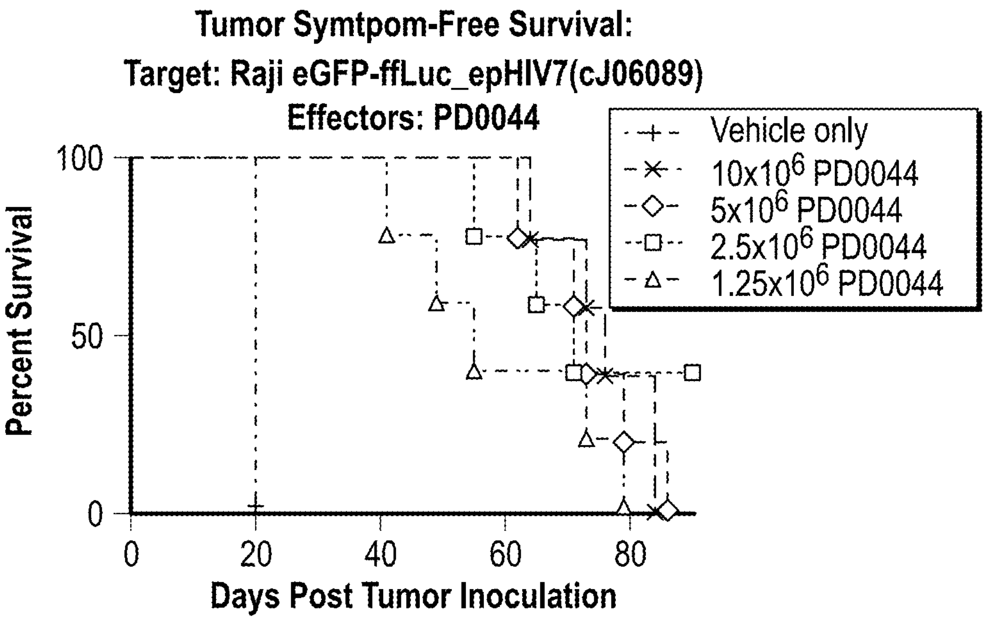
FIG. 39B1
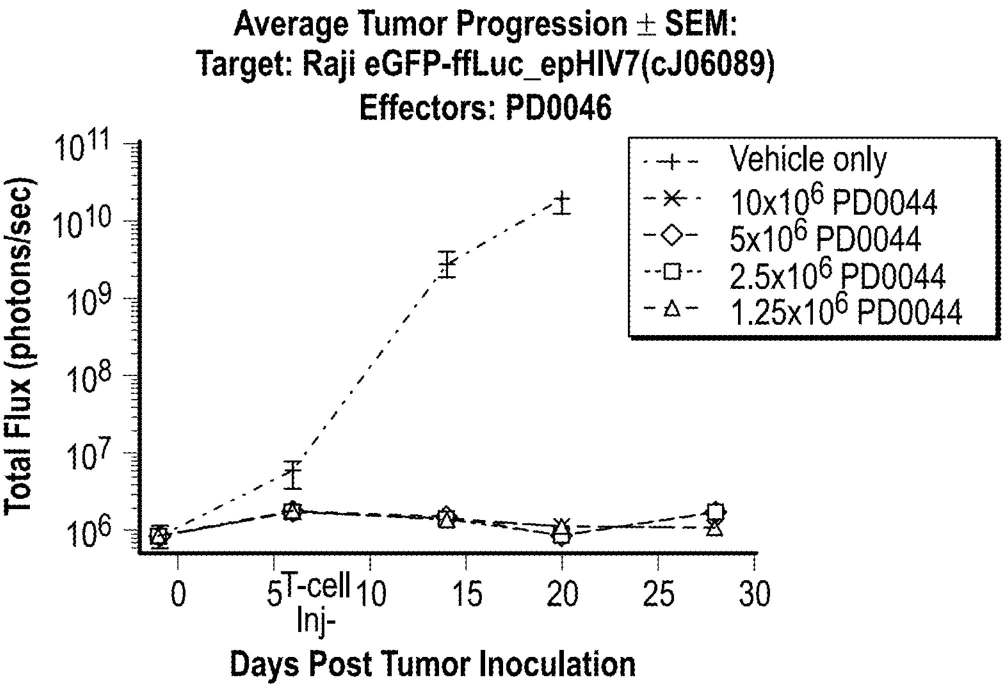
FIG. 39B2

JME13-25: Cytokine Growth Conditions

AIM(S):

1. Determine if there is an in vivo difference in killing ability between cells that have been grown in various cytokine conditions in vitro.

EXPERIMENTAL SET-UP:

(n=5 per group)

Group A: PBS only

Group B: "Normal" 1:1 EGFRt+ CD4:CD8 transduced With Zrx-014

PD0055 #1 (Donor PD0038 CD4 with 5ng/ml IL7 & 0.5ng/ml IL15, S1D14 @ 75.9% EGFRt+)

PD0051 #1 (Donor PD0038 CD8 with 50U/ml IL2 & 0.5ng/ml IL15, S1D21 @ 76.8% EGFRt+)

Group C: "Pulsed" 1:1 EGFRt+CD4:CD8 transduced with Zrx-014

PD0055 #2 (Donor PD0038 CD4 with 50U/ml IL2 pulse 5 days, then 5ng/ml IL7 & 5ng/ml IL21, S1D11 @ 81.2% EGFRt+)

PD0051 #2 (Donor PD0038 CD8 with 50U/ml IL2 pulse 5 days, then 5ng/ml IL7 & 5ng/ml IL21, S1D21 @ 89.5% EGFRt+)

*Note: Cells thawed, counted, and injected same day

Image mice before tumor

Tumor inoculation: 0.5e6 cells/mouse IV

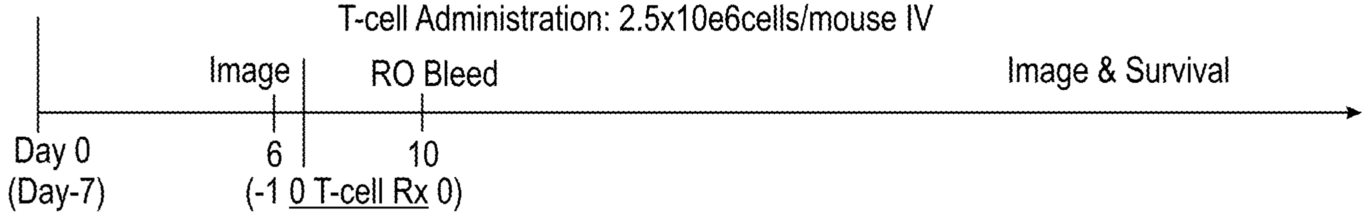

FIG. 41

JME13-25:Cytokine Growth Conditions
FACS Analysis on Cells Post Thaw that were Used for Injection into Mice in JME13-25

Cell Thawed out with Similar %EGFRt+

| cJ# | Cell Line | Day of Freezeing EGFRt+ | Day of Thaw EGFRt+ |
|---|---|---|---|
| cJ06641 | PD0051 #1 (CD8 in IL2/IL15) | 76.8% | 78.3% |
| cJ06642 | PD0051 #2 (CD8 in IL2 pulse, IL7/IL21) | 89.5% | 84.1% |
| cJ06643 | PD0055 #1 (CD4 in IL7/IL15) | 75.9% | 77.0% |
| cJ06645 | PD0055 #2 (CD4 in IL2 pulse, IL7/IL21) | 81.2% | 82.9% |

Samples collected on mixed samples left over from preparation for injection into mice.
Data acquired but not analyzed.

FIG. 42E

CD8 T-Cell Persistance in Peripheral Blood 3 Days After T-Cell Transfer

Caveats to Note:

- <u>This staining is prior to inclusion of the Live/Dead stain and switching from CD3 to CD45 in optimized mouse panel.</u>
- Lymphocyte gate is not confirmed.
- EGFRt staining in Cd3- population.
- CD4-CD8- population is present in CD3+EGFRt+ population.

AIM(S):

1. Determine if there is an in vivo difference in killing ability between cells that have been grown in various cytokine conditions in vitro with repeat antigen encounters.

EXPERIMENTAL SET-UP:

(n=3 per group)

Group A: PBS only

Group B: "Normal"1:1 EGFRt+CD4:CD8 transduced With Zrx-014

PD0055 #1 (Donor PD0038 CD4 with 5ng/ml IL7 & 0.5ng/ml IL15, S1D14 @ 75.9% EGFRt+)

PD0051 #1 (Donor PD0038 CD8 with 50U/ml IL2 & 0.5ng/ml IL15, S1D21 @ 76.8% EGFRt+)

Group C: "Pulsed" 1:1 EGFRt+CD4: CD8 transduced with Zrx-014

PD0055 #2 (Donor PD0038 CD4 with 50U/ml IL2 pulse 5 days, then 5ng/ml IL7& 5ng/ml IL21, S1D11 @ 81.2% EGFRt+)

PD0051 #2 (Donor PD0038 CD8 with 50U/ml IL2 pulse 5 days, then 5ng/ml IL7& 5ng/ml IL21, S1D21 @ 89.5% EGFRt+)

*Note:Cells thawed, counted, and injected same day

Image mice before tumor

Tumor inoculation: 0.5e6 cells/mouse IV

T-cells Administration: 10e6 cells/mouse IV

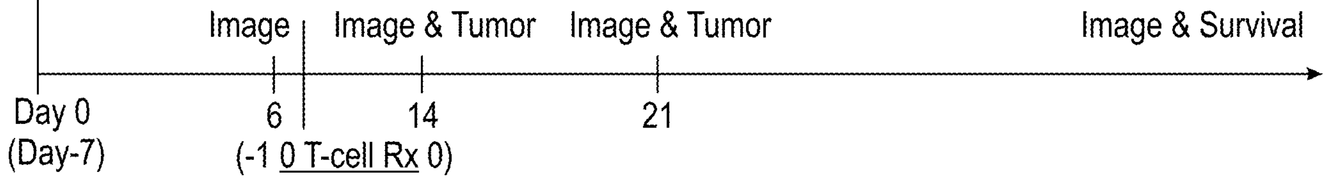

FIG. 45

Experiment Timeline

Day 0: Tumor Inoculation

Day 6: Image mice

Day 7:T-cell administration

Day 14(AM): Image mice

Day 14(PM): Tumor Inoculation

Day 20: Image mice

Day 21: Tumor Inoculation

Day 28, 35, 49, 63, 78, 92, 105, 120: Image mice

AIM(S):

1. Determine if there is an in vivo difference in killing ability between cells that have been grown under the same conditions as PLAT-01 and PLAT-02 as well as "in between" protocols.

CONDITIONS:

| Product | CD4 select (%) | CD8 select (%) | EGFRt select (CD4%/CD8%) | PD#'s |
|---|---|---|---|---|
| PLAT-1.0 | No (28.9%) | No (72.0%) | No (79.5%) | PD0066 #6 |
| PLAT-1.33 | **Yes** (87.4%) | **Yes** (99.8%) | No (95.0%/48.0%) | PD0069 #1 & PD0070#2 |
| PLAT-1.67 | No (24.3%) | No (77.8%) | **Yes** (66.7%) | PD0069 #3 |
| PLAT-2.0 | **Yes** (99.8%) | **Yes** (99.1%) | **Yes** (94.2/94.9%) | PD0063 CD4 & PD0063 CD8 |

Note: All products initiated from the same donor.

EXPERIMENTAL SET-UP:

- n=5 per group
- 17 groups total
    - Dose of 1.25e6/2.5e6/5e6/10e6 per product condition
    - Additional vehicle control group
- Cells thawed, counted, and injected on same day.
- Cells injected based on EGFRt+ [and 1:1 CD4:CD8 (for selected) cells]

Tumor inoculation: 0.5e6 cells/mouse IV

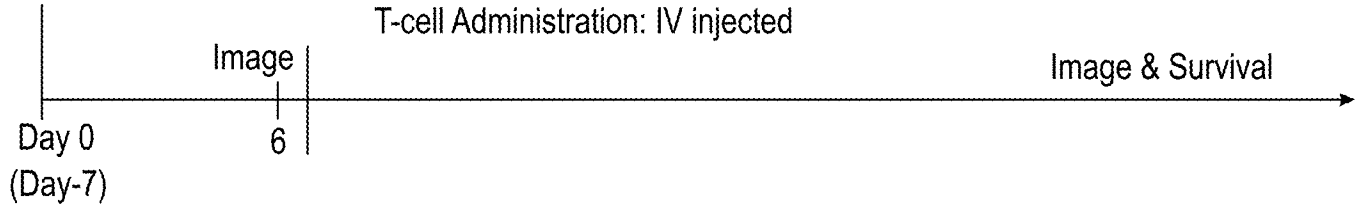

FIG. 49

| Product | CD4 select (%) | CD8 select (%) | EGFRt select (CD4%/CD8%) | PD#'s |
|---|---|---|---|---|
| ⇨ PLAT-1.0 | No (28.9%) | No (72.0%) | No (79.5%) | PD0066 #6 |
| PLAT-1.33 | **Yes** (87.4%) | **Yes** (99.8%) | No (95.0%/48.0%) | PD0069 #1 & PD0070#2 |
| PLAT-1.67 | No (24.3%) | No (77.8%) | **Yes** (66.7%) | PD0069 #3 |
| ⇨ PLAT-2.0 | **Yes** (99.8%) | **Yes** (99.1%) | **Yes** (94.2/94.9%) | PD0063 CD4 & PD0063 CD8 |

1. Data from PLAT-1.33 is questionable as although the cells were selected for CD4 and CD8, the final %EGFRt+CD8 cells appears unusually low at 48%.

2. Data from PLAT-1.67 is questionable as final %EGFRt+ is only 66.7% even though bulk cells underwent mid-process enriched for EGFRt.

3. Animals receiving PLAT-2.0 cells developed xGvHD in both the 10 million and 5 million dose groups with the first group coming mid-study as a result of the xGvHD and the later group being confirmed for xGvHD both by physical observation and persistence of T-cells by FACS analysis of bone marrow.

FIG. 50

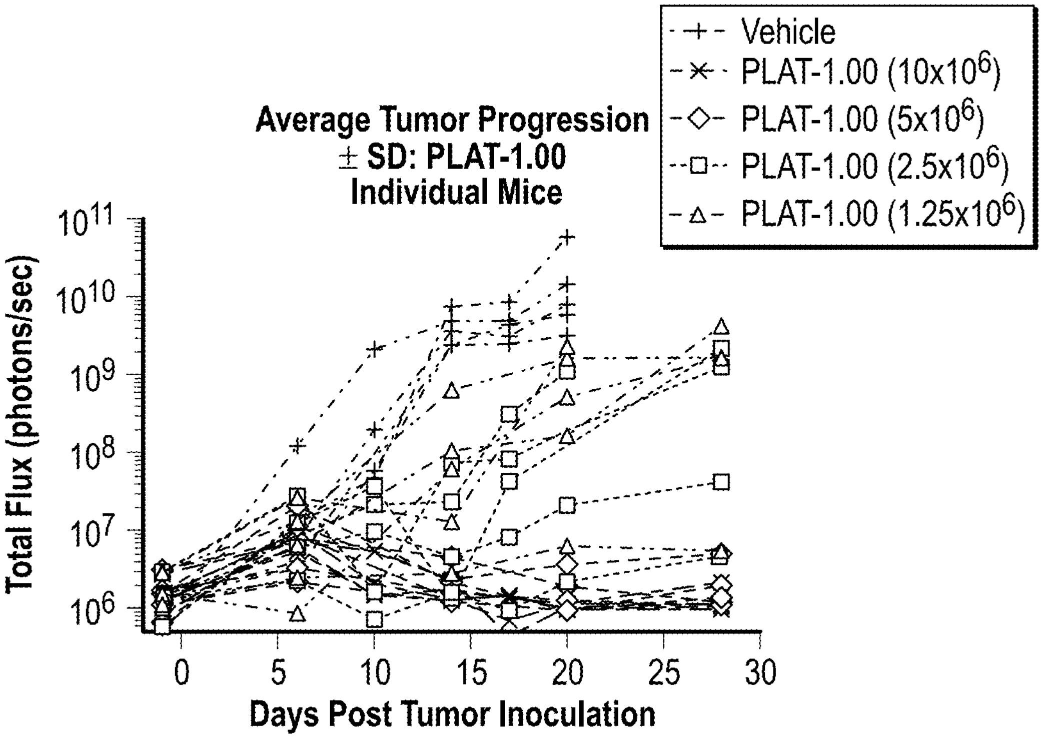
FIG. 53A1
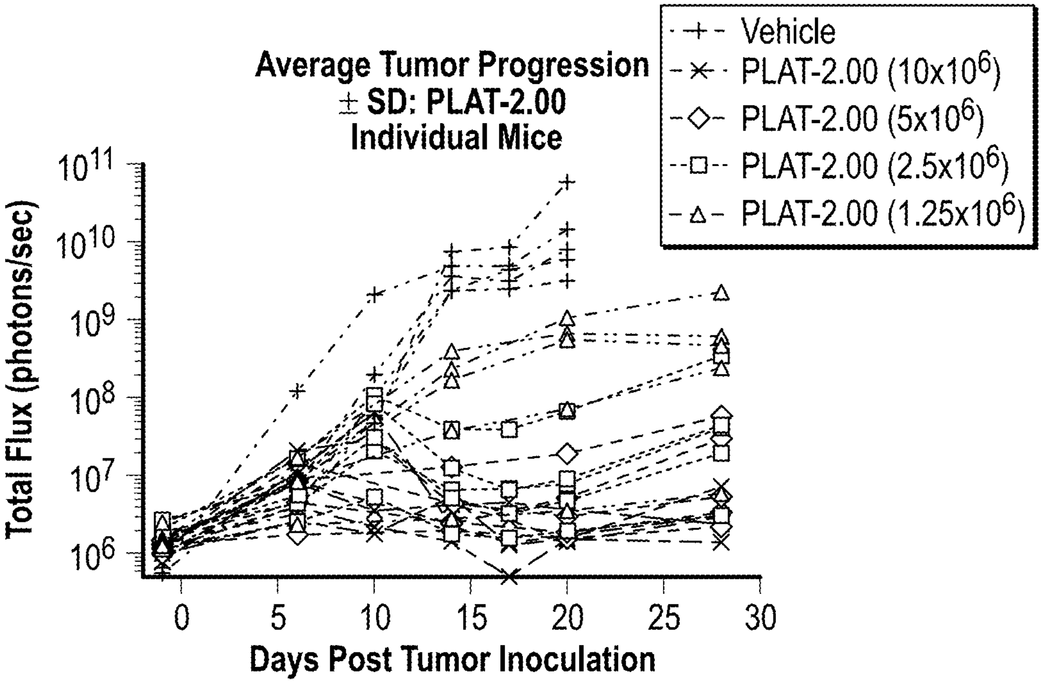
FIG. 53A2

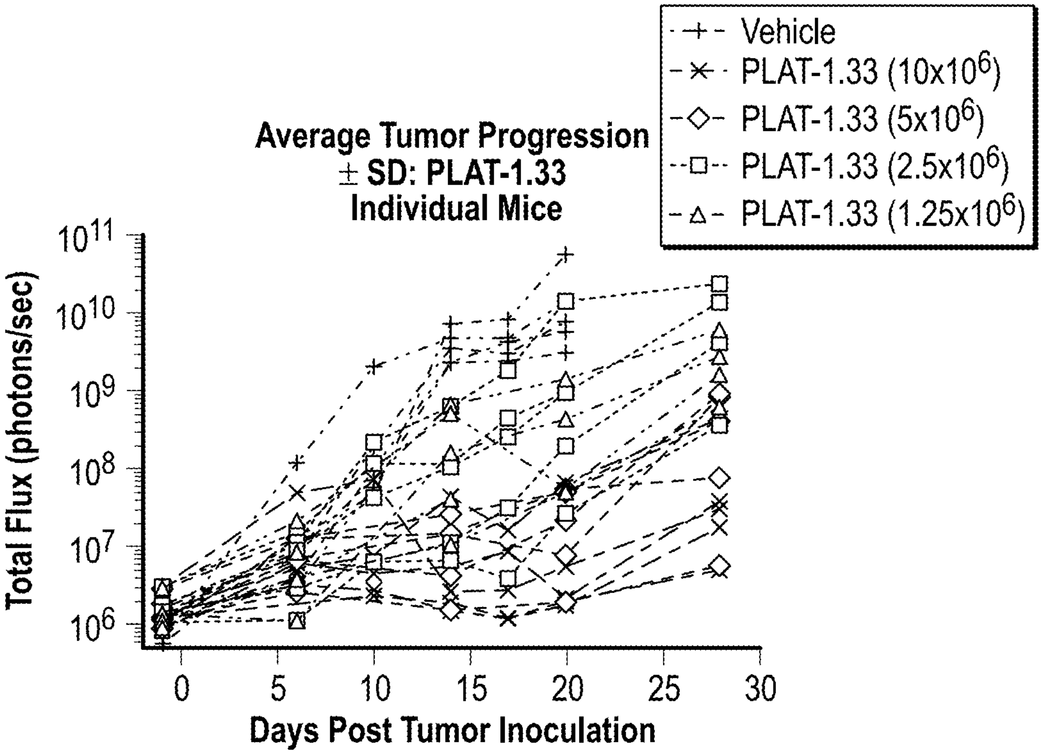
FIG. 53A3
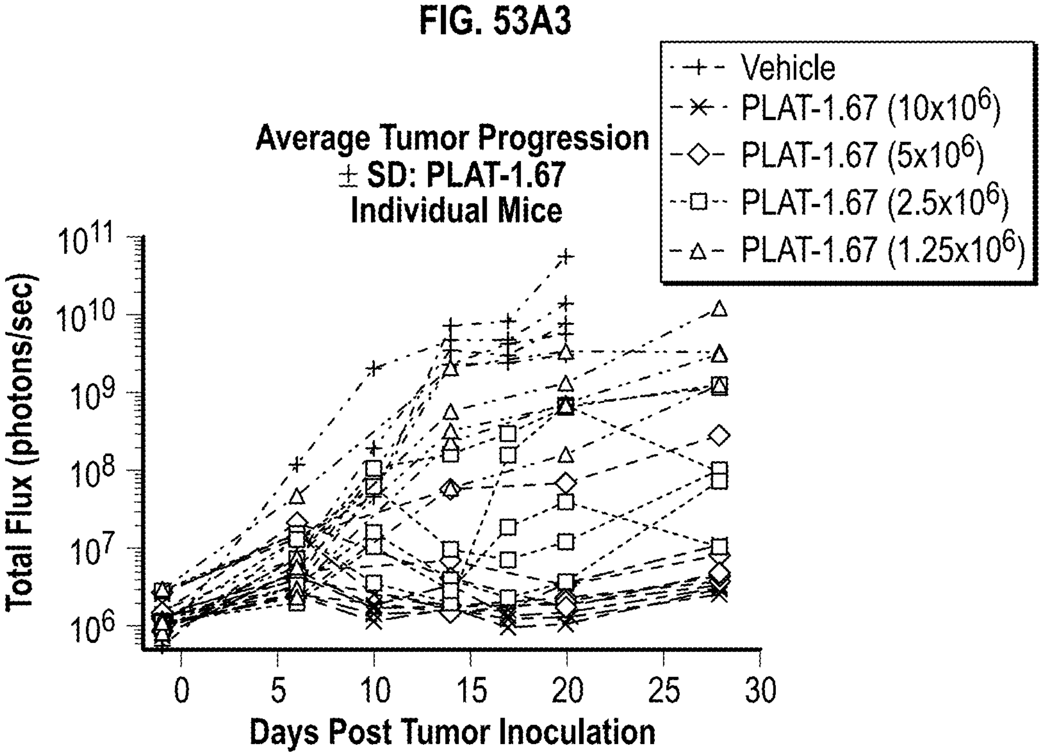
FIG. 53A4

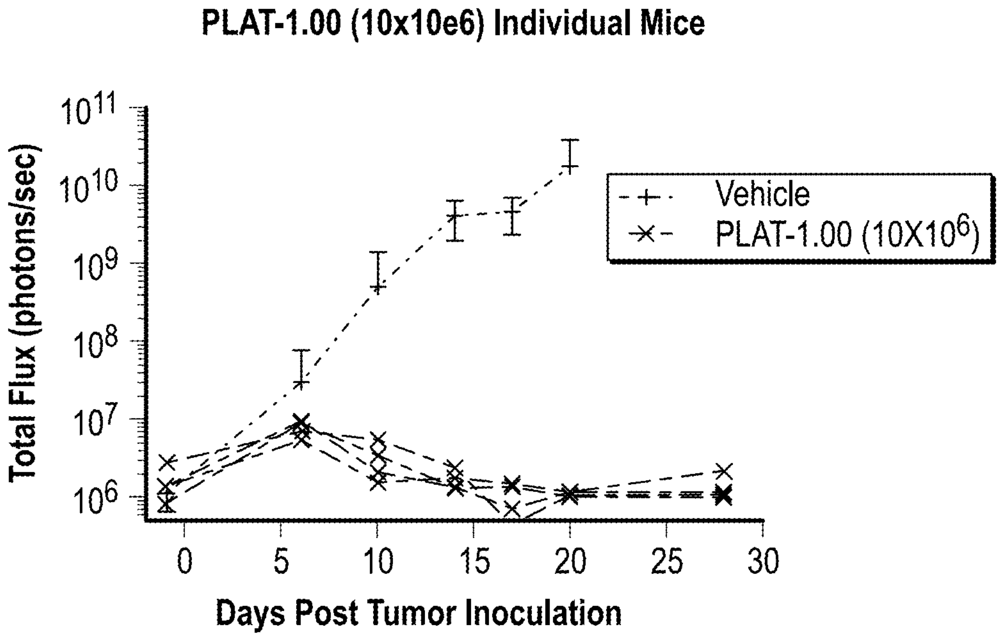
FIG. 53B1
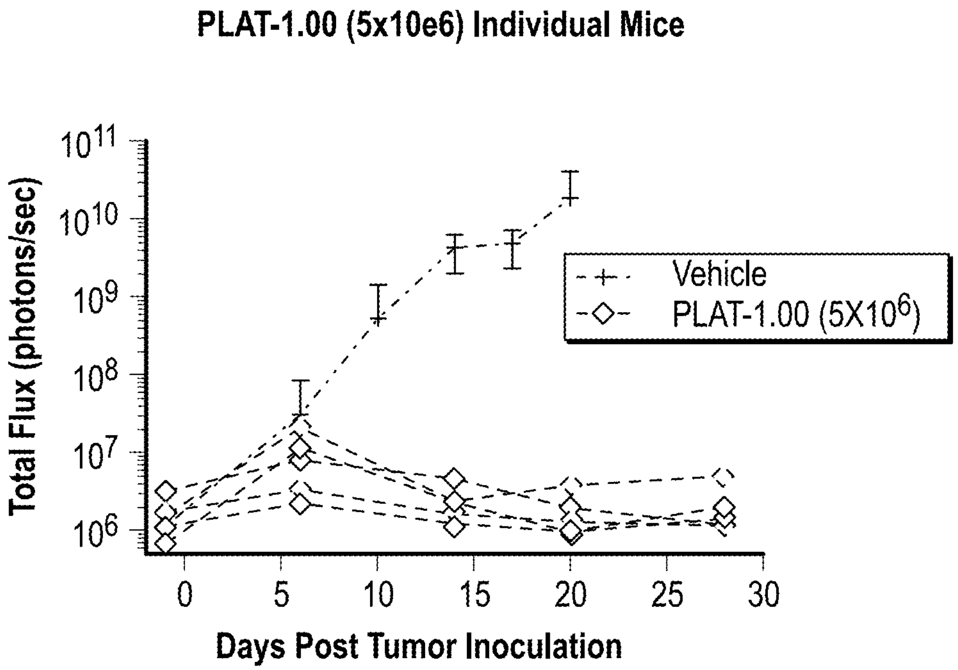
FIG. 53B2

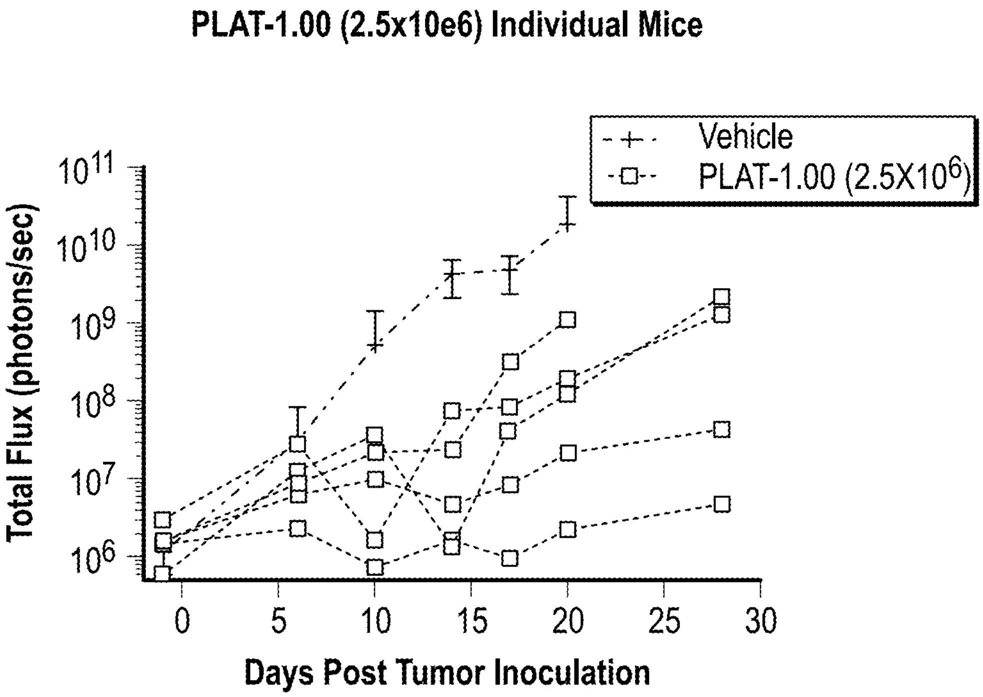
FIG. 53B3
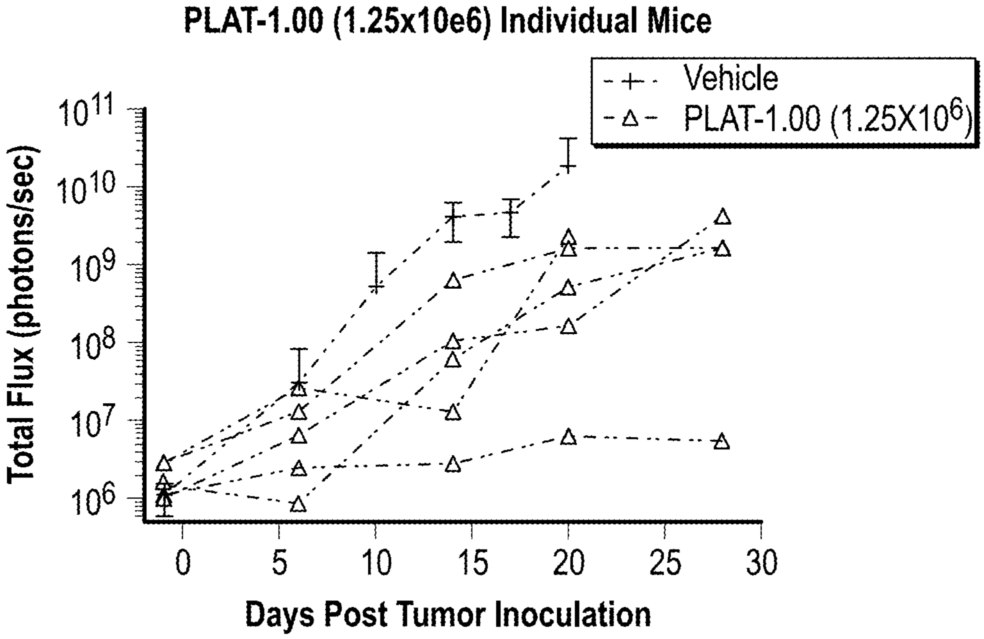
FIG. 53B4

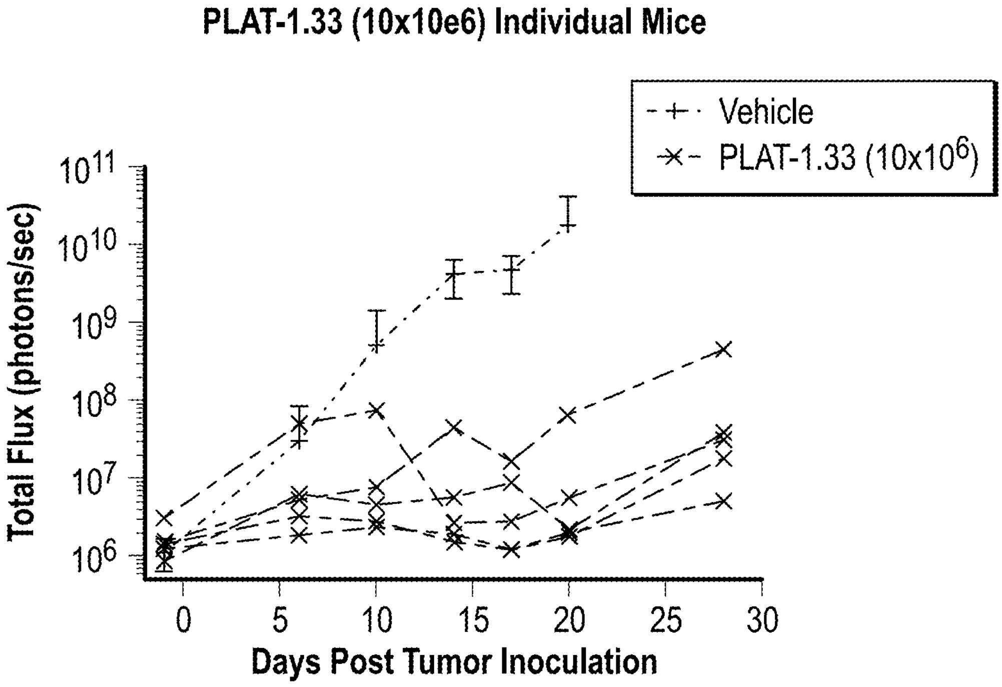
FIG. 53C1
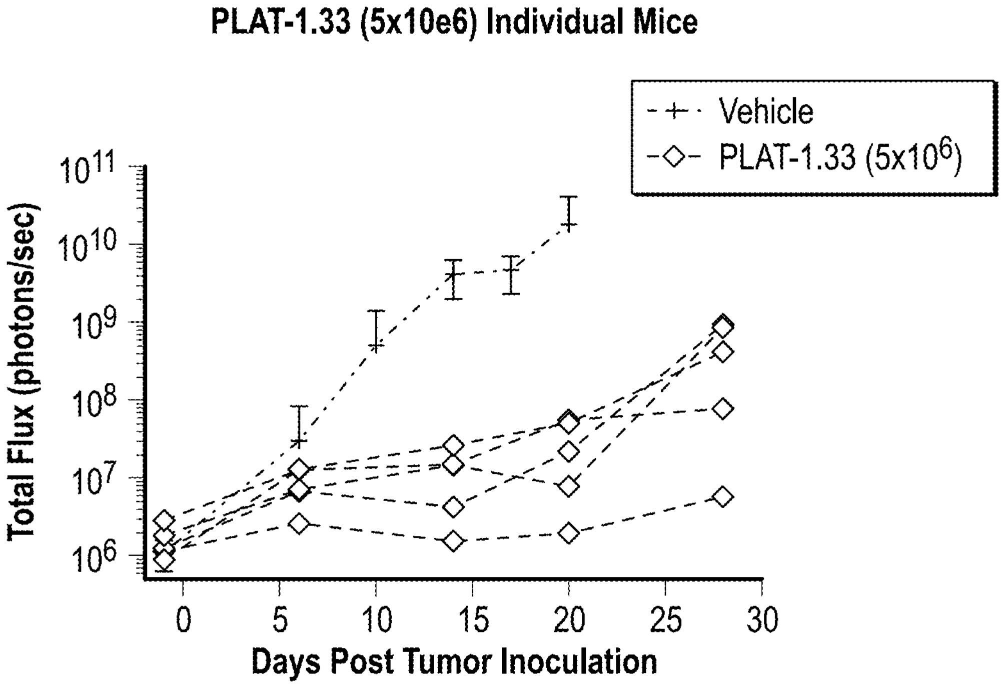
FIG. 53C2

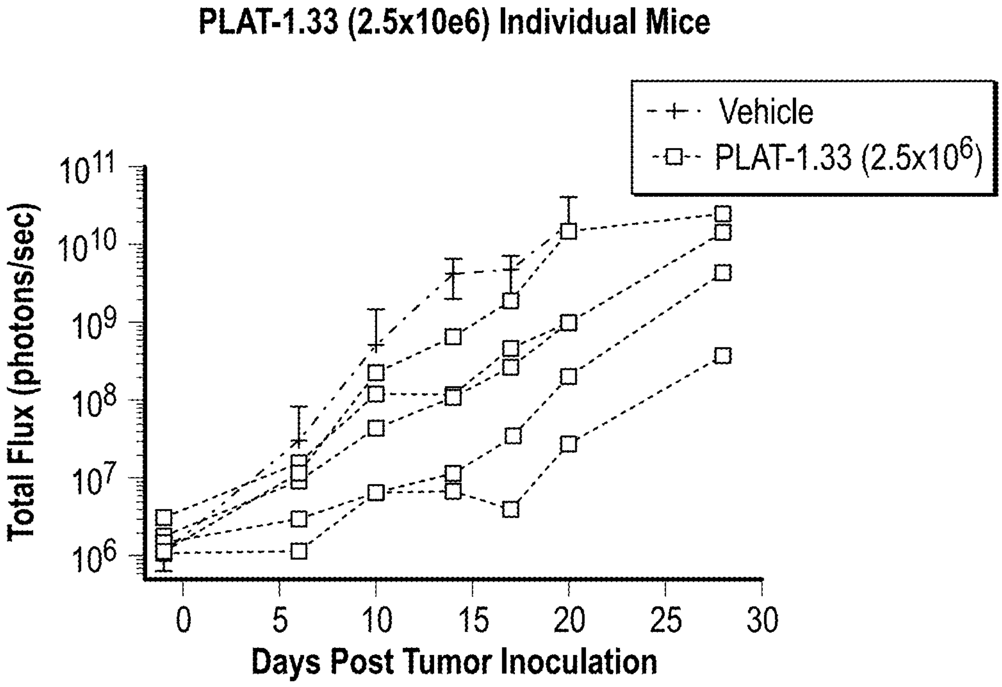
FIG. 53C3
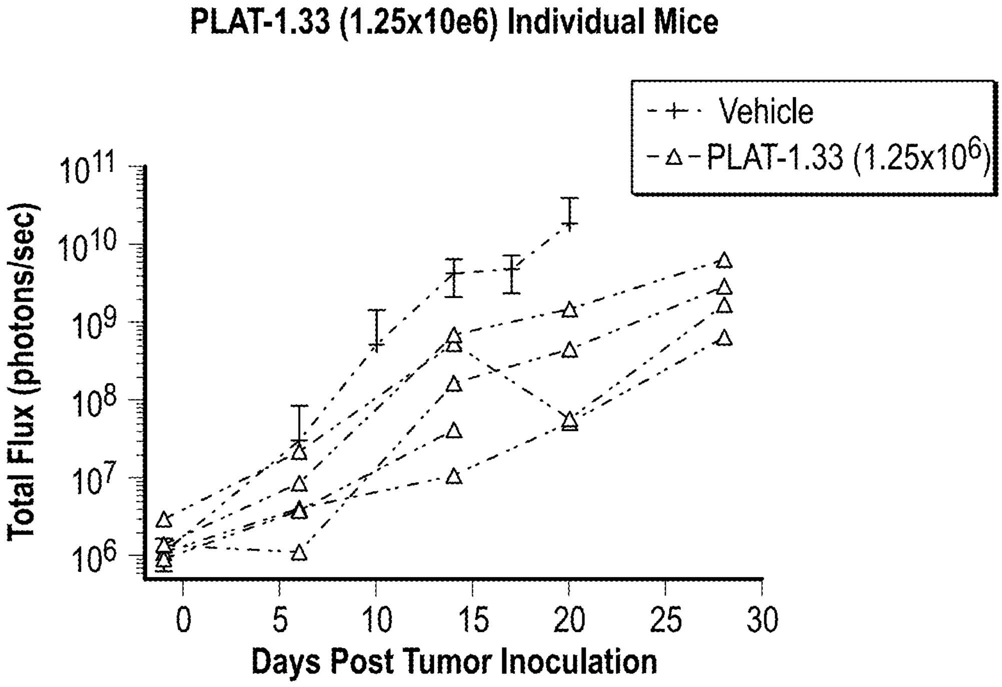
FIG. 53C4

PLAT-1.67 (10x10e6) Individual Mice
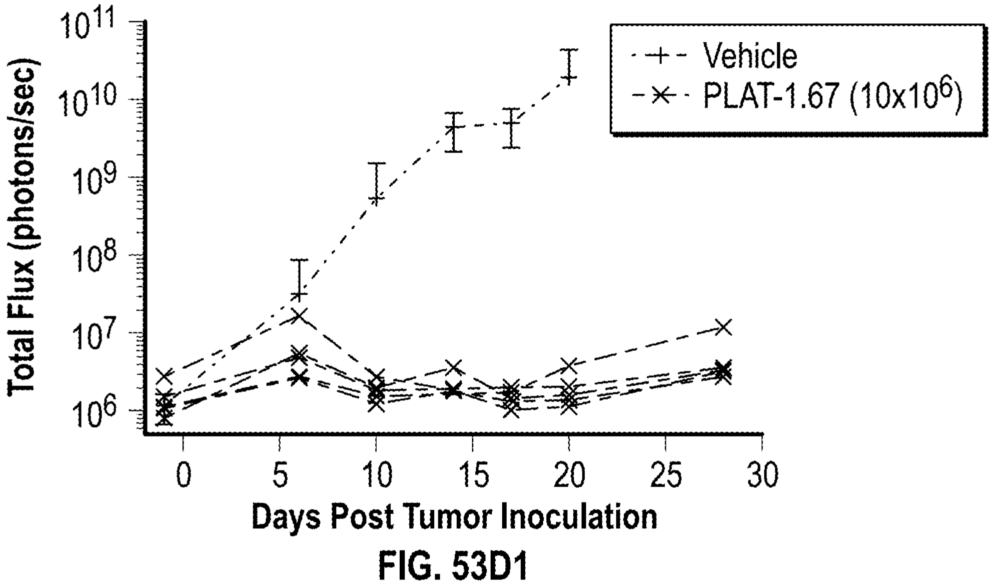
FIG. 53D1
PLAT-1.67 (5x10e6) Individual Mice
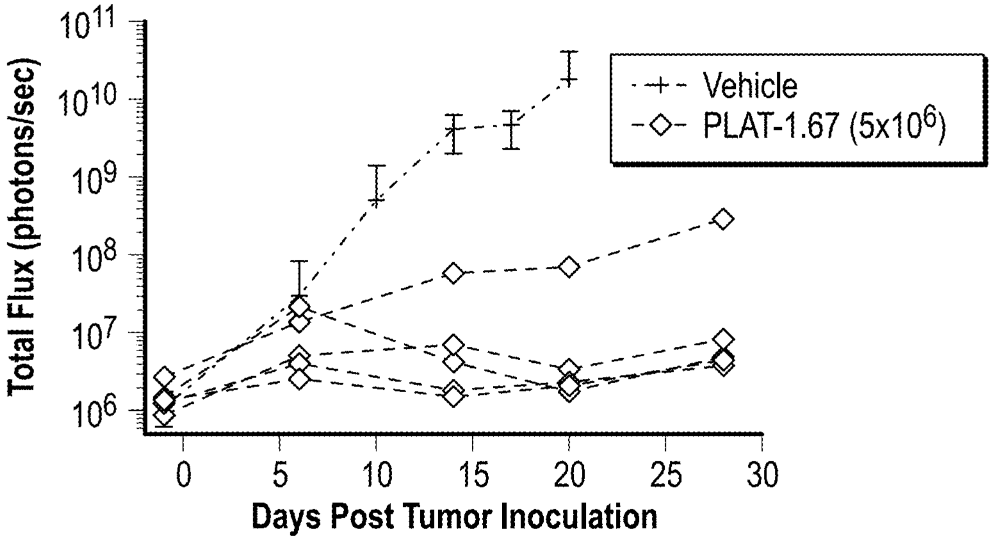
FIG. 53D2

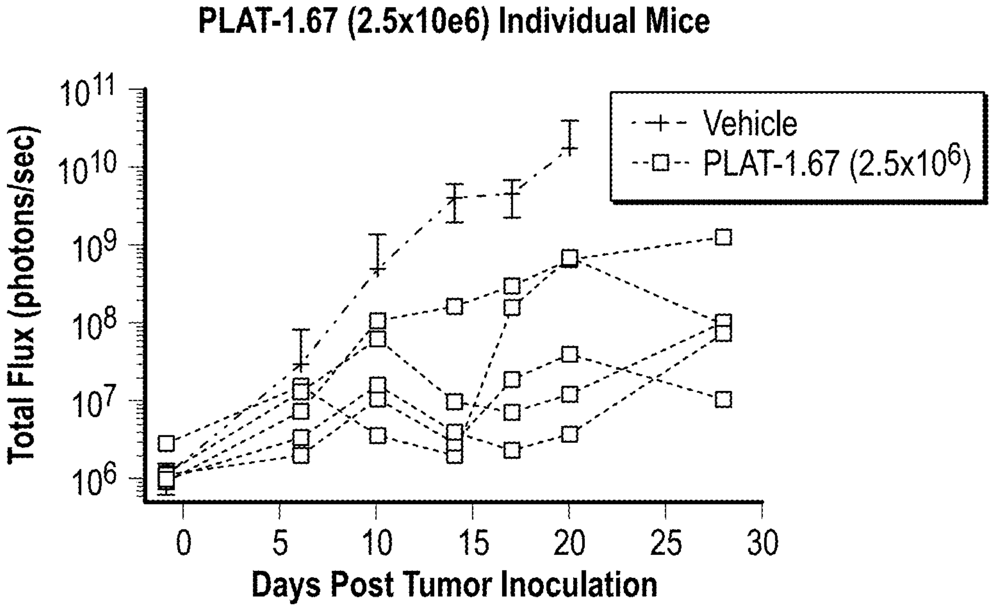
FIG. 53D3
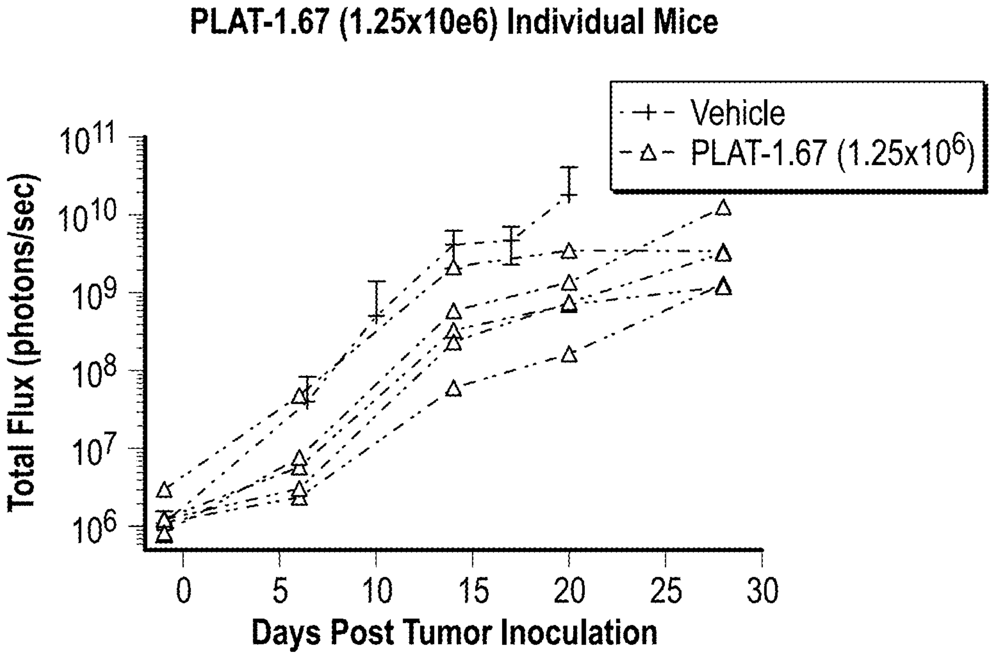
FIG. 53D4

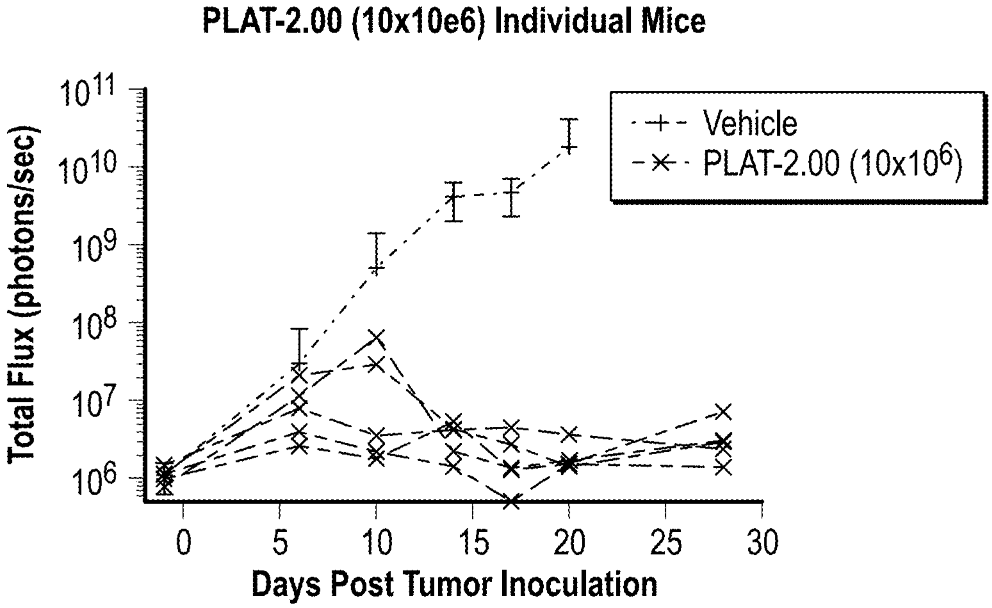
FIG. 53E1
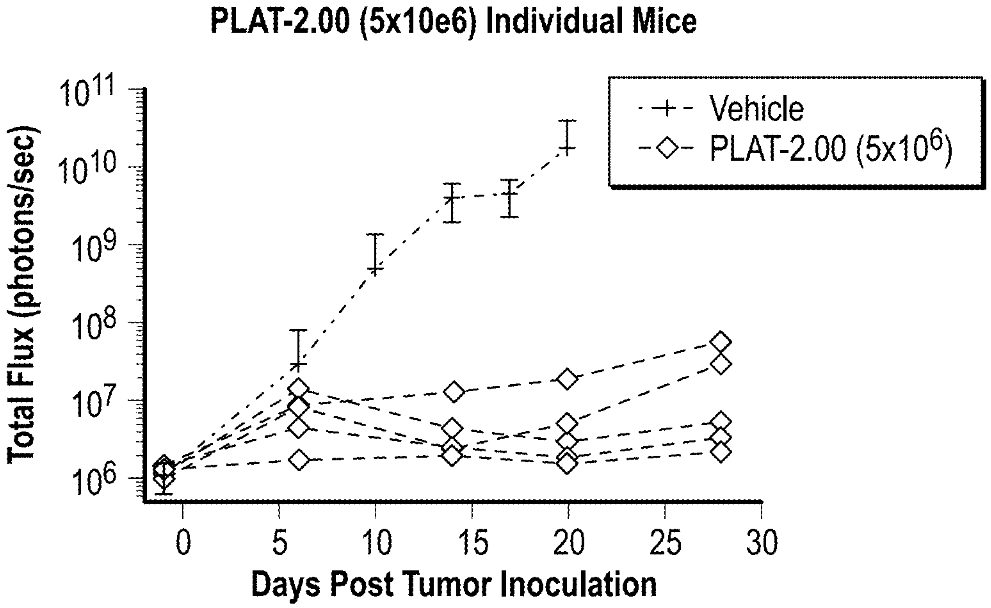
FIG. 53E2

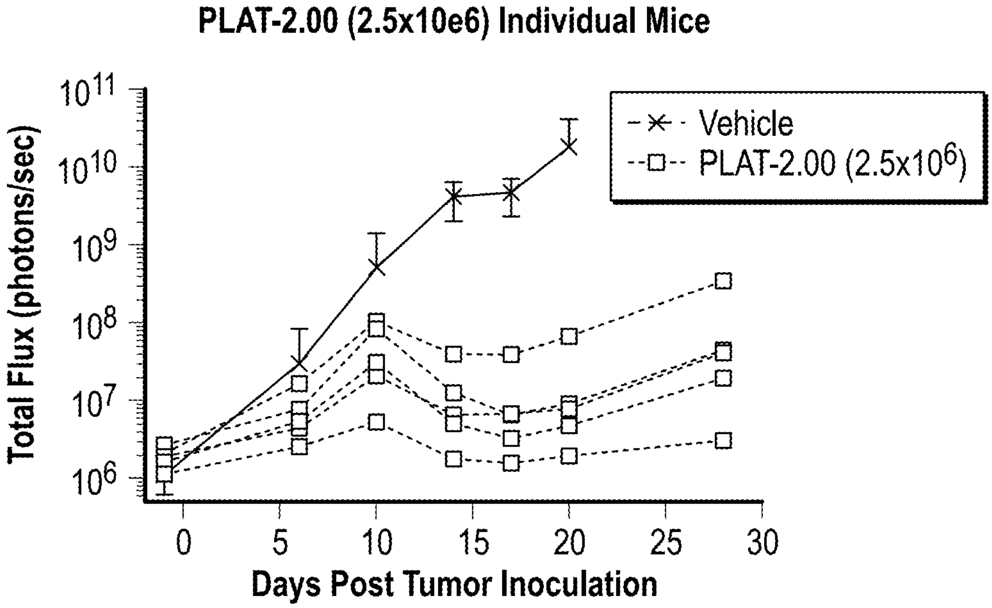
FIG. 53E3
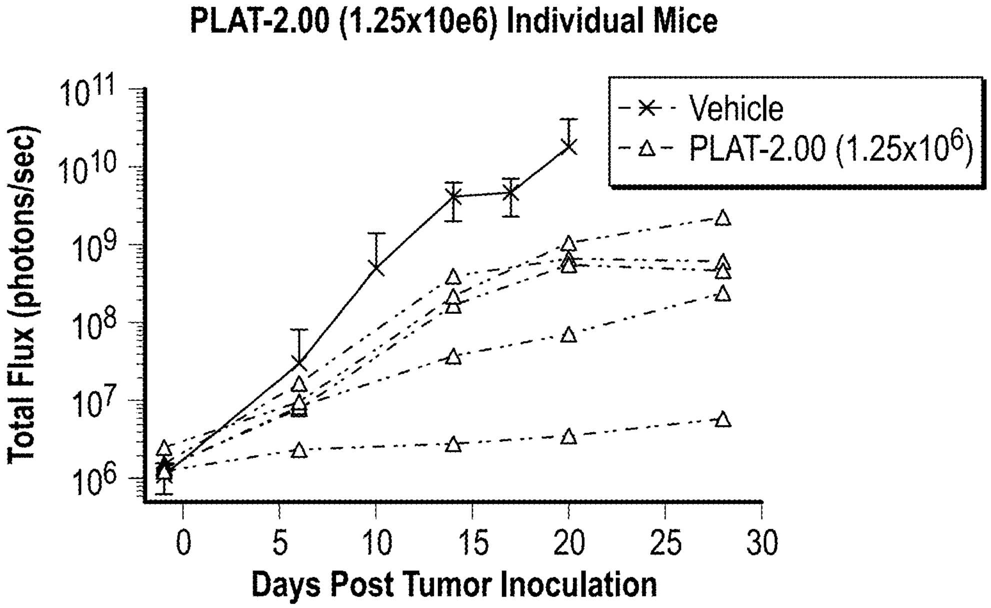
FIG. 53E4

*PLAT-2.00(10x10e6)-Death by xGVHD

JME14-03: xenoGraft-versus-Host Disease

Symptoms/Signs xGvHD in Mice:

- Flaky skin
- Eye issues (weepy looking)
- Weight loss
- Dehydration
- Hindlimb edema NOTE: Animals treated at 10 million and 5 million doses with PLAT-02 cells developed xGvHD. As a result animals receiving the 10 million dose were taken down day 58 post tumor or 51 days post T-cell administration. Those receiving 5 million dose were euthanized at end of study at 90 days post tumor or 83 days post T-cell administration.

JME14-03:Confirming xGvHD by FACS
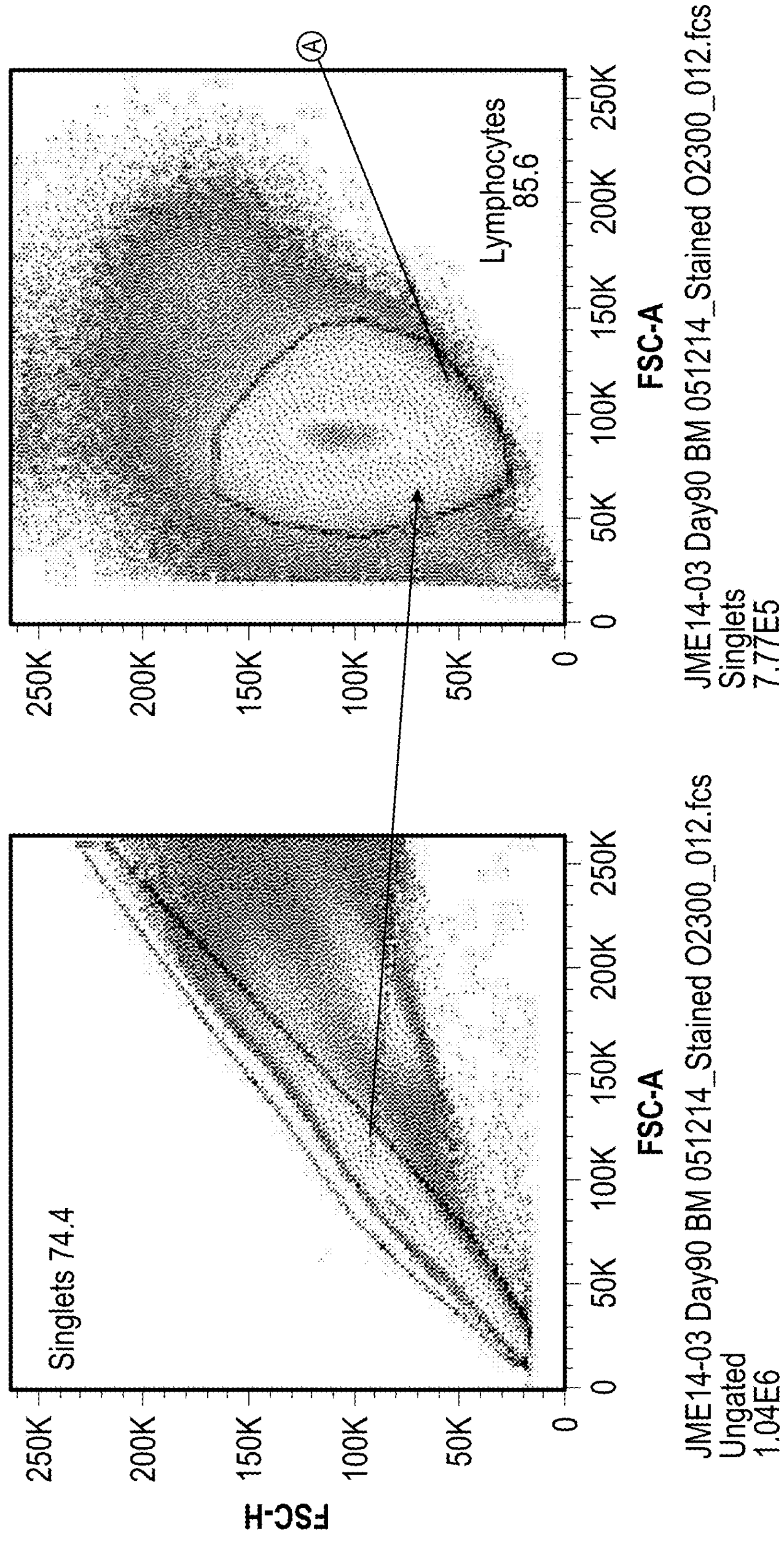
FIG. 58A1
FIG. 58A2

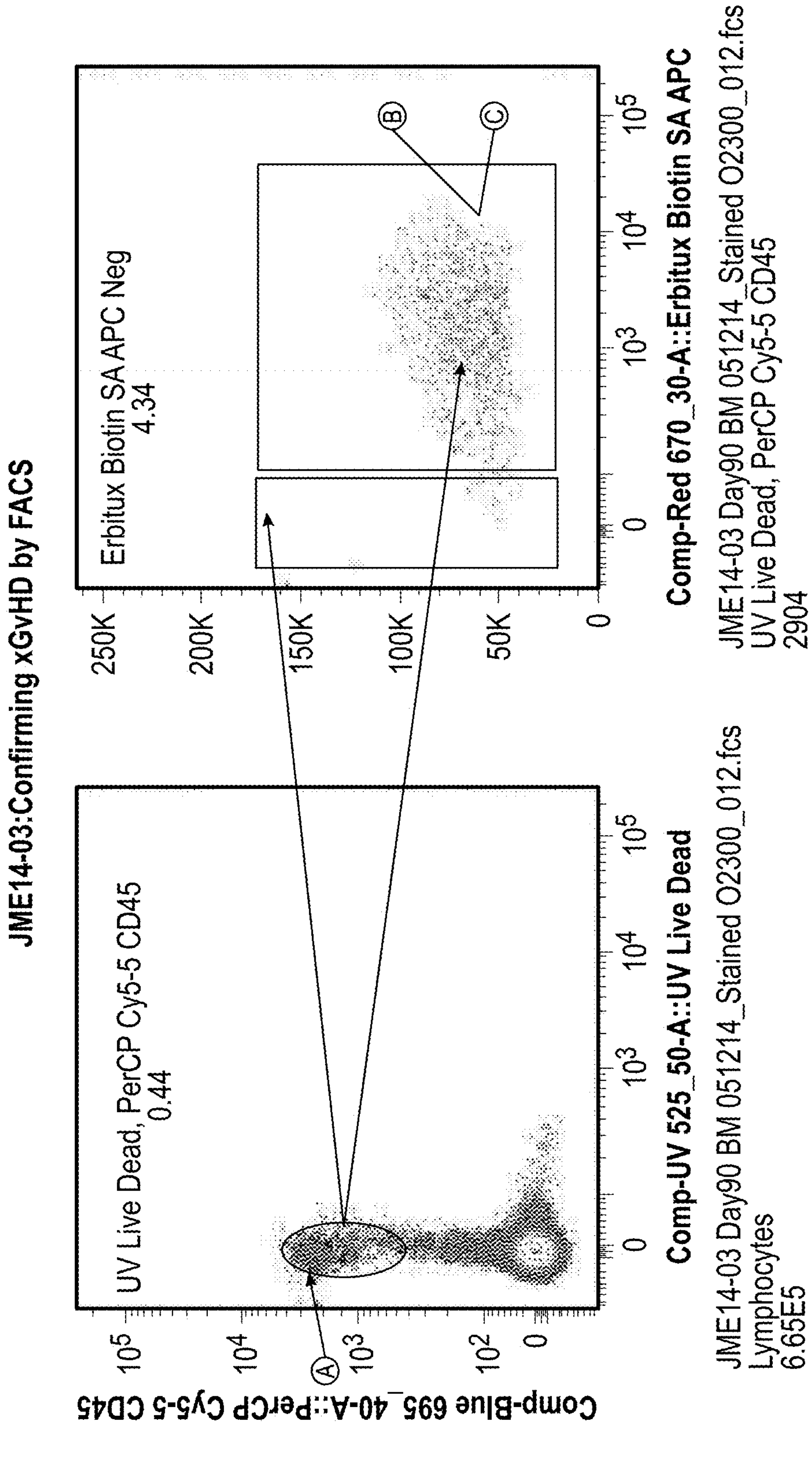
FIG. 58A3
FIG. 58A4

JME14-03:Confirming xGvHD by FACS
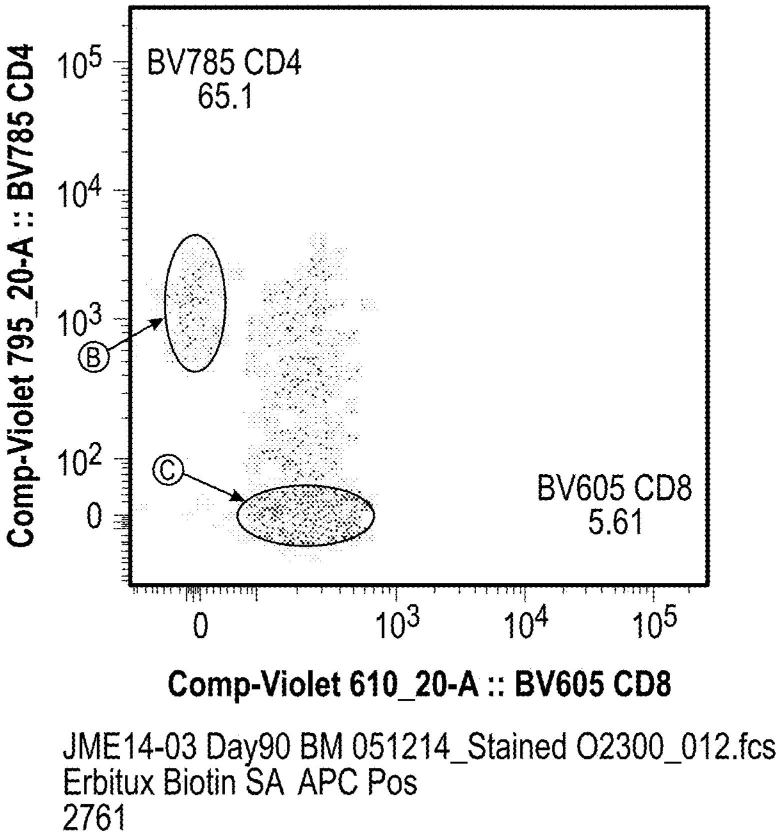
JME14-03 Day90 BM 051214_Stained O2300_012.fcs
Erbitux Biotin SA APC Pos
2761
FIG. 58A5

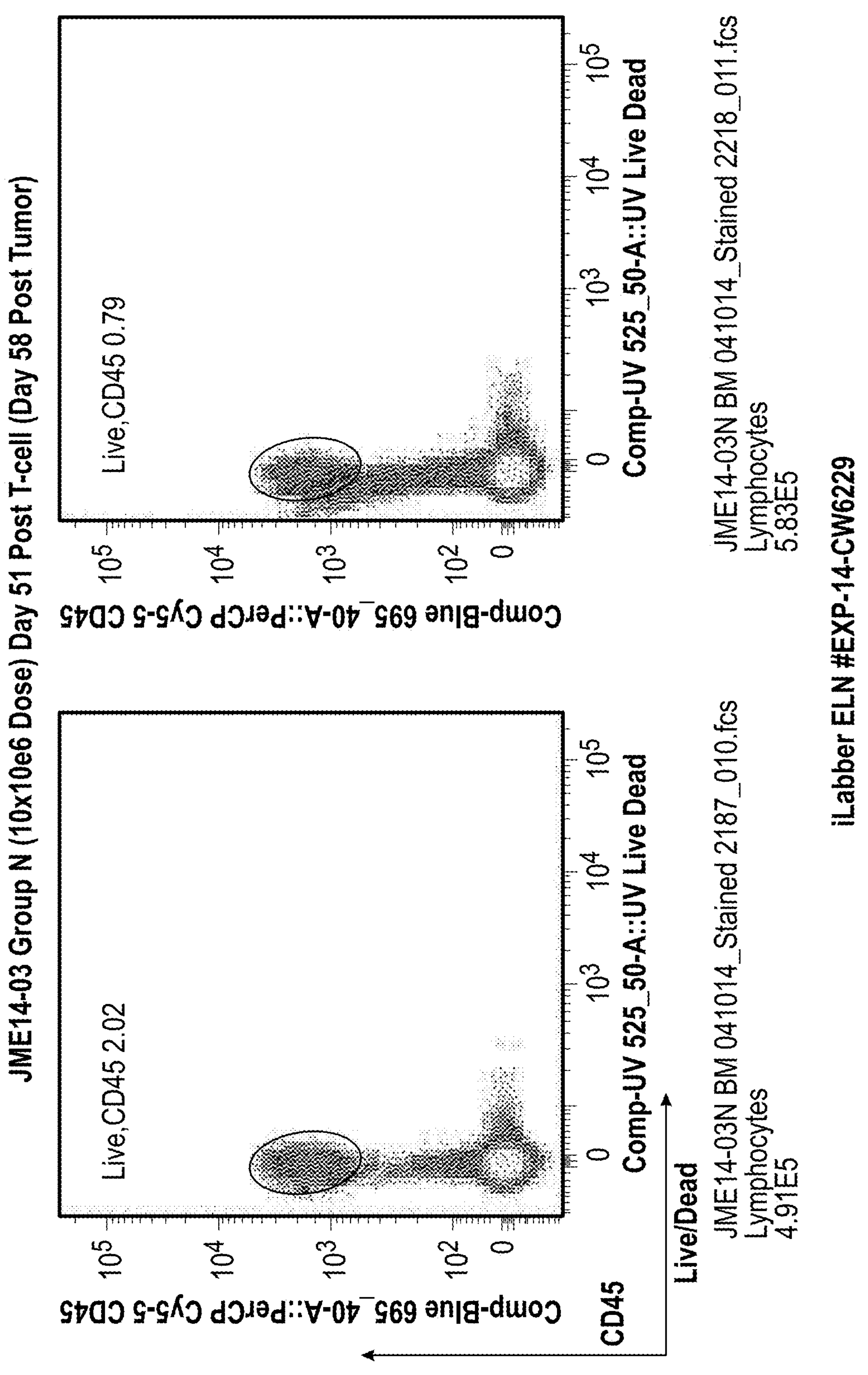
FIG. 58B1
FIG. 58B2

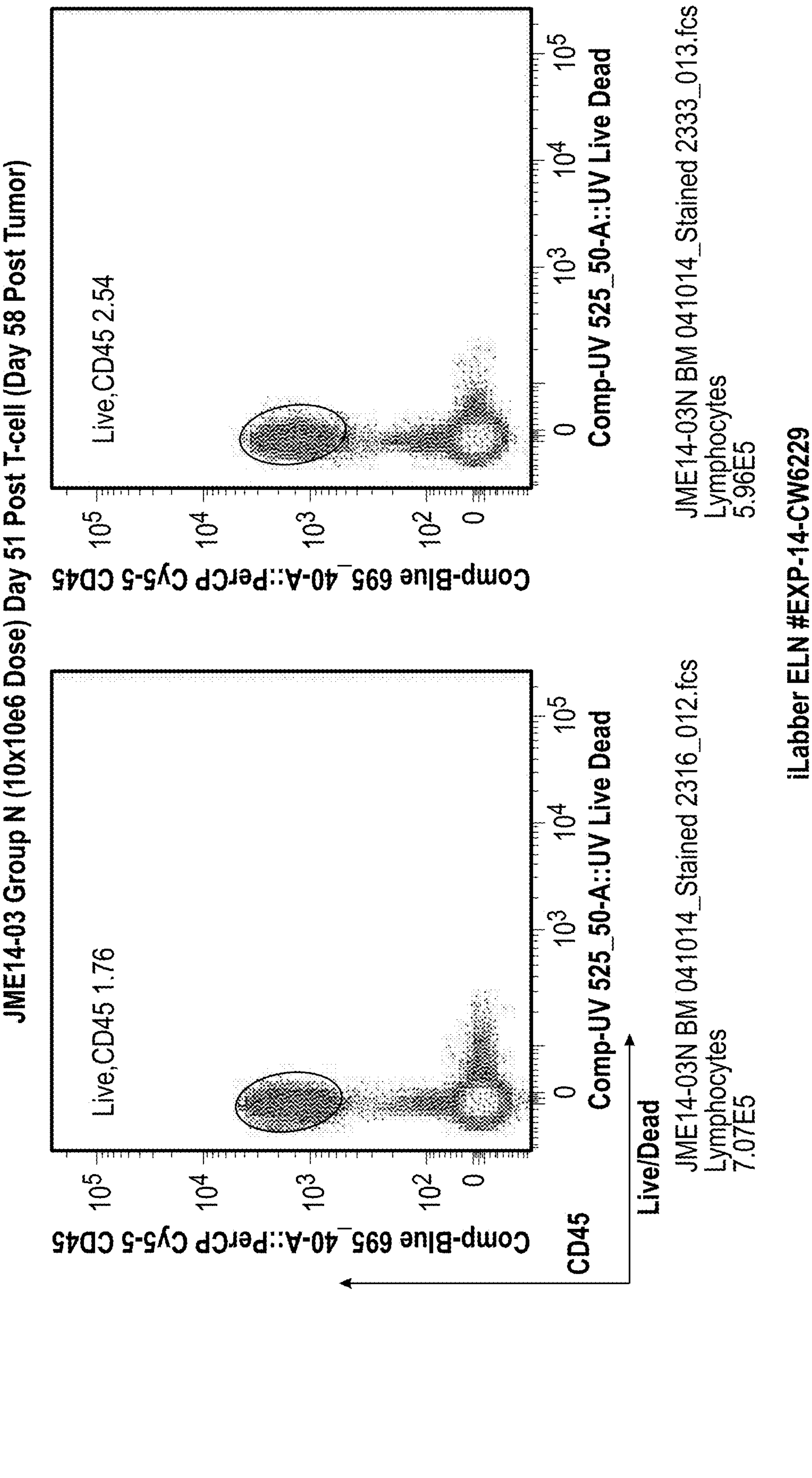
iLabber ELN #EXP-14-CW6229
FIG. 58B3
FIG. 58B4

JME14-03 Group N (10x10e6 Dose) Day 51 Post T-cell (Day 58 Post Tumor)
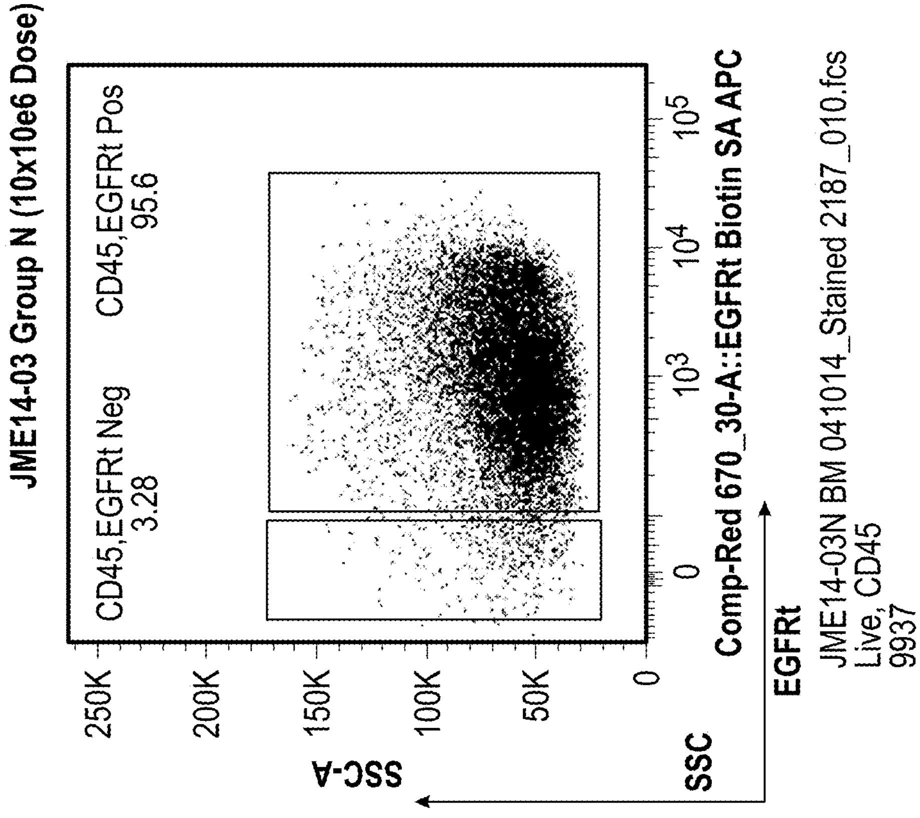
FIG. 58B5
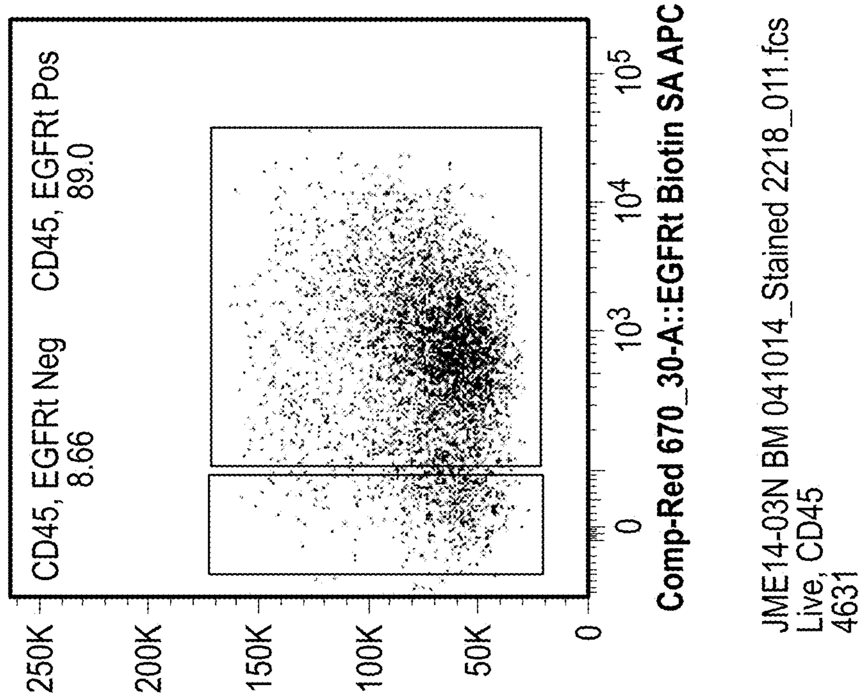
FIG. 58B6
iLabber ELN #EXP-14-CW6229

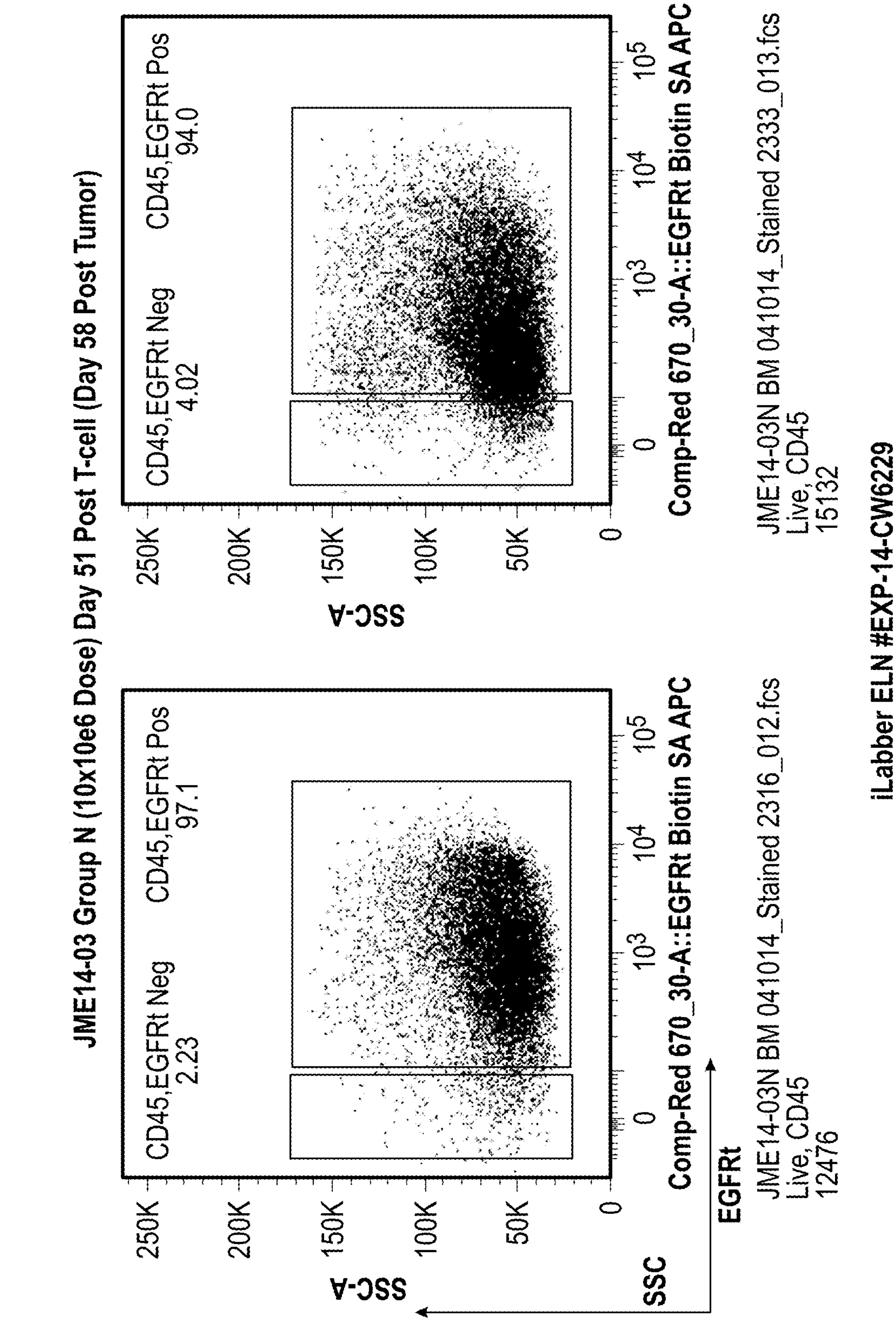
iLabber ELN #EXP-14-CW6229
FIG. 58B7
FIG. 58B8

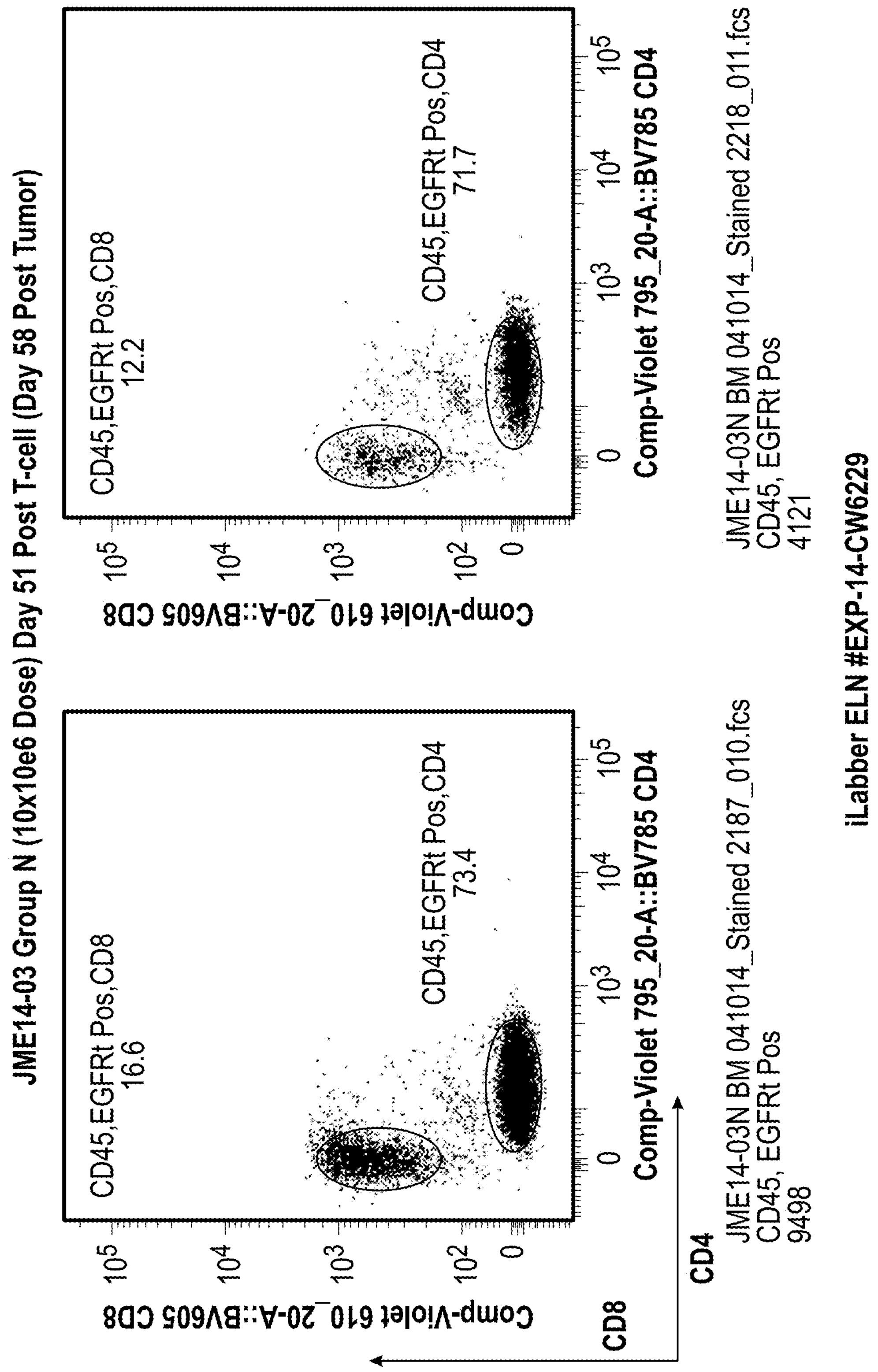
FIG. 58B9
FIG. 58B10

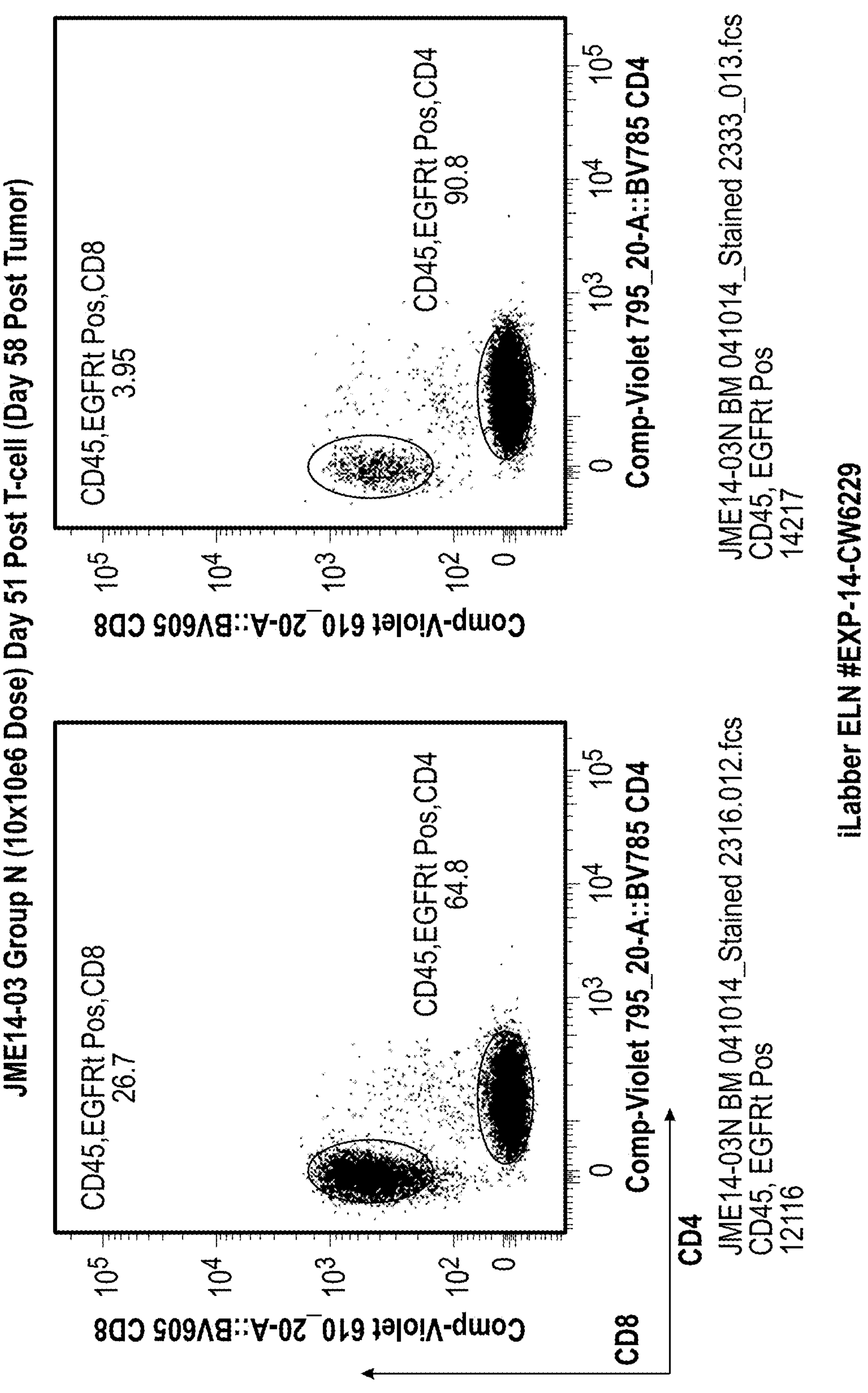
FIG. 58B11
FIG. 58B12

JME14-03 Group O (5x10e6 Dose)Day 83 Post T-cell (Day 90 post Tumor)
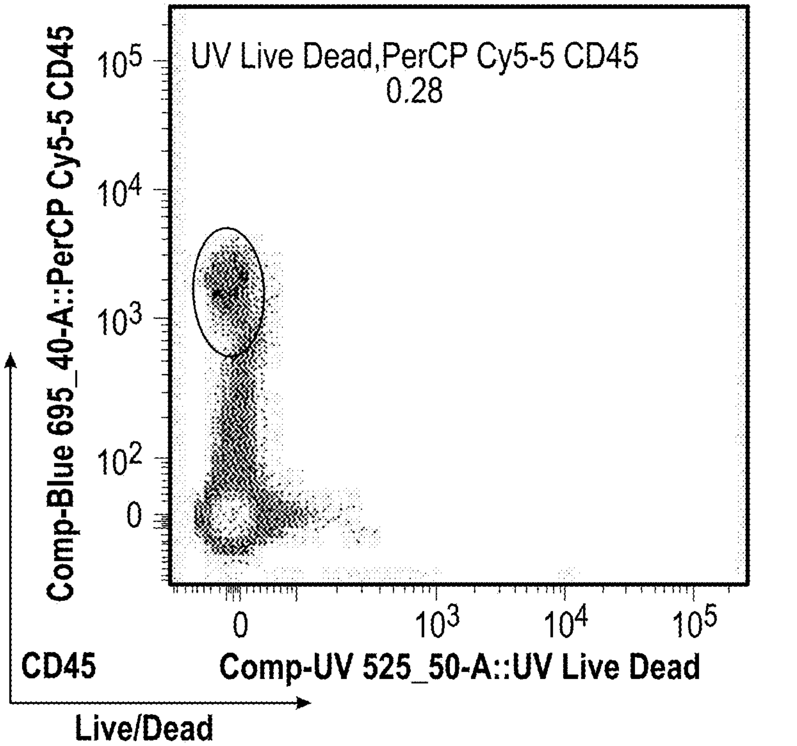
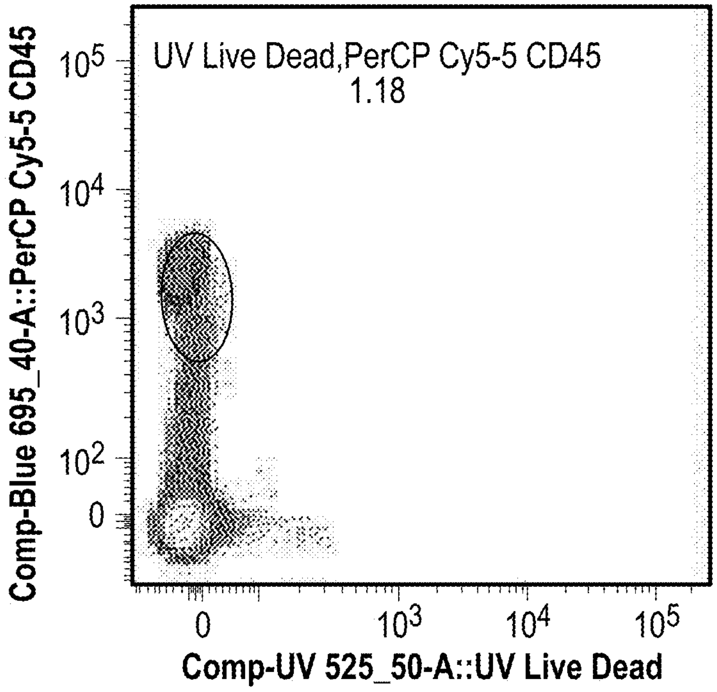
JME14-03 Day90 BM 051214_Stained O2189_010.fcs
Lymphocytes
7.91E5
JME14-03 Day90 BM 051214_Stained O2199_011.fcs
Lymphocytes
7.81E5
iLabber ELN #EXP-14-CW6241
FIG. 58C1
FIG. 58C2

JME14-03 Group O (5x10e6 Dose)Day 83 Post T-cell (Day 90 post Tumor)
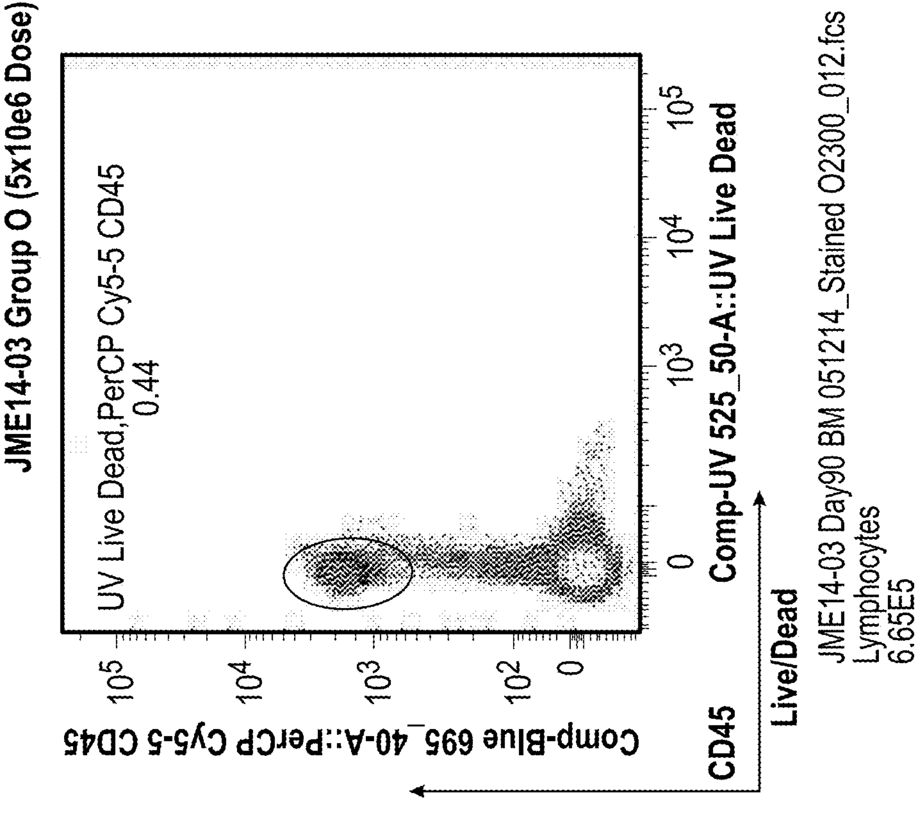
FIG. 58C3
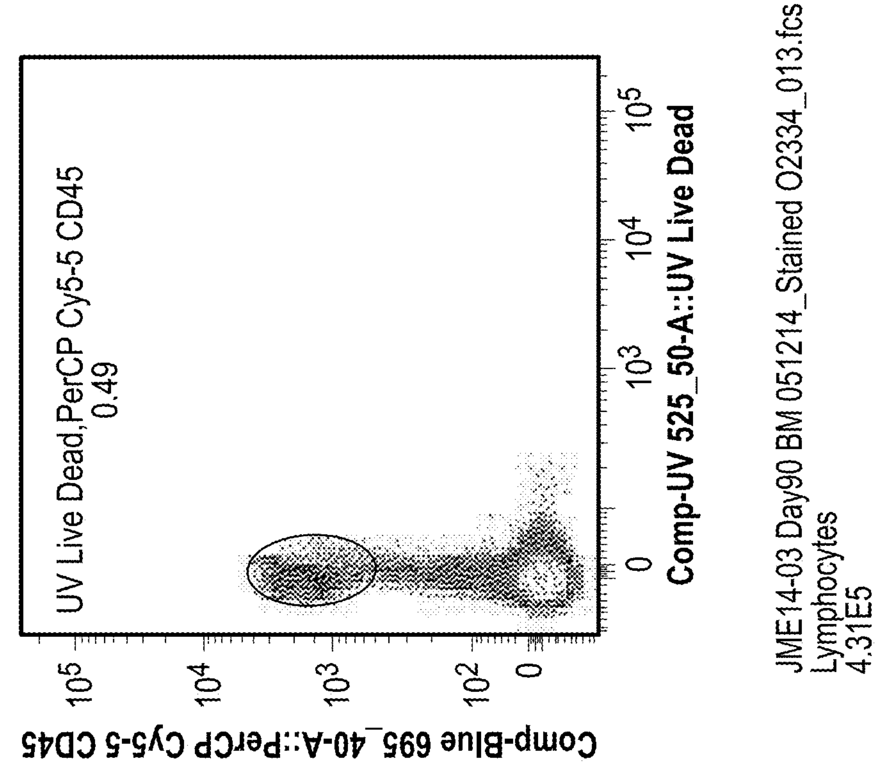
FIG. 58C4
iLabber ELN #EXP-14-CW6241

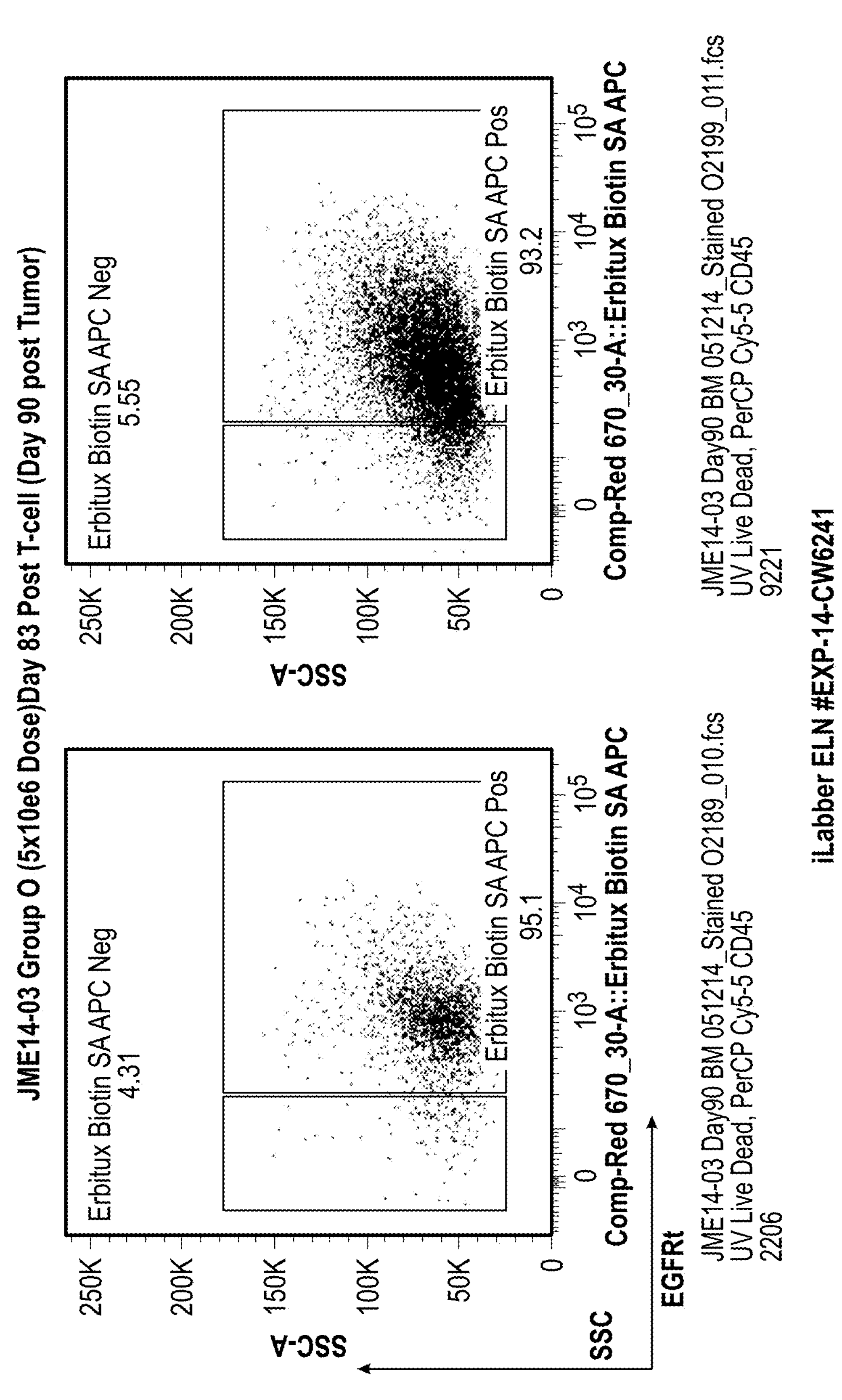
FIG. 58C5
FIG. 58C6

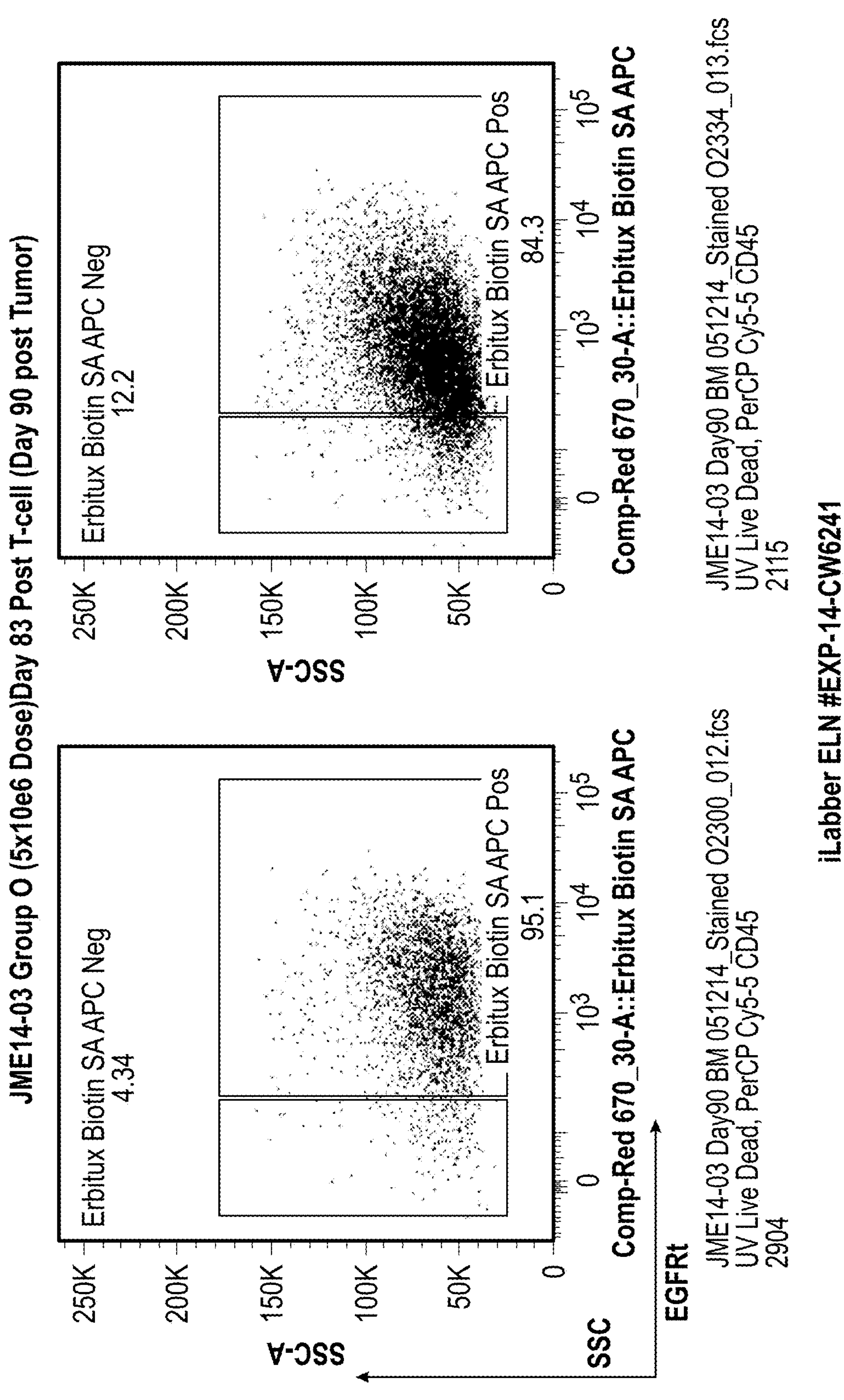
FIG. 58C7
iLabber ELN #EXP-14-CW6241
FIG. 58C8

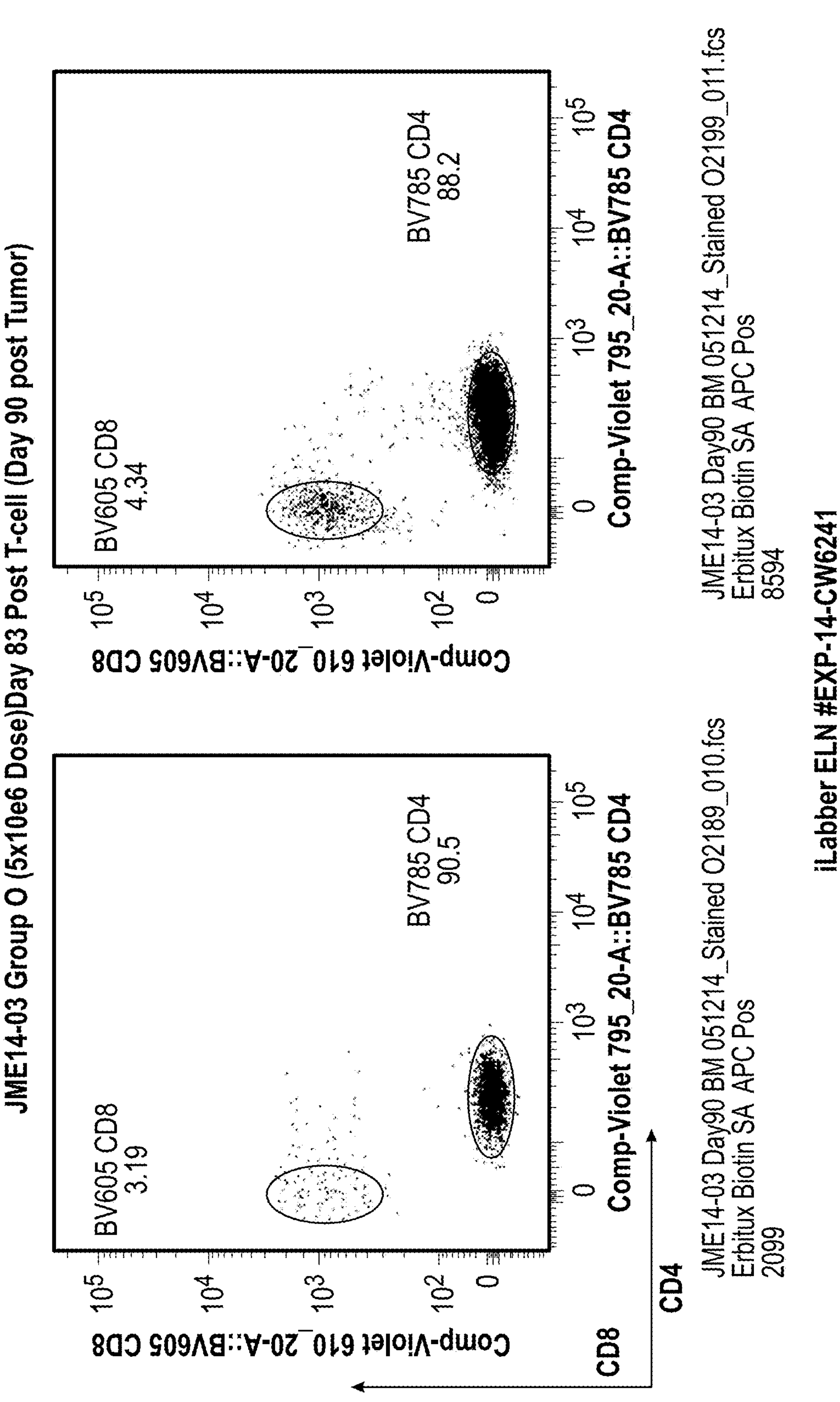
iLabber ELN #EXP-14-CW6241
FIG. 58C9
FIG. 58C10

JME14-03 Group O (5x10e6 Dose)Day 83 Post T-cell (Day 90 post Tumor)
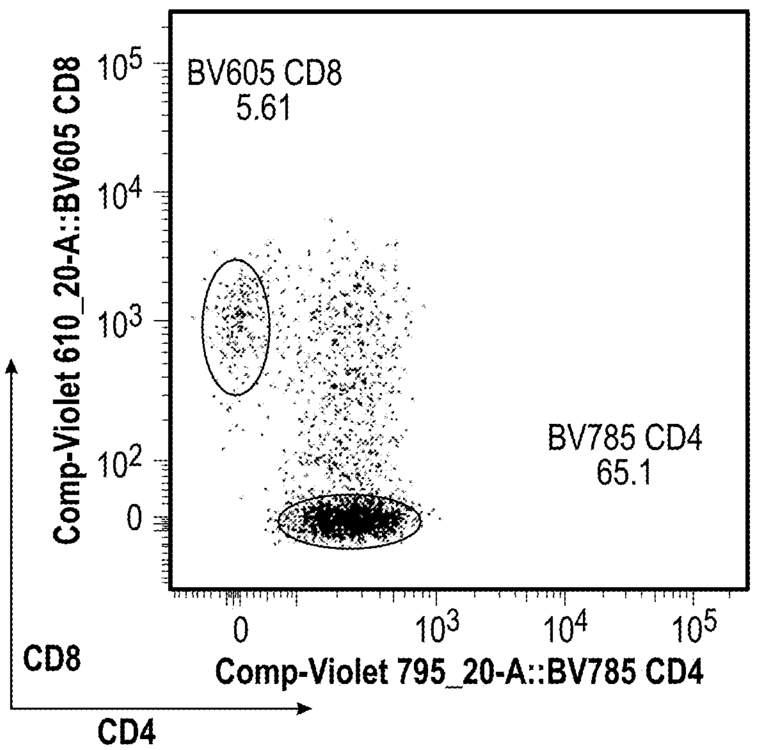
JME14-03 Day90 BM 051214_Stained O2300_012.fcs
Erbitux Biotin SA APC Pos
2761
FIG. 58C11
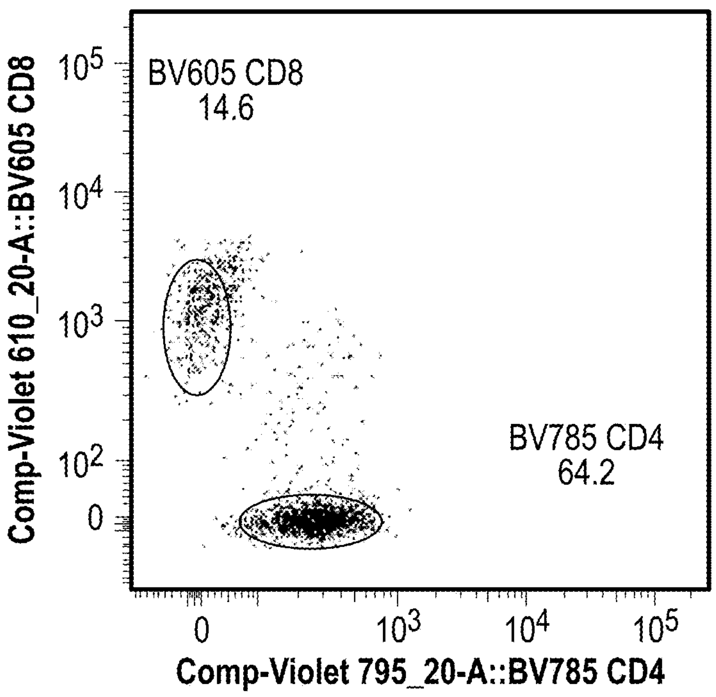
JME14-03 Day90 BM 051214_Stained O2334_013.fcs
Erbitux Biotin SA APC Pos
1783
FIG. 58C12
iLabber ELN #EXP-14-CW6241

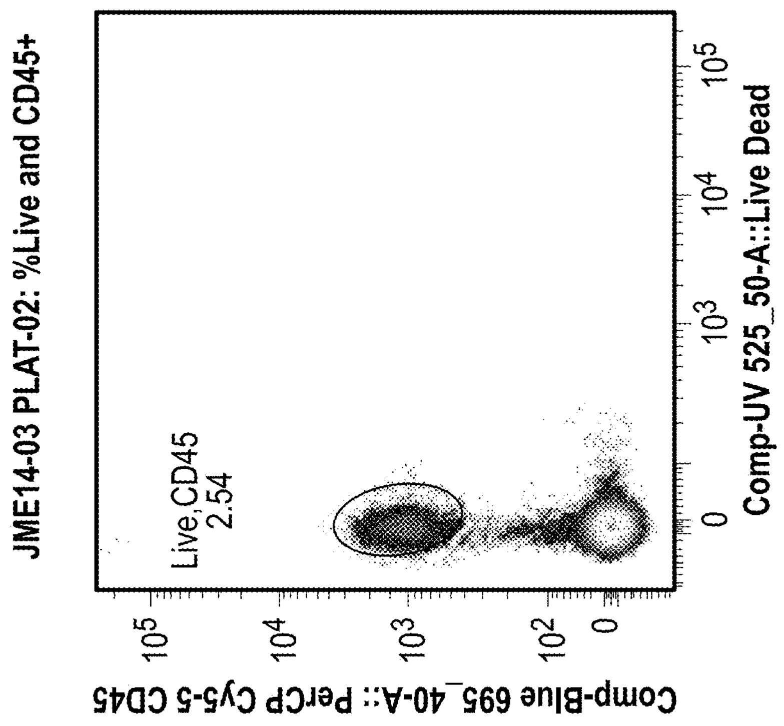
FIG. 59B1
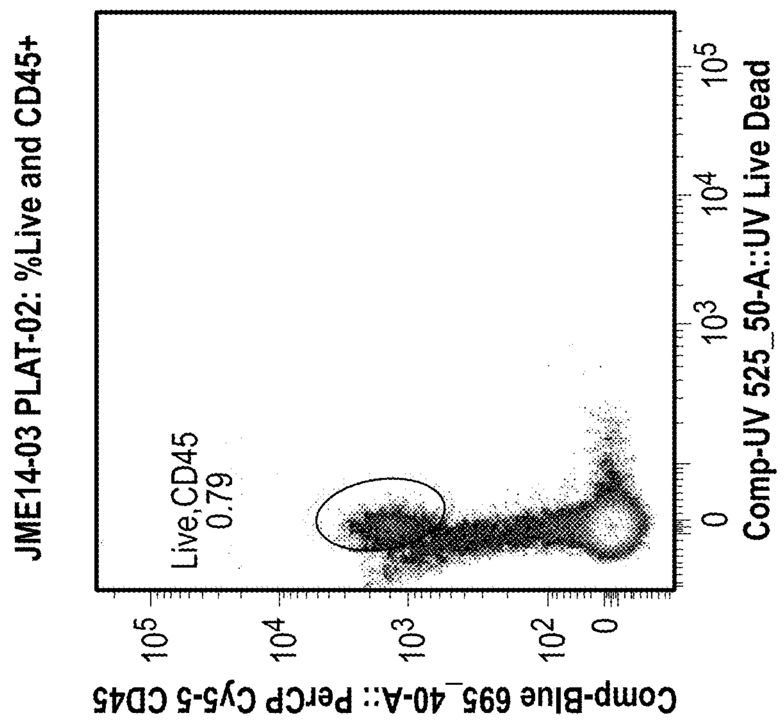
FIG. 59B2

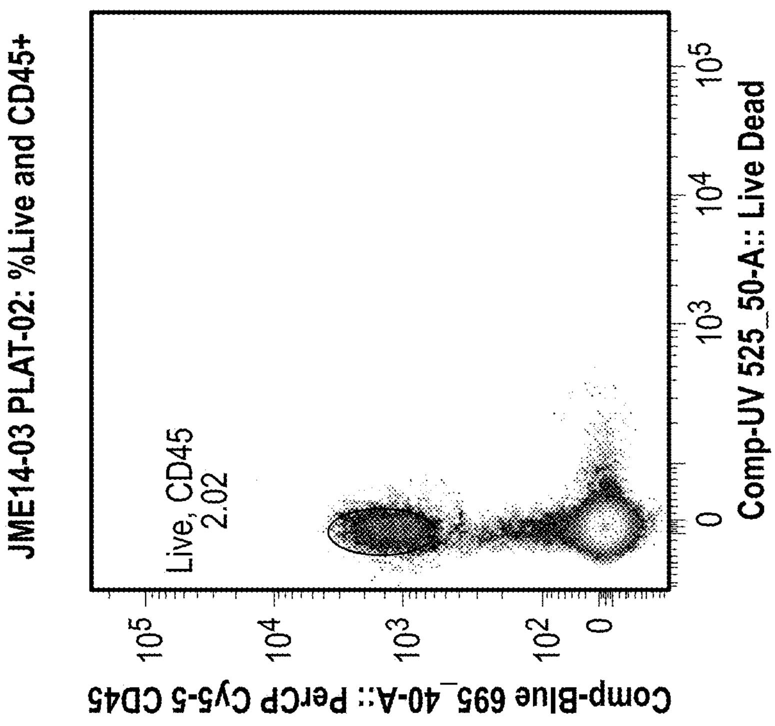
FIG. 59B3
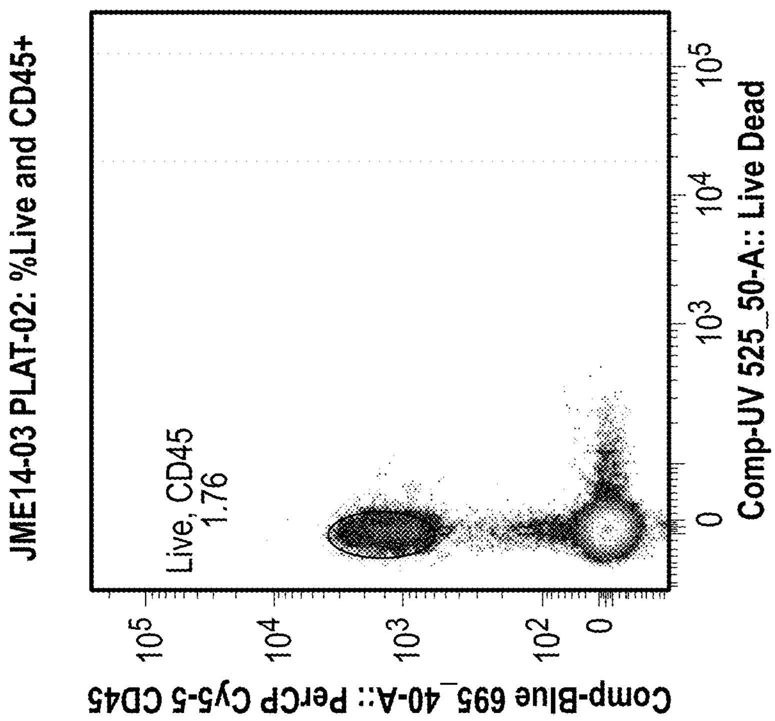
FIG. 59B4

JME14-03 PLAT-02: %Live and CD45+
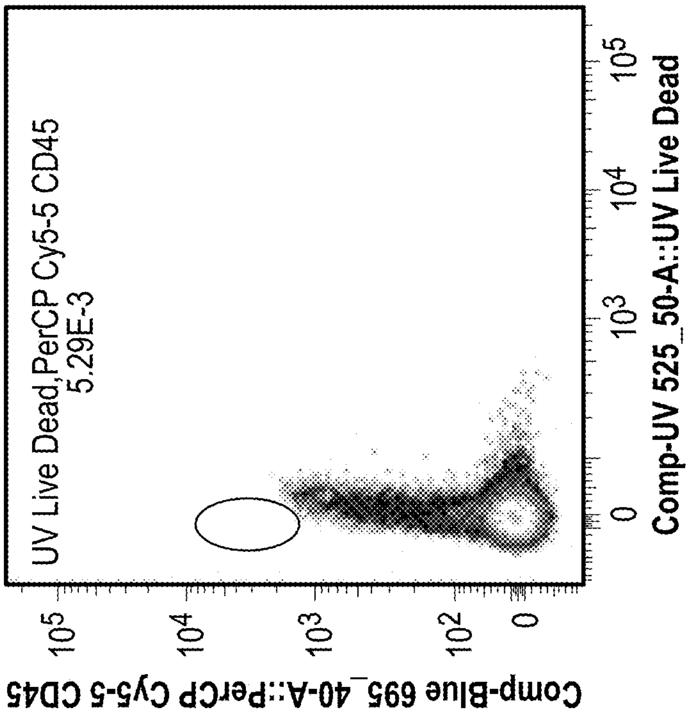
FIG. 59D1
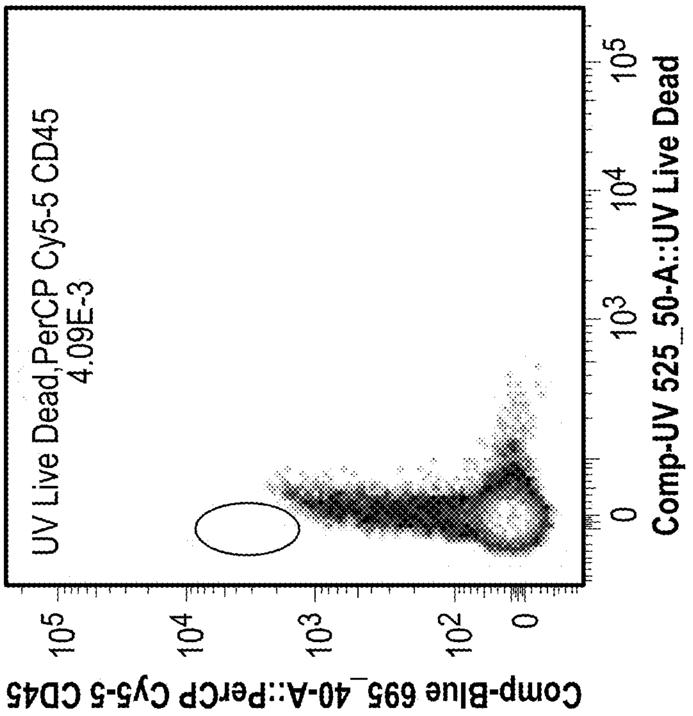
FIG. 59D2

JME14-03 PLAT-02: %Live and CD45+
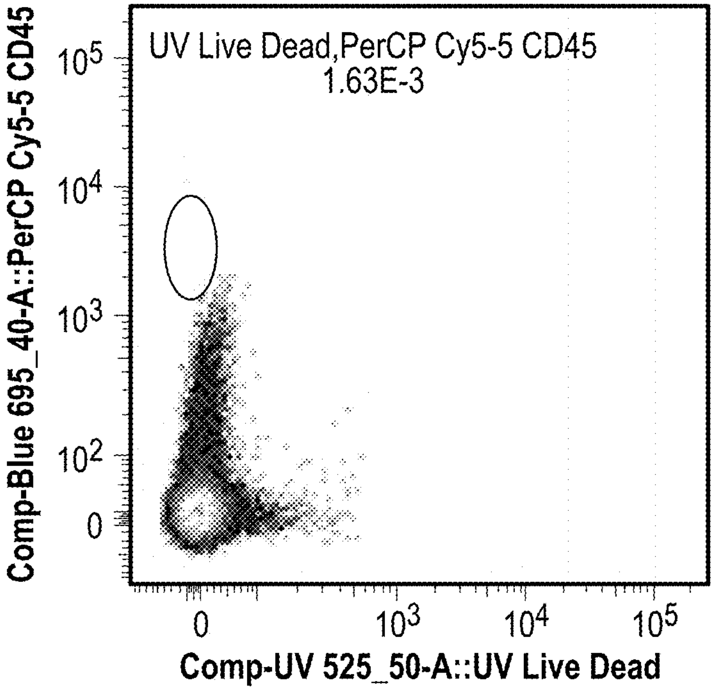
FIG. 59D3
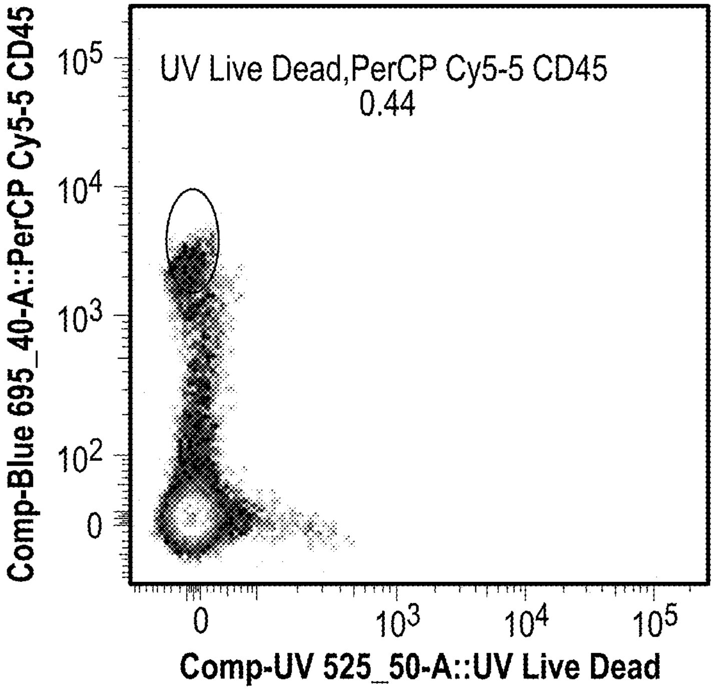
FIG. 59D4

JME14-03 PLAT-02: %Live and CD45+
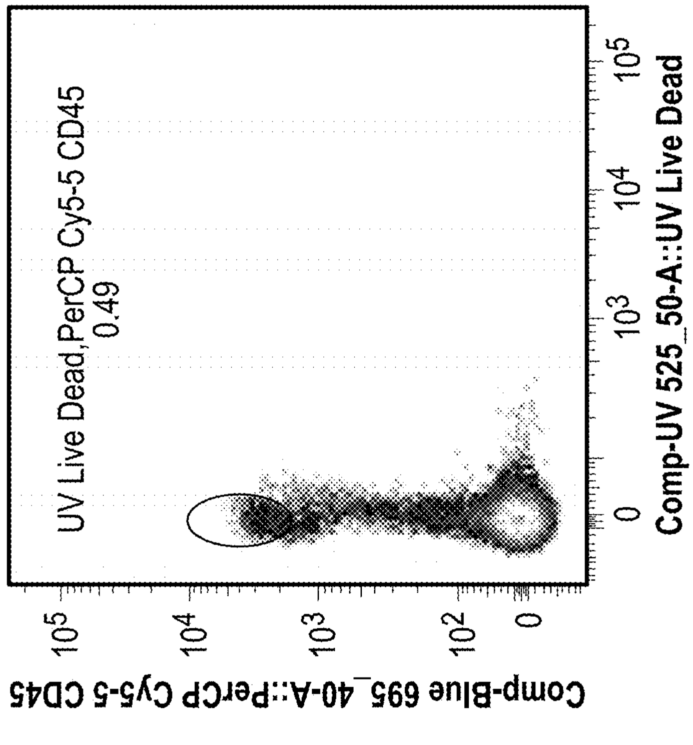
FIG. 59D5
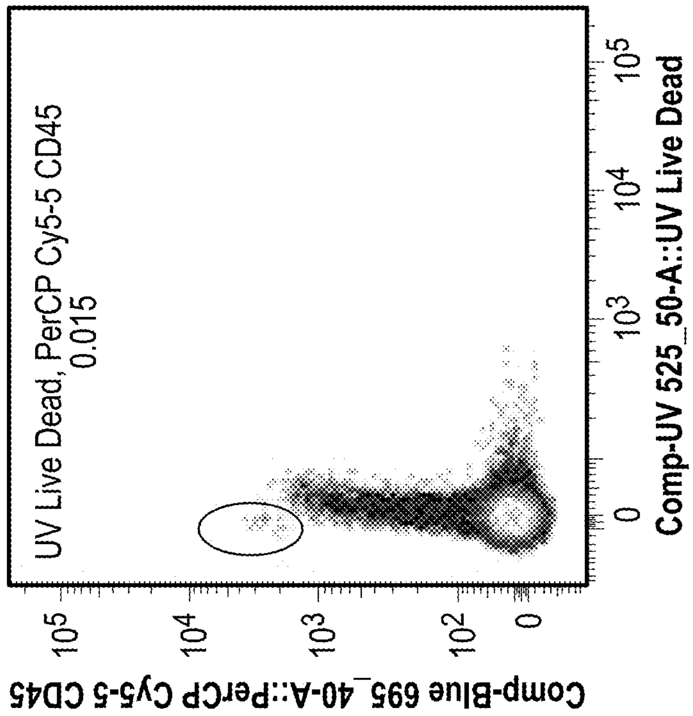
FIG. 59D6

JME14-03 PLAT-02: %Live and CD45+
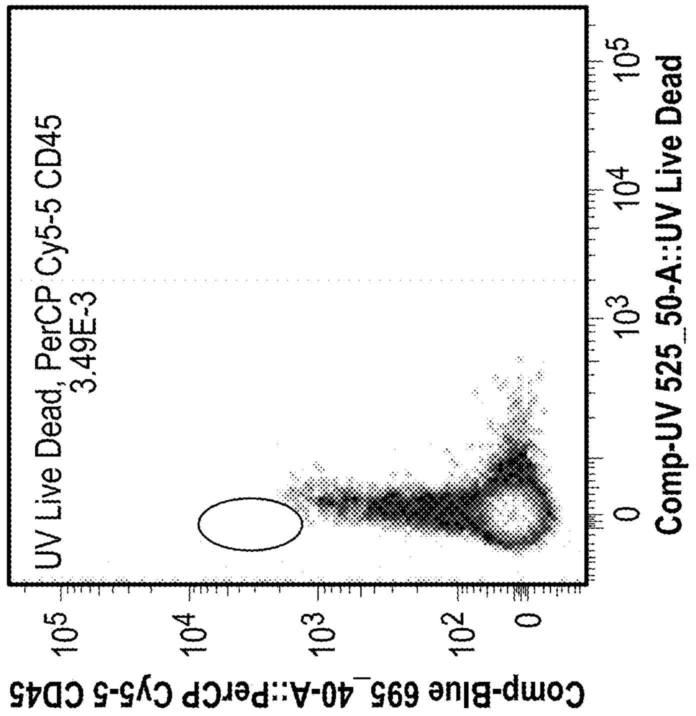
FIG. 59D7
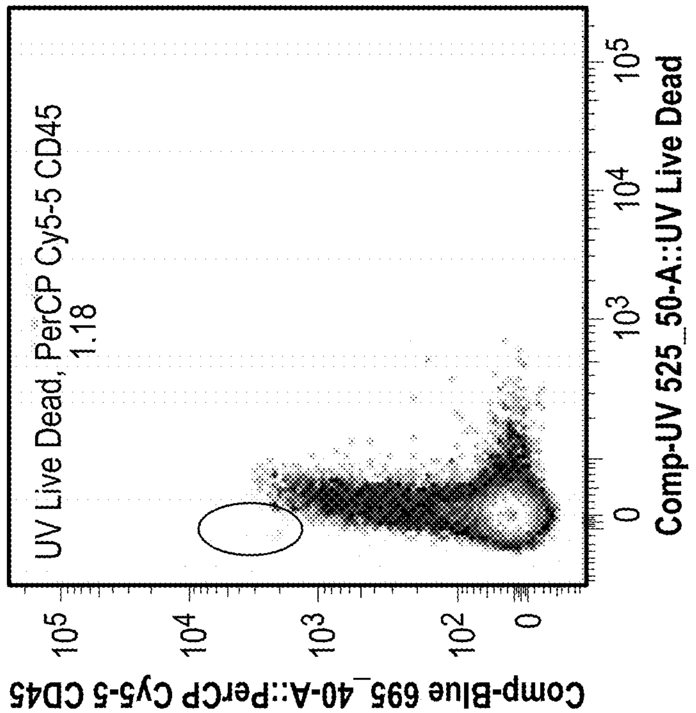
FIG. 59D8

JME14-03 PLAT-02: %Live and CD45+
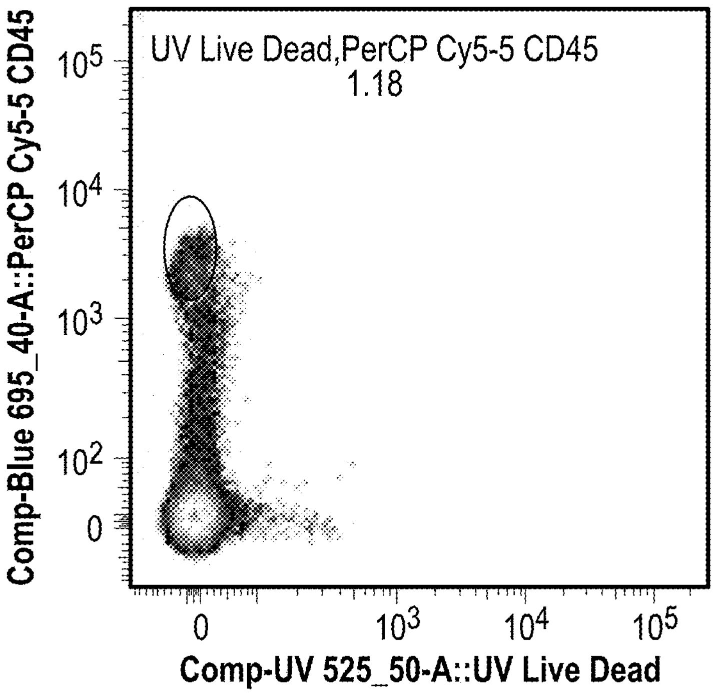
FIG. 59D9
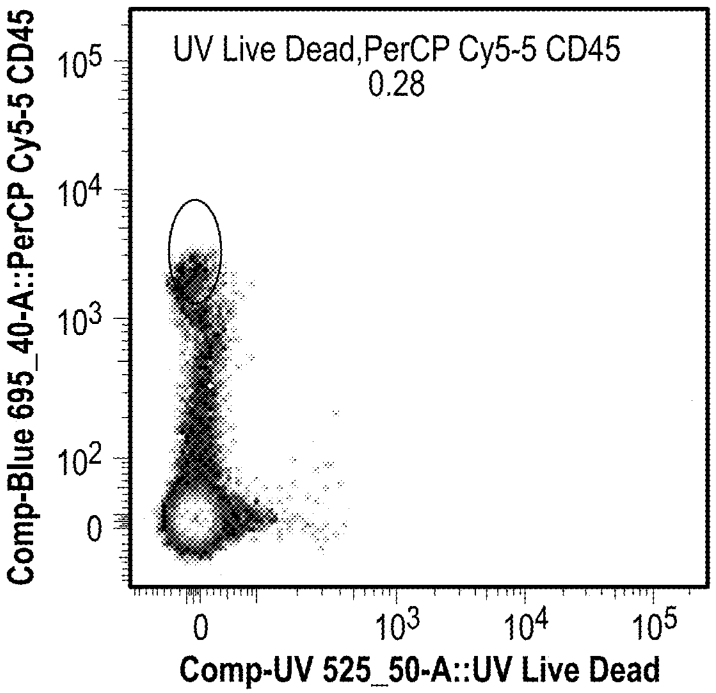
FIG. 59D10

JME14-03 PLAT-02: %Live and CD45+
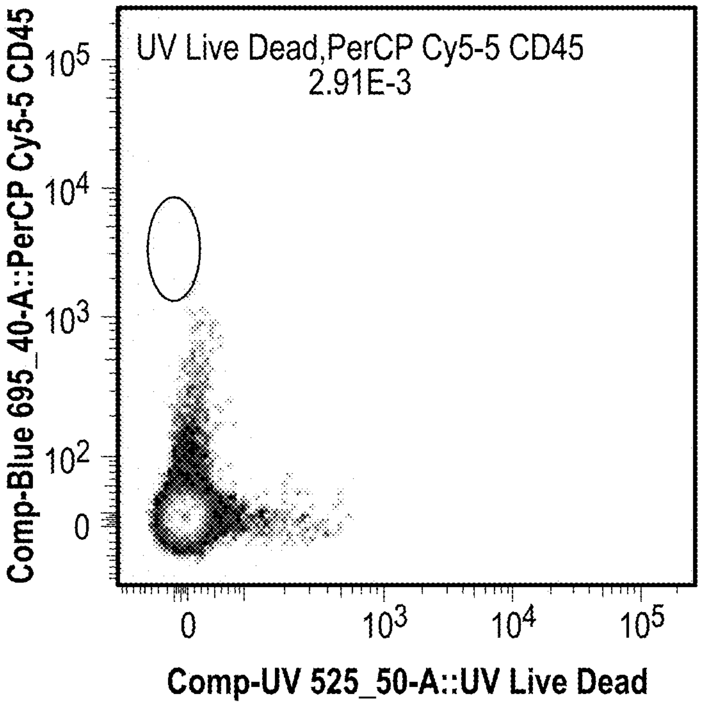
FIG. 59D11

JME14-03 PLAT-02, 5 Million T-Cell Dose Group:%EGFRt+ of Live, CD45+
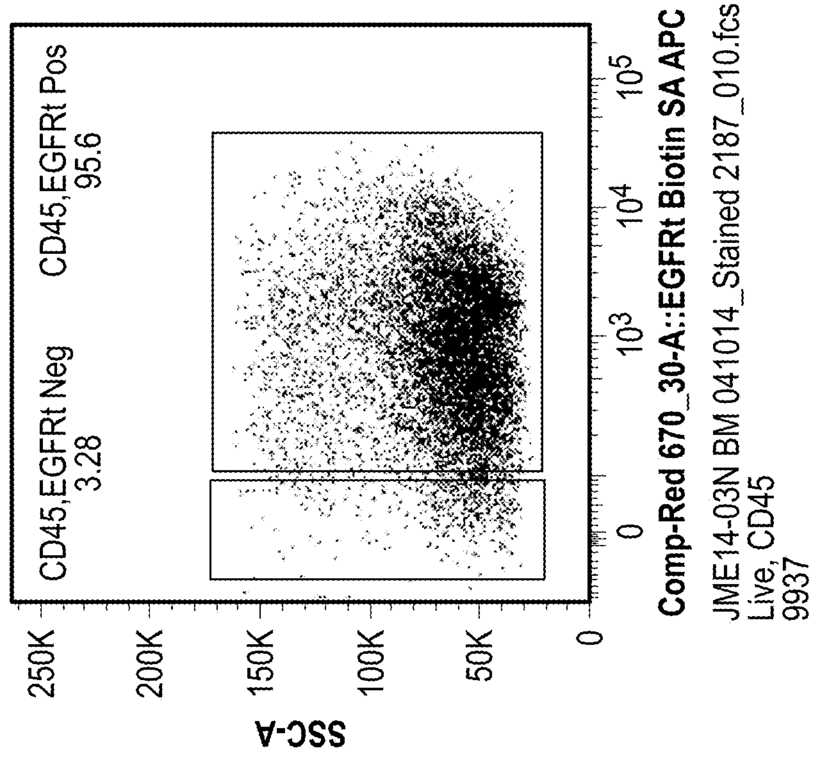
FIG. 59F1
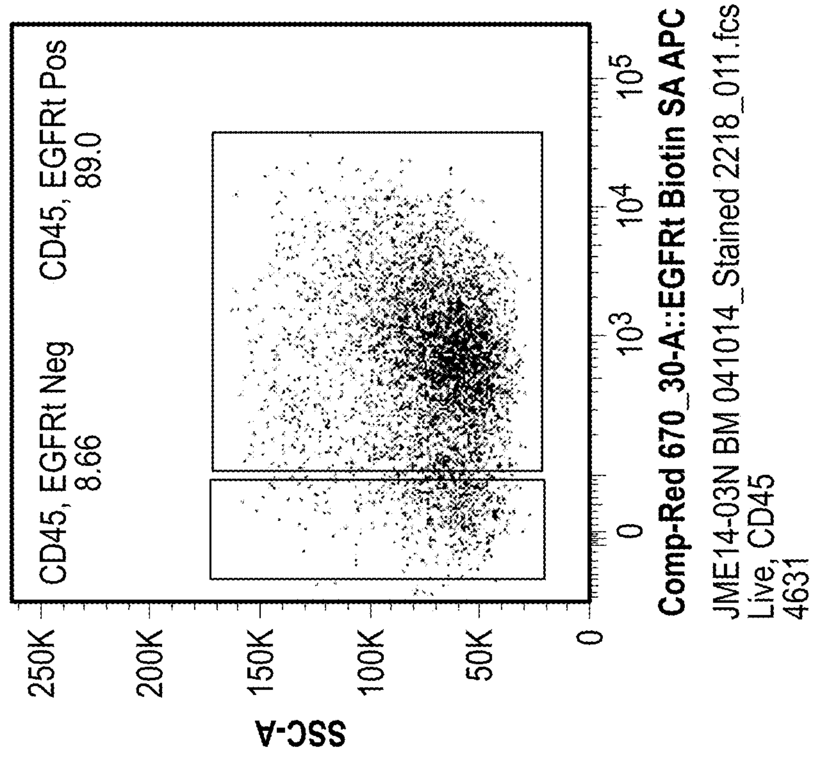
FIG. 59F2

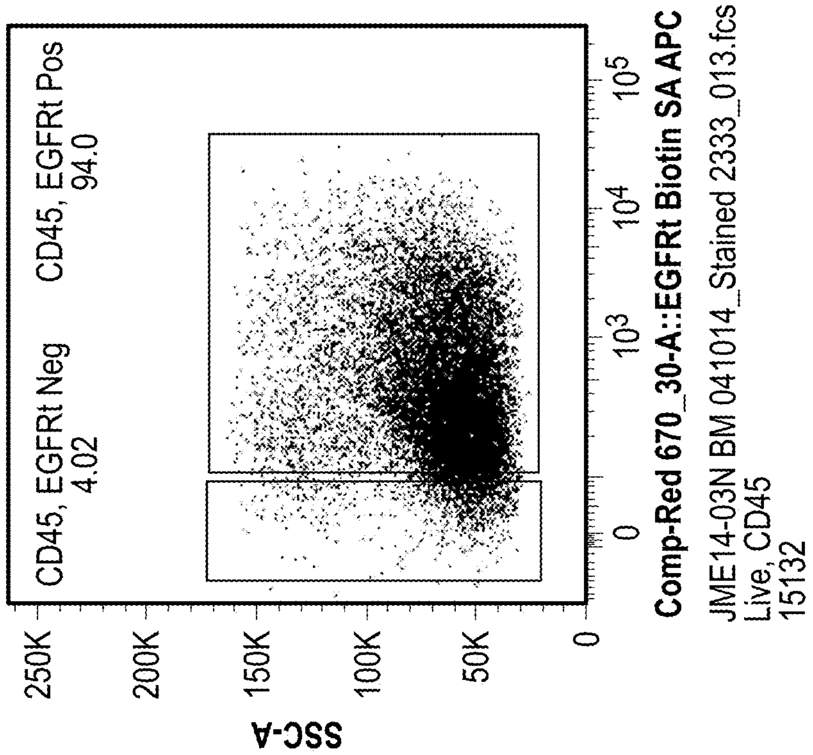
FIG. 59F4
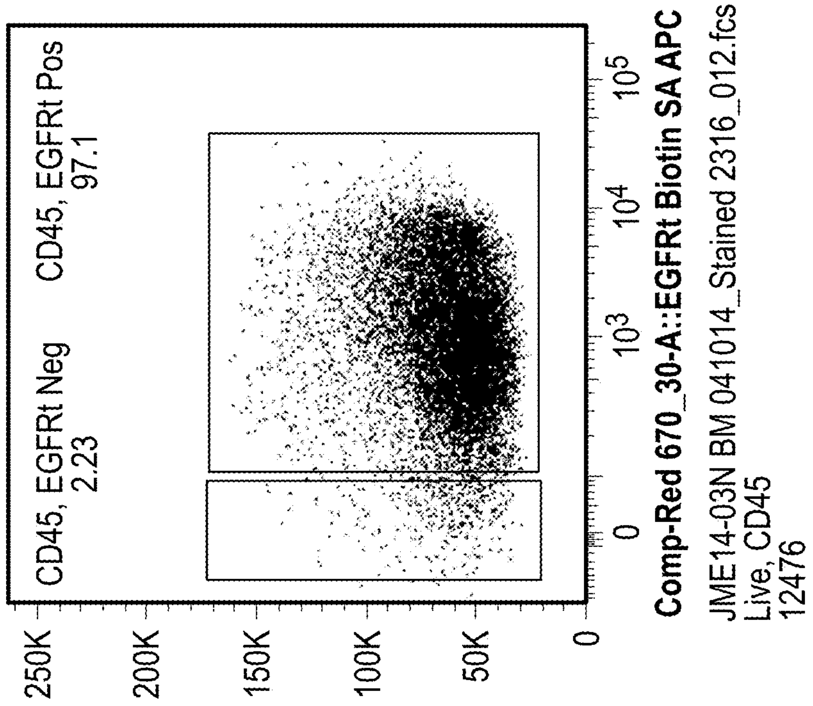
FIG. 59F3

JME14-03 PLAT-02, 5 Million T-Cell Dose Group:%EGFRt+ of Live, CD45+
83 Days Post T-Cells:
%EGFRt of CD45+ Bone Marrow JME14-03 PLAT-02, 5 Million T-Cell Dose Group:%EGFRt+ of Live, CD45+
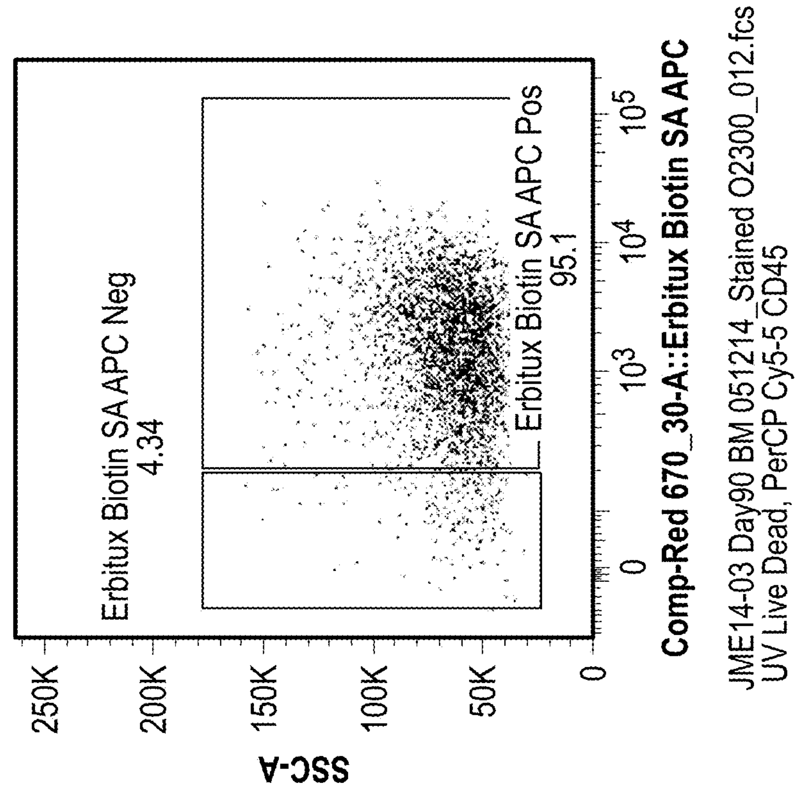
FIG. 59H1
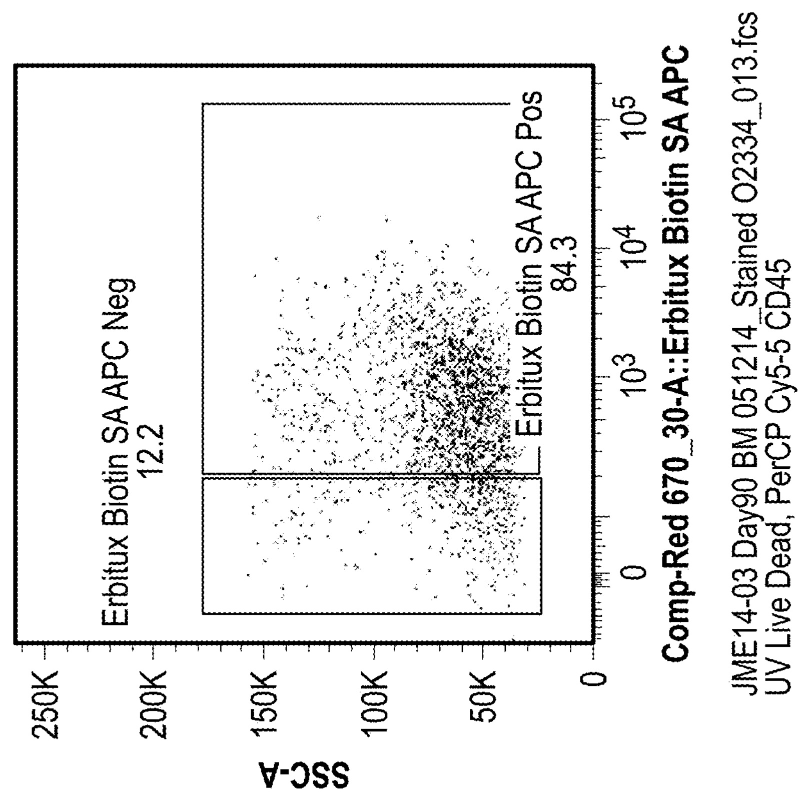
FIG. 59H2

JME14-03 PLAT-02, 5 Million T-Cell Dose Group: %EGFRt+ of Live, CD45+
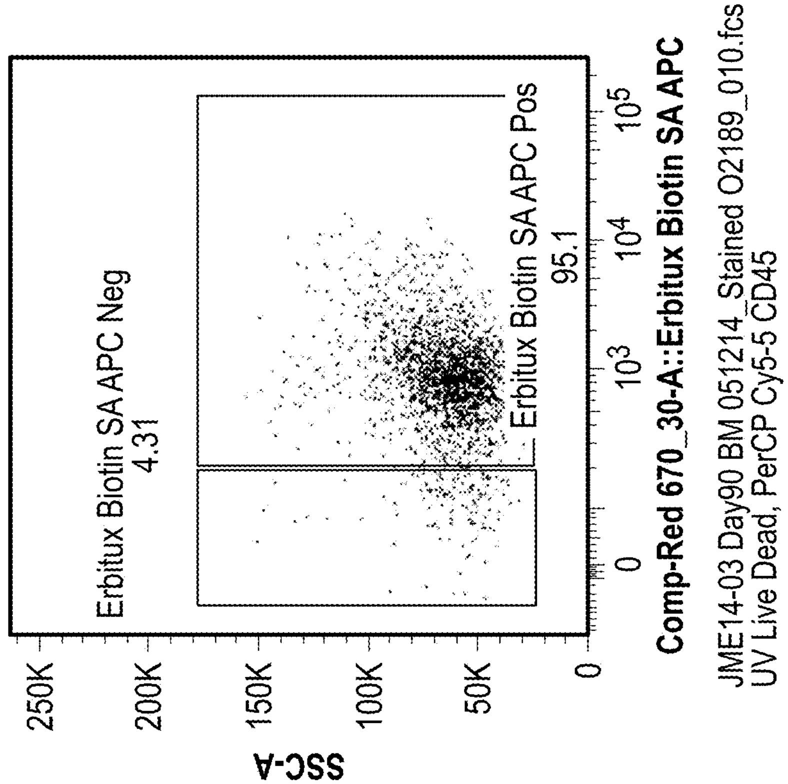
FIG. 59H3
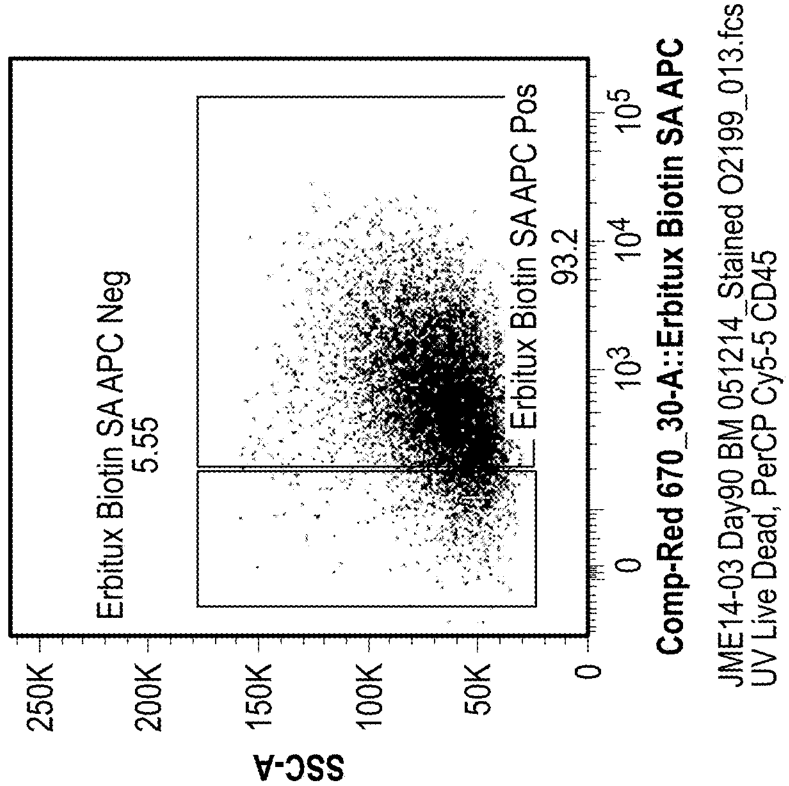
FIG. 59H4

JME14-03 PLAT-02, 5 Million Dose Group:%CD4+ vs CD8+ of Live, CD45+, EGFRt+
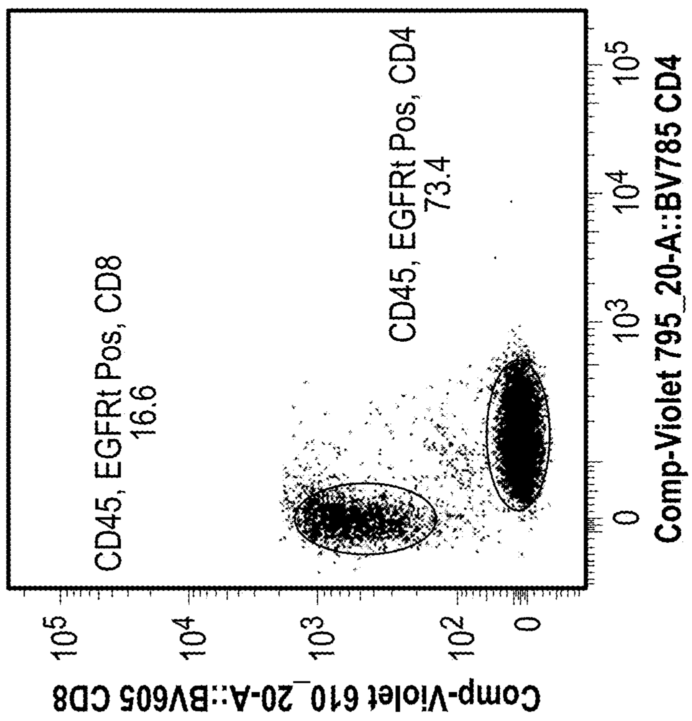
FIG. 60B1
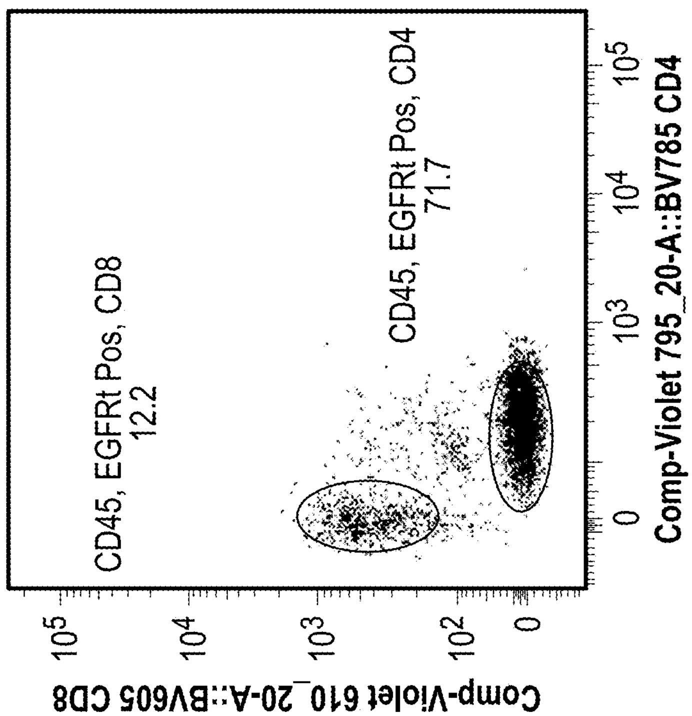
FIG. 60B2

JME14-03 PLAT-02, 5 Million Dose Group:%CD4+ vs CD8+ of Live, CD45+, EGFRt+
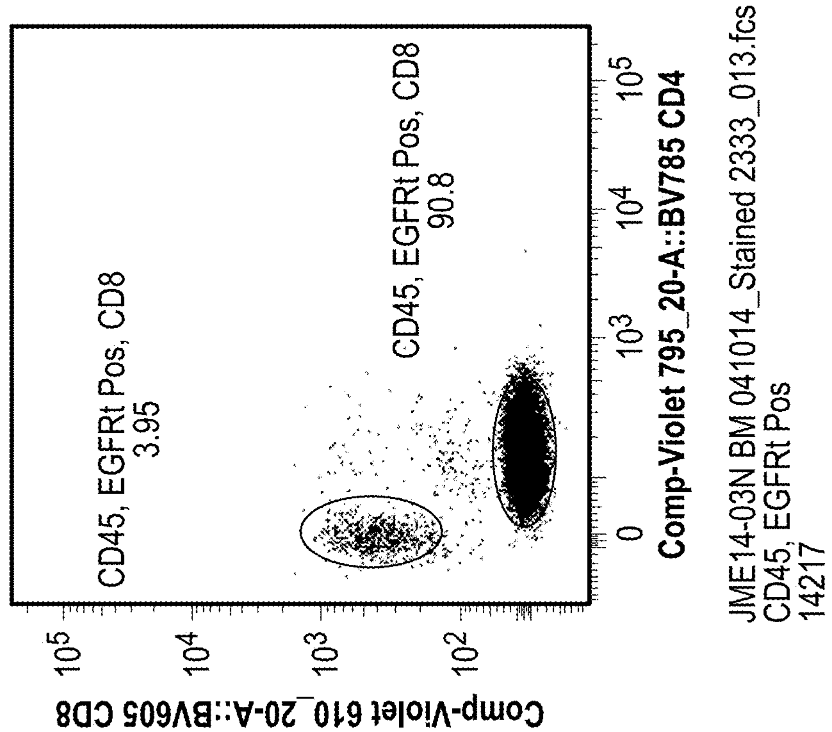
FIG. 60B4
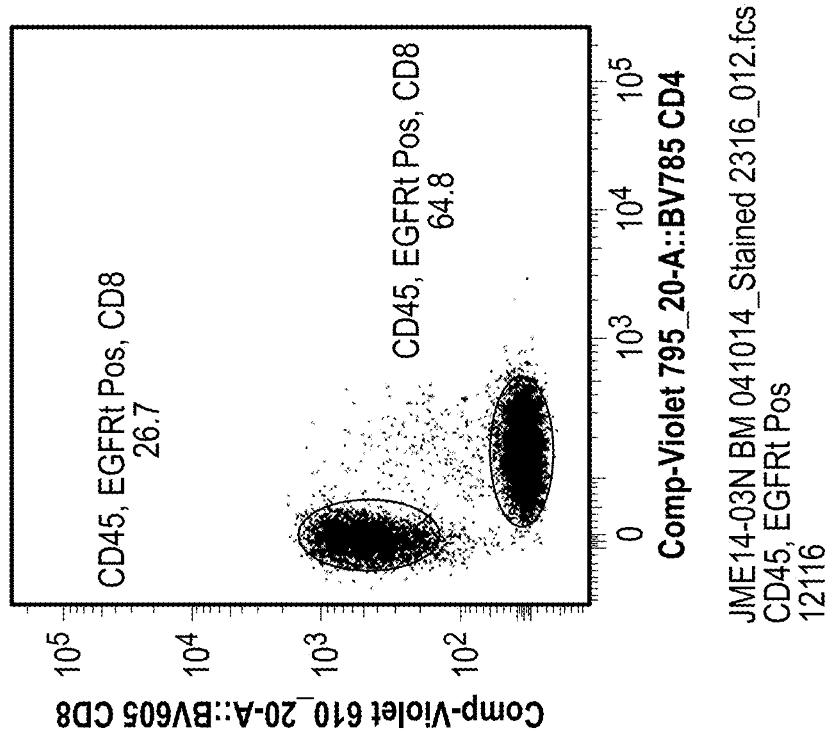
FIG. 60B3

JME14-03 PLAT-02, 5 Million Dose Group:%CD4+ vs CD8+ of Live, CD45+, EGFRt+
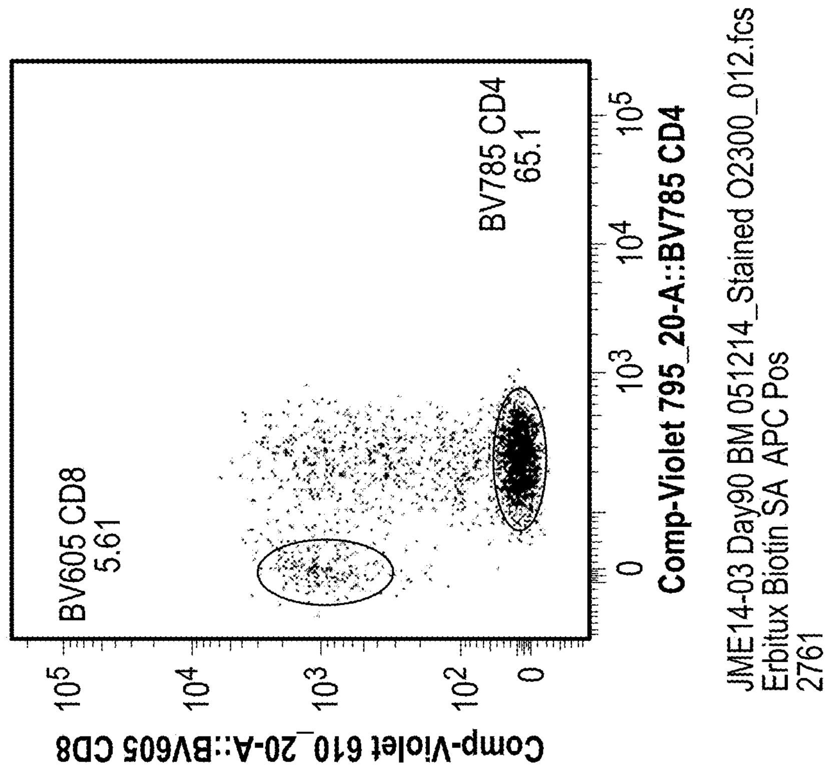
FIG. 60D1
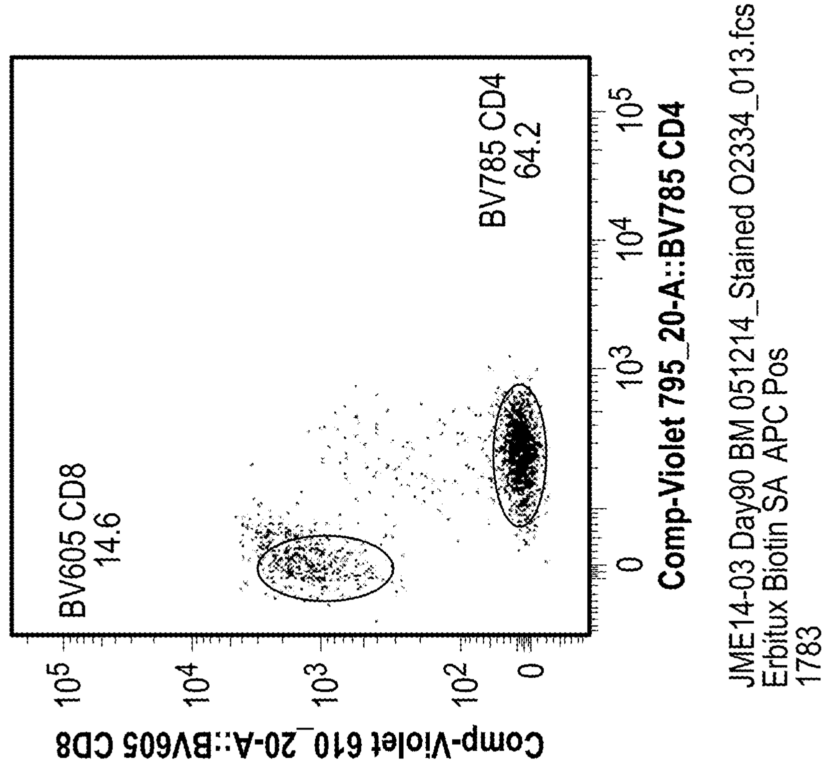
FIG. 60D2

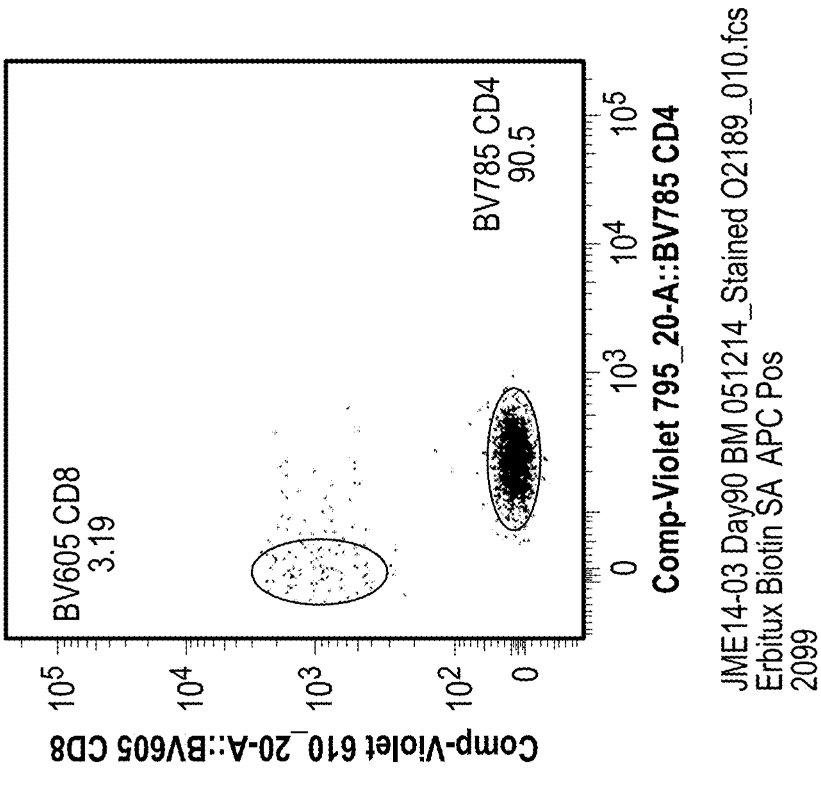
FIG. 60D3
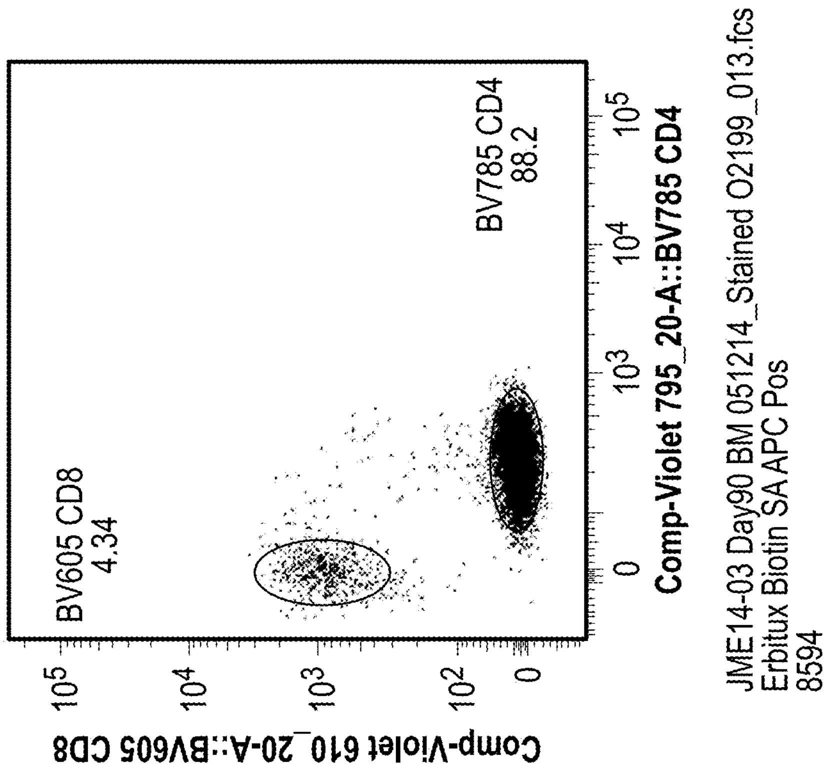
FIG. 60D4

JME14-03 Group N, Day 51 post T-cell

| Sample | Lymphocytes | Live, CD45+ | EGFRt+ | CD4+ | CD8+ |
|---|---|---|---|---|---|
| PLAT-02 (10x10e6) | 4.91e5 (87.2%) | 9937 (2.02%) | 9498 (95.6%) | 6976 (73.4%) | 1576 (16.6%) |
| PLAT-02 (10x10e6) | 5.83e5 (84.2%) | 4631 (0.79%) | 4121 (89.0%) | 3443 (71.7%) | 504 (12.2%) |
| PLAT-02 (10x10e6) | 7.07e5 (91.2%) | 12376 (1.76%) | 12116 (97.1%) | 7851 (64.8%) | 3234 (26.7%) |
| PLAT-02 (10x10e6) | 5.96e5 (88.4%) | 15132 (2.54%) | 14217 (94.0%) | 12907 (90.8%) | 561 (3.95%) |
| Neg. Control | 120212 (87.6%) | 156 (0.13%) | 145 (92.9%) | 51 (35.2%) | 45 (31.0%) |

JME14-03 Day 90 post T-cell

| Sample | Lymphocytes | Live, CD45+ | EGFRt+ | CD4+ | CD8+ |
|---|---|---|---|---|---|
| PLAT-02 (5x10e6) | 7.91e5 (87.2%) | 2206 (0.28%) | 2099 (95.1%) | 1899 (90.5%) | 67 (3.19%) |
| PLAT-02 (5x10e6) | 7.81e5 (86.9%) | 9221 (1.18%) | 8594 (93.2%) | 7583 (88.2%) | 373 (4.34%) |
| PLAT-02 (5x10e6) | 76.65e5 (85.6%) | 2904 (0.44%) | 2761 (95.1%) | 1798 (65.1%) | 155 (5.61%) |
| PLAT-02 (5x10e6) | 4.31e5 (81.5%) | 2115 (0.49%) | 1783 (84.3%) | 1145 (64.2%) | 260 (14.6%) |
| Neg. Control | 7.51e5 (83.1%) | 109 (0.015%) | 79 (72.5%) | 48 (60.8%) | 8 (10.1%) |
| Neg. Control | 5.29e5 (78.6%) | 28 (5.29e-3%) | 10 (28%) | 0 (0%) | 0 (0%) |
| PLAT-01 (10x10e6) | 6.15e6 (80.3%) | 27 (4.09e-3%) | 19 (70.4%) | 6 (31.6%) | 1 (5.26%) |
| PLAT-01 (10x10e6) | 6.44e6 (81.1%) | 26 (4.04e-3%) | 15 (57.7%) | 8 (53.3%) | 2 (13.3%) |
| PLAT-01 (5x10e6) | 6.77e5 (80.9%) | 11 (1.63e-3) | 5 (45.5%) | 1 (20.0%) | 0 (0%) |
| PLAT-01 (5x10e6) | 7.73e5 (80.3%) | 27 (3.49e-3) | 11 (40.7%) | 3 (27.3%) | 0 (0%) |
| PLAT-01 (5x10e6) | 7.56e5 (84.5%) | 22 (2.91e-3) | 16 (72.7%) | 5 (31.2%) | 8 (50%) |

FIG. 61

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Modified IgG4 hinge region

<400> SEQUENCE: 1

Glu Ser Lys Tyr Gly Pro Pro Cys Pro Pro Cys Pro
1 5 10

<210> SEQ ID NO 2
<211> LENGTH: 9
<212> TYPE: PRT
<213> ORGANISM: Artificial Sequence
<220> FEATURE:
<223> OTHER INFORMATION: Modified IgG4 hinge region

<400> SEQUENCE: 2

Tyr Gly Pro Pro Cys Pro Pro Cys Pro
1 5

<210> SEQ ID NO 3
<211> LENGTH: 10
<212> TYPE: PRT
<213> ORGANISM: Artificial Sequence
<220> FEATURE:
<223> OTHER INFORMATION: Modified IgG4 hinge region

<400> SEQUENCE: 3

Lys Tyr Gly Pro Pro Cys Pro Pro Cys Pro
1 5 10

<210> SEQ ID NO 4
<211> LENGTH: 13
<212> TYPE: PRT
<213> ORGANISM: Artificial Sequence
<220> FEATURE:
<223> OTHER INFORMATION: Modified IgG4 hinge region

<400> SEQUENCE: 4

Glu Val Val Lys Tyr Gly Pro Pro Cys Pro Pro Cys Pro
1 5 10

<210> SEQ ID NO 5
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 5

Met Phe Trp Val Leu Val Val Val Gly Gly Val Leu Ala Cys Tyr Ser
1 5 10 15

Leu Leu Val Thr Val Ala Phe Ile Ile Phe Trp Val
20 25

<210> SEQ ID NO 6
<211> LENGTH: 42
<212> TYPE: PRT
<213> ORGANISM: Artificial Sequence
<220> FEATURE:
<223> OTHER INFORMATION: 4-1BB domain

<400> SEQUENCE: 6

-continued

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 7
<211> LENGTH: 112
<212> TYPE: PRT
<213> ORGANISM: Artificial Sequence
<220> FEATURE:
<223> OTHER INFORMATION: CD3-zeta domain

<400> SEQUENCE: 7

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

DEFINED COMPOSITION GENE MODIFIED T-CELL PRODUCTS

CROSS REFERENCE TO RELATED APPLICATIONS

This is a continuation of U.S. application Ser. No. 15/302,426 filed Oct. 6, 2016 which is a U.S. National Phase of PCT/US2015/024866 filed on Apr. 8, 2015 which claims priority to U.S. Prov. App. No. 61/977,751, filed Apr. 10, 2014, U.S. Prov. App. No. 61/986,479, filed Apr. 30, 2014, U.S. Prov. App. No. 62/058,973, filed Oct. 2, 2014, U.S. Prov. App. No. 62/088,363, filed Dec. 5, 2014, U.S. Prov. App. No. 62/089,730 filed Dec. 9, 2014, and U.S. Prov. App. No. 62/090,845, filed Dec. 11, 2014. The entire disclosures of the aforementioned applications are expressly incorporated by reference in their entireties.

REFERENCE TO SEQUENCE LISTING

The present application is being filed along with a Sequence Listing in electronic format. The Sequence Listing is provided as a file entitled SCRI090C1SEQLIST, created Apr. 21, 2022, which is approximately 3.2 kilobytes in size. The information in the electronic format of the Sequence Listing is incorporated herein by reference in its entirety.

FIELD OF THE INVENTION

Aspects of the invention concern approaches to make genetically modified T-cells comprising a chimeric antigen receptor. The disclosed methods concern the selection and/or isolation of CD4+ and/or CD8+ T-cells from a mixed T-cell population, which are then activated, genetically modified, and propagated in isolated cultures in the presence of one or more cytokines, which support survival, engraftment and/or proliferation of the cells, as well as, promoting retention of cell surface receptors, such as CD62L, CD28, and/or CD27.

BACKGROUND OF THE INVENTION

Acute lymphoblastic leukemia (ALL) relapse following allogeneic hematopoietic stem cell transplantation (HSCT) can occur. Accordingly, many believe such approaches are ineffective. The adoptive transfer of human T lymphocytes that are engineered by gene transfer to express chimeric antigen receptors (CARs) specific for molecules present on the surface of tumor cells or malignant B cells has the potential to effectively treat many advanced cancers and malignancies, as well. In order to be an effective and long lasting treatment, however, the administered T-cells that comprise chimeric antigen receptors desirably have a high survival and proliferation rate after transfer to the patient. The T-cells used for therapy are also desirably fit for engraftment. Despite the tremendous effort in the field, the need for additional, effective cellular therapies remains.

SUMMARY OF THE INVENTION

Aspects of the invention described herein include methods of manufacturing genetically modified T-cells comprising a chimeric antigen receptor for human therapy. Alternatives include methods utilizing a selection, enrichment, and/or isolation of CD4+ and/or CD8+ expressing T-cells, such as T-cells that are derived from thymocytes or T-cells that are derived from engineered precursors, desirably iPS cells, from a mixed T-cell population. Once selected, enriched, or isolated, the CD4+ and/or CD8+ expressing T-cells are then activated, genetically modified, and propagated, preferably, in separated, enriched, or isolated cultures in the presence of one or more cytokines, which can be provided exogenously to the T-cells, e.g., in addition to any cytokine that may be produced by the cells or present in media and, which support, promote, induce, or contribute to survival, engraftment and/or proliferation of the cells, as well as, preferably supporting, promoting, inducing, or contributing to the retention of cell surface receptors, such as CD62L, CD28, and/or CD27. Included herein are also methods of treatment, inhibition, amelioration, or elimination of a cancer by administering to a subject in need thereof, one or more types of the genetically engineered T-cells or compositions that comprise the genetically engineered T-cell prepared as described herein.

Some aspects of the invention described herein concern methods of making genetically modified T-cells, which have a chimeric antigen receptor. By some approaches, these methods are practiced by separating, isolating, or enriching a CD8+ expressing population of T-cells and/or a CD4+ expressing population of T-cells, such as T-cells that are derived from thymocytes or T-cells that are derived from engineered precursors, desirably iPS cells, from a mixed population of T-cells so as to generate a separated, isolated, or enriched population of T-cells; stimulating these separated, enriched, or isolated populations of T-cells so as to generate a stimulated population of CD8+ expressing T-cells and/or CD4+ expressing T-cells; transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells; contacting the transduced population of CD8+ expressing T-cells and/or CD4+ expressing T-cells with at least one cytokine, which can be provided exogenously to the T-cells, e.g., in addition to any cytokine that may be produced by the cells or present in media, so as to generate a transduced, cytokine-stimulated population of CD8+ expressing T-cells and/or CD4+ expressing T-cells; enriching the transduced, cytokine-stimulated population of CD8+ expressing T-cells and/or CD4+ expressing T-cells by selection of the marker sequence so as to generate a separated, enriched, or isolated population of transduced, cytokine-stimulated CD8+ expressing T-cells and/or CD4+ expressing T-cells; and propagating the separated, enriched, or isolated population of transduced, cytokine-stimulated CD8+ expressing T-cells and/or CD4+ expressing T-cells for at least two days so as to obtain said genetically modified T-cells, which have a chimeric antigen receptor. In some alternatives, the CD8+ expressing T-cells and/or CD4+ expressing T-cells can be propagated for at least or equal to 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor. In some alternatives, the separating or enriching of the CD8+ population of T-cells and/or a CD4+ population of T-cells from a mixed population of T-cells is performed by affinity selection for T-cells having an epitope present on CD8 and/or CD4. In some alternatives, the separating or enriching of the CD8+ population of T-cells and/or a CD4+ population of T-cells from a mixed population of T-cells is performed by flow cytometry. In some alternatives, the separating or enriching of the CD8+ population of T-cells and/or a CD4+ population of T-cells from a mixed population of T-cells is performed by immuno-magnetic selection. In some alternatives, the genetically modified CD8+ T-cells and/or CD4+ T-cells comprise at least one receptor that promotes, induces, contributes to, or enhances engraftment fitness. In some alternatives, the at least one receptor is CD45 RA, CD45 RO, CCR7, CD25, CD127, CD57, CD137, CD27, CD28 and/or CD62L. In some alternatives, the at least one receptor is CD27, CD28 and/or CD62L. In some alternatives, the stimulating of the isolated population of T-cells is performed by contacting the CD8+ and/or CD4+ T-cells with an antibody-bound support, such as a bead or particle. In some alternatives, the antibody-bound support comprises anti-TCR, anti-CD2, anti-CD3, anti-CD4 and/or anti-CD28 antibodies. In some alternatives, the antibody-bound support comprises anti-CD3 and/or anti-CD28 antibodies. In some alternatives, the vector further comprises a first sequence encoding a leader sequence, a second sequence encoding a ligand binding domain, a third sequence encoding a signaling domain and a fourth sequence encoding a selectable marker. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the marker sequence encodes a truncated epidermal growth factor receptor (EGFRt). In some alternatives, the at least one cytokine comprises GM-CSF, IL-7, IL-12, IL-15, IL-18, IL-2, and/or IL-21. In some alternatives, the at least one cytokine comprises IL7, IL-15 and/or IL-21, which can be provided at 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL or in an amount that is within a range defined by any two of the aforementioned amounts and/or at 10 U/mL, 20 U/mL, 30 U/mL, 40 U/mL, 50 U/mL, 60 U/mL, 70 U/mL, 80 U/mL, 90 U/mL, or 100 U/mL or in an amount that is within a range defined by any two of the aforementioned amounts. In some alternatives, the at least one cytokine comprises IL-2, IL-15 and/or IL-21, wherein the amount of cytokine is provided at 0.5 ng/mL and/or 50 U/mL. In some alternatives, the contacting is performed for 1, 2, 3, 4, 5, 6, 7, 8, 9, 10, 11, 12, 13, 14, 15, 16, 17, 18, 19, or 20 days or a period of time within a range defined by any two of these values. In some alternatives, the method is performed with isolated, purified, enriched or separated CD4+ cells in the absence of, substantially depleted of, or enriched over CD8+ cells. In some alternatives, the method is performed with isolated, purified, enriched or separated CD8+ in the absence of, substantially depleted of, or enriched over CD4+ cells. In some alternatives, the CD4+ expressing T-cells are propagated for at least 1 day, such as 1, 2, 3, 4, 5, 6, 7, 8, 9, 10, 11, 12, 13, 14, 15, 16, 17, 18, 19, or 20 days or for a period that is within a range defined by any two of the aforementioned time periods. In some alternatives, the CD8+ T-cells are propagated at least 1 day, such as 1, 2, 3, 4, 5, 6, 7, 8, 9, 10, 11, 12, 13, 14, 15, 16, 17, 18, 19, or 20 days or for a period that is within a range defined by any two of the aforementioned time periods. In some alternatives, the method further comprises removing the antibody-bound support, such as beads or particles. In some alternatives, the ligand binding domain of the chimeric antigen receptor comprises an antibody, or a binding portion thereof. In some alternatives, the ligand binding domain of the chimeric antigen receptor comprises a single chain variable fragment (scFv), or a binding portion thereof. In some alternatives, the ligand binding domain of the chimeric antigen receptor comprises FMC63, or a binding portion thereof. In some alternatives, the ligand binding domain of the chimeric antigen receptor is specific for CD19. In some alternatives, the method further comprises cryopreserving the genetically modified CD8+ and/or CD4+ T-cells.

In some alternatives, the separating, enriching, or isolating of the CD8+ expressing population of T-cells and/or a CD4+ expressing population of T-cells, such as T-cells that are derived from thymocytes or T-cells that are derived from engineered precursors, desirably iPS cells, from a mixed population of T-cells is performed by affinity selection for T-cells having an epitope present on CD8 and/or CD4. In some alternatives, the separating, enriching, or isolating of the CD8+ expressing population of T-cells and/or a CD4+ expressing population of T-cells from a mixed population of T-cells is performed by flow cytometry. In some alternatives, the separating, enriching, or isolating of the CD8+ expressing population of T-cells and/or a CD4+ expressing population of T-cells from a mixed population of T-cells is performed by immuno-magnetic selection. In some alternatives, the genetically modified CD8+ expressing T-cells and/or CD4+ expressing T-cells comprise at least one receptor that promotes, induces, or contributes to engraftment fitness. In some alternatives, the at least one receptor that promotes, induces, or contributes to engraftment fitness is CD45 RA, CD45 RO, CCR7, CD25, CD127, CD57, CD137, CD27, CD28 and/or CD62L. In preferred alternatives, the at least one receptor that promotes, induces, or contributes to engraftment fitness is CD27, CD28 and/or CD62L. In some alternatives, the stimulating of the isolated, enriched, or separated population of T-cells is performed by contacting the CD8+ and/or CD4+ expressing T-cells with an antibody-bound support, such as a bead or particle. In some of these alternatives, the antibody-bound support comprises anti-TCR, anti-CD2, anti-CD3, anti-CD4 and/or anti-CD28 antibodies. In preferred alternatives, the antibody-bound support comprises anti-CD3 and/or anti-CD28 antibodies.

In many of the aforementioned alternatives, the vector further comprises a first sequence encoding a leader sequence, a second sequence encoding a ligand binding domain, a third sequence encoding a signaling domain and a fourth sequence encoding a selectable marker sequence. In some of these alternatives, the vector further comprises a sequence encoding a spacer, which in some alternatives may comprise an IgG4 hinge. In many of the aforementioned alternatives, the vector is a viral vector or a mini-circle.

In many of the aforementioned alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. Preferably, the viral vector is a lentivirus vector. In many of the aforementioned alternatives, the marker sequence encodes a truncated epidermal growth factor receptor (EGFRt). In many of the aforementioned alternatives, the at least one cytokine that is utilized comprises GM-CSF, IL-7, IL-12, IL-15, IL-18, IL-2, and/or IL-21 and said cytokine is provided exogenously to the T-cells e.g., in addition to any cytokine that may be produced by the cells or present in media.

In desirable alternatives, the at least one cytokine comprises IL-7, IL-15 and/or IL-21. In many of the aforementioned alternatives, the at least one cytokine comprises IL-2, IL-15 and/or IL-21. In preferred alternatives, the contacting period is performed for at least 1, 2, 3, 4, 5, 6, 7, 8, 9, 10, 11, 12, 13, 14, 15, 16, 17, 18, 19, or 20 days or a period of time within a range defined by any two of these time points. In many of the aforementioned alternatives, the methods are performed with isolated, separated, or enriched populations of CD4+ expressing T-cells, such as T-cells that are derived from thymocytes or T-cells that are derived from engineered precursors, desirably iPS cells, in the absence of or having a reduced amount CD8+ expressing T-cells, as compared to a native population of unseparated, non-enriched, or non-isolated population of T-cells. In many of the aforementioned alternatives, these methods are performed with isolated, separated, or enriched populations of CD8+ expressing T-cells, such as T-cells that are derived from thymocytes or T-cells that are derived from engineered precursors, desirably iPS cells, in the absence of or having a reduced amount of CD4+ expressing T-cells, as compared to a native population of unseparated, non-enriched, or non-isolated population of T-cells. In many of the aforementioned alternatives, the CD4+ expressing T-cells are propagated for at least 1 day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points. In many of the aforementioned alternatives, the CD8+ expressing T-cells are propagated for at least 1 day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points.

In many of the aforementioned alternatives, the methods further comprise removing the antibody-bound support, such as beads or particles. In many of the aforementioned alternatives, the ligand binding domain of the chimeric antigen receptor comprises an antibody, or a binding portion thereof. In many of the aforementioned alternatives, the ligand binding domain of the chimeric antigen receptor comprises a single chain variable fragment (scFv), or a binding portion thereof. In many of the aforementioned alternatives, the ligand binding domain of the chimeric antigen receptor comprises FMC63, or a binding portion thereof, such as is available in U.S. Pat. No. 7,446,179, herein expressly incorporated by reference in its entirety. In many of the aforementioned alternatives, the ligand binding domain of the chimeric antigen receptor is specific for CD19. In many of the aforementioned alternatives, the method further comprises cryopreserving the genetically modified CD8+ and/or CD4+ T-cells.

Additional aspects of the invention concern a population of genetically modified T-cells, such as T-cells that are derived from thymocytes or T-cells that are derived from engineered precursors, comprising a plurality of affinity selected CD8+ and/or CD4+ expressing T-cells, in an enriched form, such as enriched from, in the absence of, or isolated from CD8− and/or CD4− expressing T-cells, wherein said plurality of affinity selected CD8+ and/or CD4+ expressing T-cells have stimulated CD2, CD3, CD4 and/or CD28 receptors, wherein said plurality of affinity selected or enriched CD8+ and/or CD4+ expressing T-cells further comprise a gene encoding a chimeric antigen receptor and a gene encoding a cell surface selectable marker and, wherein said plurality of affinity selected or enriched CD8+ and/or CD4+ expressing T-cells have been re-stimulated with at least one cytokine, which can be provided exogenously to the T-cells, e.g., in addition to any cytokine that may be produced by the cells or present in media, such as, contacting the cells with an exogenously added cytokine for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points. In some alternatives, said plurality of affinity selected CD8+ and/or CD4+ expressing T-cells further comprise at least one receptor that promotes, induces, or contributes to engraftment fitness. In some alternatives, the at least one receptor that promotes, induces, improves, or contributes to engraftment fitness is CD45 RA, CD45 RO, CCR7, CD25, CD127, CD57, CD137, CD27, CD28 and/or CD62L. In some alternatives, the at least one receptor that promotes, induces, improves, or contributes to engraftment fitness is CD27, CD28 and/or CD62L. In some alternatives, the plurality of affinity selected CD8+ and/or CD4+ expressing T-cells further comprises a vector having a first sequence encoding a leader sequence, a second sequence encoding a ligand binding domain, a third sequence encoding a signaling domain and a fourth sequence encoding a selectable marker sequence.

Some alternatives relate to a population of genetically modified T-cells. In some alternatives, the population of genetically modified T-cells comprises a plurality of affinity selected CD8+ and/or CD4+ T-cells, absence of, substantially depleted of, or enriched over CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ T-cells have been re-stimulated with at least one cytokine. In some alternatives, said plurality of affinity selected CD8+ and/or CD4+ T-cells further comprise at least one receptor that promotes, enhances, improves or contributes to engraftment fitness. In some alternatives, the at least one receptor that promotes, enhances, improves or contributes to engraftment fitness is CD45 RA, CD45 RO, CCR7, CD25, CD127, CD57, CD137, CD27, CD28 and/or CD62L. In some alternatives, the at least one receptor that promotes, enhances, improves or contributes to engraftment fitness is CD27, CD28 and/or CD62L. In some alternatives, the plurality of affinity selected CD8+ and/or CD4+ T-cells further comprises a vector having a first sequence encoding a leader sequence, a second sequence encoding a ligand binding domain, a third sequence encoding a signaling domain and a fourth sequence encoding a selectable marker. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the cell surface selectable marker encodes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof. In some alternatives, the ligand binding domain is specific for CD19. In some alternatives, the population comprises isolated, purified, separated or enriched CD8+

T-cells in the absence of, substantially depleted of, or enriched over CD4+ T-cells. In some alternatives, the population comprises isolated, purified, separated or enriched CD4+ T-cells in the absence of, substantially depleted of, or enriched over CD8+ T-cells. In some alternatives, the T cell is a precursor T cell. In some alternatives, the precursor T cell is a hematopoietic stem cell. In some alternatives, the vector further comprises a sequence encoding a spacer, such as a spacer that comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector or a mini-circle. In some alternatives, the cell surface selectable marker encodes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof, such as is available in U.S. Pat. No. 7,446,179, herein expressly incorporated by reference in its entirety. In some alternatives, the ligand binding domain is specific for CD19. In some alternatives, the population of genetically modified T-cells, such as T-cells that are derived from thymocytes or T-cells that are derived from engineered precursors, comprises isolated CD8+ expressing T-cells in the absence of or having a reduced amount of CD4+ expressing T-cells, as compared to a native population of unseparated, non-enriched, or non-isolated population of T-cells. In some alternatives, the population of genetically modified T-cells, such as T-cells that are derived from thymocytes or T-cells that are derived from engineered precursors, comprises isolated CD4+ expressing T-cells in the absence of or having a reduced amount of CD8+ expressing T-cells, as compared to a native population of unseparated, non-enriched, or non-isolated population of T-cells.

Additional aspects of the invention relate to a composition or product combination for human therapy, comprising a pharmaceutical excipient; and at least one population of the genetically modified T-cells, as set forth in the preceding paragraph. In some alternatives, the composition or product combination comprises a population of genetically modified CD8+ expressing T-cells. In some alternatives, the composition or product combination comprises a population of genetically modified CD4+ expressing T-cells. In some alternatives, the composition or product combination comprises the population of genetically modified CD8+ expressing T-cells, as set forth above, and the population of genetically modified CD4+ expressing T-cells, as set forth above, in a mixed population or co-administered in a 1:1, 1:2, 1:3, 1:4, 1:5, 1:6, 1:7, 1:8, 1:9, 1:10, 2:1, 3:1, 4:1, 5:1, 6:1, 7:1, 8:1, 9:1, or 10:1 ratio or a ratio that is within a range defined by any two of the aforementioned ratios.

Additional aspects of the invention concern methods of treating, inhibiting, or ameliorating a disease in a subject in need thereof comprising administering to the subject at least one composition or product combination set forth above. In some alternatives, the methods comprise administering a composition or product combination comprising CD4+ expressing T-cells, such as T-cells that are derived from thymocytes or T-cells that are derived from engineered precursors, in advance or prior to administration of the CD8+ expressing T-cells and in other alternatives, the CD8+ expressing cells, such as T-cells that are derived from thymocytes or T-cells that are derived from engineered precursors, are administered before the CD4+ expressing T-cells. In many alternatives, the subject is identified or selected to receive an anti-cancer therapy. In many of the aforementioned methods, the approach also involves measuring or evaluating an inhibition of a disease. In many of the aforementioned methods, the approach also involves providing said subject an additional anti-cancer therapy before, during, or after administration of a composition or product combination set forth above.

In many of the aforementioned methods, a composition or product combination is administered to said subject by adoptive cell transfer. In some alternatives, a composition or product combination are administered to said subject after said subject has received another form of anti-cancer therapy. In many of the aforementioned methods, the subject is suffering from leukemia. In many of the aforementioned methods, the subject has recurrent and/or chemotherapy refractory CD19+ childhood acute lymphoblastic leukemia (ALL). In many of the aforementioned methods, the subject has recurrent and/or chemotherapy refractory CD19+ acute lymphoblastic leukemia (ALL). In many of the aforementioned methods, the subject is suffering from an autoimmune disease. In many of the aforementioned methods, the subject is suffering from a post-HSCT relapse.

Accordingly, some aspects of the present invention relate to the following alternatives:

1. A method of making genetically modified T-cells, which have a chimeric antigen receptor, comprising: separating or enriching a CD8+ expressing population of T-cells and/or a CD4+ expressing population of T-cells, such as T-cells that are derived from thymocytes or T-cells that are derived from engineered precursors, desirably iPS cells, from a mixed population of T-cells so as to generate a separated or enriched population of T-cells; stimulating the separated or enriched population of T-cells so as to generate a stimulated population of CD8+ T-cells and/or CD4+ T-cells; transducing the stimulated population of CD8+ T-cells and/or CD4+ T-cells with a vector, wherein the vector encodes a chimeric antigen receptor and a marker sequence, wherein said marker sequence encodes a cell surface selectable marker, so as to generate a transduced population of CD8+ T-cells and/or CD4+ T-cells; contacting the transduced population of CD8+ T-cells and/or CD4+ T-cells with at least one cytokine, which can be provided exogenously to the T-cells, e.g., in addition to any cytokine that may be produced by the cells or present in media, such as for 1, 2, 3, 4, 5, 6, 7, 8, 9, 10, 11, 12, 13, 14, 15, 16, 17, 18, 19, or 20 days or for a period that is within a range defined by any two of the aforementioned time periods, so as to generate a transduced, cytokine-stimulated population of CD8+ T-cells and/or CD4+ T-cells; enriching the transduced, cytokine-stimulated population of CD8+ T-cells and/or CD4+ T-cells by selection of the marker sequence so as to generate an enriched population of transduced, cytokine-stimulated CD8+ T-cells and/or CD4+ T-cells; and propagating the enriched population of transduced, cytokine-stimulated CD8+ T-cells and/or CD4+ T-cells for at least one day, such as 1, 2, 3, 4, 5, 6, 7, 8, 9, 10, 11, 12, 13, 14, 15, 16, 17, 18, 19, or 20 days or fora period that is within a range defined by any two of the aforementioned time periods, so as to obtain said genetically modified T-cells, which have a chimeric antigen receptor.

2. The method of alternative 1, wherein the separating or enriching of the CD8+ population of T-cells and/or a CD4+ population of T-cells from a mixed population of T-cells is performed by affinity selection for T-cells having an epitope present on CD8 and/or CD4.
3. The method of alternative 1 or 2, wherein the separating or enriching of the CD8+ population of T-cells and/or a CD4+ population of T-cells from a mixed population of T-cells is performed by flow cytometry.
4. The method of alternative 1 or 2, wherein the separating or enriching of the CD8+ population of T-cells and/or a CD4+ population of T-cells from a mixed population of T-cells is performed by immuno-magnetic selection.
5. The method of any one of alternatives 1-4, wherein the genetically modified CD8+ T-cells and/or CD4+ T-cells comprise at least one receptor that promotes, induces, contributes to, or enhances engraftment fitness.
6. The method of alternative 5, wherein the at least one receptor is CD45 RA, CD45 RO, CCR7, CD25, CD127, CD57, CD137, CD27, CD28 and/or CD62L.
7. The method of alternative 5 or 6, wherein the at least one receptor is CD27, CD28 and/or CD62L.
8. The method of any one of alternatives 1-7, wherein the stimulating of the isolated population of T-cells is performed by contacting the CD8+ and/or CD4+ T-cells with an antibody-bound support, such as a bead or particle.
9. The method of alternative 8, wherein the antibody-bound support comprises anti-TCR, anti-CD2, anti-CD3, anti-CD4 and/or anti-CD28 antibodies.
10. The method of alternative 8 or 9, wherein the antibody-bound support comprises anti-CD3 and/or anti-CD28 antibodies.
11. The method of any one of alternatives 1-10, wherein the vector further comprises a first sequence encoding a leader sequence, a second sequence encoding a ligand binding domain, a third sequence encoding a signaling domain and a fourth sequence encoding a selectable marker.
12. The method of any one of alternatives 1-11, wherein the vector further comprises a sequence encoding a spacer.
13. The method of alternative 12, wherein the spacer comprises an IgG4 hinge.
14. The method of any one of alternatives 1-13, wherein the vector is a viral vector.
15. The method of alternative 14, wherein the viral vector is derived from simian virus 40, adenoviruses, adeno-associated virus (AAV), lentivirus, or retroviruses.
16. The method of alternative 14 or 15, wherein the viral vector is a recombinant adenovirus, adeno-associated virus, lentivirus or retrovirus vector.
17. The method of any one of alternatives 14-16, wherein the viral vector is a lentivirus vector.
18. The method of any one of alternatives 1-17, wherein the marker sequence encodes a truncated epidermal growth factor receptor (EGFRt).
19. The method of any one of alternatives 1-18, wherein the at least one cytokine comprises GM-CSF, IL-7, IL-12, IL-15, IL-18, IL-2 and/or IL-21.
20. The method of any one of alternatives 1-19, wherein the at least one cytokine comprises IL7, IL-15 and/or IL-21, which can be provided at 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL or in an amount that is within a range defined by any two of the aforementioned amounts and/or at 10 U/mL, 20 U/mL, 30 U/mL, 40 U/mL, 50 U/mL, 60 U/mL, 70 U/mL, 80 U/mL, 90 U/mL, or 100 U/mL or in an amount that is within a range defined by any two of the aforementioned amounts.
21. The method of any one of alternatives 1-19, wherein the at least one cytokine comprises IL-2, IL-15 and/or IL-21, wherein the amount of cytokine is provided at 0.5 ng/mL and/or 50 U/mL.
22. The method of any one of alternatives 1-21, wherein the contacting is performed for 1, 2, 3, 4, 5, 6, 7, 8, 9, 10, 11, 12, 13, 14, 15, 16, 17, 18, 19, or 20 days or a period of time within a range defined by any two of these values.
23. The method of any one of alternatives 1-20 or 22, wherein the method is performed with isolated, purified, enriched or separated CD4+ cells in the absence of, substantially depleted of, or enriched over CD8+ cells.
24. The method of any one of alternatives 1-19, 21 or 22, wherein the method is performed with isolated, purified, enriched or separated CD8+ in the absence of, substantially depleted of, or enriched over CD4+ cells.
25. The method of any one of alternatives 1-20, 22 or 23, wherein the CD4+ expressing T-cells are propagated for at least 1 day, such as 1, 2, 3, 4, 5, 6, 7, 8, 9, 10, 11, 12, 13, 14, 15, 16, 17, 18, 19, or 20 days or for a period that is within a range defined by any two of the aforementioned time periods.
26. The method of any one of alternatives 1-19, 21, 22 or 24, wherein the CD8+ T-cells are propagated at least 1 day, such as 1, 2, 3, 4, 5, 6, 7, 8, 9, 10, 11, 12, 13, 14, 15, 16, 17, 18, 19, or 20 days or for a period that is within a range defined by any two of the aforementioned time periods.
27. The method of any one of alternatives 8-26, wherein the method further comprises removing the antibody-bound support, such as beads or particles.
28. The method of any one of alternatives 1-27, wherein the ligand binding domain of the chimeric antigen receptor comprises an antibody, or a binding portion thereof.
29. The method of any one of alternatives 1-28, wherein the ligand binding domain of the chimeric antigen receptor comprises a single chain variable fragment (scFv), or a binding portion thereof.
30. The method of any one of alternatives 1-29, wherein the ligand binding domain of the chimeric antigen receptor comprises FMC63, or a binding portion thereof.
31. The method of any one of alternatives 1-30, wherein the ligand binding domain of the chimeric antigen receptor is specific for CD19.
32. The method of any one of alternatives 1-31, wherein the method further comprises cryopreserving the genetically modified CD8+ and/or CD4+ T-cells.
33. A population of genetically modified T-cells comprising: a plurality of affinity selected CD8+ and/or CD4+ T-cells, absence of, substantially depleted of, or enriched over CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ T-cells have been re-stimulated with at least one cytokine.

34. The population of genetically modified T-cells of alternative 33, wherein said plurality of affinity selected CD8+ and/or CD4+ T-cells further comprise at least one receptor that promotes, enhances, improves or contributes to engraftment fitness.

35. The population of genetically modified T-cells of alternative 33 or 34, wherein the at least one receptor that promotes, enhances, improves or contributes to engraftment fitness is CD45 RA, CD45 RO, CCR7, CD25, CD127, CD57, CD137, CD27, CD28 and/or CD62L.

36. The population of genetically modified T-cells of alternative 34 or 35, wherein the at least one receptor that promotes, enhances, improves or contributes to engraftment fitness is CD27, CD28 and/or CD62L.

37. The population of genetically modified T-cells of any one of alternatives 33-36, wherein the plurality of affinity selected CD8+ and/or CD4+ T-cells further comprises a vector having a first sequence encoding a leader sequence, a second sequence encoding a ligand binding domain, a third sequence encoding a signaling domain and a fourth sequence encoding a selectable marker.

38. The population of genetically modified T-cells of alternative 37, wherein the vector further comprises a sequence encoding a spacer.

39. The population of genetically modified T-cells of alternative 38, wherein the spacer comprises an IgG4 hinge.

40. The population of genetically modified T-cells of any one of alternatives 33-39, wherein the vector is a viral vector.

41. The population of genetically modified T-cells of alternative 40, wherein the viral vector is derived from simian virus 40, adenoviruses, adeno-associated virus (AAV), lentivirus, or retroviruses.

42. The population of genetically modified T-cells of alternative 40 or 41, wherein the viral vector is a recombinant adenovirus, adeno-associated virus, lentivirus or retrovirus vector.

43. The population of genetically modified T-cells of any one of alternatives 40-42, wherein the viral vector is a lentivirus vector.

44. The population of genetically modified T-cells of any one of alternatives 33-43, wherein the cell surface selectable marker encodes for a truncated epidermal growth factor receptor (EGFRt).

45. The population of genetically modified T-cells of any one of alternatives 37-44, wherein the ligand binding domain comprises an antibody, or a binding portion thereof.

46. The population of genetically modified T-cells of any one of alternatives 37-45, wherein the ligand binding domain comprises a single chain variable fragment (scFv), or a binding portion thereof.

47. The population of genetically modified T-cells of any one of alternatives 37-46, wherein the ligand binding domain comprises FMC63, or a binding portion thereof.

48. The population of genetically modified T-cells of any one of alternatives 37-47, wherein the ligand binding domain is specific for CD19.

49. The population of genetically modified T-cells of any one of alternatives 33-48, wherein the population comprises isolated, purified, separated or enriched CD8+ T-cells in the absence of, substantially depleted of, or enriched over CD4+ T-cells.

50. The population of genetically modified T-cells of any one of alternatives 33-48, wherein the population comprises isolated, purified, separated or enriched CD4+ T-cells in the absence of, substantially depleted of, or enriched over CD8+ T-cells.

51. A composition or product combination for human therapy, comprising: a pharmaceutical excipient; and at least one population of genetically modified T-cells according to any one or more of alternatives 33-50.

52. The composition or product combination of alternative 51, wherein the composition or product combination comprises the population of genetically modified T-cells of alternative 49.

53. The composition or product combination of alternative 47, wherein the composition or product combination comprises the population of genetically modified T-cells of alternative 50.

54. The composition or product combination of alternative 47, wherein the composition or product combination comprises the population of genetically modified T-cells of alternative 49 and the population of genetically modified T-cells of alternative 50, mixed or co-administered in a 1:1 ratio.

55. A method of treating, inhibiting, or ameliorating a disease in a subject in need thereof comprising: administering to the subject at least one composition or product combination of any one or more of alternatives 51-54.

56. The method of alternative 55, wherein the method comprises administering the composition or product combination of alternative 52.

57. The method of alternative 55, wherein the method comprises administering the composition or product combination of alternative 53.

58. The method of alternative 56, wherein the method further comprises administering the composition or product combination of alternative 53.

59. The method of alternative 57, wherein the method further comprises administering the composition or product combination of alternative 52.

60. The method of alternative 55, wherein the method comprises administering the composition or product combination of alternative 54, such as by an approach, wherein the CD8+ expressing T-cells are administered in advance of the CD4+ expressing T-cells, such as 1, 2, 3, 4, 5, 6, 7, 8, 9, 10, 20, 30, 40, 50, or 60 minutes before the CD4+ T-cells are administered or a time period that is within a range defined by any two of the aforementioned times.

61. The method of any one or more of alternatives 55-60, wherein the subject is identified or selected to receive an anti-cancer therapy.

62. The method of any one or more of alternatives 55-61, further comprising measuring or evaluating an inhibition of a disease.

63. The method of any one or more of alternatives 55-62, further comprising providing said subject an additional anti-cancer therapy before, during, or after administration of the composition or product combination of any one or more of alternatives 51-54.

64. The method of any one or more of alternatives 55-63, wherein the composition or product combination of any one or more of alternatives 51-54 are administered to said subject by adoptive cell transfer.

65. The method of any one or more of alternatives 55-64, wherein the composition or product combination of any one or more of alternatives 51-54 are administered to said subject after said subject has received another form of anti-cancer therapy.

66. The method of any one or more of alternatives 55-65, wherein the composition or product combination of any one or more of alternatives 51-54 are administered to said subject after said subject has received another form of anti-cancer therapy.

67. The method of any one or more of alternatives 55-66, wherein the subject is suffering from leukemia.

68. The method of any one or more of alternatives 55-67, wherein the subject has recurrent and/or chemotherapy refractory CD19+ childhood acute lymphoblastic leukemia (ALL).

69. The method of any one or more of alternatives 55-68, wherein the subject has recurrent and/or chemotherapy refractory CD19+ acute lymphoblastic leukemia (ALL).

70. The method of any one or more of alternatives 55-69, wherein the subject is suffering from an autoimmune disease.

71. The method of any one or more of alternatives 55-70, wherein the subject is suffering from a post-HSCT relapse.

BRIEF DESCRIPTION OF THE DRAWINGS

FIG. 5 shows a table of the patient characteristics that were used in the studies.

FIGS. 6A-B show bar graphs indicate the number of patients subjected to the treatment comprising anti-CD19 CAR bearing T-cells and their severity of disease following 3 treatments.

FIG. 7A indicates the results following treatment using anti-CD19 CAR bearing T-cells.

As shown in FIG. 8A, S03 developed de novo grade 2 acute skin GVHD d17 post CAR T-cell engraftment. In FIG. 8B, a skin biopsy revealed that only 9% of skin localized T-cells marked EGFRt+ while 79% of circulating T-cells marked EGFRt+. In FIG. 8C, peripheral blood at the same time showed the majority of the T-cells were CAR+. This subject was treated with a 2 week course of 1 mg/kg of prednisone, followed by a rapid taper over a six week period and resolution of the GVHD. Despite the prednisone, the subject has ongoing persistent CAR+ T-cells.

FIG. 9 shows a table of patients experiencing Ig or TCR as a marker of minimal residual disease (MRD) following treatment using anti-CD19 CAR bearing T-cells.

FIG. 10 shows a table of patient profiles after allogeneic hematopoietic stem cell transplantation of anti-CD19CAR T-cells.

FIGS. 25A, 25B1, 25B2, 25B3, 25B4 show a cytokine comparisons for cell growth. For PD0059 donor sample the same cytokine testing experiment was performed as in PD0051 except testing a new CD4 and CD8 donor (PD0057).

FIGS. 31A-B show the expansion of cells from bulk PBMC cultures when grown in the presence of cytokines. As shown, CD4+ expressing T-cells (●) were grown in the presence of IL-2 and IL-15. CD8+ expressing T-cells (■) were grown in in the presence of IL-7 and IL-15.

FIGS. 32A-B show the expansion of enriched CD8+ and CD4+ expressing T-cells in cytokine mixtures. As shown in sample PD0044, enriched CD8+ expressing T-cells were expanded in the presence of IL-2 and IL-15. In sample PD0044, enriched CD4+ expressing T-cells were expanded in the presence of IL-7 and IL-15 for over 20 days.

FIGS. 34A-C show expansion of enriched CD4+ and CD8+ expressing T-cells using an earlier methodology as shown in the flow chart of FIGS. 18A-B. Shown are experiments of cells in sample 14602-S04/14602-S04-02, 14602-505, 14602-SO6 and 14602-S06-2/14602-S06-04.

FIGS. 39A-B shows the survival of a mouse injected with cells from the sample PD00044 and PD00046. PD00046 cells were noted for having expression of engraftment fitness markers (CD27, CD28, CD127, and CD62L).

FIG. 41 shows the experimental set up of testing tumor progression in mice treated with T-cells that are manufactured for engraftment fitness.

FIGS. 42A-E show a comparison between CD4+ and CD8+ expressing T-cells from the samples PD0051 and PD00055 on the day of administration into animals and the cytokine growth conditions.

FIG. 45 shows the experimental set up for testing three groups of mice in order to determine an in vivo difference in killing ability between cells that have been grown in various cytokine conditions in vitro with repeat antigen encounters.

FIG. 49 shows the experimental set up to determine if there is an in vivo difference in killing ability between cells that have been grown under the same conditions as PLAT-01 (Phase I clinical trial) and PLAT-02 (Phase I and Phase II clinical trial), as well as, "in between" protocols.

FIG. 50 shows a table that indicates the cell products and the levels of EGFRt from the CD8+ and CD4+ expressing T-cells.

FIGS. 53A-E show the comparison of T-cells from the products of PLAT-1.00, PLAT-1.33, PLAT-1.67 and PLAT-2.00 at similar dosing concentrations. The figures illustrate the tumor progression of individual animals. The start of each row shows the grouped for each PLAT group with the various dose titrations, followed by the individual groups teased out.

FIGS. 58A-C show the survival of the mice in response to T-cell treatment in which the T-cells were grown in normal expansion methods or grown in the presence of cytokines. The figures also show if the mice developed xenoGraft Host disease after T-cell treatment FIGS. 59A-H show the survival of the mice in response to T-cell treatment in which the T-cells were grown in normal expansion methods or grown in the presence of cytokines. The figures also show if the mice developed xenoGraft Host disease after T-cell treatment FIGS. 60A-D show the survival of the mice in response to T-cell treatment in which the T-cells were grown in normal expansion methods or grown in the presence of cytokines. The figures also show if the mice developed xenoGraft Host disease after T-cell treatment.

FIG. 61 shows a table of JME14-03 Group N, at Day 51 post-T cell treatment at 51 days and at 90 days.

DETAILED DESCRIPTION

Figure 1A:
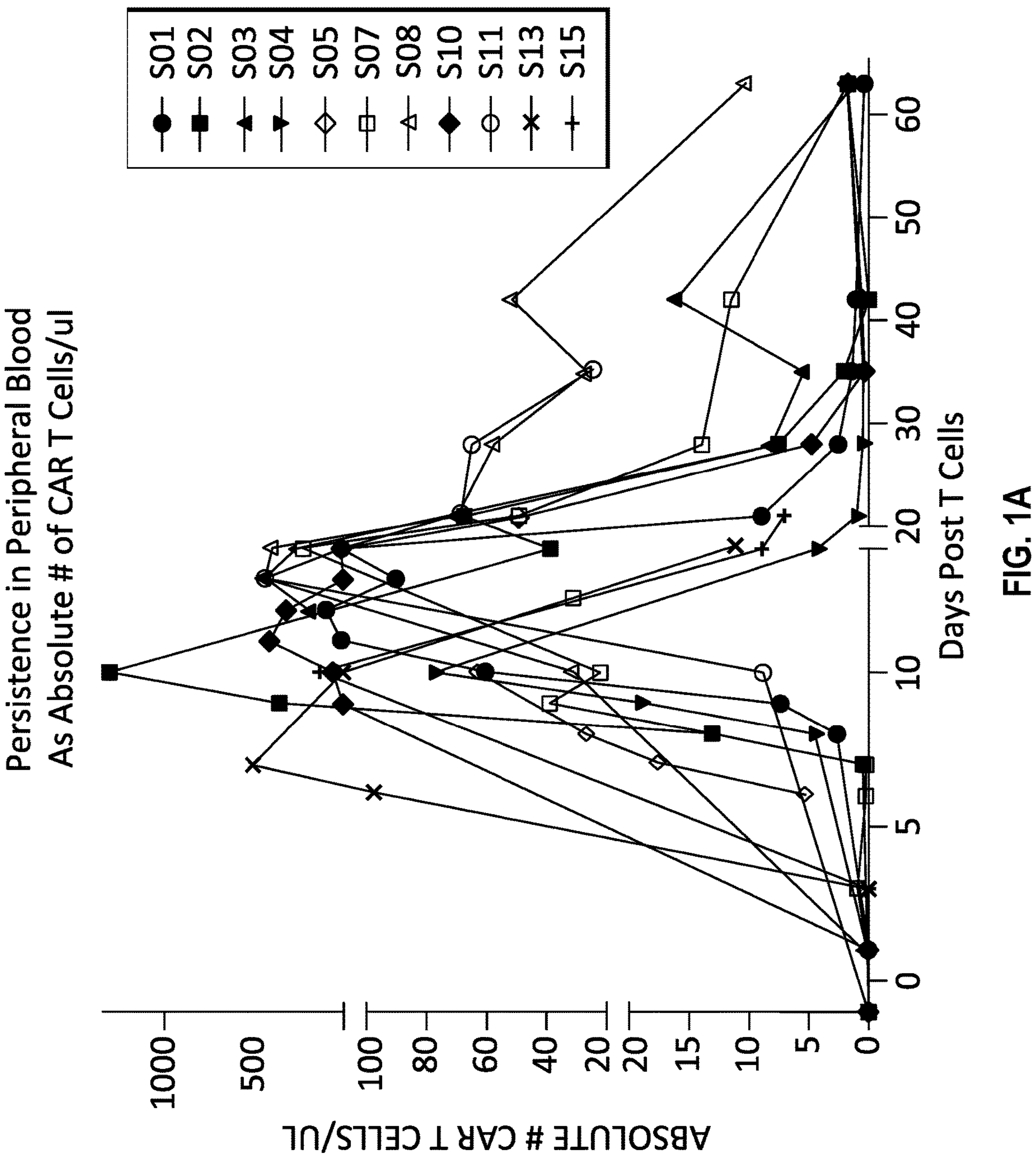
FIG. 1A shows the absolute number of anti-CD19 CAR bearing T-cells in 11 patients following adoptive transfer of the CAR bearing T-cells from Day 0 to Day 65.

The following definitions are provided to facilitate understanding of several of the alternatives described herein.

As used herein, "a" or "an" can mean one or more than one.

As used herein, "nucleic acid" or "nucleic acid molecule" refers to polynucleotides or oligonucleotides such as deoxyribonucleic acid (DNA) or ribonucleic acid (RNA), oligonucleotides, fragments generated by the polymerase chain reaction (PCR), and fragments generated by any of ligation, scission, endonuclease action, exonuclease action, and by synthetic generation. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

"Genetically modify," as used herein, refers to a process for modifying an organism or a cell such as a bacterium, T-cell, bacterial cell, eukaryotic cell, insect, plant or mammal with genetic material, such as nucleic acid, that has been altered using genetic engineering techniques. For example, nucleic acid such as DNA can be inserted in the host genome by first isolating and copying the genetic material of interest using molecular cloning methods to generate a DNA sequence, or by synthesizing the DNA, and then inserting this construct into the host organism. Genes can also be removed, or "knocked out", using a nuclease. Gene targeting is a different technique that uses homologous recombination to change an endogenous gene, and can be used to delete a gene, remove exons, add a gene, or introduce point mutations.

Genetic modification performed by transduction is described herein. "Transduction" refers to methods of transferring genetic material, such as, for example, DNA or RNA, to a cell by way of a vector. Common techniques use viral vectors, electroporation, and chemical reagents to increase cell permeability. The DNA can be transferred by a virus, or via a viral vector. As described herein, methods are provided for modifying immune CD4+ and/or CD8+ T-cells. In order to achieve high expression of therapeutic genes and/or increase the amount of chimeric antigen receptors on a cell surface, for example, T-cells can be transduced with genetic material encoding a chimeric antigen receptor. T-cells can be genetically modified using a virus. Viruses commonly used for gene therapy are adenovirus, adeno-associated virus (AAV), retroviruses and lentiviruses.

Various transduction techniques have been developed, which utilize recombinant infectious virus particles for delivery of the nucleic acid encoding a chimeric antigen receptor. This represents a currently preferred approach to the transduction of T lymphocytes. As described herein, the viral vectors used for transduction can include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Several of the above techniques can be used to transduce hematopoietic or lymphoid cells, including calcium phosphate transfection, protoplast fusion, electroporation, and infection with recombinant adenovirus, adeno-associated virus, lentivirus, or retrovirus vectors. Primary T lymphocytes have been successfully transduced by electroporation and by retroviral or lentiviral infection. As such, retroviral and lentiviral vectors can provide a highly efficient method for gene transfer in eukaryotic cells. Retroviral and lentiviral vectors provide highly efficient methods for gene transfer into T-cells. Moreover, retroviral or lentiviral integration takes place in a controlled fashion and results in the stable integration of one or a few copies of the new genetic information per cell.

An "expression vector" or a vector, as described herein, is a nucleic acid molecule encoding a gene that is expressed in a host-cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

In some alternatives, a method of making genetically modified T-cells, such as T-cells that are derived from thymocytes or T-cells that are derived from engineered precursors, which have a chimeric antigen receptor is provided, wherein the method comprises separating, isolating, or enriching a CD8+ expressing population of T-cells and/or a CD4+ expressing population of T-cells from a mixed population of T-cells so as to generate an isolated, separated, or enriched population of T-cells, stimulating the isolated, separated or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells, for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, with at least one cytokine so as to generate a transduced, cytokine-stimulated population of CD8+ expressing T-cells and/or CD4+ expressing T-cells, enriching, separating, or isolating the transduced, cytokine-stimulated population of CD8+ expressing T-cells and/or CD4+ expressing T-cells by selection of the marker encoded by the marker sequence so as to generate an enriched, separated or isolated population of transduced, cytokine-stimulated CD8+ expressing T-cells and/or CD4+ expressing T-cells and propagating the enriched, separated, or isolated population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor. In some alternatives of the method, the vector is a viral vector. In some alternatives of the method, the viral vector is derived from simian virus 40, adenoviruses, adeno-associated virus (AAV), lentivirus, or retroviruses. In some alternatives of the method, the viral vector is a recombinant adenovirus, adeno-associated virus, lentivirus or retrovirus vector. In some alternatives of the method, the viral vector is a lentivirus vector.

A "leader sequence" also known as the "5' untranslated region (5' UTR), is the region of mRNA that is located upstream from the initiation codon and is important in regulating the translation of an mRNA transcript. In some alternatives of the method of making genetically modified T-cells, which have a chimeric antigen receptor, the vector encoding the chimeric antigen receptor comprises a sequence encoding a leader sequence.

A "ligand" as described herein refers to a small molecule that can form a complex with another molecule or biomolecule for a biological purpose such as, for example, signal triggering. Binding can occur through intermolecular forces, for example ionic bonds, hydrogen bonds, and van der walls interactions. Ligand binding to a receptor protein can alter the three dimensional structure and determine its functional state.

By way of example and not of limitation, ligands can include substrates, proteins, small molecules, inhibitors, activators and neurotransmitters. The strength of binding of a ligand is referred to as the binding affinity and can be determined by direct interactions and solvent effects. A ligand can be bound by a "ligand binding domain." A ligand binding domain can refer to a conserved sequence in a structure that can bind a specific ligand. Without being limiting, a ligand binding domain can be a specific protein domain that is specific for a ligand or ligands.

Specific" or "Specificity" can refer to the characteristic of a ligand for the binding partner or alternatively, the binding partner for the ligand, and can include complementary shape, charge and hydrophobic specificity for binding. Specificity for binding can include stereo specificity, regio selectivity and chemo selectivity.

A "signaling domain," also known as a ""Co-stimulatory domain" is an intracellular or cytoplasmic domain of a protein or a receptor protein that interacts with the interior of the cells and functions by relaying a signal. The portion of the protein that resides in the intracellular portion of the cell is also referred to as the "endodomain." This interaction can occur through the intracellular domain communicating via specific protein-protein or protein-ligand interactions with an effector molecule or an effector protein, which in turn can send the signal along a signal chain to its destination.

The signaling or co-stimulatory domain also refers to a signaling moiety that provides to T-cells a signal which, in addition to the primary signal provided by for instance the CD3 zeta chain of the TCR/CD3 complex, mediates a T-cell response, such as, for example, an immune response, activation, proliferation, differentiation, cytokine secretion, cytolytic activity, perforin and/or granzyme activity and the like. A signaling or co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, and/or a ligand that specifically binds with CD83.

"Selectable marker sequence," is a gene introduced into a vector or a cell that confers a trait for artificial selection. A selectable marker sequence or marker sequence can be a screenable marker to allow a researcher to distinguish between wanted and unwanted cells, or to enrich for a specific cell type. In some alternatives of the method of making genetically modified T-cells, which have a chimeric antigen receptor, a vector is provided wherein the vector encodes a chimeric antigen receptor comprising a marker sequence, wherein said marker sequence encodes a cell surface selectable marker.

In some alternatives, a method of making genetically modified T-cells, which have a chimeric antigen receptor is provided, wherein the method comprises separating, isolating or enriching a CD8+ expressing population of T-cells and/or a CD4+ expressing population of T-cells, such as T-cells that are derived from thymocytes or T-cells that are derived from engineered precursors, desirably iPS cells, from a mixed population of T-cells so as to generate an isolated, separated, or enriched population of T-cells, stimulating the isolated, separated or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells, for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, with at least one cytokine, which is preferably an exogenously added cytokine e.g., in addition to any cytokine either produced by the T-cells or present in the media, so as to generate a transduced, cytokine-stimulated population of CD8+ expressing T-cells and/or CD4+ expressing T-cells, separating, enriching, or isolating the transduced, cytokine-stimulated population of CD8+ expressing T-cells and/or CD4+ expressing T-cells by selection of the marker encoded by the marker sequence so as to generate an enriched, separated, or isolated population of transduced, cytokine-stimulated CD8+ expressing T-cells and/or CD4+ expressing T-cells and propagating the enriched, separated, or isolated population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor.

In some alternatives of the method, the vector further comprises a first sequence encoding a leader sequence, a second sequence encoding a ligand binding domain, a third sequence encoding a signaling domain and a fourth sequence encoding a selectable marker sequence. In some alternatives of the method, the vector further comprises a sequence encoding a spacer. In some alternatives of the method, the spacer comprises an IgG4 hinge. In some alternatives of the method, the vector is a viral vector. In some alternatives of the method, the viral vector is derived from simian virus 40, adenoviruses, adeno-associated virus (AAV), lentivirus, or retroviruses. In some alternatives of the method, the viral vector is a recombinant adenovirus, adeno-associated virus, lentivirus or retrovirus vector. In some alternatives of the method, the viral vector is a lentivirus vector. In some alternatives of the method, the marker sequence encodes a truncated epidermal growth factor receptor (EGFRt). In some alternatives of the method, the ligand binding domain of the chimeric antigen receptor comprises an antibody, or a binding portion thereof. In some alternatives of the method, the ligand binding domain of the chimeric antigen receptor comprises a single chain variable fragment (scFv), or a binding portion thereof. In some alternatives of the method, the ligand binding domain of the chimeric antigen receptor comprises FMC63, or a binding portion thereof. In some alternatives of the method, the ligand binding domain of the chimeric antigen receptor is specific for CD19. In some alternatives of the method, the vector comprises a sequence encoding a maker sequence. In some of these alternatives, the marker sequence is a truncated epidermal growth factor receptor (EGFRt).

"Codon optimization" as described herein, refers to the design process of altering codons to codons known to increase maximum protein expression efficiency. In some alternatives, codon optimization for expression in human is described, wherein codon optimization can be performed by using algorithms that are known to those skilled in the art so as to create synthetic genetic transcripts optimized for high mRNA and protein yield in humans. Programs containing algorithms for codon optimization in humans are readily available. Such programs can include, for example, OptimumGene™ or GeneGPS® algorithms. Additionally human codon optimized sequences can be obtained commercially, for example, from Integrated DNA Technologies.

In some alternatives, a method of making genetically modified T-cells, which have a chimeric antigen receptor is provided, wherein the method comprises separating, isolating, or enriching a CD8+ expressing population of T-cells and/or a CD4+ expressing population of T-cells, such as T-cells that are derived from thymocytes or T-cells that are derived from engineered precursors, desirably iPS cells, from a mixed population of T-cells so as to generate an isolated, separated, or enriched population of T-cells, stimulating the isolated, separated, or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells, for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, with at least one cytokine, which is preferably an exogenously added cytokine e.g., in addition to any cytokine either produced by the T-cells or present in the media, so as to generate a transduced, cytokine-stimulated population of CD8+ expressing T-cells and/or CD4+ expressing T-cells, enriching, isolating, or separating the transduced, cytokine-stimulated population of CD8+ expressing T-cells and/or CD4+ expressing T-cells by selection of the marker encoded by the marker sequence so as to generate an enriched, isolated, or separated population of transduced, cytokine-stimulated CD8+ expressing T-cells and/or CD4+ expressing T-cells and propagating the enriched, separated, or isolated population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor. In some alternatives of the method, the vector further comprises a first sequence encoding a leader sequence, a second sequence encoding a ligand binding domain, a third sequence encoding a signaling domain and a fourth sequence encoding a selectable marker sequence. In some alternatives of the method, the sequences of the vector are codon optimized for expression in humans. In some alternatives, the sequences of the vector are optimized to have selected codons specifically for maximal protein expression in human cells, which can increase the concentration of proteins or CARs of a T-cell.

Optimization can also be performed to reduce the occurrence of secondary structure in a polynucleotide. In some alternatives of the method, optimization of the sequences in the vector can also be performed to reduce the total GC/AT ratio. Strict codon optimization can lead to unwanted secondary structure or an undesirably high GC content that leads to secondary structure. As such, the secondary structures affect transcriptional efficiency. Programs such as GeneOptimizer can be used after codon usage optimization, for secondary structure avoidance and GC content optimization. These additional programs can be used for further optimization and troubleshooting after an initial codon optimization to limit secondary structures that can occur after the first round of optimization. Alternative programs for optimization are readily available. In some alternatives of the method, the vector comprises sequences that are optimized for secondary structure avoidance and/or the sequences are optimized to reduce the total GC/AT ratio and/or the sequences are optimized for expression in humans.

Marker domains can also provide important aspects to alternatives described herein. Utilization of a marker domain on the cell surface can allow for transduced lymphocyte ablation in the event of a toxic event associated with administration or the presence of transduced T-cells. For example, in the case of an EGFRt marker sequence, full length antibodies to EGFR can be utilized to bind to cells expressing the EGFR and kill them via antibody dependent cell mediated cytotoxicity (ADCC). In some alternatives, an antibody specific for a marker domain can be linked to a cytotoxic agent, such as a radionuclide or a toxin, which results in a therapeutic capable of ablation or killing of the transduced cells in vivo. In some alternatives, a marker sequence is provided for enrichment and cell selection. In an exemplary alternative described herein, an EGFRt marker sequence is used in a purification and enrichment method allowing for immunomagnetic selection against the EGFRt marker.

A "spacer" as described herein can refer to a polypeptide chain that can range in length from a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. A spacer can comprise any 20 amino acids, for example, in any order to create a desirable length of polypeptide chain in a chimeric antigen receptor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine and/or tryptophan. A spacer sequence can be a linker between the scFv and the transmembrane domain of the chimeric antigen receptor. In some alternatives of the method of making genetically modified T-cells, which have a chimeric antigen receptor, the vector further comprises a sequence encoding a spacer. In some alternatives of the method, the spacer comprises a sequence with a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. In some alternatives of the method, the spacer resides between the scFv and the transmembrane region of the chimeric antigen receptor.

"IgG4 hinge" as described herein, refers to the polypeptide domains that are between the heavy chain and the light chains of the IgG4 antibody. In some alternatives, a method of making genetically modified T-cells, which have a chimeric antigen receptor is provided, wherein the method comprises separating, enriching, or isolating a CD8+ expressing population of T-cells and/or a CD4+ expressing population of T-cells, such as T-cells that are derived from thymocytes or T-cells that are derived from engineered precursors, desirably iPS cells, from a mixed population of T-cells so as to generate an isolated, separated, or enriched population of T-cells, stimulating the isolated, separated, or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells, for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, with at least one cytokine, which is preferably an exogenously added cytokine e.g., in addition to any cytokine either produced by the T-cells or present in the media, so as to generate a transduced, cytokine-stimulated population of CD8+ expressing T-cells and/or CD4+ expressing T-cells, enriching the transduced, cytokine-stimulated population of CD8+ expressing T-cells and/or CD4+ expressing T-cells by selection of the marker encoded by the marker sequence so as to generate an enriched, separated, or isolated population of transduced, cytokine-stimulated CD8+ expressing T-cells and/or CD4+ expressing T-cells and propagating the enriched population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor.

In some alternatives of the method, the vector further comprises a first sequence encoding a leader sequence, a second sequence encoding a ligand binding domain, a third sequence encoding a signaling domain and a fourth sequence encoding a selectable marker. In some alternatives of the method, the vector further comprises a sequence encoding a spacer. In some alternatives, the spacer comprises a hinge region of a human antibody. In some alternatives of the method, the spacer comprises an IgG4 hinge. In some alternatives, the IgG4 hinge region is a modified IgG4 hinge. A "modified IgG4 hinge" as described herein can refer to a hinge region that can have at least 90%, 92%, 95%, or 100% sequence identity or a sequence identity within a range defined by any two of the aforementioned percentages, with a hinge region amino acid sequence as set forth in SEQ ID NO: 1 (SEQ ID NO: 1; ESKYGPPCPPCP), SEQ ID NO: 2 (SEQ ID NO: 2; YGPPCPPCP), SEQ ID NO: 3 (SEQ ID NO: 3; KYGPPCPPCP), or SEQ ID NO: 4 (SEQ ID NO: 4; EVVKYGPPCPPCP). As mentioned above, any one or more of these sequences can be codon optimized for expression in humans and any one or more of these sequences can be optimized to reduce secondary structure or GC/AT ratio and any one or more of these sequences can be consensus sequences generated from at least two isotype genes.

A "transmembrane domain" is a region of a protein that is hydrophobic that can reside in the bilayer of a cell to anchor a protein that is embedded to the biological membrane. Without being limiting, the topology of the transmembrane domain can be a transmembrane alpha helix. In some alternatives of the method of making genetically modified T-cells, which have a chimeric antigen receptor, the vector comprises a sequence encoding a transmembrane domain. In some alternatives of the method, the transmembrane domain comprises a CD28 transmembrane sequence or a fragment thereof that is a length of 10, 11, 12, 13, 14, 15, 16, 17, 18, 19, 20, 21, 22, 23, 24, 25, 26, 27, or 28 amino acids or a length within a range defined by any two of the aforementioned lengths. In some alternatives of the method, the CD28 transmembrane sequence or fragment thereof comprise 28 amino acids in length. In some alternatives of the method, the transmembrane domain comprises the sequence set forth in SEQ ID NO: 5 (SEQ ID NO: 5; MFWVLVVVGGVLA-CYSLLVTVAFIIFWV).

A "signaling domain," also known as a "Co-stimulatory domain" is an intracellular or cytoplasmic domain of a protein or a receptor protein that interacts with the interior of the cells and functions by relaying a signal. The portion of the protein that resides in the intracellular portion of the cell is also referred to as the "endodomain." This interaction can occur through the intracellular domain communicating via specific protein-protein or protein-ligand interactions with an effector molecule or an effector protein, which in turn can send the signal along a signal chain to its destination. The signaling or co-stimulatory domain also refers to a signaling moiety that provides to T-cells a signal which, in addition to the primary signal provided by for instance the CD3 zeta chain of the TCR/CD3 complex, mediates a T-cell response, such as, for example, an immune response, activation, proliferation, differentiation, cytokine secretion, cytolytic activity, perforin and/or granzyme activity and the like. A signaling or co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, and/or B7-H3, and/or a ligand that specifically binds with CD83.

In some alternatives of the method of making genetically modified T-cells, which have a chimeric antigen receptor, the vector encoding the chimeric antigen receptor further comprises a sequence for a co-stimulatory domain, wherein the co-stimulatory domain is an intracellular signaling domain that interacts with other intracellular mediators to mediate a cell response including an immune response, activation, proliferation, differentiation, cytokine secretion, cytolytic activity, perforin and/or granzyme activity and the like. In some alternatives of the method, the vector comprises a sequence encoding a signaling domain. In some alternatives of the method, the signaling domain comprises a 4-1BB domain and/or CD3-zeta domain. In some alternatives, the 4-1BB domain comprises the sequence set forth in SEQ ID NO: 6 (SEQ ID NO: 6; KRGRKKLLY-IFKQPFMRPVQTTQEEDGCSCRFPEEEEGGCEL). In some alternatives, the CD3-zeta domain comprises the sequence set forth in SEQ ID NO: 7 (SEQ ID NO: 7; RVKFSRSADAPAYQQGQNQLYNELNLGRREEY-DVLDKRRGRDPEMGGKPRRKNPQ EGLYNELQKDK-MAEAYSEIGMKGERRRGKGHDGLYQGLSTATKDTY-DALHMQAL PPR).

A "chimeric antigen receptor" (CAR) described herein, also known as chimeric T-cell receptor, refers to an artificial T-cell receptor or a genetically engineered receptor, which grafts a desired specificity onto an immune effector cell. These receptors can be used to graft the specificity of a monoclonal antibody or a binding portion thereof onto a T-cell, for example; with transfer of the coding sequence for the CAR to a recipient cell being facilitated by a retroviral vector. The structure of the CAR can comprise single-chain variable fragments (scFv) derived from monoclonal antibodies, fused to CD3-zeta transmembrane and endodomain. Such molecules result in the transmission of a zeta signal in response to recognition by the scFv of its target.

In some alternatives, a method of making genetically modified T-cells, which have a chimeric antigen receptor is provided, wherein the method comprises separating, isolating, or enriching a CD8+ expressing population of T-cells and/or a CD4+ expressing population of T-cells, such as T-cells that are derived from thymocytes or T-cells that are derived from engineered precursors, desirably iPS cells, from a mixed population of T-cells, from a mixed population of T-cells, so as to generate an isolated, separated, or enriched population of T-cells, stimulating the isolated, separated, or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells with at least one cytokine, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to generate a transduced, cytokine-stimulated population of CD8+ expressing T-cells and/or CD4+ expressing T-cells, enriching, separating or isolating the transduced, cytokine-stimulated population of CD8+ expressing T-cells and/or CD4+ expressing T-cells by selection of the marker encoded by the marker sequence so as to generate an enriched, separated, or isolated population of transduced, cytokine-stimulated CD8+ expressing T-cells and/or CD4+ expressing T-cells and propagating the enriched, separated, or isolated population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor. In some alternatives of the method, the chimeric antigen receptor is specific for CD19.

These artificial T-cell receptors, or CARs, can be used as a therapy for cancer or a viral infection using a technique called "adoptive cell transfer." T-cells are removed from a patient and modified so that they express receptors specific for a molecule displayed on a cancer cell or a virus, or a virus-infected cell. The genetically engineered T-cells, which can then recognize and kill the cancer cells or the virus infected cells or promote clearance of the virus, are reintroduced into the patient. In some alternatives, a method of treating, inhibiting, or ameliorating a disease in a subject in need thereof is provided.

In some aspects, the method can comprise administering to the at least one composition or product combination, wherein the at least one composition or product combination comprises a population of genetically modified T-cells, wherein the population of genetically modified T-cells comprises a plurality of affinity selected CD8+ and/or CD4+ expressing T-cells, in the absence of, enriched from, substantially separated from or substantially isolated from CD8− and/or CD4− expressing T-cells, wherein said plurality of affinity selected CD8+ and/or CD4+ expressing T-cells have stimulated CD2, CD3, CD4 and/or CD28 receptors, wherein said plurality of affinity selected CD8+ and/or CD4+ expressing T-cells further comprise a gene encoding a chimeric antigen receptor and a cell surface selectable marker and, wherein said plurality of affinity selected CD8+ and/or CD4+ expressing T-cells have been re-stimulated with at least one cytokine, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points. In some alternatives, the at least one composition or product combination is administered to said subject by adoptive cell transfer.

An "antibody" as described herein refers to a large Y-shape protein produced by plasma cells that is used by the immune system to identify and neutralize foreign objects such as bacteria and viruses. The antibody protein can comprise four polypeptide chains; two identical heavy chains and two identical light chains connected by disulfide bonds. Each chain is composed of structural domains called immunoglobulin domains. These domains can contain 70-110 amino acids and are classified into different categories according to their size and function. In some alternatives, the ligand binding domain is an antibody fragment, desirably, a binding portion thereof. In some alternatives, the antibody fragment or binding portion thereof present on a CAR is specific for CD19.

A "single chain variable fragment" or scFv is a fusion protein that comprises the variable regions of the heavy chain (VH) and the light chains (VL) of an immunoglobulin that is connected with a short linker peptide. Without being limiting, the linker can comprise glycine for flexibility and hydrophilic amino acids, for example serine or threonine for solubility. The linker can connect the N-terminus of the VH with the C-terminus of the VL or it can connect the C-terminus of the VH with the N-terminus of the VL. In some alternatives, the ligand binding domain present on a CAR is a single chain variable fragment (scFv). In some alternatives, the scFv domain present on a CAR is specific for a CD19 present on a tumor cell.

"FMC63" is a CD19 specific monoclonal antibody. CD19 is a protein that is found on the surface of white blood cells and can assemble with the antigen receptor of B lymphocytes in order to decrease the threshold for antigen receptor-dependent stimulation. CD19 is expressed on follicular dendritic cells and B cells. CD19 is present on B cells from earliest recognizable B-lineage cells during development to B-cell blasts but is lost on maturation to plasma cells. CD19 primarily acts as a B cell co-receptor in conjunction with CD21 and CD81. Upon activation, the cytoplasmic tail of CD19 becomes phosphorylated, which leads to binding by Src-family kinases and recruitment of PI-3 kinase. As on T-cells, several surface molecules form the antigen receptor and form a complex on B lymphocytes.

Mutations in CD19 are associated with severe immunodeficiency syndromes characterized by diminished antibody production. For example, aberrant expression of CD19 is a marker of monocytic lineage in acute myelogenous leukemia. Since CD19 is a hallmark of B-cells, the protein can be used to diagnose cancers that arise from this type of cell, notably B-cell lymphomas. Since 2011, treatments targeting CD19 have begun to enter trials. Most current experimental anti-CD19 drugs in development work by exploiting the presence of CD19 to direct treatment specifically towards B-cell cancers. However, it is now emerging that the protein plays an active role in driving the growth of these cancers, by stabilizing the concentrations of the MYC oncoprotein. Thus, CD19 and its downstream signaling can be attractive therapeutic targets.

In some alternatives, a method of making genetically modified T-cells, which have a chimeric antigen receptor is provided, wherein the method comprises separating, enriching, isolating, or purifying a population of CD8+ expressing T-cells and/or a population of CD4+ expressing T-cells, such as T-cells that are derived from thymocytes or T-cells that are derived from engineered precursors, desirably iPS cells, from a mixed population of T-cells, from a mixed population of T-cells, from a mixed population of T-cells so as to generate an isolated, separated, enriched, or purified population of T-cells, stimulating the isolated, separated, enriched, or purified population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells with at least one cytokine, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to generate a transduced, cytokine-stimulated population of CD8+ expressing T-cells and/or CD4+ expressing T-cells, enriching the transduced, cytokine-stimulated population of CD8+ expressing T-cells and/or CD4+ expressing T-cells by selection of the marker so as to generate an enriched population of transduced, cytokine-stimulated CD8+ expressing T-cells and/or CD4+ expressing T-cells and propagating the enriched population of transduced, cytokine-stimulated CD8+ expressing T-cells and/or CD4+ expressing T-cells for at least one day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor.

In some alternatives of the method, the vector further comprises a first sequence encoding a leader sequence, a second sequence encoding a ligand binding domain, a third sequence encoding a signaling domain and a fourth sequence encoding a selectable marker sequence. In some alternatives of the method, the vector further comprises a sequence encoding a spacer. In some alternatives of the method, the ligand binding domain of the chimeric antigen receptor comprises an antibody, or a binding portion thereof. In some alternatives of the method, the ligand binding domain of the chimeric antigen receptor comprises a single chain variable fragment (scFv), or a binding portion thereof. In some alternatives of the method, the ligand binding domain of the chimeric antigen receptor comprises FMC63, or a binding portion thereof. In some alternatives of the method, the ligand binding domain of the chimeric antigen receptor is specific for CD19.

"Purification" of T-cells as described herein, refers to the isolation of highly purified, functional T-cells for research or for methods for generating T-cells for therapy. "Isolation" of T-cells, or "separating" of T-cells, as described herein, refers to a procedure of isolating or separating the desired T-cells, T-cell populations, or subpopulations from contaminating cell populations or other components, for example by using techniques, such as indirect panning. In this method, cells can be isolated, separated, or selected by their capacity to bind to an antibody that is attached to a support, such as a plastic or poly carbonate surface, bead, particle, plate, or well. Cells can bind on the basis of particular cell surface markers. In some cases the desired T-cell populations are "enriched" meaning that the population of the desired T-cells is greater after enrichment than that of the native population from which the T-cells originated.

In some alternatives of the method of making a genetically modified T-cell, the CD8+ expressing population of T-cells and/or CD4+ expressing population of T-cells are isolated, enriched, purified or separated from undesired components using CD8 specific antibodies and/or CD4 specific antibodies. In some alternatives of the method, the CD8+ expressing population of T-cells and/or CD4+ expressing population of T-cells are isolated, enriched, or purified using flow cytometry. In some alternatives, the CD8+ expressing population of T-cells and/or CD4+ expressing population of T-cells are isolated, enriched, purified, or separated using immunomagnetic selection. In some alternatives of the method, the CD8+ expressing population of T-cells and/or CD4+ expressing population of T-cells are isolated, enriched, purified, or separated using antibodies against CD45 RA, CD45 RO, CCR7, CD25, CD127, CD57, CD137, CD27, CD28, CD8, CD4, and/or CD62L. In some alternatives of the method, the CD8+ expressing population of T-cells and/or CD4+ expressing population of T-cells are isolated, enriched, purified, or separated by using antibodies against CD27, CD28 and/or CD62L. In some alternatives, the method is performed with isolated, enriched, or separated CD4+ expressing T-cells in the absence of or in greater abundance than the amount of CD8+ expressing cells in the mixed population of T-cells used for the isolation, enrichment, or purification. In some alternatives, the method is performed with isolated, enriched, or separated CD8+ in the absence of or in greater abundance than the amount of CD4+ expressing cells in the mixed population of T-cells used for the isolation, enrichment, or purification.

"Stimulation" or activation of T-cells refers to the method of inducing a T-cell to initiate a response, such as a signal transduction response, e.g., proliferation, while preserving T-cell viability and immune function. For example, simultaneous signaling to TCR/CD3 and CD8 can trigger a physiological activation and expansion of human T-cells. Following appropriate stimulation, T-cells may proliferate extensively in vitro. In some alternatives, a method of making genetically modified T-cells, which have a chimeric antigen receptor is provided wherein the method comprises isolating, separating, enriching, or purifying a CD8+ expressing population of T-cells and/or a CD4+ expressing population of T-cells, such as T-cells that are derived from thymocytes or T-cells that are derived from engineered precursors, desirably iPS cells, from a mixed population of T-cells, so as to generate an isolated, separated, purified, or enriched population of T-cells, stimulating the isolated, separated, purified, or enriched population of T-cells so as to generate a stimulated population of CD8+ expressing T-cells and/or CD4+ expressing T-cells, transducing the stimulated population of CD8+ expressing T-cells and/or CD4+ expressing T-cells with a vector, wherein the vector encodes a chimeric antigen receptor and a marker sequence, wherein said marker sequence encodes a cell surface selectable marker, so as to generate a transduced population of CD8+ expressing T-cells and/or CD4+ expressing T-cells, contacting the transduced population of CD8+ expressing T-cells and/or CD4+ expressing T-cells with at least one cytokine, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to generate a transduced, cytokine-stimulated population of CD8+ expressing T-cells and/or CD4+ expressing T-cells, enriching, separating, or isolating the transduced, cytokine-stimulated population of CD8+ expressing T-cells and/or CD4+ expressing T-cells by selection of the marker encoded by the marker sequence so as to generate an enriched population of transduced, cytokine-stimulated CD8+ T-cells and/or CD4+ T-cells and propagating the enriched, isolated, or separated population of transduced, cytokine-stimulated CD8+ expressing T-cells and/or CD4+ expressing T-cells for at least one day, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points, so as to obtain said genetically modified T-cells, which have a chimeric antigen receptor. In some alternatives, the stimulating is performed with an antibody-bound support, such as a bead or particle. In some alternatives, the stimulating is performed with an antibody-bound support comprising anti-TCR, anti-CD2, anti-CD3, anti-CD4 and/or anti-CD28 antibodies. In some alternatives, the stimulating is performed with an antibody-bound support comprising anti-CD3 and/or anti-CD28 antibodies. In some alternatives, the method further comprises removing the antibody-bound support, such as beads or particles.

"T-cells" or "T lymphocytes" as used herein can be from any mammal, preferably a primate, including monkeys or humans, a companion animal such as a dog, cat, or horse, or a domestic animal, such as a sheep, goat, or cattle. In some alternatives the T-cells are allogeneic (from the same species but different donor) as the recipient subject; in some alternatives the T-cells are autologous (the donor and the recipient are the same); in some alternatives the T-cells arc syngeneic (the donor and the recipients are different but are identical twins).

"CD8+ expressing T-cell" or "CD8+ T-cell," used synonymously throughout, is also known as a TC, cytotoxic T lymphocyte, CTL, T-killer cell, cytolytic T-cell or killer T-cell. As described herein, CD8+ T-cells are T-lymphocytes that can kill cancer cells, virally infected cells, or damaged cells. CD8+ T-cells express T-cell receptors (TCRs) that can recognize a specific antigen. CD8+ T-cells express CD8 on the surface. CD8+ expressing T-cells have the ability to make some cytokines, however the amounts of cytokines made by CD8+ T-cells are not at a concentration that promotes, improves, contributes to, or induces engraftment fitness.

"CD4+ expressing T-cell," or "CD4+ T-cell," used synonymously throughout, is also known as T helper cells, which play an important role in the immune system, and in the adaptive immune system. CD4+ T-cells also help the activity of other immune cells by releasing T-cell cytokines. These cells help, suppress or regulate immune responses. They are essential in B cell antibody class switching, in the activation and growth of cytotoxic T-cells, and in maximizing bactericidal activity of phagocytes, such as macrophages. CD4+ expressing T-cells have the ability to make some cytokines, however the amounts of cytokines made by CD4+ T-cells are not at a concentration that promotes, improves, contributes to, or induces engraftment fitness.

Mature T cells express the surface protein CD4 and are referred to as CD4+ T-cells. CD4+ T-cells are generally treated as having a pre-defined role as helper T-cells within the immune system. For example, when an antigen-presenting cell expresses an antigen on MHC class II, a CD4+ cell will aid those cells through a combination of cell to cell interactions (e.g. CD40 and CD40L) and through cytokines. Nevertheless, there are rare exceptions; for example, subgroups of regulatory T-cells, natural killer cells, and cytotoxic T-cells express CD4. All of the latter CD4+ expressing T-cell groups are not considered T helper cells.

"Central memory" T-cell (or "$T_{CM}$") as used herein refers to an antigen experienced CTL that expresses CD62L or CCR-7 and CD45RO on the surface thereof, and does not express or has decreased expression of CD45RA as compared to naïve cells. In some alternatives, central memory cells are positive for expression of CD62L, CCR7, CD28, CD127, CD45RO, and/or CD95, and have decreased expression of CD54RA as compared to naïve cells.

"Effector memory" T-cell (or "$T_{EM}$") as used herein refers to an antigen experienced T-cell that does not express or has decreased expression of CD62L on the surface thereof as compared to central memory cells, and does not express or has decreased expression of CD45RA as compared to naïve cell. In some alternatives, effector memory cells are negative for expression of CD62L and/or CCR7, as compared to naïve cells or central memory cells, and have variable expression of CD28 and/or CD45RA.

"Naïve" T-cells as used herein refers to a non-antigen experienced T lymphocyte that expresses CD62L and/or CD45RA, and/or does not express CD45RO− as compared to central or effector memory cells. In some alternatives, naïve CD8+ T lymphocytes are characterized by the expression of phenotypic markers of naïve T-cells including CD62L, CCR7, CD28, CD127, and/or CD45RA.

"Effector" "$T_E$" T-cells as used herein refers to a antigen experienced cytotoxic T lymphocyte cells that do not express or have decreased expression of CD62L, CCR7, CD28, and are positive for granzyme B and/or perforin, as compared to central memory or naïve T-cells.

"Engraftment fitness" as described herein, refers to the ability of a cell to grow and proliferate after the cells have entered the body, e.g., blood stream, through adoptive transfer. Engraftment can usually occur within two to four weeks after the transfer. Engraftment can be monitored by checking blood counts for a specific cell on a frequent basis. In some alternatives of the method of treating, inhibiting, or ameliorating a disease in a subject is provided, the method can comprise administering a composition or product combination comprising the genetically modified T-cells, as described herein. In some alternatives, the method can further comprise monitoring the subject by checking the blood counts for the genetically modified T-cells that expresses a chimeric antigen receptor e.g., by identifying the presence or absence of a marker associated with the transferred T-cells.

T-cells with improved engraftment fitness may have specific markers on the cell surface that confer generation and long term maintenance of T-cell immunity. There are several proteins that are known for T-cell activation and survival. CD28 is a protein expressed on T-cells that provide co-stimulatory signals required for T-cell activation and survival. CD27 is required for generation and long-term maintenance of T-cell immunity. It binds to ligand CD70, and plays a key role in regulating B-cell activation and immunoglobulin synthesis. L-selectin, also known as CD62L is a cell adhesion molecule found on lymphocytes. L-selectin functions as a "homing receptor" for lymphocytes or T-cells to enter secondary lymphoid tissues via high endothelial venues. Ligands present on endothelial cells will bind to lymphocytes expressing L-selectin, slowing lymphocyte trafficking through the blood, and can facilitate entry into a secondary lymphoid organ at that point. In some alternatives, of the method of making genetically modified T-cells, which have a chimeric antigen receptor, the T-cells comprise at least one receptor that promotes, induces, improves, or contributes to engraftment fitness. In some alternatives, the at least one receptor is CD45 RA, CD45 RO, CCR7, CD25, CD127, CD57, CD137, CD27, CD28 and/or CD62L. In some alternatives, the at least one receptor is CD27, CD28 and/or CD62L. In some alternatives provided herein, methods are described in which CD4+ and CD8+ expressing T-cells are genetically modified by transduction of genetic material in the form of a vector such that the genetically modified CD4+ and CD8+ expressing T-cells expresses a specific chimeric antigen receptor. In some alternatives of the genetically modified CD4+ and CD8+ T-cells, the genetically modified CD4+ and CD8+ T-cells are further modified to improve or enhance engraftment fitness.

"Cytokines" as described herein, refers to small proteins (5-25 kDa) that are important in cell signaling. Cytokines are released by cells and affect the behavior of other cells, and sometimes the releasing cell itself, such as a T-cell. Cytokines can include, for example, chemokines, interferons, interleukins, lymphokines, and tumor necrosis factor. Cytokines can be produced by a broad range of cells, which can include, for example, immune cells like macrophages, B lymphocytes, T lymphocytes and mast cells, as well as, endothelial cells, fibroblasts, and various stromal cells.

Cytokines can act through receptors, and are important in the immune system as the cytokines can modulate the balance between humoral and cell-based immune responses, and they can regulate the maturation, growth, and responsiveness of particular cell populations. Some cytokines enhance or inhibit the action of other cytokines in complex ways. Without being limiting, cytokines can include, for example, Acylation stimulating protein, Adipokine, Albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, Chemokine, Colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, Erythropoietin, Gc-MAF, Granulocyte colony-stimulating factor, Granulocyte macrophage colony-stimulating factor, Hepatocyte growth factor, IL 10 family of cytokines, IL 17 family of cytokines, IL1A, IL1B, Inflammasome, Interferome, Interferon, Interferon beta 1a, Interferon beta 1b, Interferon gamma, Interferon type I, Interferon type II, Interferon type III, Interleukin, Interleukin 1 family, Interleukin 1 receptor antagonist, Interleukin 10, Interleukin 12, Interleukin 12 subunit beta, Interleukin 13, Interleukin 15, Interleukin 16, Interleukin 2, Interleukin 23, Interleukin 23 subunit alpha, Interleukin 34, Interleukin 35, Interleukin 6, Interleukin 7, Interleukin 8, Interleukin 36, Leukemia inhibitory factor, Leukocyte-promoting factor, Lymphokine, Lymphotoxin, Lymphotoxin alpha, Lymphotoxin beta, Macrophage colony-stimulating factor, Macrophage inflammatory protein, Macrophage-activating factor, Monokine, Myokine, Myonectin, Nicotinamide phosphoribosyltransferase, Oncostatin M, Oprelvekin, Platelet factor 4, Proinflammatory cytokine, Promegapoietin, RANKL, Stromal cell-derived factor 1, Talimogene laherparepvec, Tumor necrosis factor alpha, Tumor necrosis factors, XCL1, XCL2, GM-CSF, and/or XCR1. In some alternatives of the method of making genetically modified T-cells, a transduced population of CD8+ expressing T-cells and/or CD4+ expressing T-cells is contacted with at least one cytokine so as to generate a transduced, cytokine-stimulated population of CD8+ T-cells and/or CD4+ T-cells. In some alternatives of the method, the at least one cytokine utilized comprises GM-CSF, IL-7, IL-12, IL-15, IL-18, IL-2, and/or IL-21. In some alternatives, the period of contact with the cytokine is at least one day, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points.

"Interleukins" or IL as described herein, are cytokines that the immune system depends largely upon. Examples of interleukins, which can be utilized herein, for example, include IL-1, IL-2, IL-3, IL-4, IL-5, IL-6, 11-7, IL-8/CXCL8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. Contacting T-cells with interleukins can have effects that promote, support, induce, or improve engraftment fitness of the cells. IL-1, for example can function in the maturation & proliferation of T-cells. IL-2, for example, can stimulate growth and differentiation of T-cell response. IL-3, for example, can promote differentiation and proliferation of myeloid progenitor cells. IL-4, for example, can promote proliferation and differentiation. IL-7, for example, can promote differentiation and proliferation of lymphoid progenitor cells, involved in B, T, and NK cell survival, development, and homeostasis. IL-15, for example, can induce production of natural killer cells. IL-21, for example, co-stimulates activation and proliferation of CD8+ T-cells, augments NK cytotoxicity, augments CD40-driven B cell proliferation, differentiation and isotype switching, and promotes differentiation of Th17 cells.

In some alternatives, a method of making a genetically modified T-cell is provided, wherein the method comprises purifying, separating, enriching, or isolating a CD8+ population of T-cells and/or a CD4+ population of T-cells from a mixed population of T-cells, such as T-cells that are derived from thymocytes or T-cells that are derived from engineered precursors, desirably iPS cells, from a mixed population of T-cells, so as to generate an isolated, separated, enriched, or purified population of T-cells, stimulating the isolated, separated, enriched, or purified population of T-cells so as to generate a stimulated population of CD8+ T-cells and/or CD4+ T-cells, transducing the stimulated population of CD8+ T-cells and/or CD4+ T-cells with a vector, wherein the vector encodes a chimeric antigen receptor and a marker sequence, wherein said marker sequence encodes a cell surface selectable marker, so as to generate a transduced population of CD8+ T-cells and/or CD4+ T-cells, contacting the transduced population of CD8+ T-cells and/or CD4+ T-cells with at least one cytokine so as to generate a transduced, cytokine-stimulated population of CD8+ T-cells and/or CD4+ T-cells, enriching, isolating, or separating the transduced, cytokine-stimulated population of CD8+ T-cells and/or CD4+ T-cells by selection of the marker encoded by the marker sequence so as to generate an enriched, isolated or separated population of transduced, cytokine-stimulated CD8+ T-cells and/or CD4+ T-cells and propagating the enriched, isolated, or separated population of transduced, cytokine-stimulated CD8+ T-cells and/or CD4+ T-cells for at least one day, such as for at least 1, 2, 3, 4, 5, 6, 7, 8, 9, 10, 11, 12, 13, 14, 15, 16, 17, 18, 19, or 20 days or any time that is between a range of times defined by any two of the aforementioned time points, so as to obtain said genetically modified T-cells, which have a chimeric antigen receptor. In some alternatives, the at least one cytokine comprises GM-CSF, IL-7, IL-12, IL-18, IL-15, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives of the method, the cytokine contacting is performed for 1, 2, 3, 4, 5, 6, 7, 8, 9, 10, 11, 12, 13, 14, 15, 16, 17, 18, 19, or 20 days or a period of time within a range defined by any two of these time periods. In some alternatives, the addition of the at least one cytokine improves, enhances, promotes, or induces engraftment fitness. In some alternatives, the enriched CD4+ expressing T-cells are contacted, for example propagated, in 5 ng/mL recombinant human IL-7 (rhIL-7) and/or 0.5 ng/mL recombinant human IL-15 (rhIL-15). In some alternatives, the enriched CD8+ expressing T-cells are contacted, for example propagated, in 50 U/mL recombinant human IL-2 (rhIL-2) and/or 0.5 ng/mL recombinant human IL-15 (rhIL-15). In more alternatives, the enriched CD4+ expressing T-cells are contacted, for example propagated, in 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL rhIL-7 or in an amount that is within a range defined by any two of the aforementioned amounts of rhIL-7 and/or 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL rhIL-15 or in an amount that is within a range defined by any two of the aforementioned amounts of rhIL-15. In more alternatives, the enriched CD8+ expressing T-cells are contacted, for example propagated, in 10 U/mL, 20 U/mL, 30 U/mL, 40 U/mL, 50 U/mL, 60 U/mL, 70 U/mL, 80 U/mL, 90 U/mL, or 100 U/mL of rhIL-2 or in an amount that is within a range defined by any two of the aforementioned amounts of rhIL-2 and/or 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL rhIL-7 and/or 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, or 1.0 ng/mL rhIL-15 or in an amount that is within a range defined by any two of the aforementioned amounts of rhIL-15. In some alternatives the aforementioned cytokines and amounts are co-administered to the T-cells, e.g., in a mixture or added shortly after one another, and in other alternatives, the aforementioned cytokines are contacted with the T cells separately, e.g., separated by a time period of 1-10 minutes or 1-10 hours.

"Enriched" and "depleted" are also used herein to describe amounts of cell types in a mixture refers to the subjecting of the mixture of the cells to a process or step, which results in an increase in the number of the "enriched" type and a decrease in the number of the "depleted" cells. Thus, depending upon the source of the original population of cells subjected to the enriching process, a mixture or composition can contain 60, 70, 80, 90, 95, or 99 percent or more, or any value within a range defined by any two of these values (in number or count) of the "enriched" cells and 40, 30, 20, 10, 5 or 1 percent or less or any value within a range defined by any two of these values (in number or count) of the "depleted" cells. In some alternatives of the method of making genetically modified T-cells, enriching the transduced, cytokine-stimulated population of CD8+ T-cells and/or CD4+ T-cells by affinity selection of a cell surface marker is contemplated, such that an enriched population of transduced, cytokine-stimulated CD8+ T-cells and/or CD4+ T-cells is generated.

"Propagating cells" or propagation refers to steps to allow proliferation, expansion, growth and reproduction of cells. For example, cultures of CD8+ T-cells and CD4+ T-cells can typically be incubated under conditions that are suitable for the growth and proliferation of T lymphocytes. In some alternatives of the method of making genetically modified T-cells, which have a chimeric antigen receptor, the CD4+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or fora period that is within a range defined by any two of the aforementioned time periods. In some alternatives of the method of making genetically modified T-cells, which have a chimeric antigen receptor, the CD8+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or for a period that is within a range defined by any two of the aforementioned time periods.

"Affinity selection," as described herein, refers to the selection of a specific molecule or cell having a selectable cell surface marker by binding to the molecule or marker or an epitope present thereon with a binding affinity agent, which allows for one to select out the specific molecule or cell of interest. Affinity selection can be performed by, for example, antibodies, conjugated antibodies, lectins, aptamers, and/or peptides. In some alternatives, of the method of making genetically modified T-cells, the separating of the CD8+ population of T-cells and/or a CD4+ population of T-cells from a mixed population of T-cells is performed by affinity selection for T-cells having an epitope present on CD8 and/or CD4. In some alternatives of the method, anti-CD8 or anti-CD4 antibodies or binding portions thereof are used to select out the cells of interest. In some alternatives of the method, the separating of the CD8+ population of T-cells and/or a CD4+ population of T-cells from a mixed population of T-cells is performed by flow cytometry. In some alternatives of the method, the separating of the CD8+ population of T-cells and/or a CD4+ population of T-cells from a mixed population of T-cells is performed by immunomagnetic selection. In some alternatives of the method, the anti-CD8 or the anti-CD4 antibodies are conjugated to a solid support such as, for example, an inert bead or an inert particle.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative ($CD4^{-}CD8^{-}$) cells. As they progress through their development, they become double-positive thymocytes ($CD4^{+}CD8^{+}$), and finally mature to single-positive ($CD4^{+}CD8^{-}$ or $CD4^{-}CD8^{+}$) thymocytes that are then released from the thymus to peripheral tissues. About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged β-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

"Cryopreservation" is a process of preserving cells, whole tissues, or substances susceptible to damage by cooling to sub-zero temperatures. At the low temperatures any enzymatic or chemical activity, which can cause damage to the cells, tissue or substances in question are effectively stopped. Cryopreservation methods seek to reach low temperatures without causing additional damage caused by the formation of ice during freezing. Traditional cryopreservation has relied on coating the material to be frozen with a class of molecules termed cryoprotectants. New methods are constantly being investigated due to the inherent toxicity of many cryoprotectants. Cryopreservation methods are known to those skilled in the art. In some alternatives of the method of making genetically modified T-cells, which have a chimeric antigen receptor, the method can further comprise cryopreserving the genetically modified T-cells.

In some alternatives, a population of genetically modified T-cells is provided, wherein the population of genetically modified T-cells, such as T-cells that are derived from thymocytes or T-cells that are derived from engineered precursors, desirably iPS cells, comprises a plurality of affinity selected CD8+ and/or CD4+ expressing T-cells, in the absence of, enriched over, or isolated from CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ expressing T-cells have been re-stimulated with at least one cytokine, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points. In some alternatives, the selected CD8+ and/or CD4+ T-cells are generated by methods provided herein. In some alternatives, the at least one cytokine comprises GM-CSF, IL-7, IL-12, IL-15, IL-18, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives of the population of genetically modified T-cells, the plurality of affinity selected CD8+ and/or CD4+ T-cells further comprise at least one receptor that promotes, induces, enhances or contribute to engraftment fitness. In some alternatives, the at least one receptor that promotes, enhances, induces, or contributes to engraftment fitness is CD45 RA, CD45 RO, CCR7, CD25, CD127, CD57, CD137, CD27, CD28 and/or CD62L. In some alternatives, the at least one receptor that promotes, enhances, contributes to, or induces engraftment fitness is CD27, CD28 and/or CD62L. In some alternatives, the plurality of affinity selected CD8+ and/or CD4+ expressing T-cells further comprises a vector having a first sequence encoding a leader sequence, a second sequence encoding a ligand binding domain, a third sequence encoding a signaling domain and a fourth sequence encoding a selectable marker. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the cell surface selectable marker codes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof. In some alternatives, the ligand binding domain is specific for CD19. In some alternatives, the population comprises isolated or enriched CD8+ expressing T-cells in the absence of, enriched over, substantially depleted of CD4+ T-cells. In some alternatives, the population comprises isolated or enriched CD4+ T-cells in the absence of, enriched over, or substantially depleted of CD8+ T-cells.

In some alternatives, the adoptive cellular immunotherapy compositions are useful in the treatment of a disease or cancer. In some alternatives, a composition or product combination for human therapy is provided, wherein the composition or product combination comprises a pharmaceutical excipient and at least one population of genetically modified T-cells according to any one or more of the alternative T-cells or population of genetically modified T-cells prepared or obtained as described herein. In some alternatives of the composition or product combination for human therapy, the composition or product combination comprises a population of genetically modified T-cells, such as T-cells that are derived from thymocytes or T-cells that are derived from engineered precursors, desirably iPS cells, wherein the population comprises isolated CD8+ T-cells in the absence of enriched over, substantially depleted of CD4+ T-cells. In some alternatives of the composition or product combination for human therapy, the composition or product combination comprises a population of genetically modified T-cells, such as T-cells that are derived from thymocytes or T-cells that are derived from engineered precursors, desirably iPS cells, wherein the population comprises isolated CD4+ T-cells in the absence of, enriched over, or substantially depleted of CD8+ T-cells. In some alternatives of the composition or product combination for human therapy, the composition or product combination comprises a combination of isolated CD8+ T-cells in the absence of, enriched over, or substantially depleted of CD4+ T-cells and isolated CD4+ T-cells absence of, enriched over, or substantially depleted of CD8+ T-cells in a 1:1 ratio. In some alternatives, the population of genetically modified T-cells are mixed and administered or co-administered as separate formulations to a subject in need thereof in a CD4+ T-cell to CD8+ T-cell ratio that is 1:1, 1:2, 1:3, 1:4, 1:5, 1:6, 1:7, 1:8, 1:9, 1:10 or a ratio within a range defined by any two of these ratios. In some alternatives, the population of genetically modified T-cells are mixed and administered or co-administered as separate formulations to a subject in need thereof in a CD8+ T-cell to CD4+ T-cell ratio that is 1:1, 1:2, 1:3, 1:4, 1:5, 1:6, 1:7, 1:8, 1:9, 1:10 or a ratio within a range defined by any two of these ratios.

"Pharmaceutical excipient," or pharmaceutical vehicle as described herein can refer to a carrier or inert medium used as a solvent in which the medicinally active agent or T-cells for treatment is formulated and or administered. Vehicles can include polymeric micelles, liposomes, lipoprotein-based carriers, nano-particle carriers, dendrimers, and/or other vehicles for T-cells that are known to one skilled in the art. An ideal vehicle or excipient can be non-toxic, biocompatible, non-immunogenic, biodegradable, and can avoid recognition by the host's defense mechanisms.

In some alternatives, a composition or product combination for human therapy is provided, wherein the composition or product combination comprises a pharmaceutical excipient and at least one population of genetically modified T-cells of any of the alternatives described herein. In some alternatives, the excipients are pharmaceutical vehicles. In some alternatives, the pharmaceutical vehicles include pharmaceutical compositions.

Acute lymphoblastic leukemia (ALL) or acute lymphoid leukemia is a cancer of the white blood cells, characterized by the overproduction of cancerous, immature white blood cells, also known as lymphoblasts. In patients with ALL, lymphoblasts are overproduced in the bone marrow and continuously multiply, causing damage and death by inhibiting the production of normal cells, such as, for example, red and white blood cells and platelets, in the bone marrow and by spreading to other organs. ALL is most common in childhood with a peak incidence at 2-5 years of age, and another peak at an older age.

The symptoms of ALL are indicative of a reduced production of functional blood cells, because the leukemia wastes the resources of the bone marrow, which are normally used to produce new, functioning blood cells. Symptoms can include fever, increased risk of infection, increased tendency to bleed, anemia, tachycardia, fatigue and headache. Between 50 to 70% of children and 40-50% of adults who achieve complete remission after initial therapy but then suffer a relapse can be able to go into a second complete remission. Treatment for relapse after a first remission can be standard chemotherapy or experimental drugs, or more aggressive treatments such as stem cell transplants. Treatment for relapse after a first remission can be standard chemotherapy or experimental drugs, or more aggressive treatments such as stem cell transplants. However, for others such as acute myeloid leukemia and ALL the reduced mortality of the autogenous relative to allogeneic hematopoietic stem cell transplantation (HSCT) can be outweighed by an increased likelihood of cancer relapse and related mortality, and therefore the allogeneic treatment can be preferred for those conditions. As such methods are needed to improve the cells for treatment of leukemia, myeloid leukemia and ALL.

In some alternatives, a method of treating, inhibiting, or ameliorating a disease, such as a cancer, such as ALL, in a subject in need thereof is provided, wherein the method comprises administering to the subject at least one composition or product combination of any one or more of the alternatives described herein, wherein the composition or product combination comprises genetically modified T-cells, which have a chimeric antigen receptor, wherein the T-cells are transduced, cytokine-stimulated CD8+ T-cells and/or CD4+ T-cells. In some alternatives of the method, the method comprises administering a composition or product combination, wherein the composition or product combination comprises a population of genetically modified T-cells comprising isolated CD8+ T-cells absence of, enriched over, or substantially depleted of CD4+ T-cells. In some alternatives of the method, the method comprises administering a composition or product combination, wherein the composition or product combination comprises a population of genetically modified T-cells comprising isolated CD4+ T-cells absence of, enriched over, or substantially depleted of CD8+ T-cells. In some alternatives, the method further comprises administering a composition or product combination, wherein the composition or product combination comprises a population of genetically modified T-cells comprising isolated CD4+ T-cells absence of, enriched over, or substantially depleted of CD8+ T-cells. In some alternatives of the method, the method further comprises administering a composition or product combination, wherein the composition or product combination comprises a population of genetically modified T-cells comprising isolated CD8+ T-cells absence of, enriched over, or substantially depleted of CD4+ T-cells. In some alternatives of the method, the method further comprises administering the composition or product combination, wherein the composition or product combination comprises isolated CD8+ T-cells absence of, enriched over, or substantially depleted of CD4+ T-cells and isolated CD4+ T-cells absence of, enriched over, or substantially depleted of CD8+ T-cells in a 1:1 ratio. In some alternatives, the population of genetically modified T-cells are mixed and administered or co-administered as separate formulations to a subject in need thereof in a CD4+ T-cell to CD8+ T-cell ratio that is 1:1, 1:2, 1:3, 1:4, 1:5, 1:6, 1:7, 1:8, 1:9, 1:10 or a ratio within a range defined by any two of these ratios. In some alternatives, the population of genetically modified T-cells are mixed and administered or co-administered as separate formulations to a subject in need thereof in a CD8+ T-cell to CD4+ T-cell ratio that is 1:1, 1:2, 1:3, 1:4, 1:5, 1:6, 1:7, 1:8, 1:9, 1:10 or a ratio within a range defined by any two of these ratios. In some alternatives, the subject is identified or selected to receive an anti-cancer therapy. In some alternatives, the method further comprises measuring or evaluating an inhibition of a disease. In some alternatives, the method further comprises providing said subject an additional anti-cancer therapy before, during, or after administration of the composition or product combination of any one or more of the alternatives described herein. In some alternatives of the method, the composition or product combination of any one or more of the alternatives described herein, are administered to said subject by adoptive cell transfer. In some alternatives, the composition or product combination of any one or more of the alternatives described herein, are administered to said subject after said subject has received another form of anti-cancer therapy. In some alternatives, the composition or product combination of any one or more of the alternatives described herein, are administered to said subject after said subject has received another form of anti-cancer therapy. In some alternatives, the subject is suffering from leukemia. In some alternatives, the subject has recurrent and/or refractory CD19+ childhood acute lymphoblastic leukemia (ALL). In some alternatives of the method, the subject has recurrent and/or chemotherapy refractory CD19+ acute lymphoblastic leukemia (ALL). In some alternatives of the method, the subject is suffering from an autoimmune disease. In some alternatives of the method, the subject is suffering from a post-HSCT relapse.

Additional Alternatives

Vectors, Cells and Methods of Transducing Cells

The compositions described herein provide for CD4+ and/or CD8+ expressing T lymphocytes, such as T-cells that are derived from thymocytes or T-cells that are derived from engineered precursors, desirably iPS cells. T lymphocytes can be collected in accordance with known techniques and enriched or depleted by known techniques, such as affinity binding to antibodies such as flow cytometry and/or immunomagnetic selection. After enrichment and/or depletion steps, in vitro expansion of the desired T lymphocytes can be carried out in accordance with known techniques (including but not limited to those described in U.S. Pat. No. 6,040,177 to Riddell et al., hereby expressly incorporated by reference in its entirety). In some alternatives, the T-cells are autologous T-cells i.e., obtained from the patient to which the cells are delivered. In some alternatives, the T cells are precursor T cells. In some alternatives, the precursor T cells are a hematopoietic stem cells (HSC).

For example, the desired T-cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T-cells). The non-dividing feeder cells can comprise gamma-irradiated PBMC feeder cells. In some alternatives, the PBMC are irradiated with gamma rays at 3000, 3200, 3300, 3400, 3500, or 3600 rads to prevent cell division, or within a range of rads defined by any two of the aforementioned rads. The order of addition of the T-cells and feeder cells to the culture media can be reversed if desired. The culture can be incubated under conditions that are suitable for the growth of T lymphocytes. For the growth of human T lymphocytes, for example, the temperature will generally be at least 25 degrees Celsius, preferably at least 30 degrees, more preferably 37 degrees, or any other temperature within a range defined by any two of these temperatures.

The T lymphocytes expanded include CD8+ cytotoxic T lymphocytes (CTL) and CD4+ helper T lymphocytes that can be specific for an antigen present on a human tumor or a pathogen and express a chimeric antigen receptor.

In another alternative, the expansion method or propagation can further comprise adding non-dividing EBV-transformed lymphoblastoid cells (LCL) as feeder cells. LCL can be irradiated with gamma rays in the range of 6000, 7000, 8000, 9000, or 10,000 rads, or within a range of rads defined by any two of the aforementioned rads. The LCL feeder cells can be provided in any suitable amount, such as a ratio of LCL feeder cells to initial T lymphocytes of at least 10:1.

In another alternative, the expansion method or propagation can further comprise adding anti-CD3 and/or anti CD28 antibody to the culture medium (e.g., at a concentration of at least 0.5 ng/ml). In another alternative, the method of making genetically modified T-cells, which have a chimeric antigen receptor method can further comprise adding IL-2, IL-15, and/or IL-21 to the culture medium (e.g., wherein the concentration of IL-2 is at least 10 units/ml). In another alternative, the method of making genetically modified T-cells, which have a chimeric antigen receptor method can further comprise adding IL-7, IL-15, and/or IL21 to the culture medium (e.g., wherein the concentration of IL-2 is at least 10 units/ml). After isolation of T lymphocytes, both cytotoxic and helper T lymphocytes can be sorted into naïve, memory, and effector T-cell subpopulations either before or after expansion.

CD8+ cells can also be obtained by using standard methods. In some alternatives, CD8+ cells are further sorted into naïve, central memory, and effector memory cells by identifying cell surface antigens that are associated with each of those types of CD8+ cells. In some alternatives, memory T-cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some alternatives, the expression of phenotypic markers of central memory $T_{CM}$ include CD45RO, CD62L, CCR7, CD28, CD3, and/or CD127 and/or are negative or low for granzyme B and/or CD45RA. In some alternatives, central memory T-cells are CD28+, CD27+, CD45RO+, CD62L+, and/or CD8+ T-cells. In some alternatives, naïve CD8+ T lymphocytes are characterized by the expression of phenotypic markers of naïve T-cells including CD62L, CCR7, CD27, CD28, CD3, CD127, and/or CD45RA.

Whether a cell or cell population is positive for or expresses a particular cell surface marker can be determined by flow cytometry using a specific antibody that is specific for the surface marker and an isotype matched control antibody. A cell population negative for a marker refers to the absence of significant binding of the cell population with the specific antibody above the isotype control, indicative of a lack of expression of said marker; positive refers to uniform binding of the cell population above the isotype control indicative of the expression of the marker. In some alternatives, a decrease in expression of one or markers refers to loss of 1 log 10 in the mean fluorescence intensity and/or decrease of percentage of cells that exhibit the marker of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % within a range of % s defined by any two of these values when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % within a range of % s defined by any two of these values when compared to a reference cell population.

CD4+ T helper cells are sorted into naïve, central memory, and effector cells by identifying cell populations that have cell surface antigens. CD4+ lymphocytes can be obtained by standard methods. In some alternatives, naïve CD4+ T lymphocytes are CD45RO−, CD45RA+, CD62L+, CD27+, CD28+, and/or CD4+ T-cells. In some alternatives, central memory CD4+ cells are CD62L+ and/or CD45RO+. In some alternatives, effector CD4+ cells are CD62L- and/or CD45RO−. In some alternatives, effector CD4+ cells are CD28+, CD27+ and/or CD62L+.

In some alternatives, populations of CD4+ and CD8+ that are antigen specific can be obtained by stimulating naïve or antigen specific T lymphocytes with antigen. For example, antigen-specific T-cell lines or clones can be generated to Cytomegalovirus antigens by isolating T-cells from infected subjects and stimulating the cells in vitro with the same antigen. Naïve T-cells can also be used. Any number of antigens from tumor cells can be utilized as targets to elicit T-cell responses. In some alternatives, the adoptive cellular immunotherapy compositions are useful in the treatment of a disease or disorder including a solid tumor, hematologic malignancy, breast cancer or melanoma.

Modification of T Lymphocyte Populations

In some alternatives it can be desired to introduce functional genes into the T-cells to be used in immunotherapy in accordance with the present disclosure. For example, the introduced gene or genes can improve the efficacy of therapy by promoting the viability and/or function of transferred T-cells; or they can provide a genetic marker to permit selection and/or evaluation of in vivo survival or migration; or they can incorporate functions that improve the safety of immunotherapy, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker, both references hereby expressly incorporated by reference in their entireties. This can be carried out in accordance with known techniques (see, e.g., U.S. Pat. No. 6,040,177 to Riddell et al. at columns 14-17, hereby expressly incorporated by reference in its entirety) or variations thereof that will be apparent to those skilled in the art based upon the present disclosure. In some alternatives, the T cells are precursor T cells. In some alternatives, the precursor T cells are a hematopoietic stem cells (HSC).

In some alternatives, T-cells are modified with chimeric receptors, as described herein. In some alternatives, the T-cells are obtained from the subject to be treated, in other alternatives, the lymphocytes are obtained from allogeneic human donors, preferably healthy human donors. In some alternatives, the T cells are precursor T cells. In some alternatives, the precursor T cells are a hematopoietic stem cells (HSC).

In some alternatives, chimeric receptors comprise a ligand binding domain that specifically binds to surface molecule on a cell, a polypeptide spacer region, a transmembrane domain and an intracellular signaling domain as described herein. In some alternatives, the ligand binding domain is a single-chain antibody fragment (scFv) that is derived from the variable heavy (VH) and variable light (VL) chains of a monoclonal antibody (mAb). Co-stimulatory signals can also be provided through the chimeric receptor by fusing the co-stimulatory domain of CD28 and/or 4-1BB to the CD3ζ chain. Chimeric receptors are specific for cell surface molecules independent from HLA, thus overcoming the limitations of TCR-recognition including HLA-restriction and low levels of HLA-expression on tumor cells.

In some alternatives, the same or a different chimeric receptor can be introduced into each of population of CD4+ and CD8+ T lymphocytes. In some alternatives, the chimeric receptor in each of these populations has a ligand binding domain that specifically binds to the same ligand on the cell. The cellular signaling modules can differ. In some alternatives, the intracellular signaling domain of the CD8+ cytotoxic T-cells is the same as the intracellular signaling domain of the CD4+ helper T-cells. In other alternatives, the intracellular signaling domain of the CD8+ cytotoxic T-cells is different than the intracellular signaling domain of the CD4+ helper T-cells. In some alternatives, an anti-CD19 CAR is introduced into one population of lymphocytes and an EGFR specific CAR is introduced into another population of lymphocytes.

In some alternatives each of the CD4 or CD8 T lymphocytes are sorted in to naïve, central memory, effector memory or effector cells prior to transduction, as described herein. In some alternatives, each of the CD4 or CD8 T lymphocytes are sorted into naïve, central memory, effector memory, or effector cells after transduction.

Various transduction techniques have been developed, which utilize recombinant infectious virus particles for gene delivery. This represents a currently preferred approach to the transduction of T lymphocytes described herein. The viral vectors, which have been used in this way include virus vectors derived from simian virus 40, adenoviruses, adeno-associated virus (AAV), lentiviral vectors, and retroviruses.

Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

In some alternatives it can be useful to include in the T-cells a positive marker that enables the selection of cells of the negative selectable phenotype in vitro. The positive selectable marker can be a gene that upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene. In some alternatives, the positive marker is an EGFR truncated protein for cell selection.

A variety of methods can be employed for transducing T lymphocytes, as is well known in the art. In some alternatives, transduction is carried out using lentiviral vectors. In some alternatives, CD4+ and CD8+ cells each can separately be modified with an expression vector encoding a chimeric receptor to form defined populations. In some alternatives, these cells are then further sorted into subpopulations of naïve, central memory and effector cells as described above by sorting for cell surface antigens unique to each of those cell populations.

In some alternatives, CD4+ and CD8+ cells that proliferate in response to antigen or tumor targets are selected. For example, CD4+ cells that proliferate vigorously when stimulated with antigen or tumor targets as compared to sham transduced cells, or CD8+ transduced cells are selected. In some alternatives, CD4+ and CD8+ cells are selected that are cytotoxic for antigen bearing cells. In some alternatives, CD4+ are expected to be weakly cytotoxic as compared to CD8+ cells.

In another alternative, transduced lymphocytes, such as CD8+ central memory cells, are selected that provide for cell killing in vivo using an animal model established for the particular type of cancer. Such animal models are known to those of skill in the art and exclude human beings. As described herein, not all chimeric receptor constructs transduced into lymphocytes confer the ability to kill tumor cells in vivo despite the ability to become activated and kill cells in vitro.

The disclosure contemplates that combinations of CD4+ and CD8+ T-cells will be utilized in compositions. In one alternative, combinations of chimeric receptor transduced CD4+ cells can be combined with chimeric receptor transduced CD8+ cells of the same ligand specificity or combined with CD8+ T-cells that are specific for a distinct tumor ligand. In other alternatives, chimeric receptor transduced CD8+ cells are combined with chimeric receptor transduced CD4+ cells specific for a different ligand expressed on the tumor. In yet another alternative, chimeric receptor modified CD4+ and CD8+ cells are combined. In some alternatives CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+ or any other ratio within a range defined by any two of the aforementioned ratio values. In some alternatives, the combined population is tested for cell proliferation in vitro and/or in vivo, and the ratio of cells that provides for proliferation of cells is selected.

As described herein, the disclosure contemplates that CD4+ and CD8+ cells can be further separated into subpopulations, such as naïve, central memory, and effector memory cell populations. As described herein, in some alternatives, naïve CD4+ cells are CD45RO−, CD45RA+, CD62L+, CD28+, CD27+, and/or CD4+ positive T-cells. In some alternatives, central memory CD4+ cells are CD62L positive and/or CD45RO positive. In some alternatives, effector CD4+ cells are CD62L negative and/or CD45RO positive. Each of these populations can be independently modified with a chimeric receptor. In some alternatives, central memory CD4+ cells are CD62L+, CD28+ and/or CD27+.

After transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg. In some alternatives, the transduced cells are cultured in the presence of antigen bearing cells, anti CD3, anti CD28, IL 2, IL-7, IL 15, and/or IL-21 and/or combinations thereof. In some alternatives, the T-cells are stimulated in the presence of an antibody-bound support, such as a bead or particle. In some alternatives, the T-cells are stimulated with an antibody-bound support, wherein the antibody-bound support comprises anti-TCR, anti-CD2, anti-CD3, anti-CD4 and/or anti-CD28 antibodies. In some alternatives, the T-cells are stimulated with an antibody-bound support, wherein the antibody-bound support comprises anti-CD3 and/or anti-CD28 antibodies.

Each of the subpopulations of CD4+ and CD8+ cells can be combined with one another. In a specific alternative, modified naïve or central memory CD4+ cells are combined with modified central memory CD8+ T-cells to provide a synergistic cytotoxic effect on an antigen bearing cells, such as a B-cell comprising CD19 on the cell surface.

Compositions

The disclosure provides for an adoptive cellular immunotherapy composition comprising a genetically modified T lymphocyte cell preparation as described herein.

In some alternatives, the T lymphocyte cell preparation comprises CD4+ T-cells that have a chimeric receptor comprising an extracellular antibody variable domain specific for a ligand associated with the disease or disorder, a customizable spacer region, a transmembrane domain, and an intracellular signaling domain of a T-cell receptor or other receptors as described herein. In other alternatives, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T-cells that have a chimeric receptor comprising an extracellular single chain antibody specific for a ligand associated with the disease or disorder, a customizable spacer region, a transmembrane domain, and an intracellular signaling domain of a T-cell receptor, as described herein.

In some alternatives, an adoptive cellular immunotherapy composition comprises a chimeric receptor modified tumor-specific CD8+ cytotoxic T lymphocyte cell preparation that provides a cellular immune response, wherein the cytotoxic T lymphocyte cell preparation comprises CD8+ T-cells that have a chimeric receptor comprising an extracellular single chain antibody specific for a ligand associated with the disease or disorder, a customizable spacer region, a transmembrane domain, and an intracellular signaling domain of a T-cell receptor, in combination with an antigen-reactive chimeric receptor modified naïve CD4+ T helper cell derived from CD45RO− CD62L+ and/or CD4+ T-cells, and a pharmaceutically acceptable carrier.

In other alternatives, an adoptive cellular immunotherapy composition comprises an antigen specific CD8+ cytotoxic T lymphocyte cell preparation that provides a cellular immune response derived from the patient combined with an antigen-reactive chimeric receptor modified naïve CD4+ T helper cell that augments the CD8+ immune response, wherein the helper T lymphocyte cell preparation comprises CD4+ T-cells that have a chimeric receptor comprising an extracellular antibody variable domain specific for the antigen associated with the disease or disorder, a customizable spacer region, a transmembrane domain, and an intracellular signaling domain of a T-cell receptor.

In a further alternative, an adoptive cellular immunotherapy composition comprises an antigen-reactive chimeric receptor modified naïve CD4+ T helper cell that augments the CD8+ immune response, wherein the helper T lymphocyte cell preparation comprises CD4+ T-cells that have a chimeric receptor comprising an extracellular antibody variable domain specific for a ligand associated with a disease or disorder, a customizable spacer region, a transmembrane domain, and an intracellular signaling domain of a T-cell receptor.

In some alternatives, the CD4+ T helper lymphocyte cell is selected from the group consisting of naïve CD4+ T-cells, central memory CD4+ T-cells, effector memory CD4+ T-cells, and bulk CD4+ T-cells. In some alternatives, CD4+ helper lymphocyte cell is a naïve CD4+ T-cell, wherein the naïve CD4+ T-cell comprises a CD45RO−, CD45RA+, CD62L+CD28+, CD27+, and/or CD4+. In some alternatives, the CD8+ T cytotoxic lymphocyte cell is selected from the group consisting of naïve CD8+ T-cells, central memory CD8+ T-cells, effector memory CD8+ T-cells and bulk CD8+ T-cells. In some alternatives, the CD8+ cytotoxic T lymphocyte cell is a central memory T-cell wherein the central memory T-cell comprises a CD45RO+, CD62L+, CD27+, CD28+ and/or CD8+. In yet other alternatives, the CD8+ cytotoxic T lymphocyte cell is a central memory T-cell and the CD4+ helper T lymphocyte cell is a naïve or central memory CD4+ T-cell.

The disclosure provides methods of making adoptive immunotherapy compositions and uses or methods of using these compositions for performing cellular immunotherapy in a subject having a disease or disorder. Proliferation and persistence of the chimeric receptor modified T-cells can be determined by using an animal model of the disease or disorder and administering the cells and determining persistence and/or proliferative capacity of the transferred cells. In other alternatives, proliferation and activation can be tested in vitro by going through multiple cycles of activation with antigen bearing cells.

In some alternatives, a method of manufacturing the compositions comprises obtaining a modified naïve CD4+ T helper cell, wherein the modified helper T lymphocyte cell preparation comprises CD4+ T-cells that have a chimeric receptor comprising a ligand binding domain specific for a tumor cell surface molecule, a customized spacer domain, a transmembrane domain, and an intracellular signaling domain as described herein.

In another alternative, a method further comprises obtaining a modified CD8+ cytotoxic T cell, wherein the modified cytotoxic T lymphocyte cell preparation comprises CD8+ cells that have a chimeric receptor comprising a ligand binding domain specific for a tumor cell surface molecule, a customized spacer domain, a transmembrane domain, and an intracellular signaling domain as described herein.

In another alternative, a method comprises obtaining a modified CD8+ cytotoxic T-cell, wherein the modified cytotoxic T lymphocyte cell preparation comprises CD8+ T-cells that have a chimeric receptor comprising a ligand binding domain specific for a tumor cell surface molecule, a customized spacer domain, a transmembrane domain, and an intracellular signaling domain, as described herein, and further comprising combining the modified CD8+ cytotoxic T-cells with a CD4+ helper cell lymphocyte cell preparation.

The preparation of the CD4+ and CD8+ cells that are modified with a chimeric receptor has been described above, as well as, in the examples. Antigen specific T lymphocytes can be obtained from a patient having the disease or disorder or can be prepared by in vitro stimulation of T lymphocytes in the presence of antigen. Subpopulations of CD4+ and CD8+ T lymphocytes that are not selected for antigen specificity can also be isolated as described herein and combined in the methods of manufacturing. In some alternatives, the combination of cell populations can be evaluated for uniformity of cell surface makers, the ability to proliferate through at least two generations, to have a uniform cell differentiation status. Quality control can be performed by co-culturing a cell line expressing the target ligand with chimeric receptor modified T-cells to determine if the chimeric receptor modified T-cells recognize the cell line using cytotoxicity, proliferation, or cytokine production assays that are known in the field. Cell differentiation status and cell surface markers on the chimeric receptor modified T-cells can be determined by flow cytometry. In some alternatives, the markers and cell differentiation status on the CD8+ cells include CD3, CD8, CD62L, CD28, CD27, CD69, CD25, PD-1, CTLA-4, CD45RO, and/or CD45RA. In some alternatives, the markers and the cell differentiation status on the CD4+ cells include CD3, CD4, CD62L, CD28, CD27, CD69, CD25, PD-1, CTLA-4 CD45RO, and/or CD45RA. In some alternatives, the markers include CD45 RA, CD45 RO, CCR7, CD25, CD127, CD57, CD137, CD27, CD28 and/or CD62L. In some alternatives, the markers include CD27, CD28 and/or CD62L.

Some alternatives relate to approaches for treating, inhibiting, or ameliorating a disease, such as cancer, such as ALL in a subject in need thereof, including methods of inhibiting or delaying progression and/or metastasis of a cancer, methods of inhibiting or reducing the presence of a tumor or cancer cell, and/or a methods of inhibiting or reducing a target population of CD19 expressing cells in a patient in need thereof. Such methods involve administering to a subject or a patient in need thereof a genetically modified cytotoxic T lymphocyte cell preparation that provides a cellular immune response, wherein the cytotoxic T lymphocyte cell preparation comprises CD8+ T-cells that have a chimeric receptor comprising a polynucleotide coding for a ligand binding domain, wherein the ligand is a tumor specific antigen, or any other molecule expressed on a target-cell population (e.g. CD19) that is suitable to mediate recognition and elimination by a lymphocyte; a polynucleotide coding for a polypeptide spacer wherein the polypeptide spacer is of a customized length, wherein the spacer provides for enhanced T-cell proliferation and/or cytokine production as compared to a reference chimeric receptor; a polynucleotide coding for a transmembrane domain; and a polynucleotide coding for one or more intracellular signaling domains.

The disclosure also provides methods of performing cellular immunotherapy in a subject having a disease or disorder such as cancer, such as ALL comprising: administering a composition of lymphocytes expressing a chimeric receptor as described herein. In other alternatives, a method comprises administering to the subject a genetically modified cytotoxic T lymphocyte cell preparation that provides a cellular immune response, wherein the cytotoxic T lymphocyte cell preparation comprises CD8+ T-cells that have a chimeric receptor comprising a ligand binding domain specific for a cell surface molecule, a customized spacer domain, a transmembrane domain, and an intracellular signaling domain as described herein, and a genetically modified helper T lymphocyte cell preparation that elicits direct recognition and augments the genetically modified cytotoxic T lymphocyte cell preparations ability to mediate a cellular immune response, wherein the helper T lymphocyte cell preparation comprises CD4+ T-cells that have a chimeric receptor comprising a ligand binding domain specific for a cell surface molecule, a customized spacer domain, a transmembrane domain, and an intracellular signaling domain, as described herein.

While not limiting the scope of the disclosure, it is believed by selecting the chimeric receptor modified T-cell population that can persist and proliferate in vivo prior to administration can result in the ability to use a lower dose of T-cells and provide more uniform therapeutic activity. In some alternatives, the dose of T-cells can be reduced at least 10%, 20%, or 30% or greater. Reduction in the dose of T-cells can be beneficial to reduce the risk or tumor lysis syndrome and cytokine storm.

In another alternative, a method of performing cellular immunotherapy in subject having a disease or disorder comprises: administering to the subject a genetically modified helper T lymphocyte cell preparation, wherein the modified helper T lymphocyte cell preparation comprises CD4+ T-cells that have a chimeric receptor comprising a ligand binding domain specific for a tumor cell surface molecule, a customized spacer domain, a transmembrane domain, and an intracellular signaling domain as described herein. In some alternatives, the method further comprises administering to the subject a genetically modified cytotoxic T lymphocyte cell preparation, wherein the modified cytotoxic T lymphocyte cell preparation comprises CD4+ cells that have a chimeric receptor comprising a ligand binding domain specific for a tumor cell surface molecule, a customized spacer domain, a transmembrane domain, and an intracellular signaling domain as described herein.

Another alternative describes a method of performing cellular immunotherapy in a subject having a disease or disorder comprising: analyzing a biological sample of the subject for the presence of a target molecule (e.g. CD19) associated with the disease or disorder and administering the adoptive immunotherapy compositions described herein, wherein the chimeric receptor specifically binds to the target molecule (CD19).

In some alternatives, the CD4+ T helper lymphocyte cell is selected prior to introduction of the chimeric receptor from the group consisting of naïve CD4+ T-cells, central memory CD4+ T-cells, effector memory CD4+ T-cells and bulk CD4+ T-cells. In a specific alternative, CD4+ helper lymphocyte cell is a naïve CD4+ T-cell, wherein the naïve CD4+ T-cell comprises a CD45RO−, CD45RA+, CD28+, CD27+, CD62L+ and/or CD4+. In yet other alternatives, the CD8+ T cytotoxic lymphocyte cell is selected prior to introduction of the chimeric receptor from the group consisting of naïve CD8+ T-cells, central memory CD8+ T-cells, effector memory CD8+ T-cells and bulk CD8+ T-cells. In a specific alternative, the CD8+ cytotoxic T lymphocyte cell is a central memory T-cell wherein the central memory T-cell comprises a CD45RO+, CD62L+, CD28+, CD28+, and/or CD8+. In a specific alternative, the CD8+ cytotoxic T lymphocyte cell is a central memory T-cell and the CD4+ helper T lymphocyte cell is a naïve CD4+ T-cell.

In some alternatives, the CD8+ T-cell and the CD4+ T-cell are both genetically modified with a chimeric receptor comprising an antibody heavy chain domain that specifically binds a cell surface molecule. In other alternatives, the intracellular signaling domain of the CD8 cytotoxic T-cells is the same as the intracellular signaling domain of the CD4 helper T-cells. In yet other alternatives, the intracellular signaling domain of the CD8 cytotoxic T-cells is different than the intracellular signaling domain of the CD4 helper T-cells.

The subjects that can be administered the alternatives described herein include humans, other primates, such as monkeys and apes, companion animals, such as dogs, cats, and horses, and domestic animals such as pigs, goats, sheep, and cattle. The subjects can be male or female and can be any suitable age, including infant, juvenile, adolescent, adult, and geriatric subjects. The methods are useful in the treatment of, for example, CD19 bearing cancer or cells.

Cells prepared as described above can be utilized in methods and compositions for adoptive immunotherapy in accordance with known techniques, or variations thereof that will be apparent to those skilled in the art based on the instant disclosure.

In some alternatives, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with fetal calf serum. Cells are then treated with cytokines to produce a transduced, cytokine-stimulated population of CD8+ T-cells and/or CD4+ T-cells with an increased or improved engraftment fitness as compared to non-cytokine stimulated populations of CD8+ T-cells and/or CD4+ T-cells. In order to generate cells with the desired improvement in engraftment fitness, the cytokines are desirably added in vitro during the propagation of the T-cells. As such, separated CD4+ and CD8+ T-cells are cytokine stimulated by the addition of cytokines during the propagation of the genetically modified T-cells. In some alternatives, the CD4+ T cells are stimulated with at least one cytokine, wherein the at least one cytokine comprises IL/7, IL-15 and/or IL-21. In some alternatives, the CD8+ T cells are stimulated with at least one cytokine, wherein the at least one cytokine comprises IL-2, IL-15 and/or IL-21.

A treatment or inhibitory effective amount of cells in the composition is at least 2 cell subsets (for example, 1 CD8+ central memory T-cell subset and 1 CD4+ helper T-cell subset) or is more typically greater than $10^2$ cells, and up to $10^6$, up to and including $10^8$ or $10^9$ cells and can be more than $10^{10}$ cells or any other value in a range defined by any of these two values. The number of cells will depend upon the ultimate use for which the composition is intended as will the type of cells included therein. For example, if cells that are specific for a particular antigen are desired, then the population will contain greater than 70%, generally greater than 80%, 85% and/or 90-95% of such cells. For uses provided herein, the cells are generally in a volume of a liter or less, can be 500 mls or less, even 250 mls or 100 mls or less, or any other value within a range defined by any two of these values. Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^9$, $10^{10}$ or $10^{11}$ cells or any other amount within a range defined by any of these two values.

In some alternatives, the lymphocytes of the invention can be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3\times10^{10}$ cells, preferably in the range of at least $10^7$ to $10^9$ cells. The T-cells can be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17, hereby expressly incorporated by reference in its entirety.

In some alternatives, the compositions, as described herein are administered intravenously, intraperitoneally, intratumorly, into the bone marrow, into the lymph node, and/or into cerebrospinal fluid.

In some alternatives, the compositions, as described herein are administered with chemotherapeutic agents and/or immunosuppressants. In an alternative, a patient is first administered a chemotherapeutic agent that inhibits or destroys other immune cells followed by the compositions described herein. In some cases, chemotherapy can be avoided entirely.

Administration to Patients of ALL

CD4 and CD8 T cell subsets were immunomagnetically isolated from apheresis products obtained from the research participant. Following anti-CD3×CD28 bead stimulation, T cell lines were transduced with a SIN lentiviral vector that directs the co-expression of the FMC63scFv:IgG4hinge:CD28tm:4-1BB:ζ CAR and the selection and tracking suicide construct EGFRt. Transduced cells were propagated using recombinant human cytokines to numbers suitable for clinical use over 10-20 days during which time they were subjected to EGFRt immunomagnetic positive selection. Shortly following lymphodepleting chemotherapy, cryopreserved CD4/EGFRt+ and CD8/EGFRt+ T cell products were thawed and infused at the bedside such that patients received a 1:1 ratio of EGFRt+CD4 and CD8 T cells at the indicated protocol-prescribed dose level ($1=0.5\times10^6$/kg; $2=1\times10^6$/kg; $3=5\times10^6$/kg). In some alternatives, the enriched CD4+ expressing T-cells were contacted, for example propagated, in 5 ng/mL recombinant human IL-7 (rhIL-7) and/or 0.5 ng/mL recombinant human IL-15 (rhIL-15). In some alternatives, the enriched CD8+ expressing T-cells were contacted, for example propagated, in 50 U/mL recombinant human IL-2 (rhIL-2) and/or 0.5 ng/mL recombinant human IL-15 (rhIL-15).

All enrolled subjects (n=16) had cell products that met dosing specification and had been cleared for infusion. 13 subjects (6 m-3 yr s/p HSCT) had been treated at varying dose levels (range of $0.5\times10^6$/kg-$5\times10^6$/kg). The infusions were well tolerated with only 1 AE>grade 2 (grade 3 anaphylaxis related to the DMSO). 12 out of 13 subjects had responses for an ORR of 92%. 11 out of 13 subjects achieved MRD negative CRs (85%). Subjects with higher disease burden had higher peak PB CAR T cell levels compared to those with MRD negative marrows (62.7% v 19.6%). Accumulation with expansion of CAR T cells in bone marrow (n=12), peripheral blood (n=12) and CSF was observed. The average duration of persistence for the 5 subjects who lost their T cell grafts was 63 days (range of 42-150 d).

Each of the twelve responding subjects developed some degree of CRS with fever and hypotension as the hallmark symptoms. Two subjects, S02 and S09, required immunomodulatory treatment for sCRS (tocilizumab for two, and addition of dexamethasone in one). Four of 13 of these patients developed encephalopathy (2 grade 1, 1 grade 3 and 1 grade 4). The grade 4 encephalopathy was a DLT, and accompanied by seizures and abnormal MRI findings similar to PRES. MRI findings were normalized by 9 weeks post therapy, but the subject, at the time of last assessment, continued to have seizures, 6 months from therapy.

As shown, infusions of prescribed dose levels of defined composition CD4:CD8 CD19CAR/EGFRt+ T cells/kg produced encouraging rates of MRD-negative CRs in pediatric and young adult ALL patients who have suffered a post-HSCT relapse. As such, it is feasible to generate donor-derived products from each of the sixteen enrolled patients. The expected toxicities for the 13 evaluable patients include CRS with ~30% ICU admission rate and encephalopathy with severity ranging from mild to severe. MRD negative responses have been seen at all dose levels, although early data suggests enhanced persistence at escalating doses.

Although one patient developed acute GVHD post T cell therapy, the preliminary assessment suggested that CAR T cells were not mediators of this response. Interestingly, prednisone did not affect persistence of the T cell graft. As such, the cells that maintained the markers CD28, CD27, and CD62L showed high persistence in comparison to cells that were not treated with the defined cytokine mixtures and lack the markers for engraftment fitness, which are the T-cells that are used for the current method of treatment.

Figure 18A:
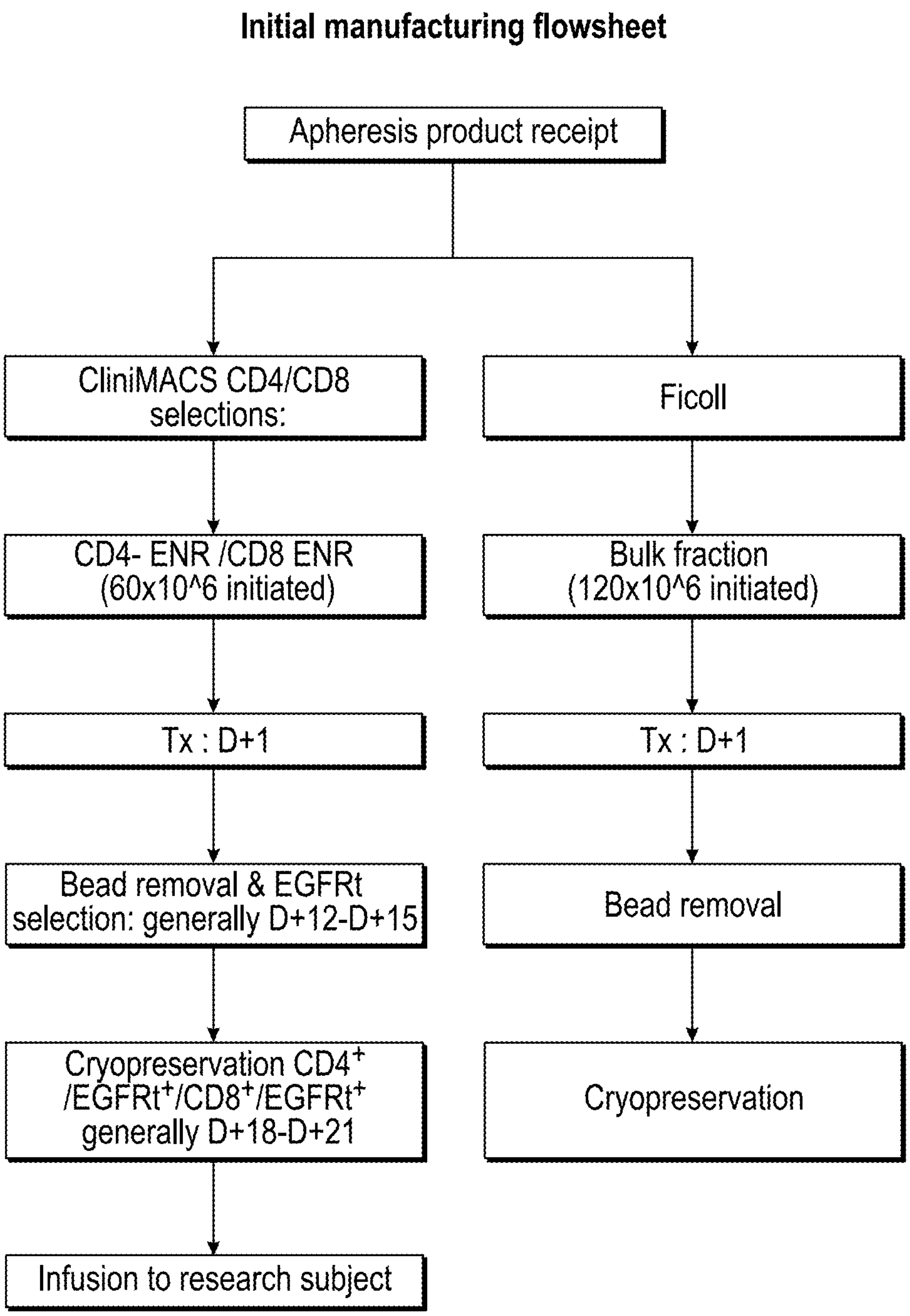
FIGS. 18A-B each show a flow diagram illustrating the manufacturing of genetically modified T-cells. As depicted, for the initial expansion methodology bulk processing was not always initiated immediately. A portion of the apheresis product was always taken for Ficoll processing. If no bulk cultures were to be initiated then that product separated by Ficoll was cryopreserved.
Figure 18B:
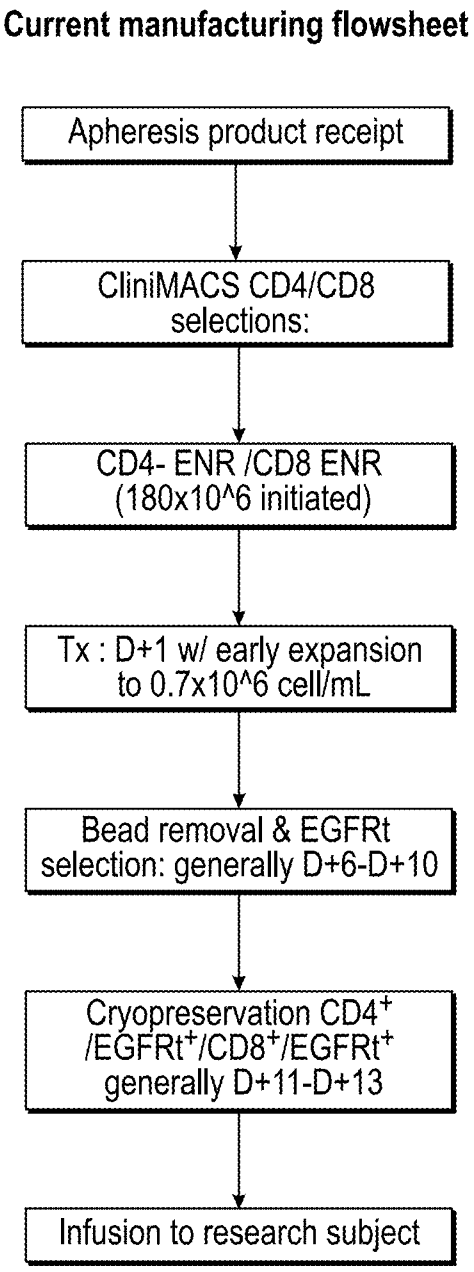
Figure 19:
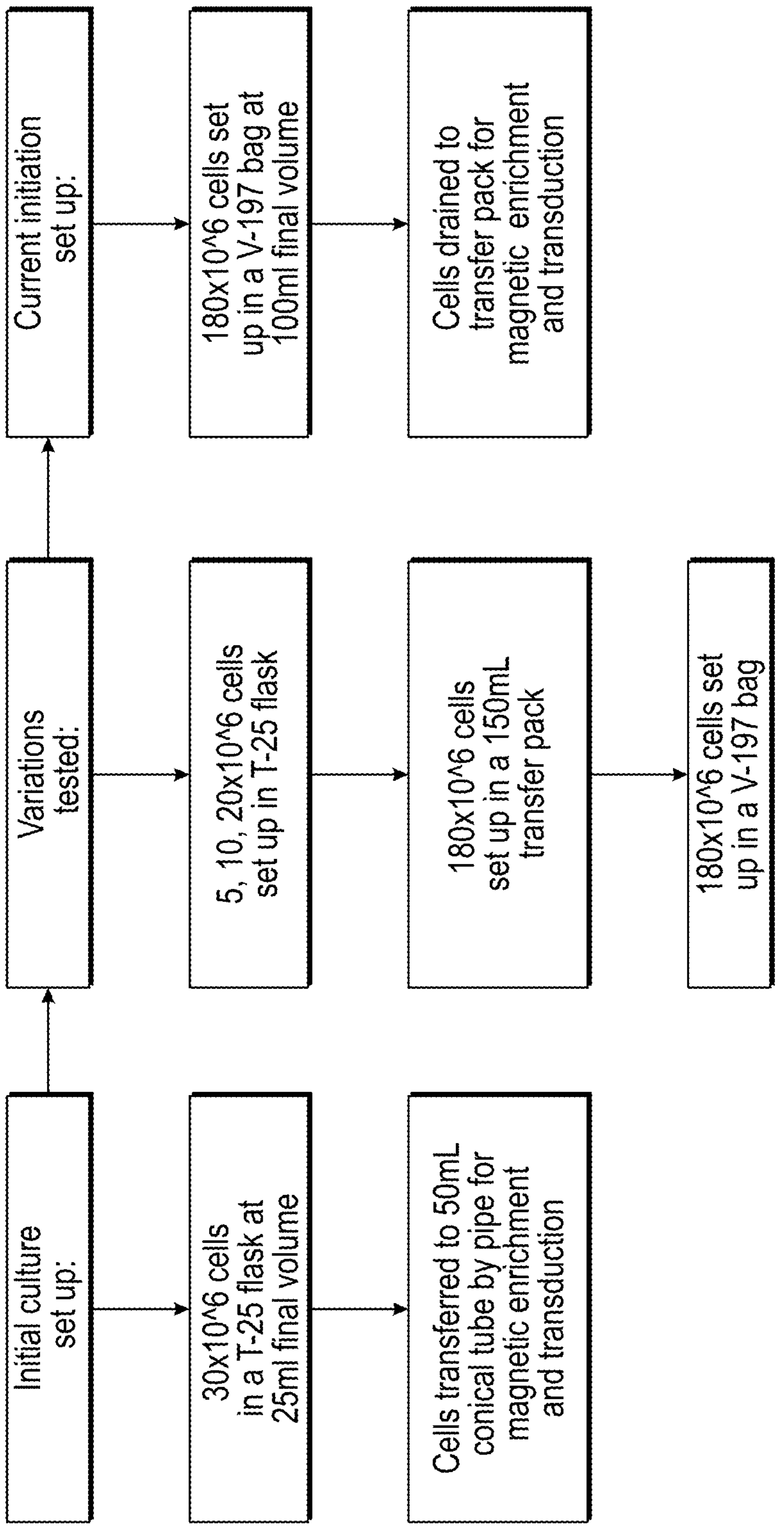
FIG. 19 shows a flow diagram of comparisons of different methods of making genetically modified T-cells that have chimeric antigen receptors.
Figure 20A:
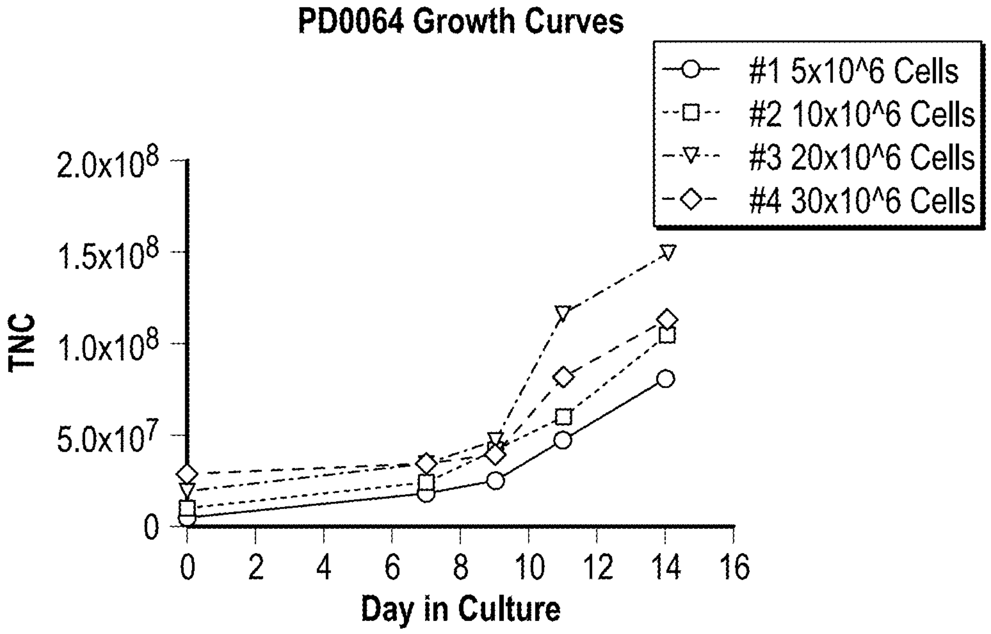
FIGS. 20A-D show the initial comparisons in cell growth using different concentrations of cells in the starter culture. As shown, PD0064 are the PD0063 donor which are enriched CD8+ expressing T-cells were used to test starting cell density in T25 flask on initiation. The experiments tested two cell densities and both showed greater viability and expansion when the volume was increased early during the experiment.
Figure 20B:
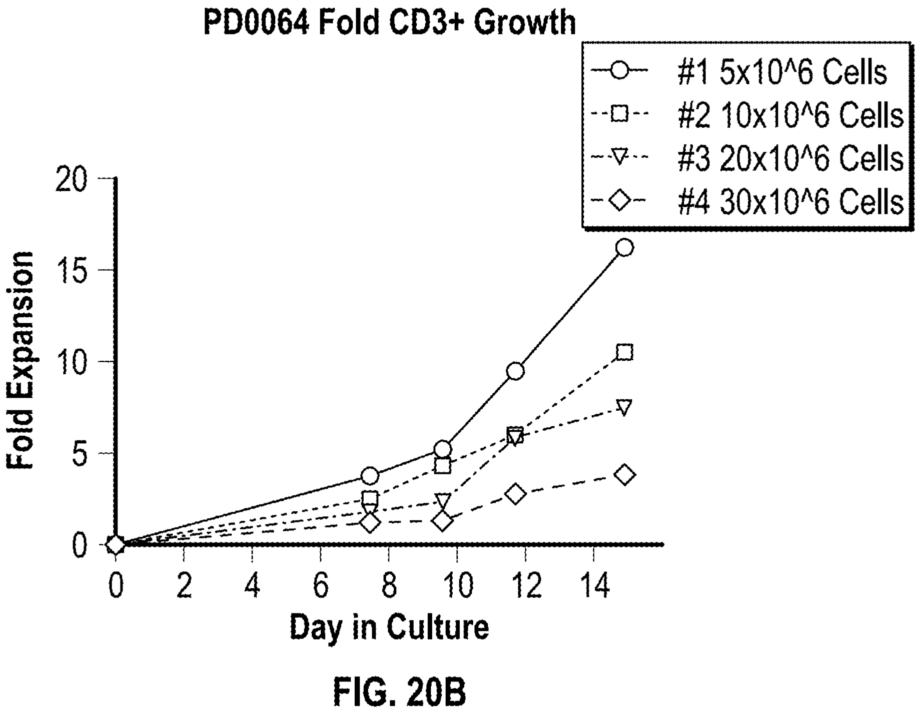
Figure 20C:
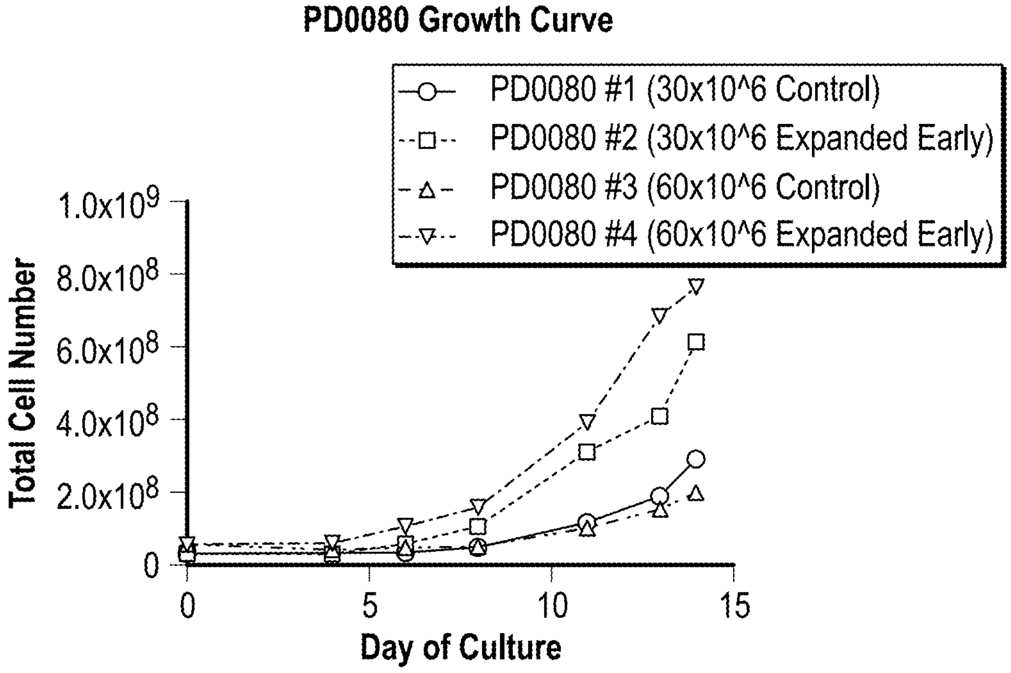
Figure 20D:
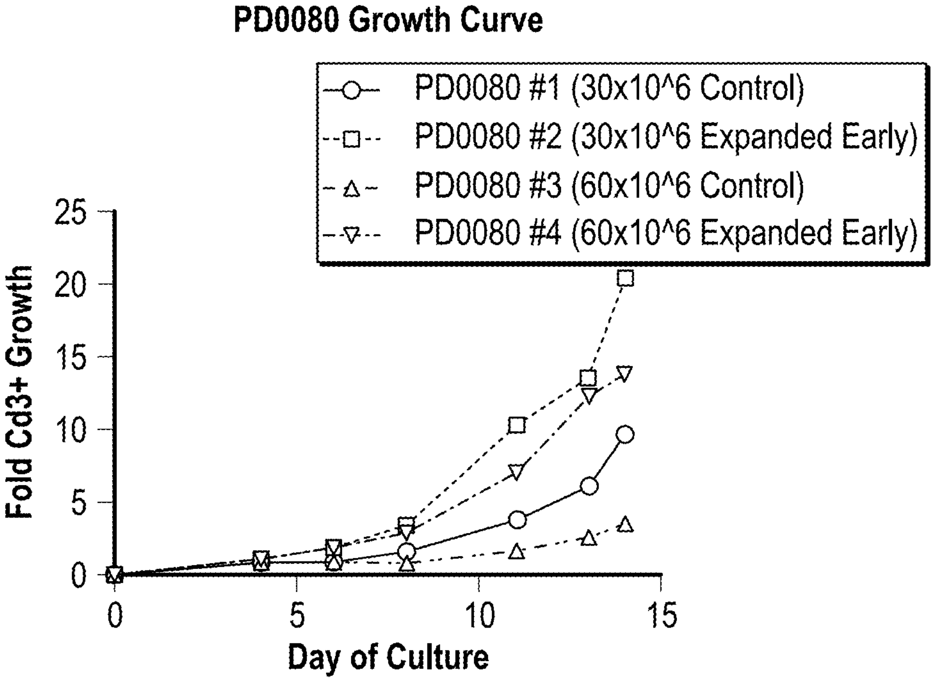
Figure 21A:
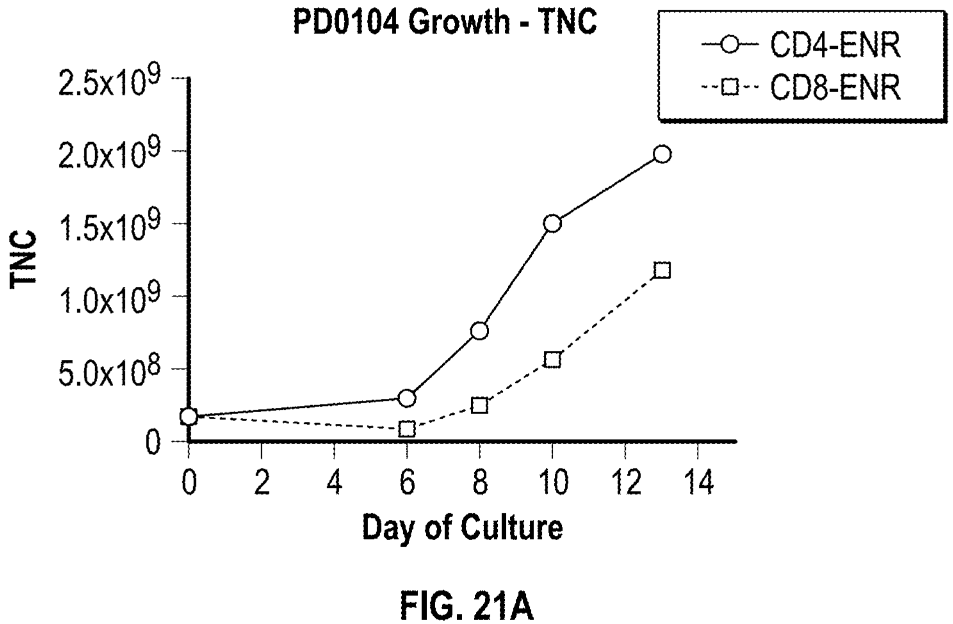
FIGS. 21A-D show an initiation comparison of cell growth. This was the full scale data used to transition to the update manufacturing process currently being used.
Figure 21B:
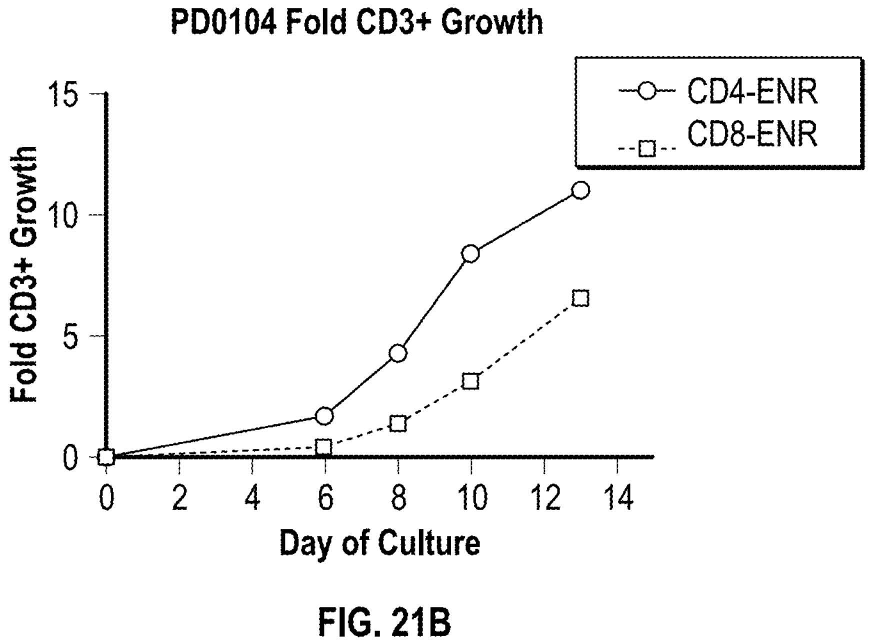
Figure 21C:
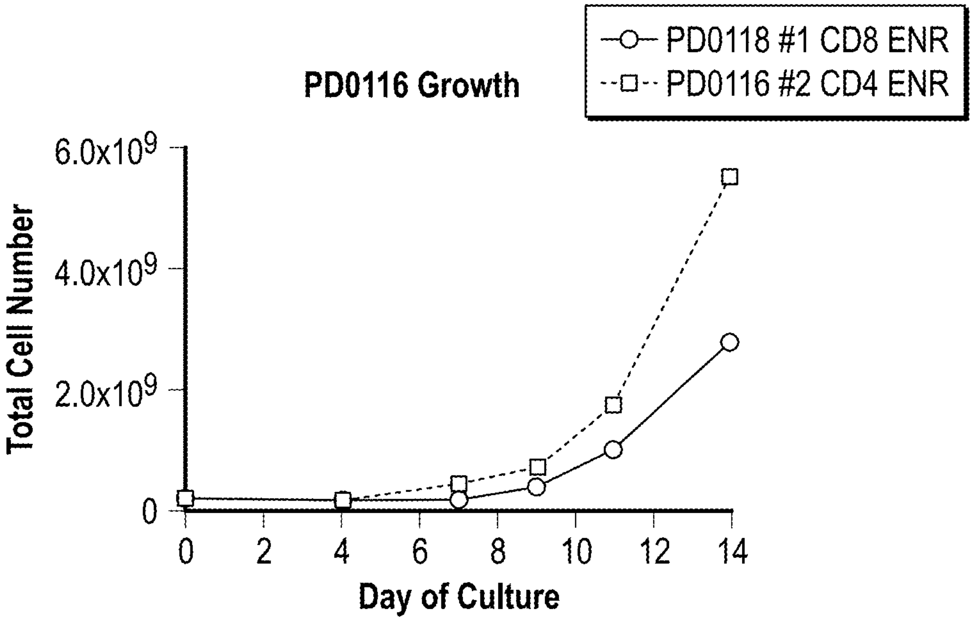
Figure 21D:
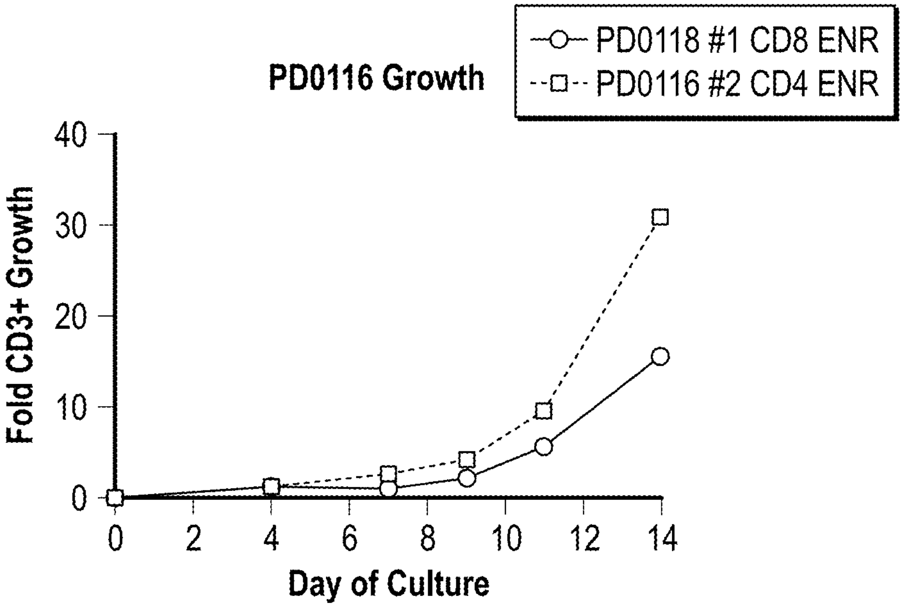

Shown in FIGS. 18A-B are a flow diagram depicting the development history of a process used to manufacture the genetically modified T-cell comprising a chimeric antigen receptor. As indicated, the current manufacturing procedure does not have the Ficoll processing, whereas initial experimental processes included a Ficoll processing step. The initial variations of cell concentrations were also tested as shown in the flow diagram of FIG. 19. Cells were also expanded in the presence of cytokines (FIGS. 20A-D).

As shown in FIGS. 20A-D, donor sample PD0064: PD0063 CD8+ enriched T-cells were used to test starting cell density in a T25 flask on initiation. Both cells (from PD0064, PD0063) were tested under normal PLAT-02 culture conditions, IL-2 (50 U/ml)+IL-15 (0.5 ng/mL). Cells from donor sample PD0080, were used in a study to test the expansion of cells on Tx day, by adding media and cytokines for a final cell concentration of to 0.7×10^6 cell/mL ("early expansion"). By "Tx" it is meant throughout to refer to Day+1, based on the day of stimulation beads being defined as Day+0. PD0063 CD8+ cells were used as the enriched starting material The same cytokine conditions were used as with the PD0064:PD0063 CD8+ enriched cells. The experiment tested two cell densities both showing greater viability and expansion when the cells were volumed up early in the presence of the cytokines. In this context "volume up" refers to the volume of media/cytokine addition for initial feeding following Tx was greater in the "early expansion" conditions, leading to decreased cell density at this point in culture for "early expansion" conditions.

As shown in FIGS. 21A-D, are the growth of cell samples PD104 and PD0116 and the comparison of cell growth under experimental conditions. PD0104: PD0063 CD8+ and CD4+ enriched cells were used to repeat previous experiments to test the expansion of cells on Tx day to $0.7\times10^{6}$ cell/mL ("early expansion"), with the following cytokines and respective concentrations being added: IL-2 (50 U/ml)+IL-15 (0.5 ng/mL) for CD8+ T-cells and IL-7 (5 ng/mL)+IL-15 (0.5 ng/mL) for CD4+ T-cells. Growth and viability were increased dramatically. These curves mimic what was seen in clinical products as far as timing of growth/bead removal/selection/cryopreservation.

The PD0116: PD0046 CD8+ and CD4+ enriched cells were used to repeat the experiment to test the expansion of cells on Tx day to 0.7×10^6 cell/mL ("early expansion"). Normal PLAT-02 culture conditions, IL-2 (50 U/ml)+IL-15 (0.5 ng/mL) for CD8 cells and IL-7 (5 ng/mL)+IL-15 (0.5 ng/mL) for CD4's. PD116 was initiated at 180×10^6 cells in a V-197 bag and magnetic enrichment and spinoculation were performed in a transfer pack. As shown, from these conditions, growth and viability were increased dramatically. These curves mimic what was seen in clinical products as far as timing of growth, bead removal, selection, and cryopreservation of T-cells.

Figure 22:
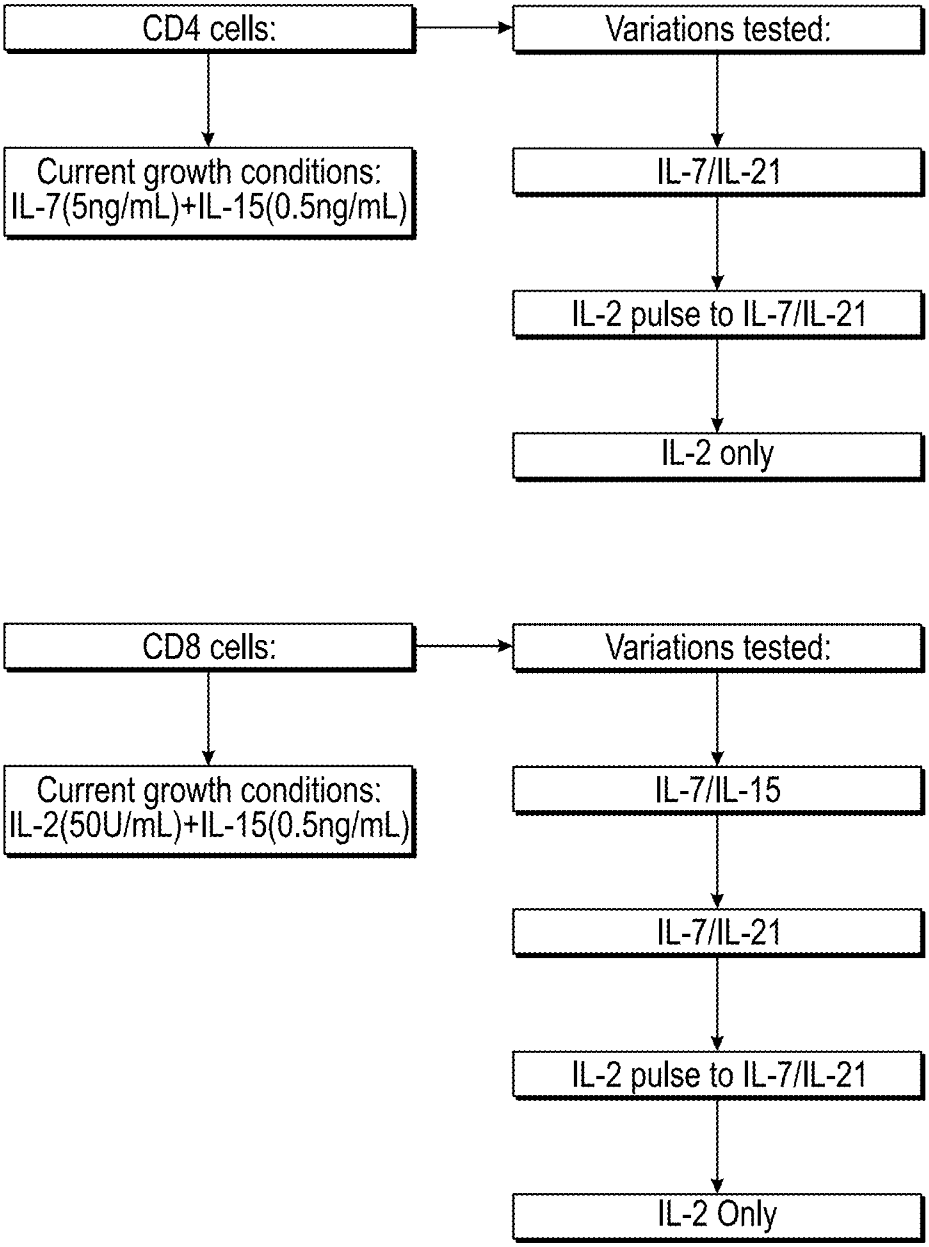
FIG. 22 shows a flow diagram illustrating the variations of cocktails of cytokines that were used to test CD4+ and CD8+ expressing T-cells for growth.
Figure 23A:
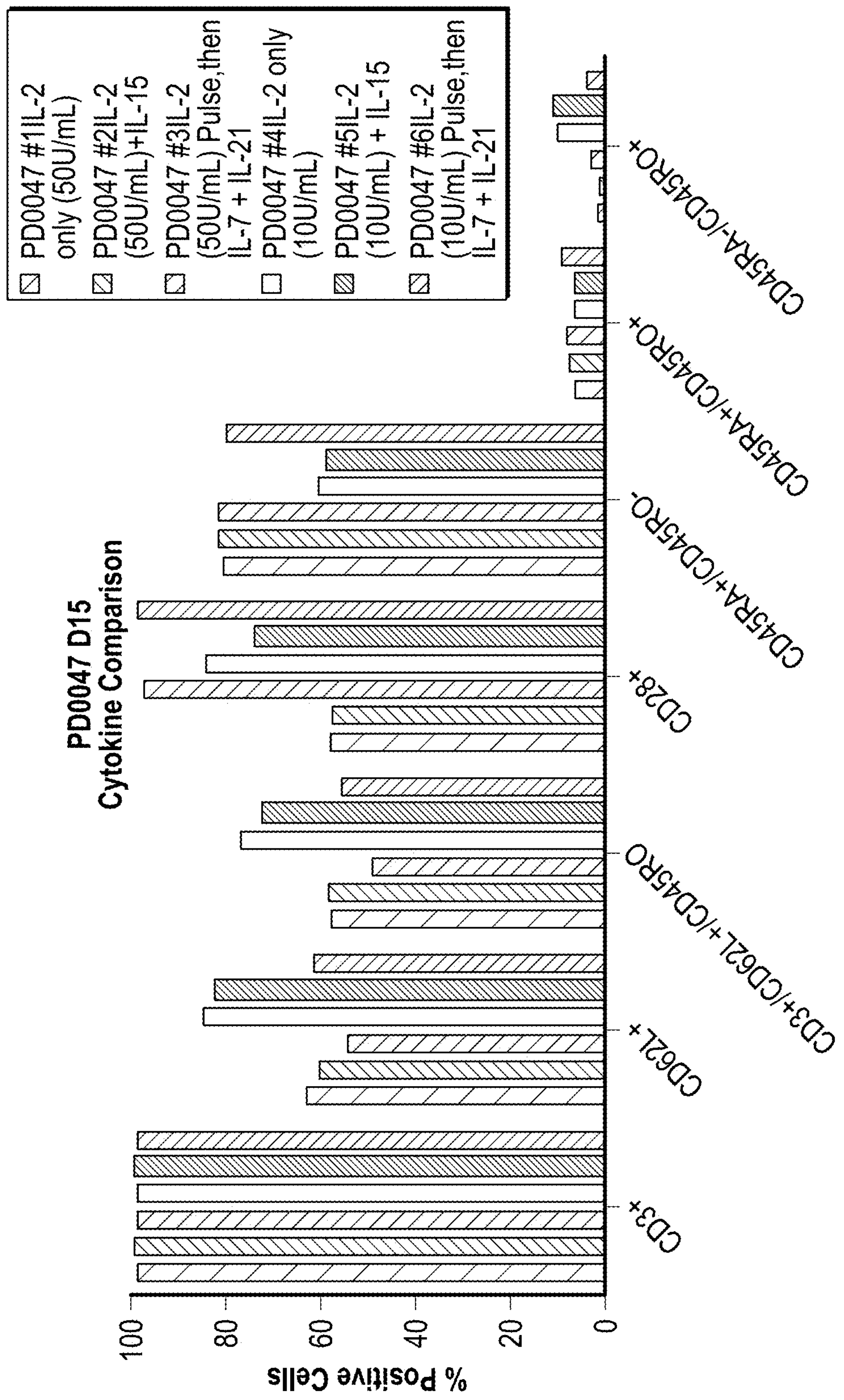
FIGS. 23A-F illustrate the comparison of cytokines that were tested during the growth of CD4+ and CD8+ expressing T-cells.
Figure 23B:
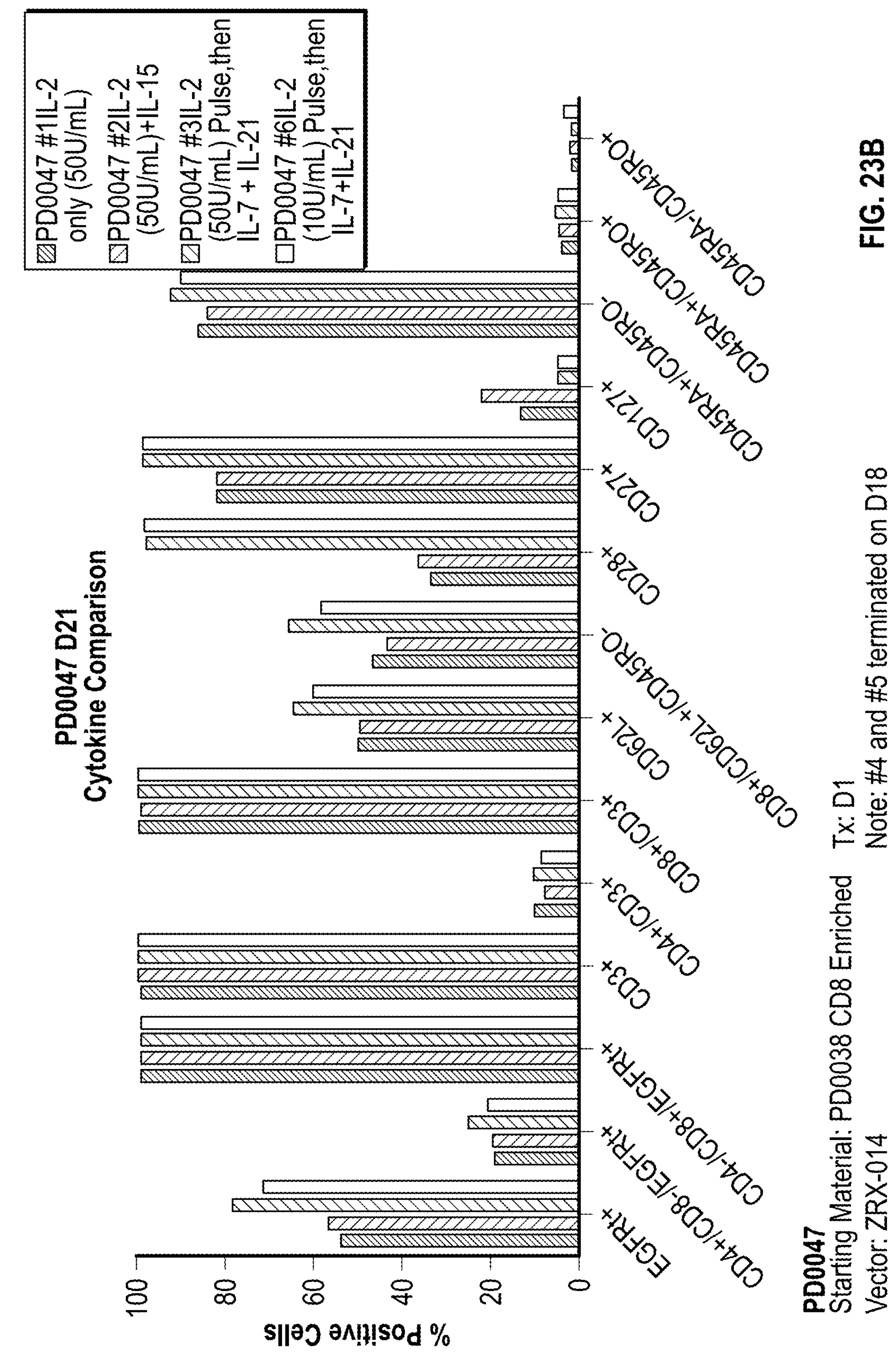
Figure 23C:
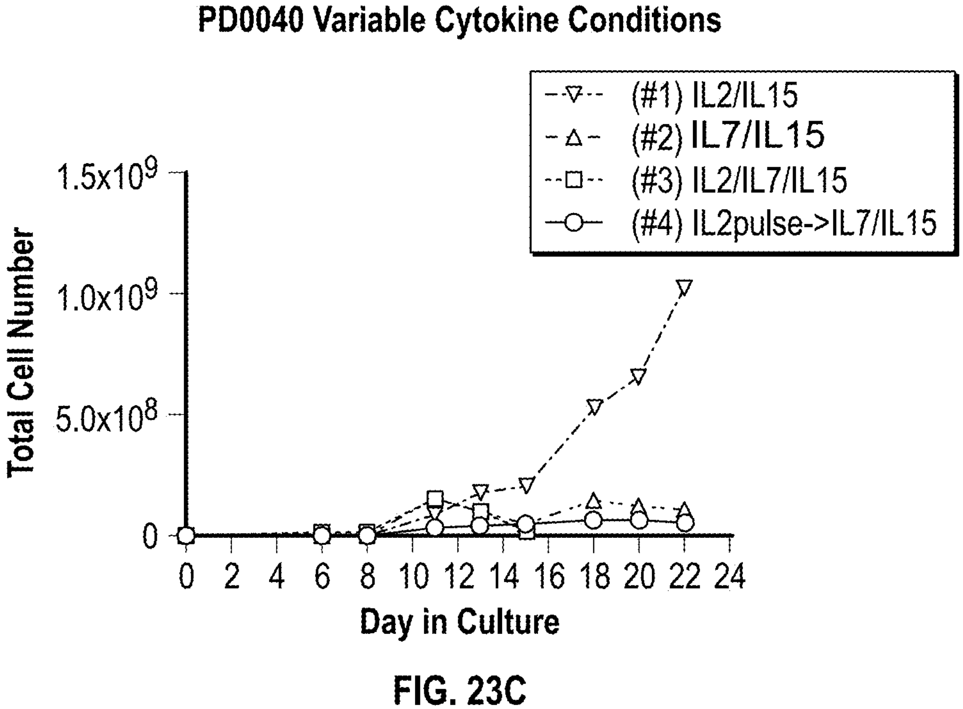
Figure 23D:
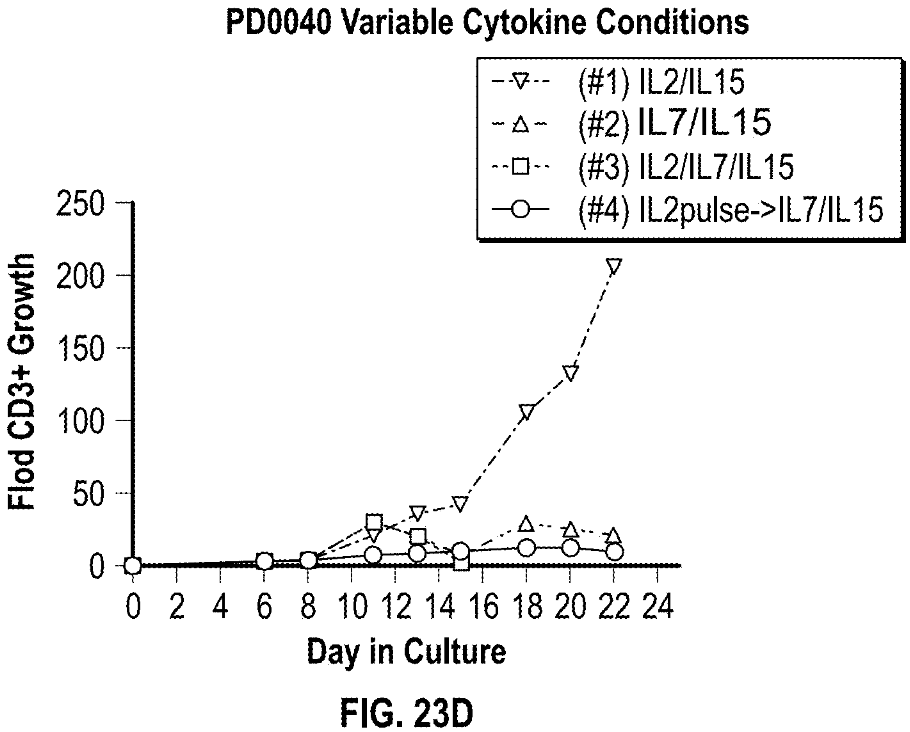
Figure 23E:
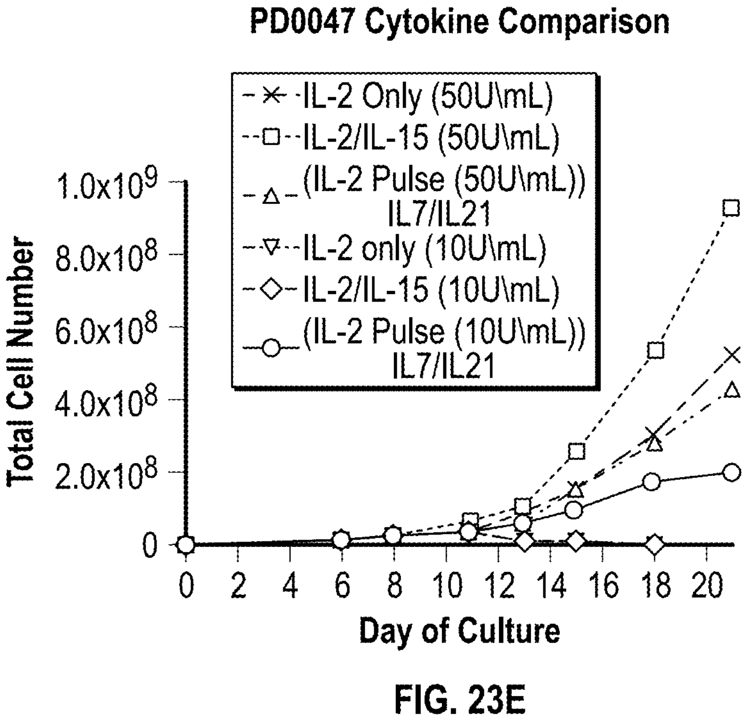
Figure 23F:
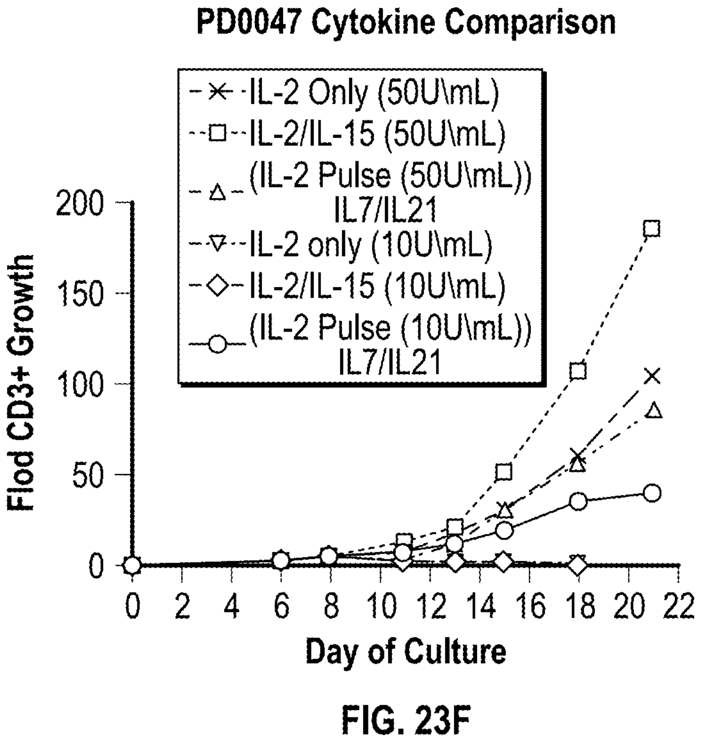
Figure 24A:
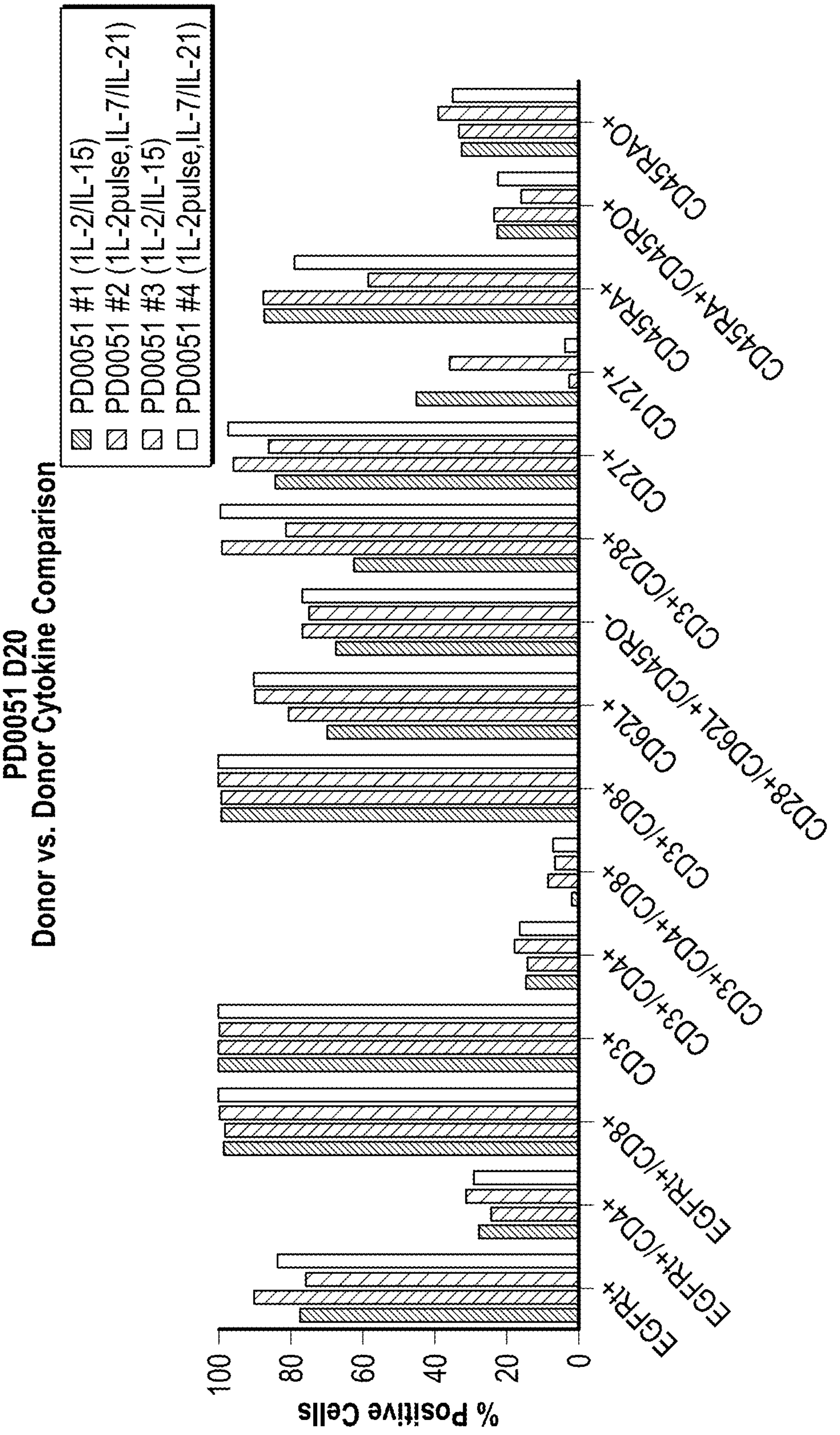
FIGS. 24A-F illustrate the comparison of cytokines that were tested during the growth of CD4+ and CD8+ expressing T-cells.
Figure 24B:
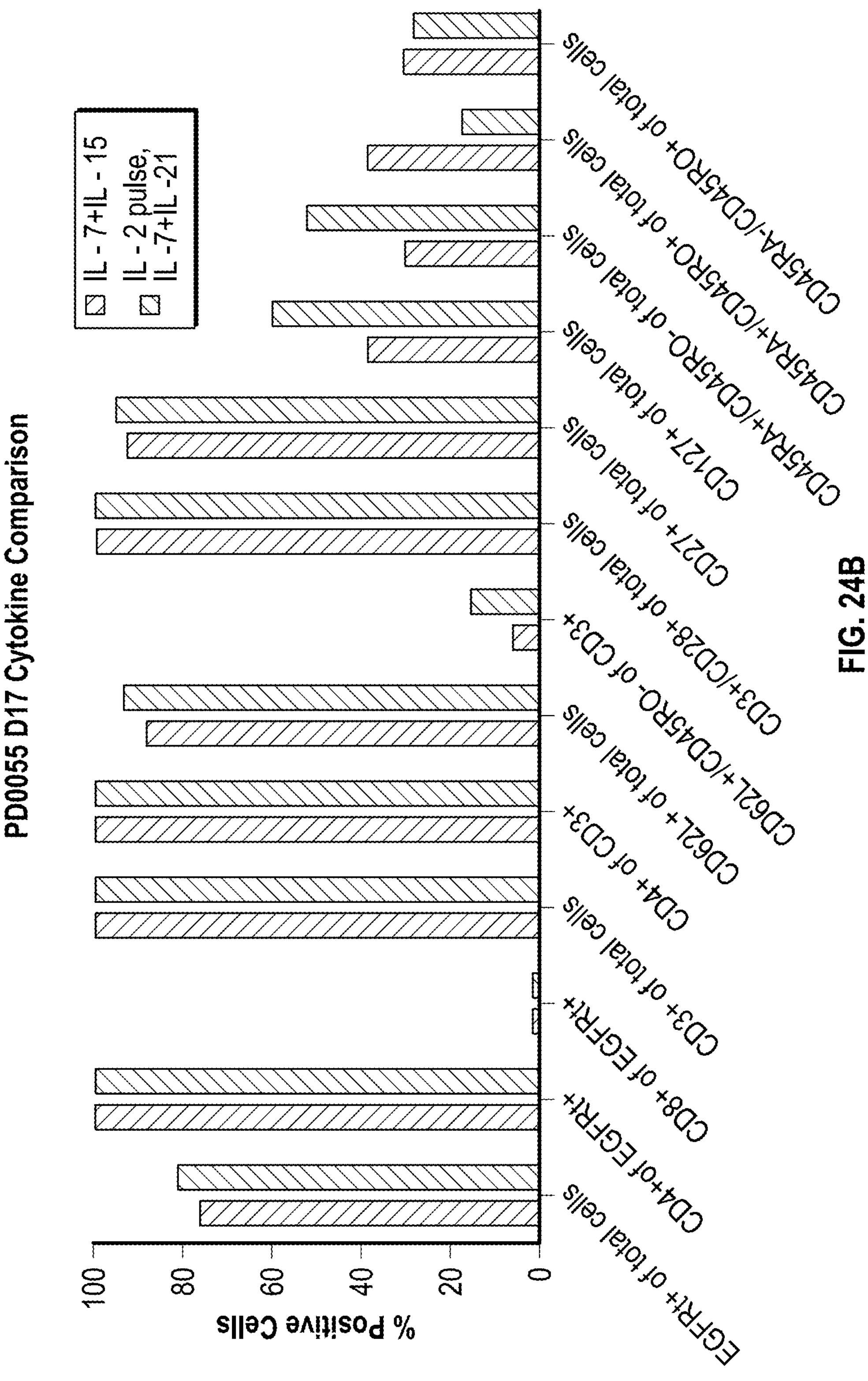
Figure 24C:
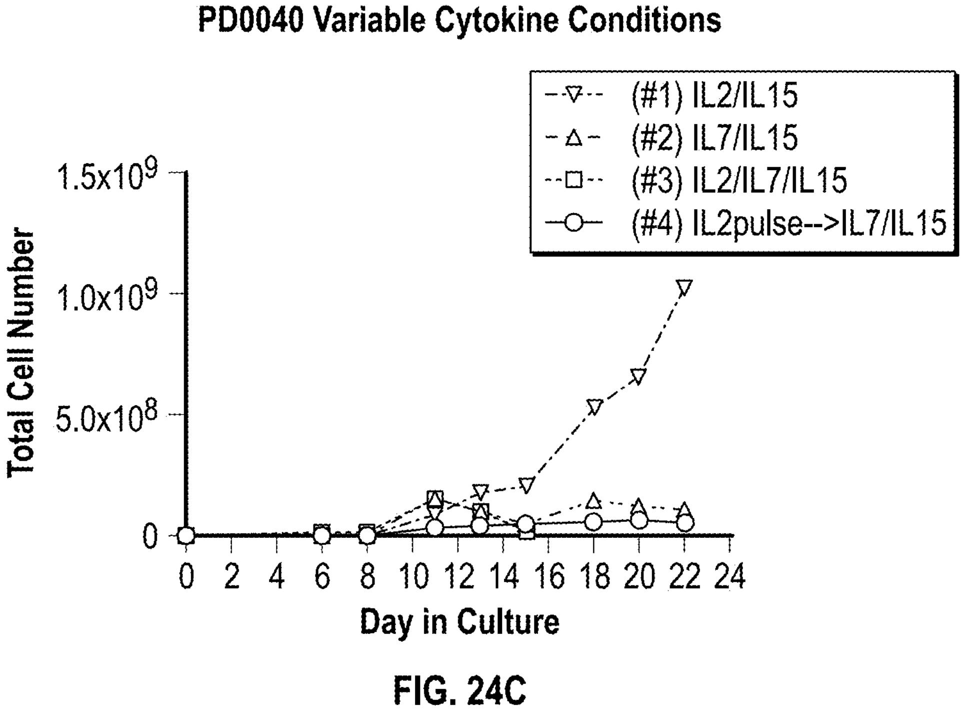
Figure 24D:
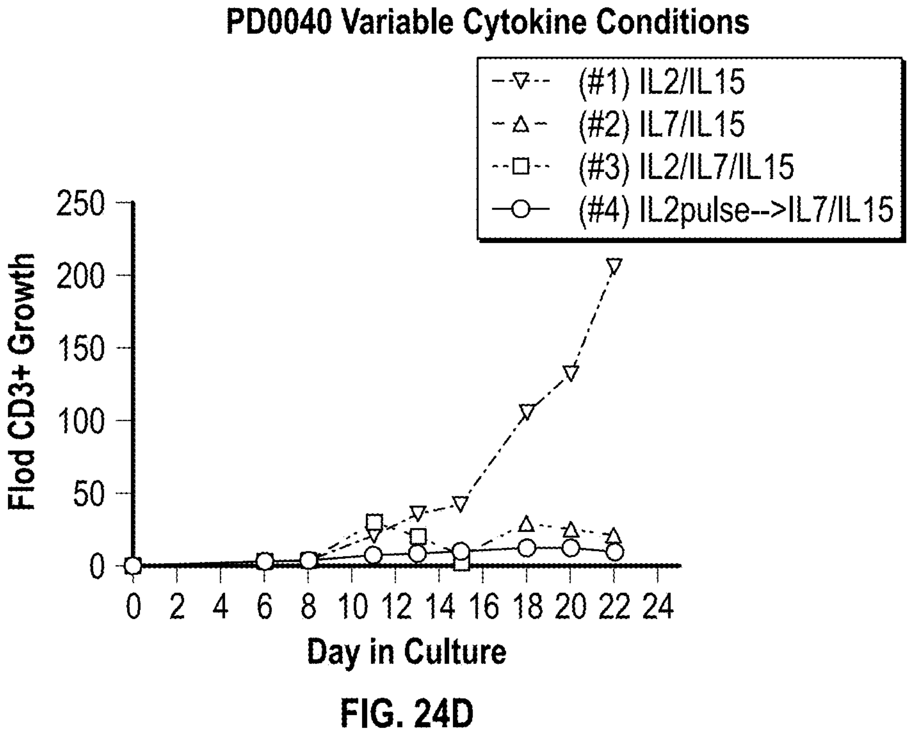
Figure 24E:
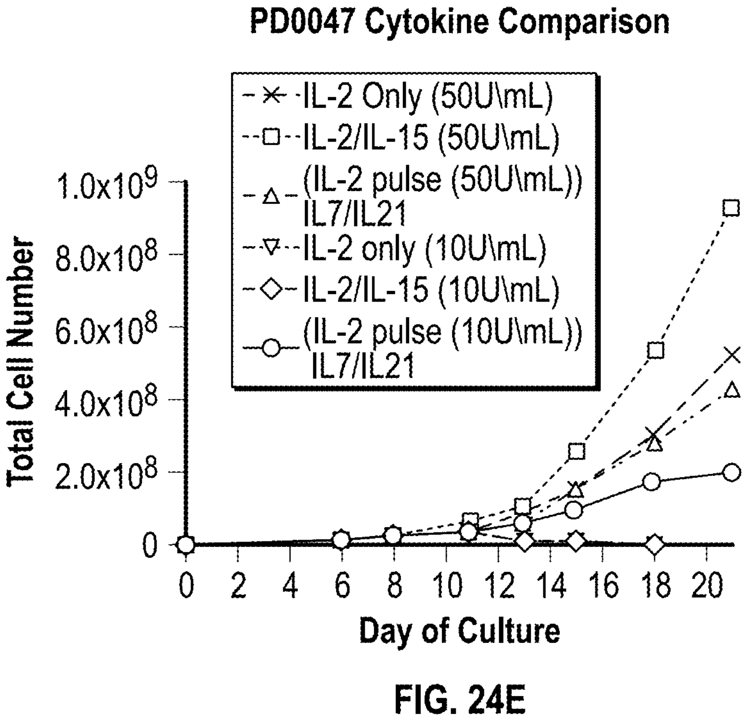
Figure 24F:
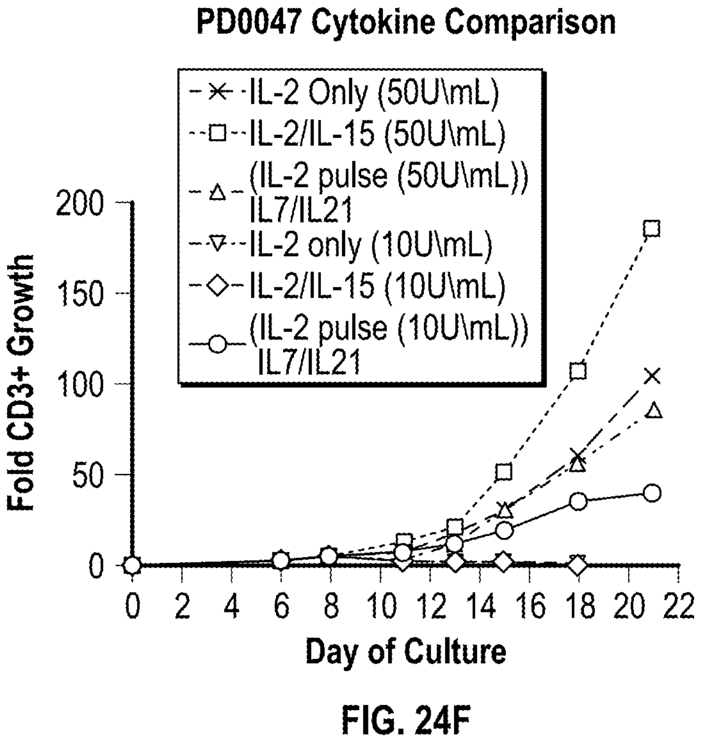

PD0116: PD0046 CD8+ and CD4+ enriched cells were also used to repeat an experiment to test the expansion of cells on Tx day by the addition of media and cytokines for a final volume of to $0.7\times10^{6}$ cell/mL ("early expansion"). Normal PLAT-02 culture conditions in which additions of IL-2 (50 U/ml)+IL-15 (0.5 ng/mL) for CD8 cells and IL-7 (5 ng/mL)+IL-15 (0.5 ng/mL) for CD4's was performed. PD116 was initiated at $180\times10^{6}$ cells in a V-197 bag and magnetic enrichment and spinoculation were performed in a transfer pack. This was the full scale data used to transition to an updated manufacturing process. As shown in FIGS. 21A-D, growth expansion was increased for CD8+ cells in comparison to the CD4+ cells. The cytokines used for the CD4_ and the CD8+ cells and the variations of the combinations of the cytokines used are depicted in a flow chart as shown in FIG. 22.

Various cytokine conditions were also tested on the CD8+ and the CD4+ cells from donors. As shown in FIG. 23-F, samples from PD0047 and PD0040 were tested with IL2/IL15, IL7/IL15, IL2/IL7/IL15, IL2 pulse with IL7/IL15, IL2 only, IL2 pulse with IL7/IL21 and IL2/IL15. This included incubation with IL-2 alone (pulse) for 5 days, followed by the addition of IL-7/IL-21, which then were present throughout the remainder of the culture, incubation with IL-2 alone (pulse) for 5 days, followed by the addition of IL-7/IL-21 and IL2/IL15, which then were present throughout the remainder of the culture. PD0040: PD0038 CD8+ enriched T-cells were used to test various cytokine cocktails. Concentrations for each condition were: IL-2 (50 U/mL), IL-7 (5 ng/mL), IL-15 (0.5 ng/mL). Condition #4 was an IL-2 pulse for 5 days followed by IL-7/IL-15 throughout the remainder of the culture. Fold growth and TNC were extrapolated from small scale experiment. Currently used IL-2/IL-15 combination showed best expansion. In this study, the IL-2/IL-15 combination was demonstrated to result in the best expansion.

As shown, the PD0047: PD0038 CD8+ enriched cells were used to test various cytokine cocktails. The same cytokine cocktails were tested using "low dose" IL-2 at 10 U/mL final. Concentrations of the individual cytokines used in the various combinations were: IL-2 (50 U/mL) and (10 U/mL) as stated in the legend, IL-7 (5 ng/mL), IL-15 (0.5 ng/mL), IL-21 (5 ng/mL). Pulse conditions were an IL-2 pulse for 5 days followed by IL-7/IL-21 throughout the remainder of the culture. Fold growth and TNC are extrapolated from a small scale experiment. The IL-2/IL-15 combination showed the best expansion and was used for following experimentations. The "normal" dose of IL-2 showed best growth. Panel A shows results from incubation of PD0047 cells at day 15 (D15) and the comparison of growth with various cytokines and the percent positive cells (CD3+, CD62L+, CD3+/CD62L+/CD45RO−, CD28+, CDD45RA+/CD4RO−, CD45RA+/CD45RO_ and CD45RA−/CD45RO+), following incubation with the various cytokine conditions.

Panel B shows results following incubation of PD0047 cells at day 21 (D21) and the comparison of growth with various cytokines and the percent positive cells as indicated above. Panel C shows PD0040 D21 and the comparison of growth with various cytokines, in which the total cell number is examined after 22 days of growth in culture. Panel D shows PD0040 D21 and the comparison of growth with various cytokines, as indicated the CD3+ cell growth is examined after 22 day of culture growth. Panel E shows PD0047 and the comparison of growth with various cytokines, in which the total cell number is examined after 22 days of growth in culture. Panel F shows PD0047 and the comparison of growth with various cytokines, as indicated the CD3+ cell growth is examined after 22 day of culture growth. As shown for PD0040: PD0038 CD8+ enriched cells, were used to test various cytokine cocktails. Concentrations for each condition were: IL-2 (50 U/mL), IL-7 (5 ng/mL), IL-15 (0.5 ng/mL). Condition #4 was an IL-2 pulse for 5 days followed by IL-7/IL-15 throughout the remainder of the culture. Fold growth and TNC were extrapolated from small scale experiments. IL-2/IL-15 combination showed the best expansion and was used for future experiments. Additionally, PD0047: PD0038 CD8+ enriched cells were used to test various cytokine cocktails. The same cytokine cocktails were tested using "low dose" IL-2 at 10 U/mL final. Concentrations for each condition were: IL-2 (50 U/mL) and (10 U/mL) stated in legend, IL-7 (5 ng/mL), IL-15 (0.5 ng/mL), IL-21 (5 ng/mL). Pulse conditions were an IL-2 pulse for 5 days followed by IL-7/IL-21 throughout the remainder of the culture. Fold growth and TNC were then extrapolated from small scale experiments. The IL-2/IL-15 cytokine combination used in the study described above showed the best expansion. The "normal" dose of IL-2 also showed the best growth. Flow cytometry for phenotypic growth is available and indicated in further experiments herein.

Shown in FIGS. 24A-F, are results from a series of experiments to test the different combination of cytokines. PD0051: CD8+ cells from two different donors were used to test the "normal" cytokine conditions using IL-2 (50 U/mL) and IL-15 (0.5 ng/mL) were used. Pulse conditions were an IL-2 pulse for 5 days followed by IL-7 (5 ng/mL), IL-21 (5 ng/mL), throughout the remainder of the culture. Fold growth and TNC that are shown, are from a scaled experiment that started with 30×10ˆ6 cells. The currently used IL-2/IL-15 combination showed the best expansion, but expansion was also seen from the cultures pulsed with IL-2 and switched to IL-7/IL-21. Fold expansion was similar in the pulsed conditions to PD0047.

For PD0055, the same cytokine conditions were tested as those assessed for PD0051 but with CD4+ donor cells (same donor PD0038 as above). Cytokine conditions were IL-7 (5 ng/mL) and IL-15 (0.5 ng/mL) for the experiments. Pulse conditions were an IL-2 pulse for 5 days followed by IL-7 (5 ng/mL), IL-21 (5 ng/mL), throughout the remainder of the culture. Fold growth and TNC are from a scaled experiment that started with 30×10ˆ6 cells. The currently used IL-7/IL-15 combination showed the usual expansion, however better expansion was seen from the cultures pulsed with IL-2 and switched to IL-7/IL-21. Panel A shows PD0051 at day 15 (D15) and the comparison of growth with various cytokines and the percent positive cells (EGFRt+, EGFRt+/CD4+, EGFRt+/CD8+, CD3+, CD3+/CD4+, CD3+/CD4+/CD8+, CD3+/CD8+, CD62L+, CD3+/CD8+, CD62L+, CD3+/CD28+, CD27+, CD127+, CD45RA+/CD45RO−, CD45RA+/CD45RO_/CD45RO_/CD45RA−, CD62+/CD28+) in a donor versus donor cytokine comparison. Panel B shows PD0055 at day 17 (D17) and the comparison of growth with various cytokines and the percent positive cells. Panel C shows the PD0051 growth curve and the comparison of growth with various cytokines, in which the total cell number is examined after 20 days of growth in culture. Panel D shows PD0051 and the comparison of growth with various cytokines, as indicated the CD3+ cell growth is examined after 20 days of culture growth. Panels C and D show a growth curves (total cells and CD3+) for PD0051, comparing growth following incubation of the cells with the indicated various cytokines, through 20 days in culture. Panel E and F shows growth curves (total cells and CD3+ respectively) for donor PD0055 following incubation with the indicated various cytokines, at the indicated time point at day 17 of growth in culture.

Figure 1B:
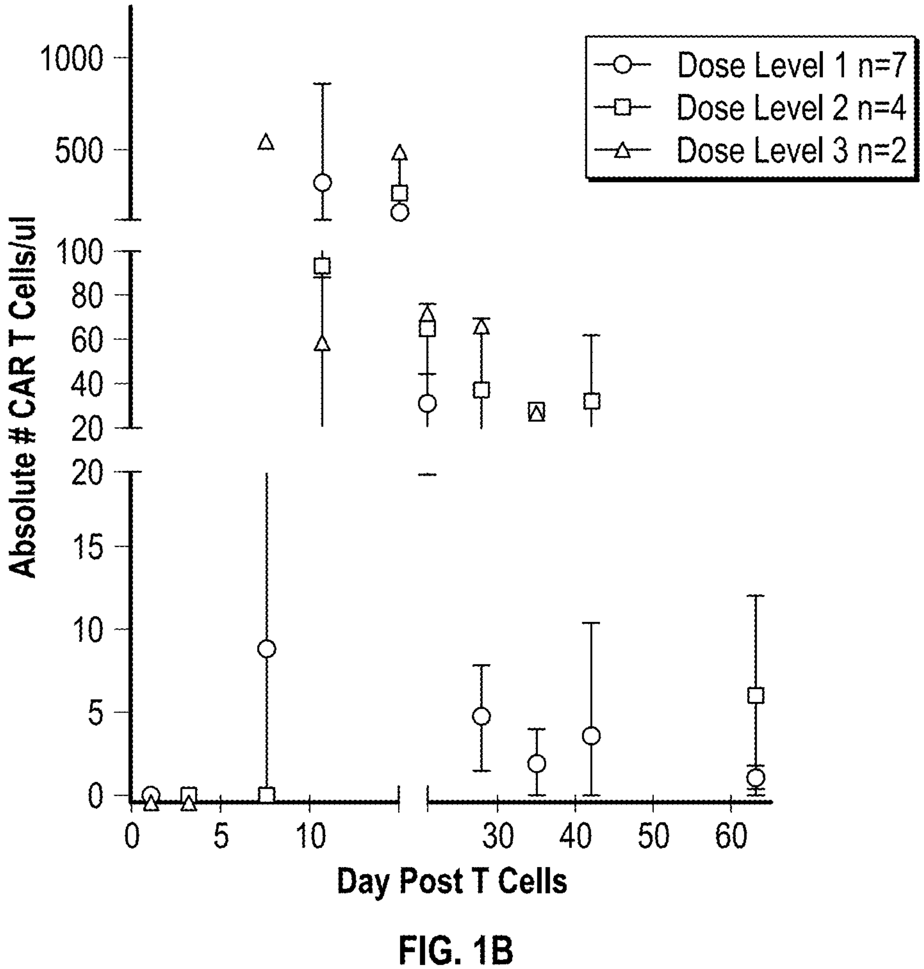
FIG. 1B shows the absolute number of anti-CD19 CAR bearing T-cells following three doses of treatment.
Figure 2A:
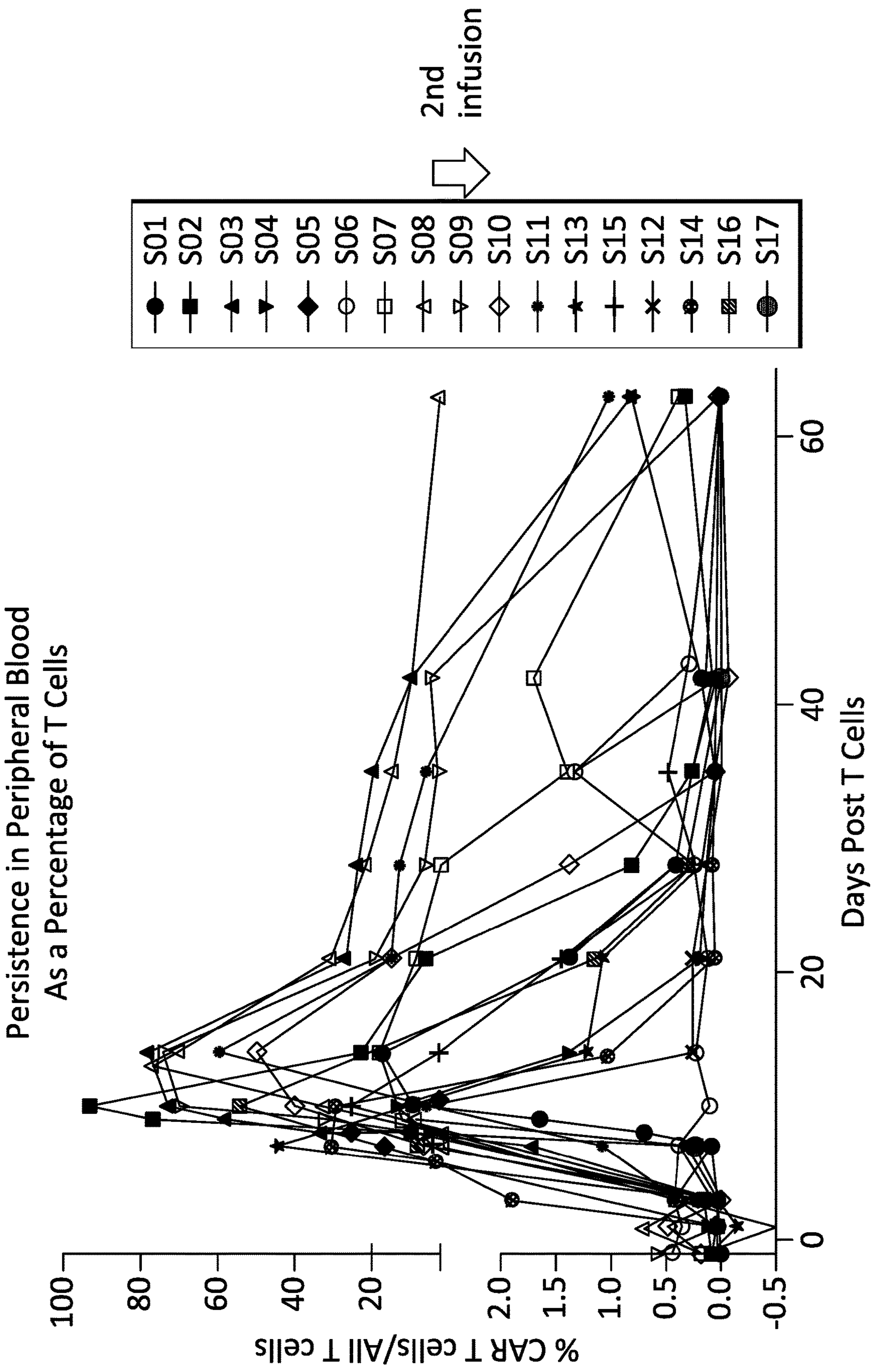
FIG. 2A shows the persistence of anti-CD19 CAR bearing T-cells in peripheral blood of patients following adoptive transfer of the CAR bearing T-cells from Day 0 to Day 65.
Figure 2B:
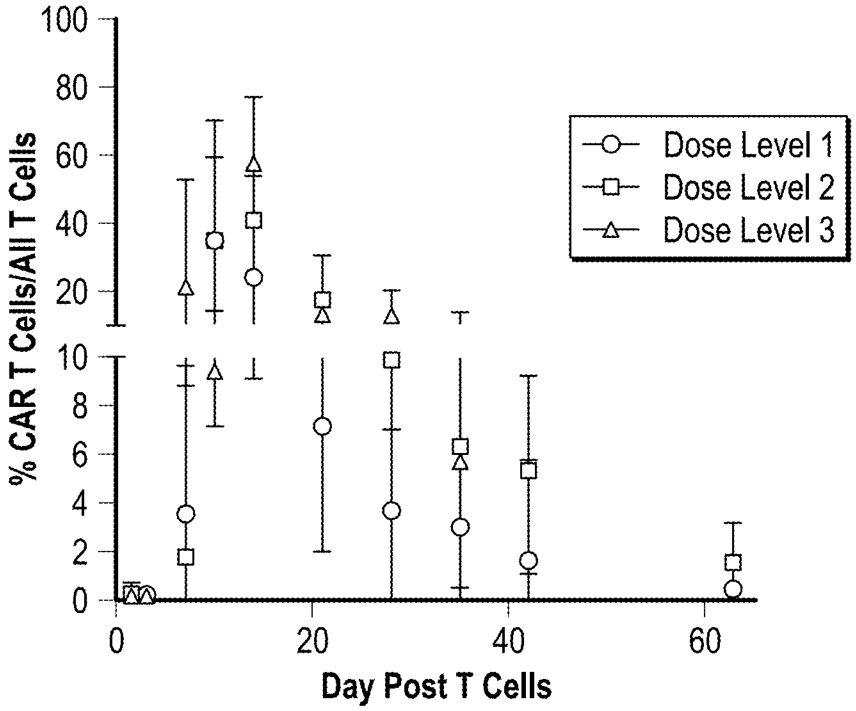
FIG. 2B shows the persistence of anti-CD19 car bearing T-cells following three doses of treatment.
Figure 25A:
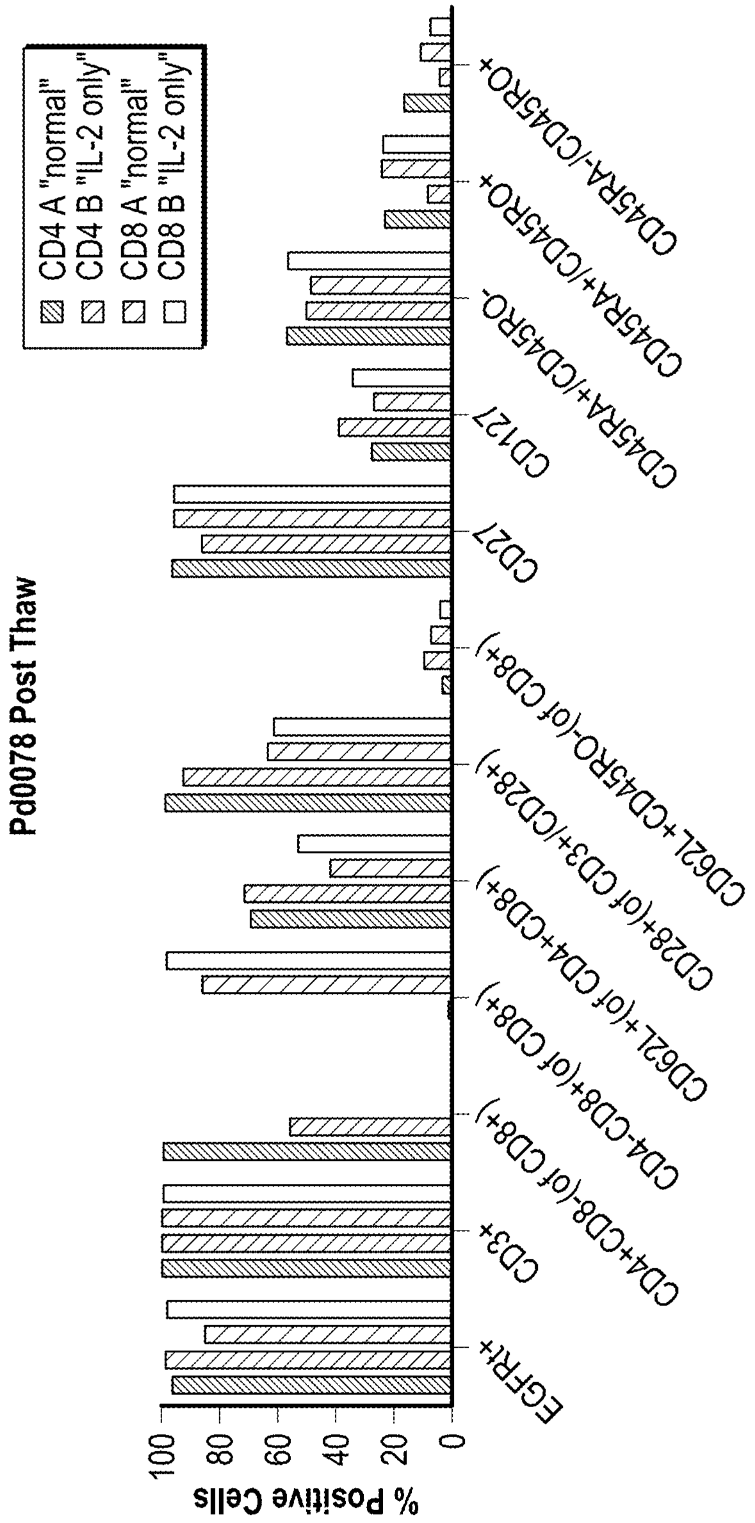

Shown in FIGS. 25A, 25B1-B4, is a cytokine testing experiment in which different combinations of cytokines were evaluated for their influence on cell expansion. For sample PD0059, the same cytokine testing experiment as shown for PD0051 was performed except that this experiment involved testing a new CD4+ and CD8+ donor (PD0057). Testing the "normal" cytokine conditions using IL-7 (5 ng/mL) and IL-15 (0.5 ng/mL) for CD4's and IL-2 (50 U/mL) and IL-15 (0.5 ng/mL) for CD8+ cells were performed. Pulse conditions were an IL-2 pulse for 5 days followed by IL-7 (5 ng/mL), IL-21 (5 ng/mL), throughout the remainder of the culture. Fold growth and TNC are from a scaled experiment that started with $30\times10^6$ cells. The "normal" cytokine combinations in this study resulted in expansion; good expansion was seen following pulsing with IL-2 and switching to IL-7/IL-21.

For PD0078, a similar cytokine study was performed as in PD0051, except that the experiment was performed with a different CD4+ and CD8+ donor (PD0063). The test was performed using "normal" cytokine conditions using IL-7 (5 ng/mL) and IL-15 (0.5 ng/mL) for CD4's and IL-2 (50 U/mL) and IL-15 (0.5 ng/mL) for CD8's versus an IL-2 only condition. All growth through day 14 (D+14) was on a normal plane, cultures were then EGFRt selected. Recovery of viability and growth was not seen following selection for the CD8+ cells. As shown in Panel A, are the percent of positive cells after thawing the cells. Panel B shows the PD0059 PLAT-02 cytokine comparison. Panel C shows PD0059 PLAT-02 cytokine comparison and the CD3+ cell growth. Panel D shows the PD0078 growth curves. Panel D shows the PD0078 growth curves and the CD3+ cell growth.

Figure 26:
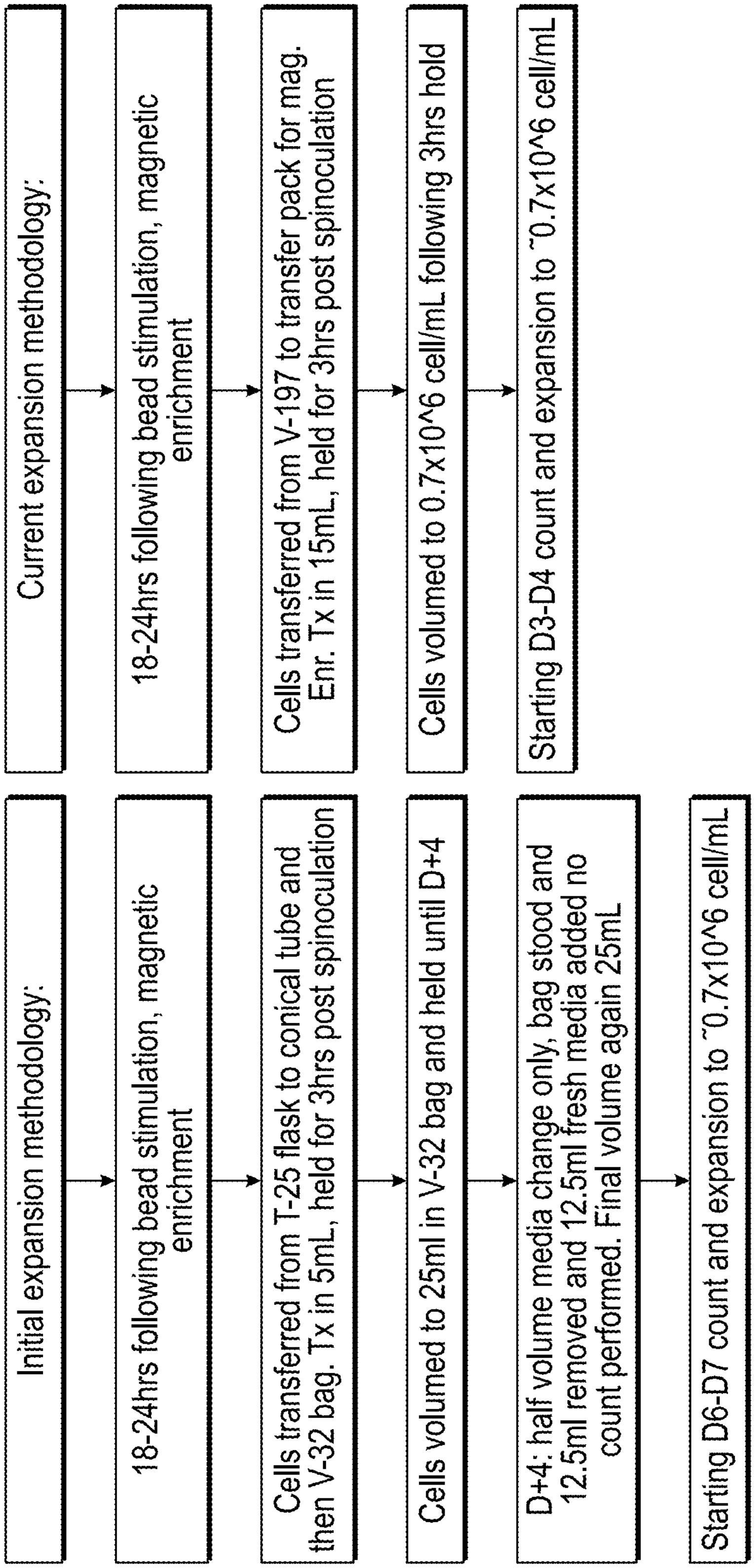
FIG. 26 shows a flow diagram illustrating the initial expansion methodology and the current expansion methodology derived from the experimentation of testing different cytokine mixtures.

Shown in FIG. 26, are two flow charts illustrating an initial expansion methodology and the updated (or "current") expansion methodology of cell expansion based on experimentation, which was then used for future experimentations.

Figure 3A:
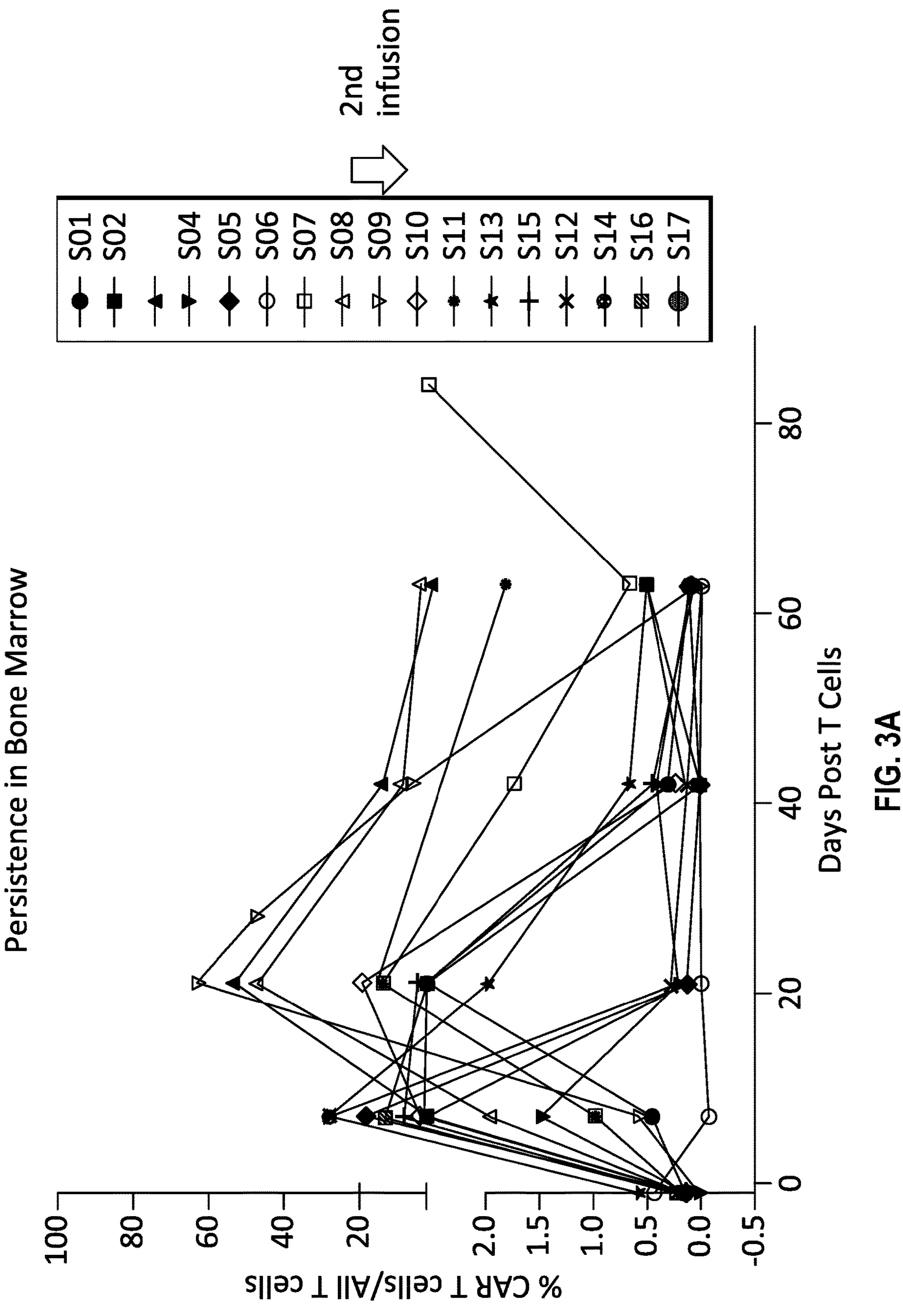
FIG. 3A shows the persistence of anti-CD19 CAR bearing T-cells in bone marrow of patients following adoptive transfer of the CAR bearing T-cells from Day 0 to Day 65.
Figure 3B:
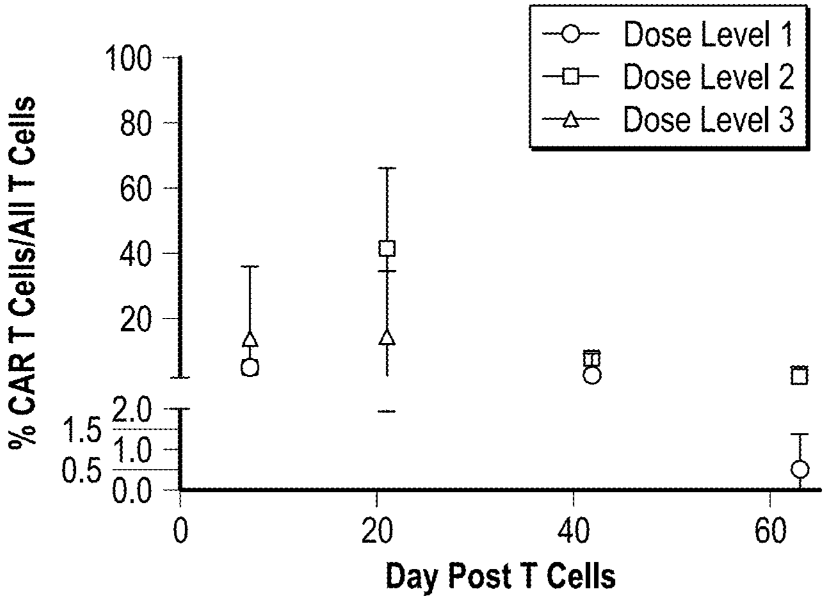
FIG. 3B shows the persistence of anti-CD19 CAR bearing T-cells in bone marrow patients following three doses of treatment.
Figure 4:
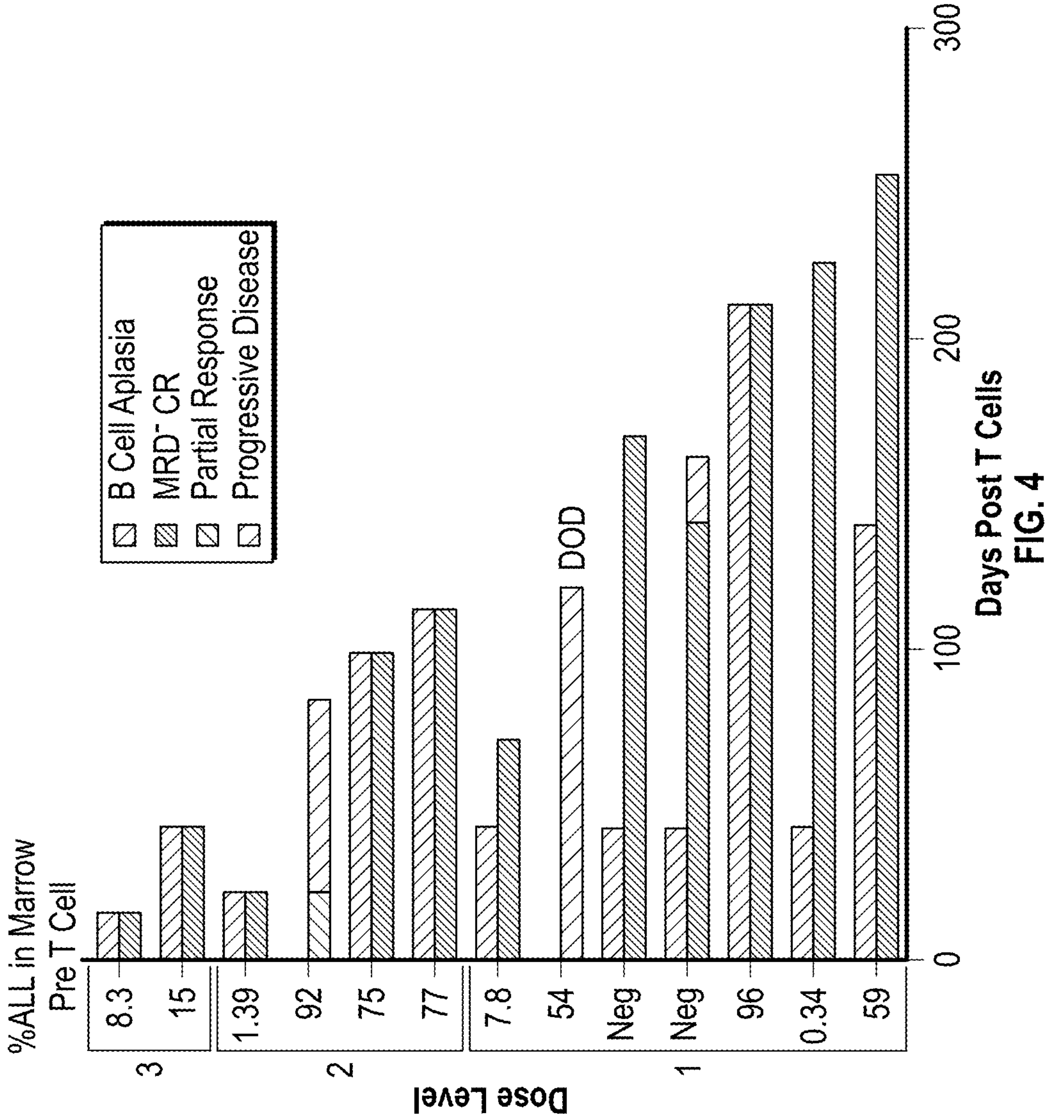
FIG. 4 shows the percent acute lymphoblastic leukemia (ALL) in patient X following three doses.
Figure 6A:
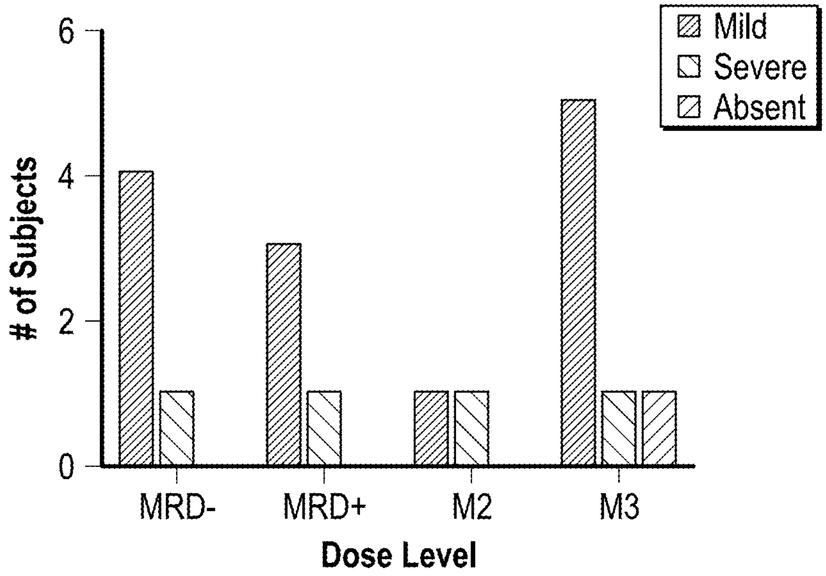
FIGS. 6A-B show the development of CNS lymphoma, as related to disease and dosage.
Figure 6B:
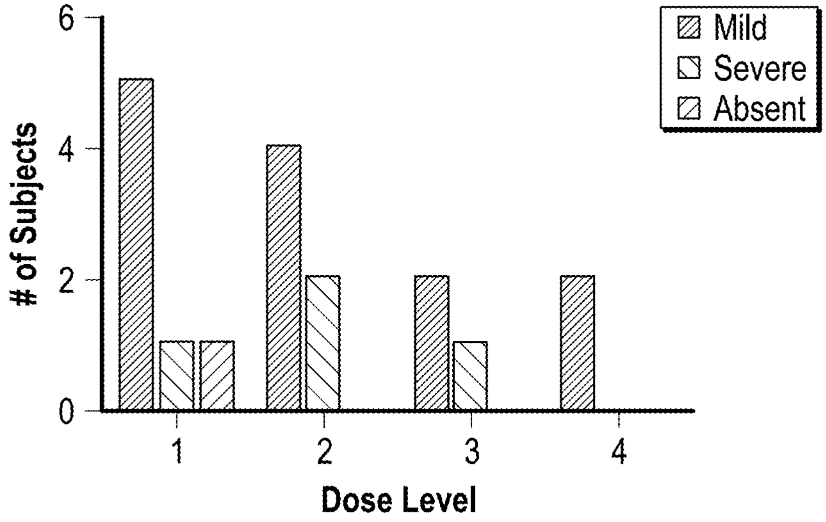
Figure 7A:
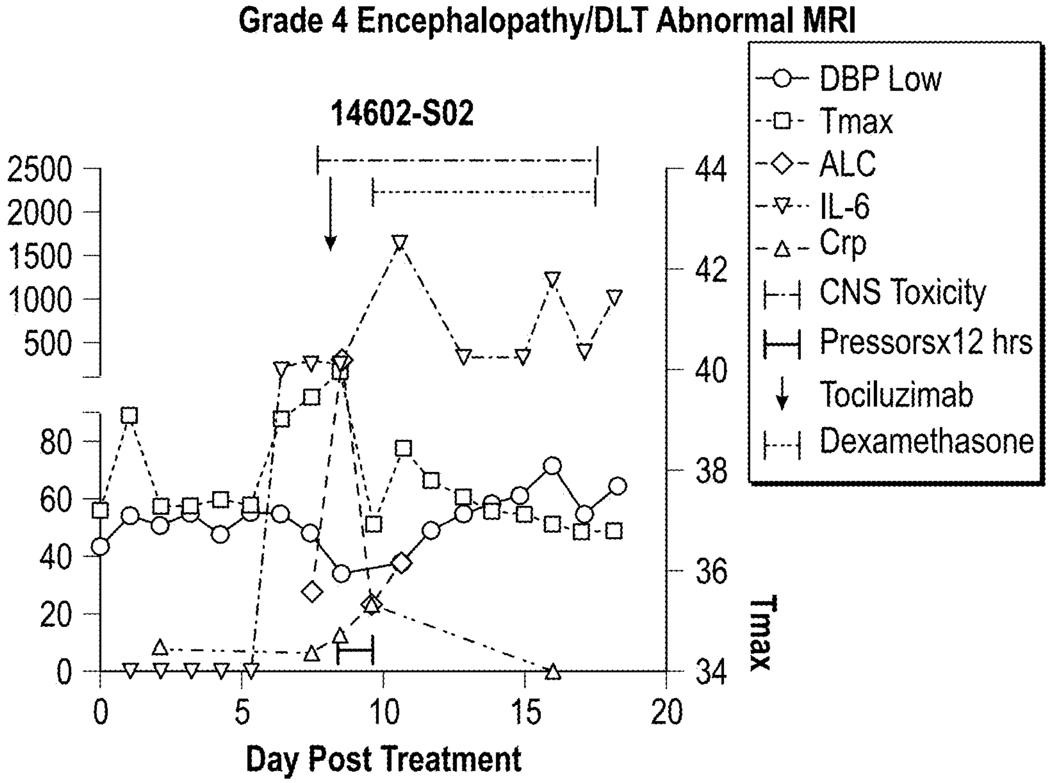
FIGS. 7A-B show grade 4 encephalopathy in an abnormal MRI of a patient suffering from ALL.
Figure 7B:
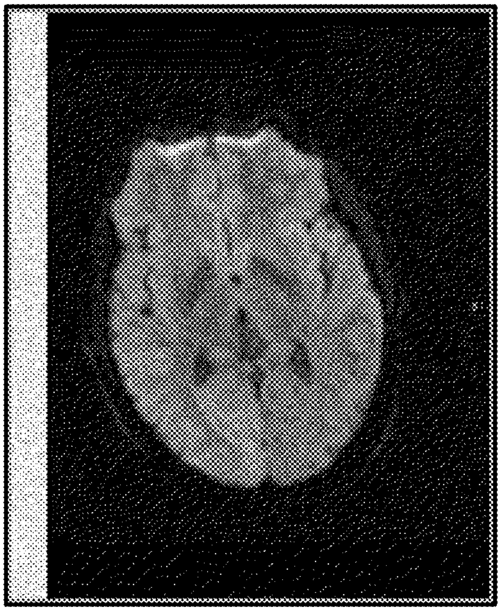
Figure 8A:
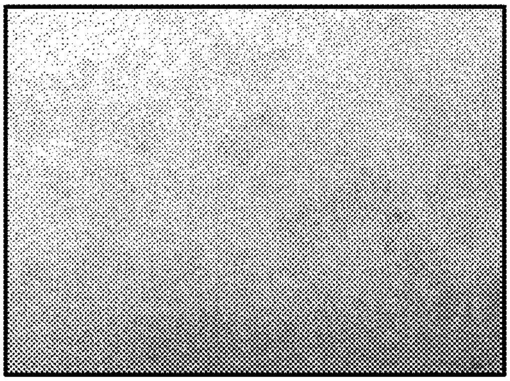
FIGS. 8A-8C shows acute Skin Graft-versus-host disease (GVHD) following treatment with anti-CD19 CAR bearing T-cells.
Figure 8B:
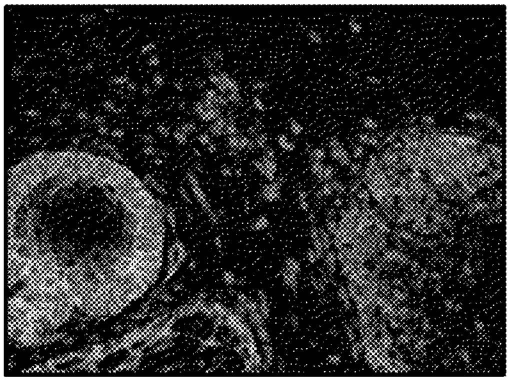
Figure 8C:
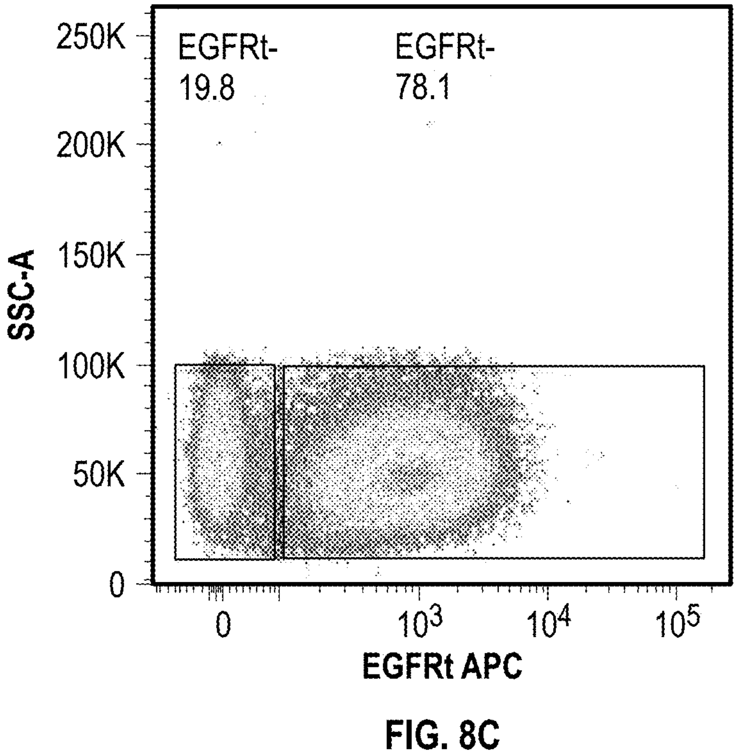
Figure 11A:
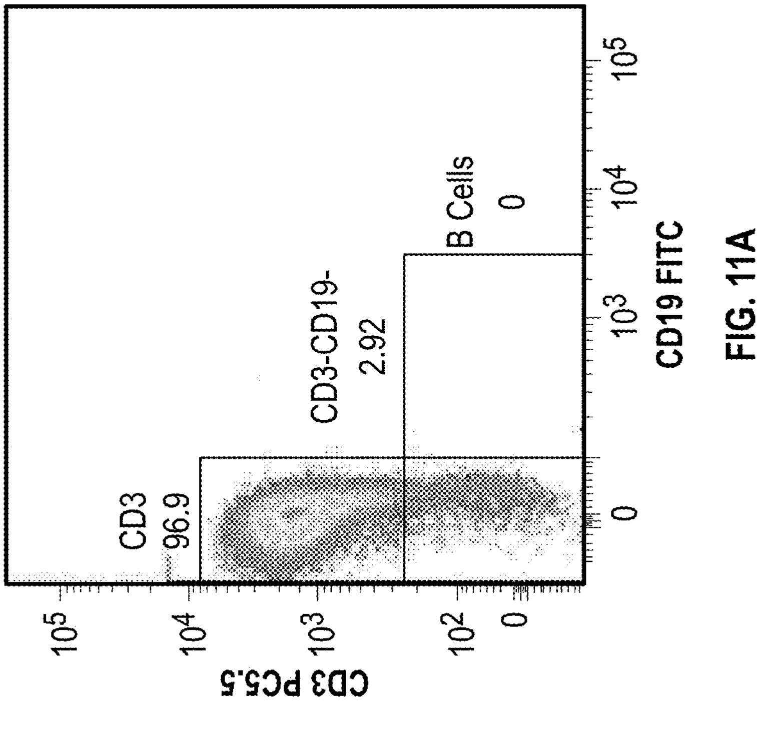
FIGS. 11A-G show the FACS scatter analysis of the cells isolated from the peripheral blood and CSF following hematopoietic stem cell transplantation (HSCT) of anti-CD19 CAR T-cells.
Figure 11B:
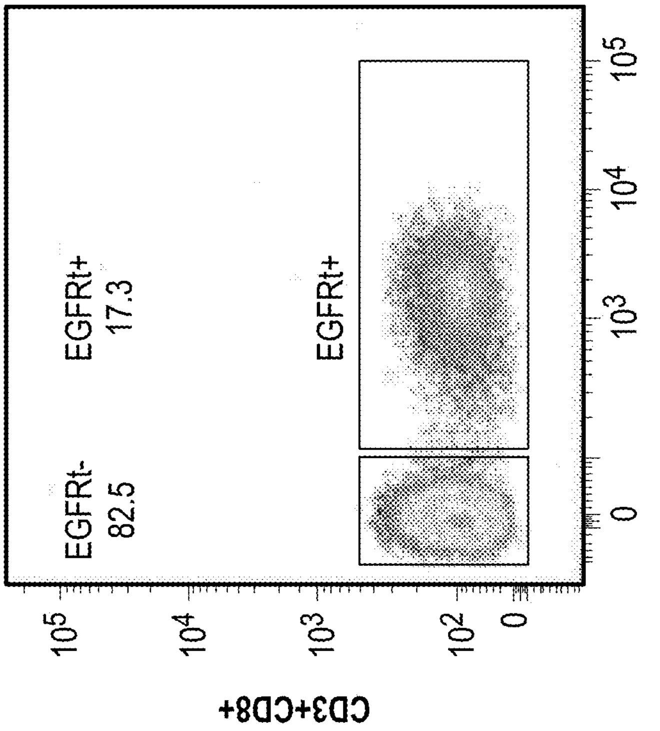
Figure 11C:
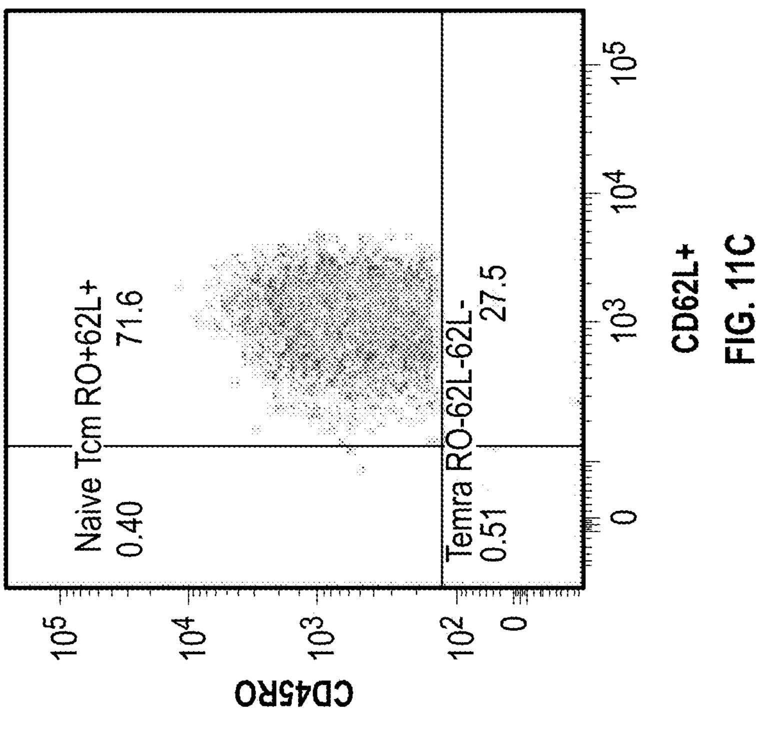
Figure 11D:
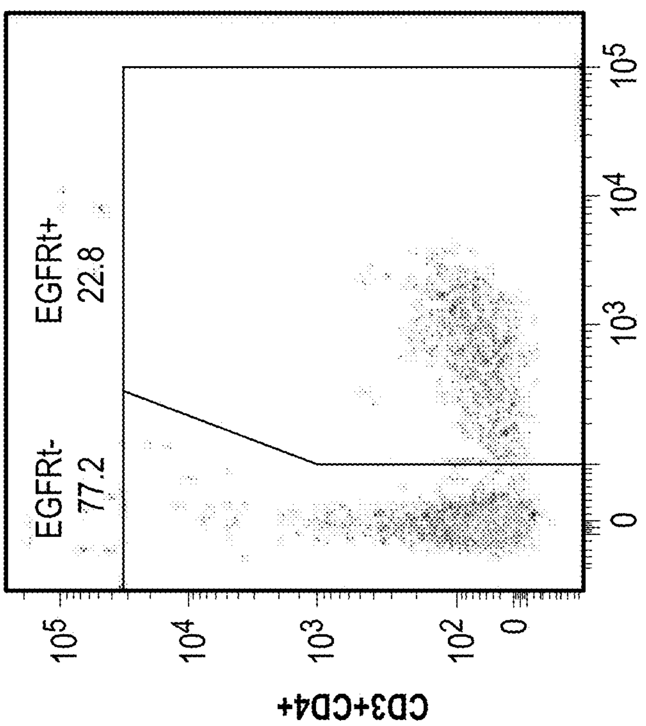
Figures 11E, 11F, 11G:
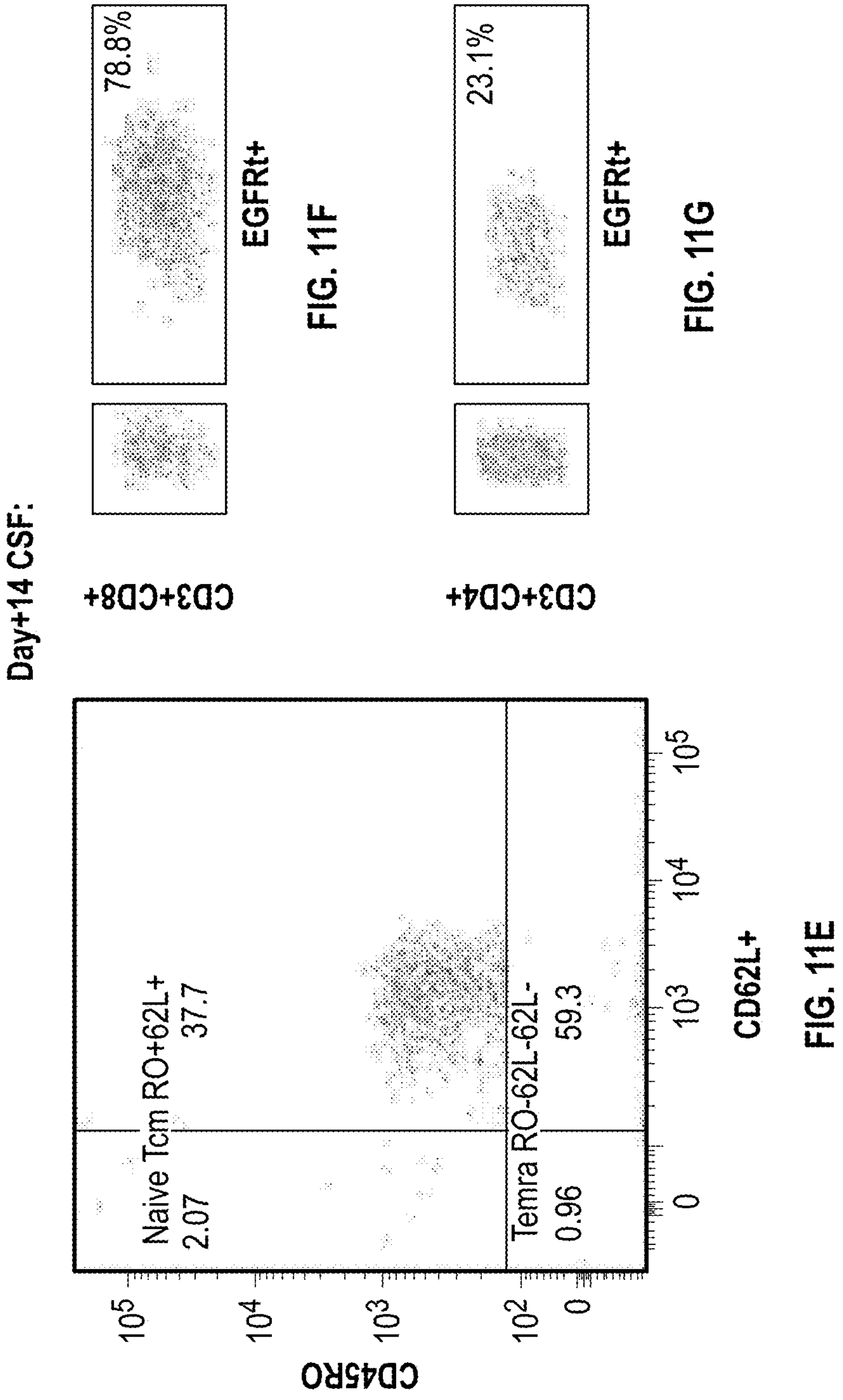
Figure 12:
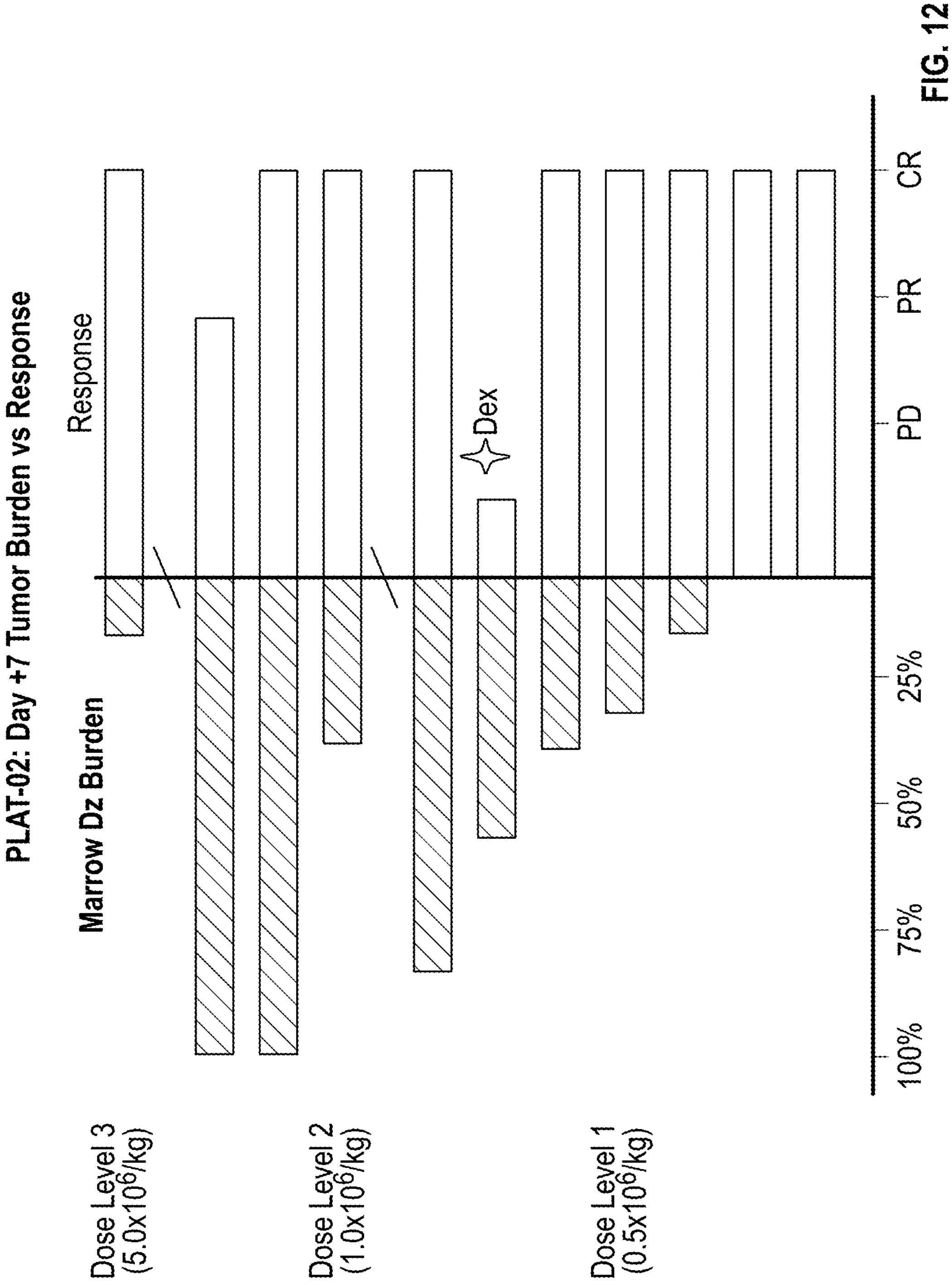
FIG. 12 shows the tumor burden vs the response after three doses of hematopoietic stem cell transplantation of anti-CD19 CAR T-cells.
Figure 13:
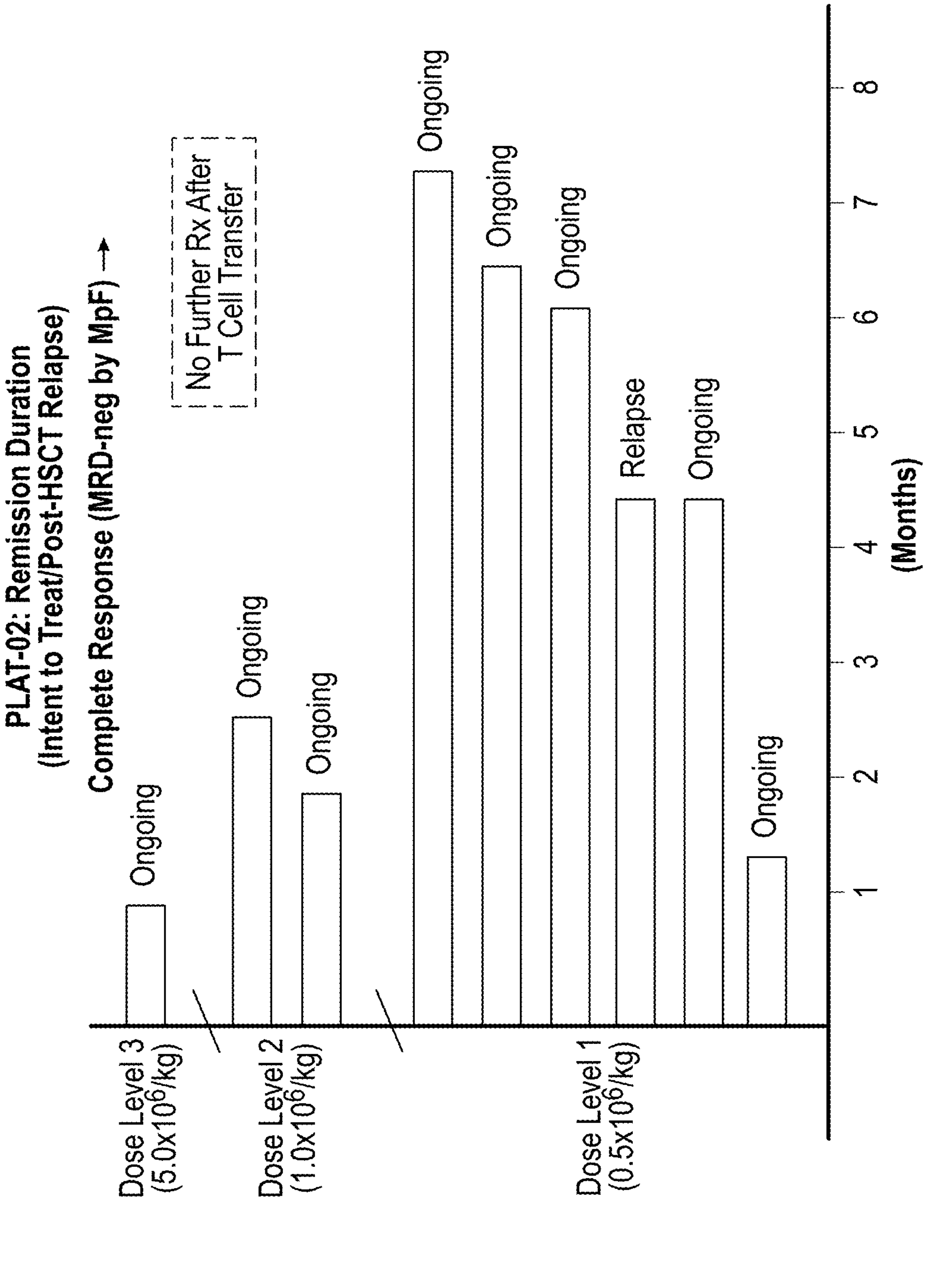
FIG. 13 shows the remission duration of patients following three doses of hematopoietic stem cell transplantation.
Figure 14:
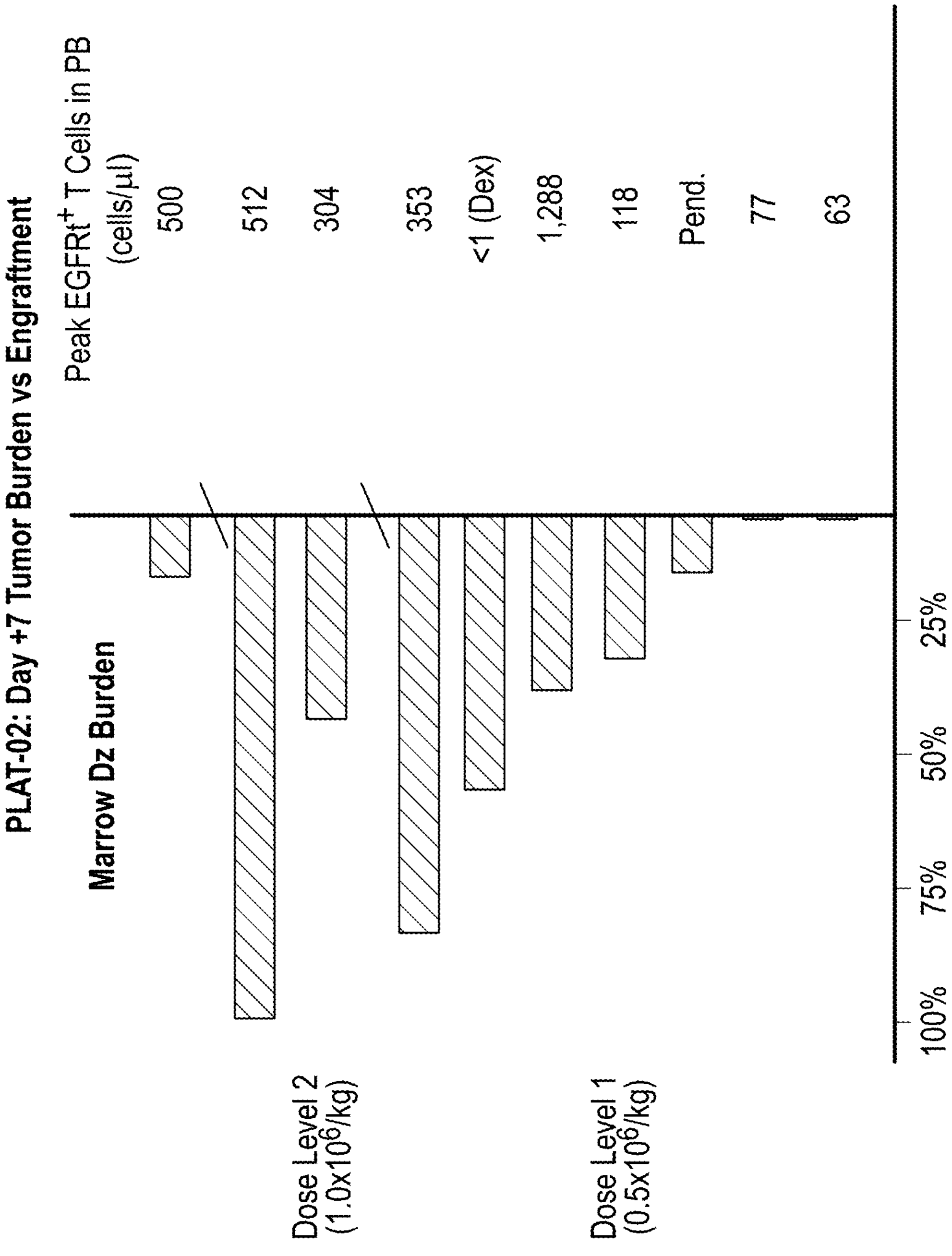
FIG. 14 shows the tumor burden vs the response after two doses of hematopoietic stem cell transplantation of anti-CD19CAR T-cells at day 7.
Figure 15:
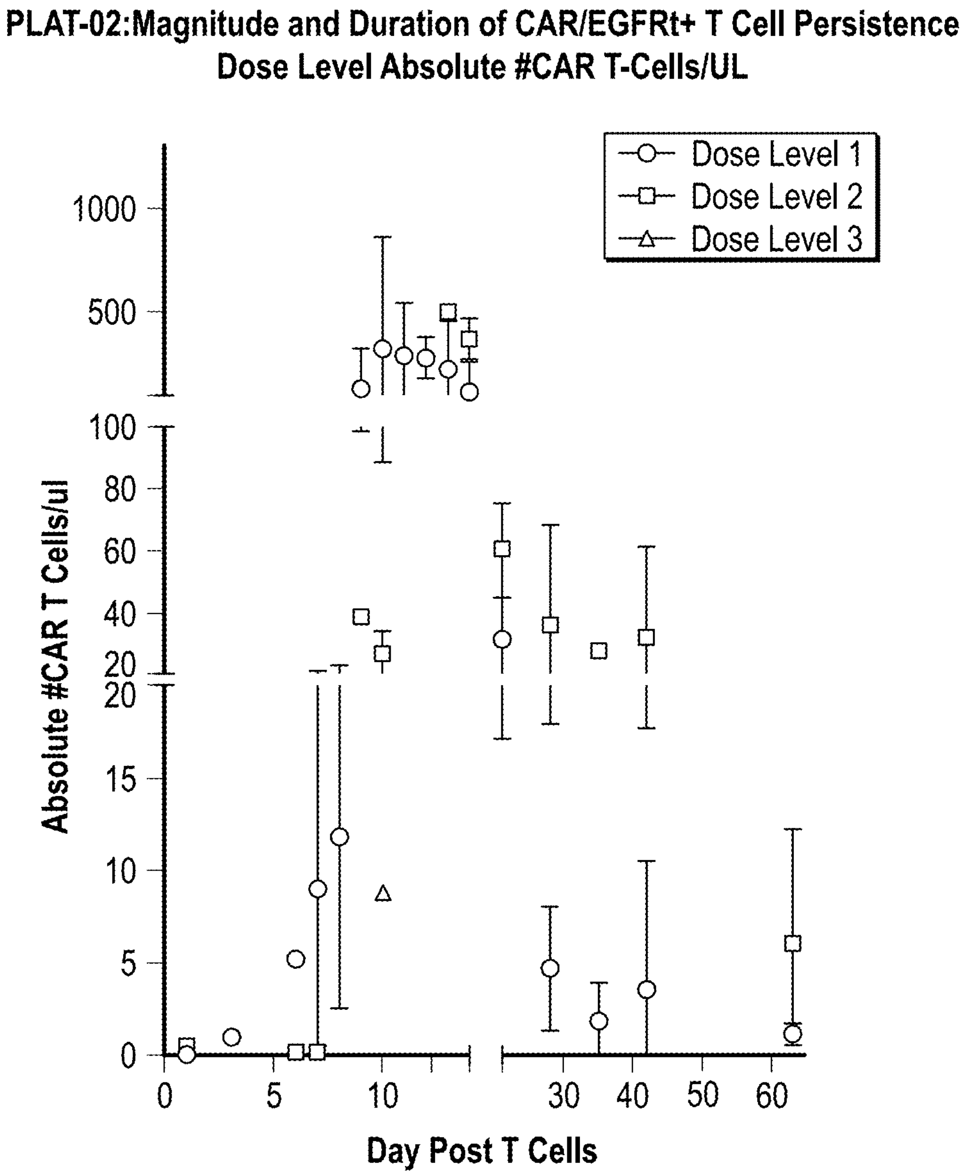
FIG. 15 shows the magnitude and duration of CAR/EGFRt+ T-cell persistence in a patient after three doses of hematopoietic stem cell transplantation of anti-CD19 CAR T-cells.
Figure 16:
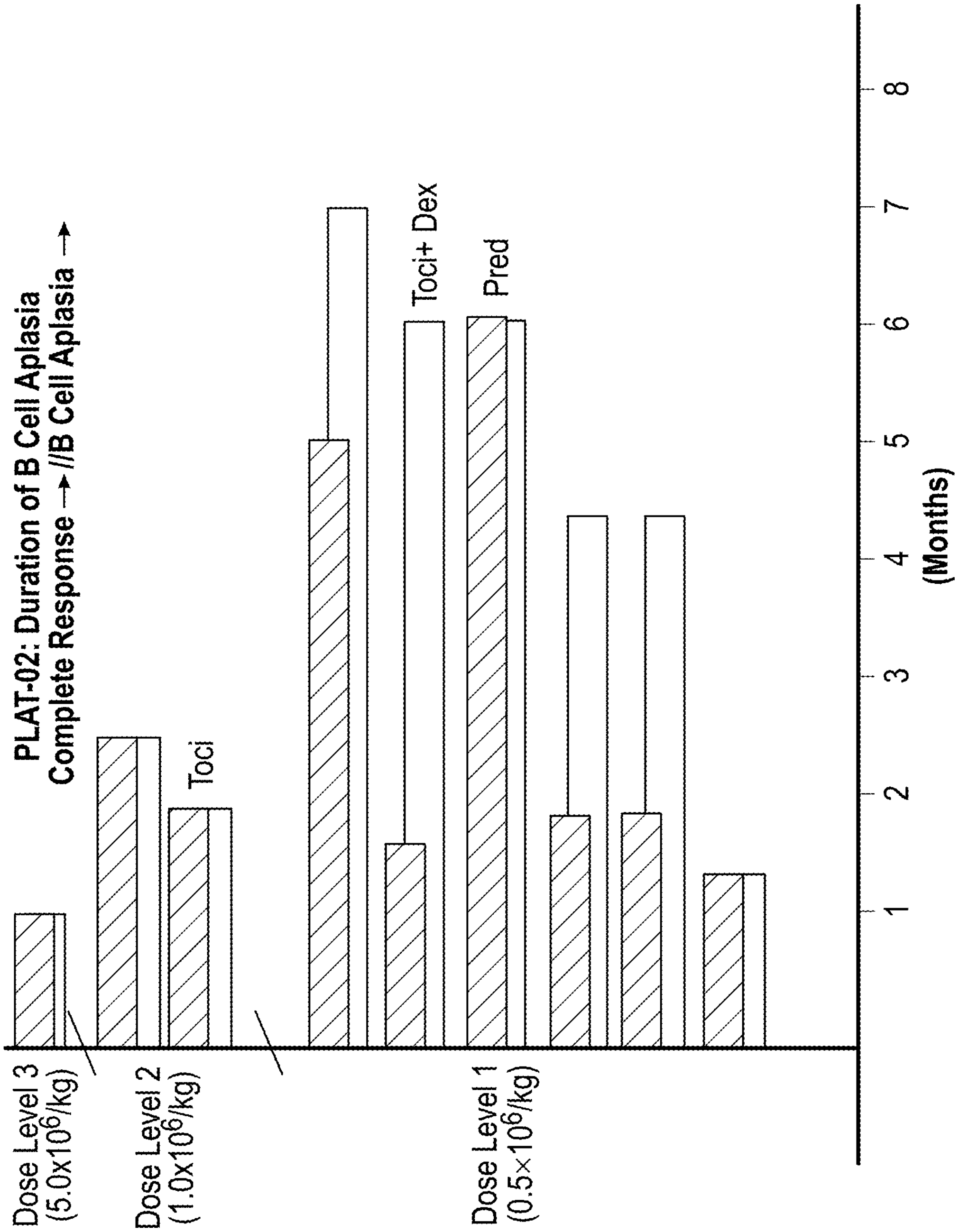
FIG. 16 shows the duration of B cell aplasia after three doses of hematopoietic stem cell transplantation of anti-CD19 CAR T-cells.
Figure 17:
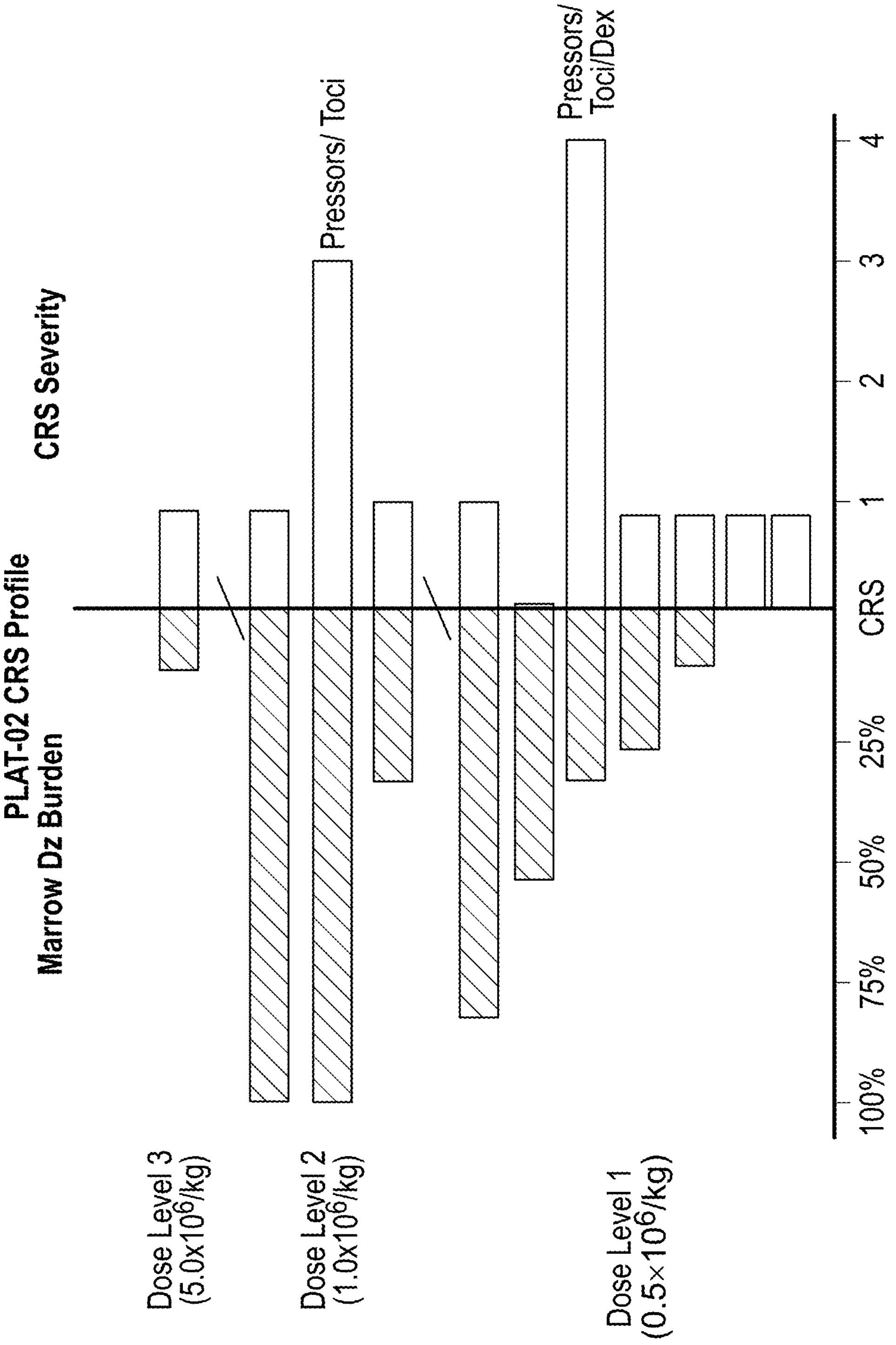
FIG. 17 shows the CRS profile of a patient after three doses of hematopoietic stem cell transplantation of anti-CD19 CAR T-cells.
Figure 27A:
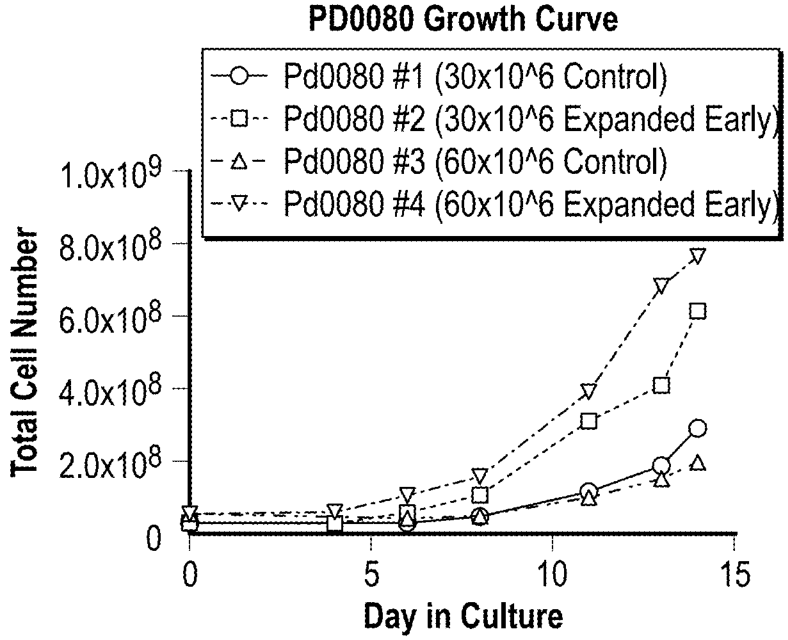
FIGS. 27A-C show expansion comparisons of samples PD0080, PD084 and PD0085. These experiments were repeats of the "early expansion" methodology.
Figure 27B:
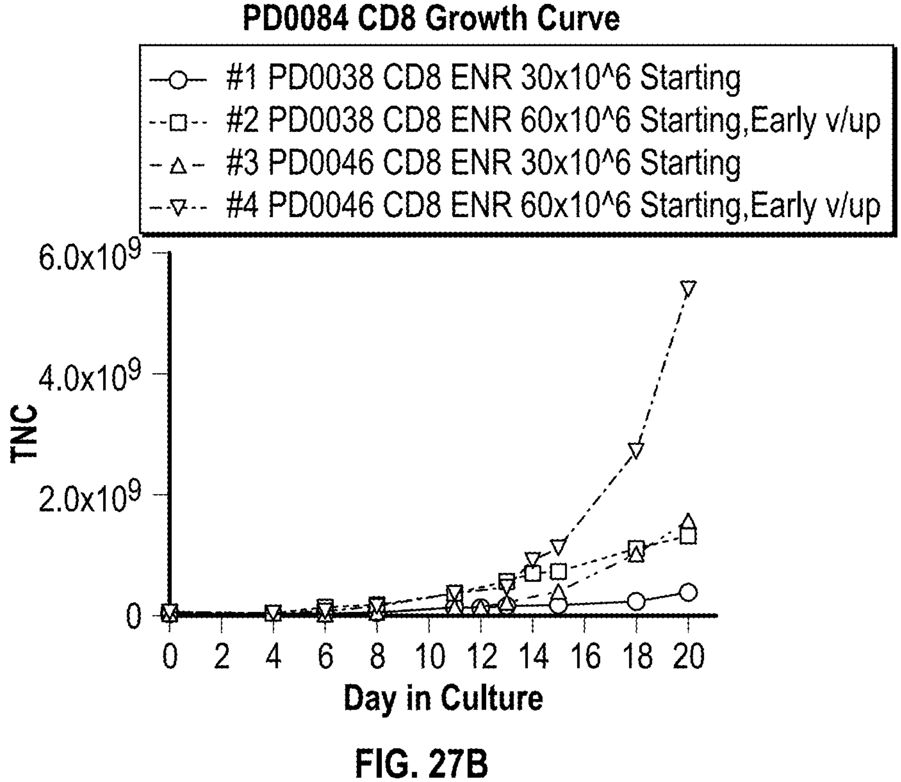
Figures 27C, 28A:
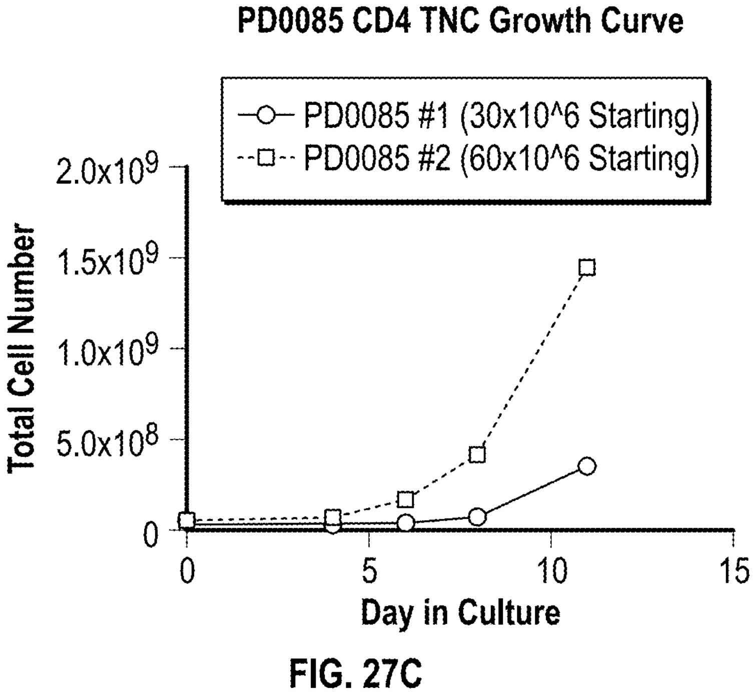
FIGS. 28A-D show the tests on PD0044 for producing the genetically modified cells. For the first scale up PLAT-02 (Phase I and Phase II trial) "pre-qual" from cryopreserved selected cells were used.
Figure 28B:
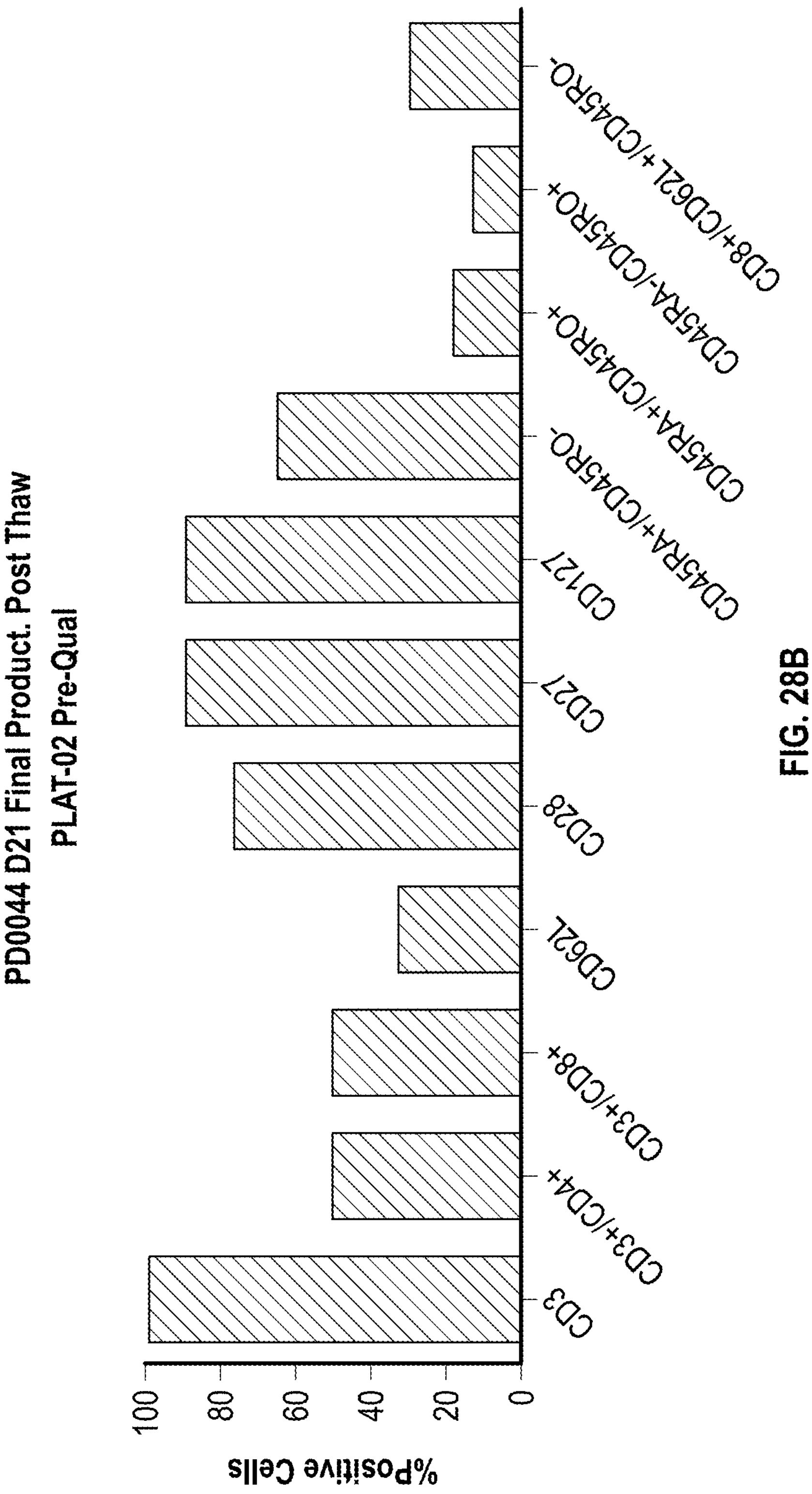
Figure 28C:
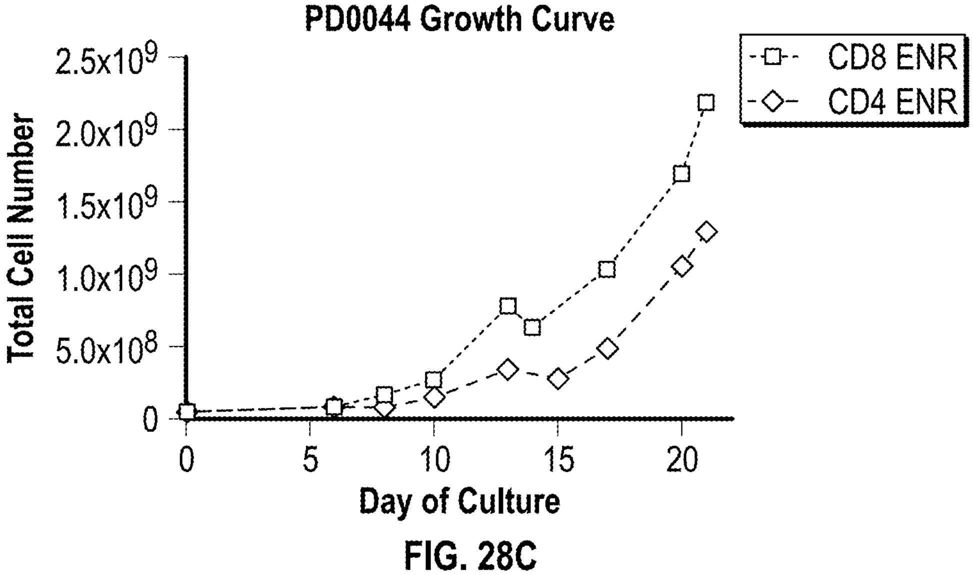
Figure 28D:
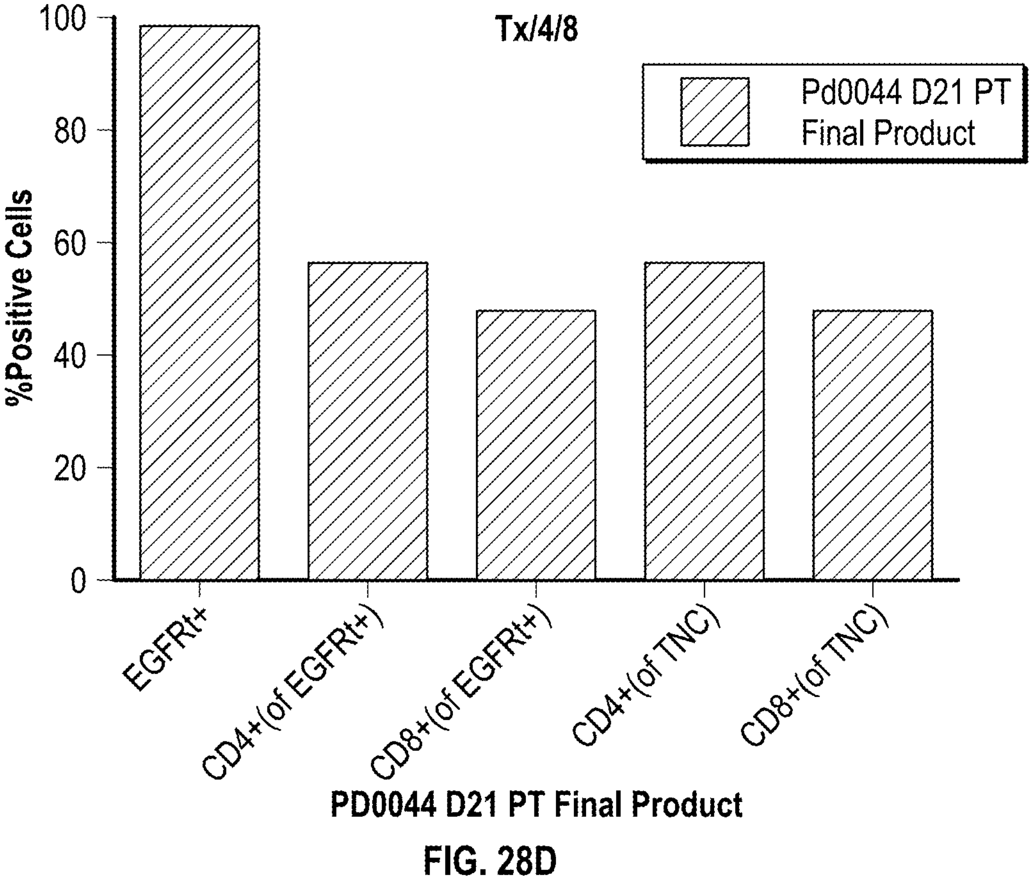

Shown in FIGS. 27A-3, are growth curves for samples from PD0080, PD0084, and PD0085 and a comparison between all three. These three experiments were repeated experiments of the "early expansion" methodology. For these experiments, the standard cytokine conditions were used: IL-2 (50 U/mL)+IL-15 (0.5 ng/mL) for CD8+ T-cells and IL-7 (5 ng/mL)+IL-15 (0.5 ng/mL) for CD4+ T-cells. For PD0080, two starting densities were tested in duplicate using PD0063 CD8+ T-cells. One of each of the cell duplicates received volumes of up to $\sim0.7\times10^6$ cell/mL following a 3-hour incubation on transduction day. For PD0084, two additional CD8+ donor T-cells were assessed for effects of early expansion. $30\times10^6$ cell starting conditions were used as a control for each donor and a $60\times10^6$ cell starting density was used with early expansion as test conditions. For PD0085, a similar test to PD0084 was performed except the CD4+ T-cells were used to test early expansion. Again $30\times10^6$ starting cell density were used as "normal" control condition and $60\times10^6$ cell starting density was used as a test condition.

As shown in FIGS. 28A-D, the starting material of PD0038 included selected CD4+ and CD8+ T-cells. The growth curves show TNC from both V-197 bags of cells that were pooled together. From the early development, it was intended to pool to 50:50 CD4:CD8 product prior to cryopreservation. Flow data shows post thaw of the pooled product. Bead removal and EGFRt enrichment occurred D+14 for CD4+ and D+15 for CD8+ T-cells. CD8+ T-cells were grown in IL-2 (50 U/mL)/IL-15 (0.5 ng/mL) and CD4+ T-cells were grown in IL-7 (5 ng/mL)/IL-15 (0.5 ng/mL). This process was changed to a cryopreservation of separate products and infusing a 50:50 product upon thawing.

Figures 29A, 29B:
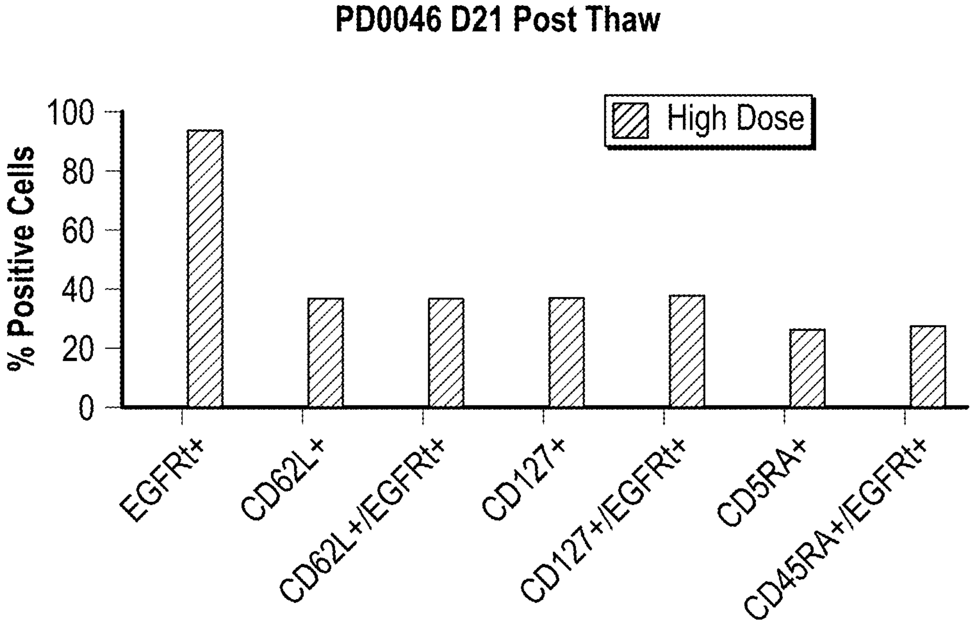
FIGS. 29A-C show the tests on PD0046 for producing the genetically modified cells from the scale up of PLAT-02 "Qual run #1".
Figure 29C:
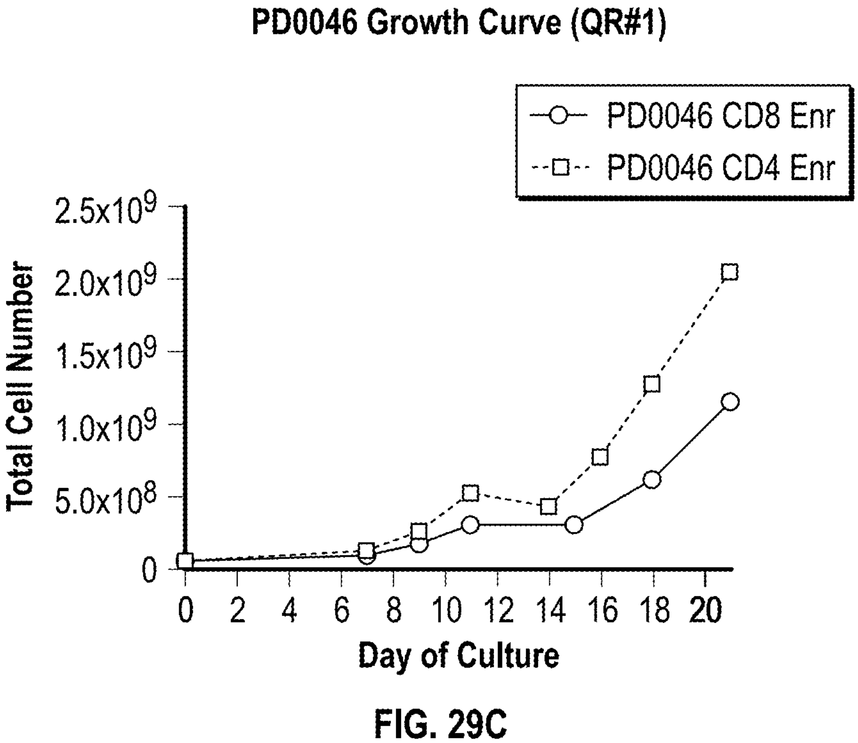

Shown in FIGS. 29A-C are the growth curve for PD0046. Growth curves show TNC from both V-197 bags of cells together. In early development there was an intent to pool a 50:50 CD4:CD8 product prior to cryopreservation. Flow data shows post thaw of the pooled product. Bead removal and EGFRt enrichment then occurred. D+14 for CD4+ T-cells and D+15 for CD8+ T-cells. CD8+ T-cells were grown in IL-2 (50 U/mL)/IL-15 (0.5 ng/mL) and CD4+ T-cells were grown in IL-7 (5 ng/mL)/IL-15 (0.5 ng/mL). However, not much was done following this product, due to the donor cells thawing poorly. Cells were used later to test 10% HA thawing and proved to be much better.

Figures 30A, 30B:
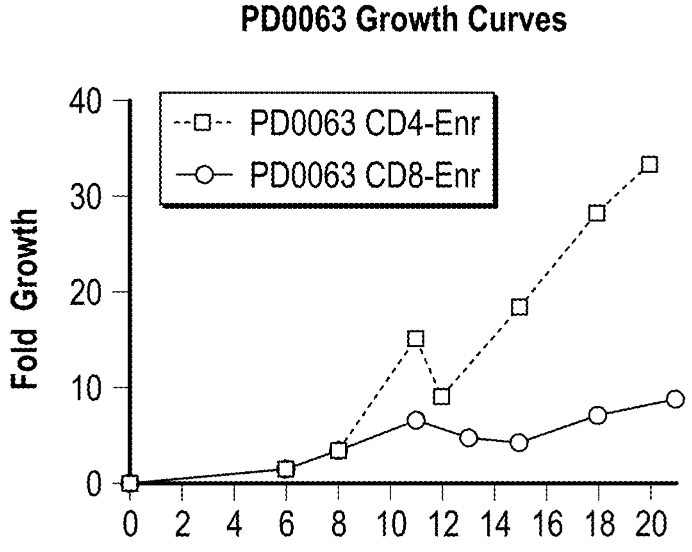
FIGS. 30A-C show the tests on PD0063 for producing the genetically modified cells. From the scale up or PLAT-02 "Qual run #2". Growth curves show TNC from both V-197 bags of cells together. Bead removal and EGFRt enrichment occurred afterward. D+14 for CD4+ expressing T-cells and D+15 for CD8+ expressing T-cells. CD8+ expressing T-cells grown in IL-2 (50 U/mL)/IL-15 (0.5 ng/mL), CD4+ expressing T-cells grown in IL-7 (5 ng/mL)/IL-15 (0.5 ng/mL). Bead removal and EGFRt enrichment occurred at D12 for CD4+ expressing T-cells and D13 for CD8+ expressing T-cells.
Figure 30C:
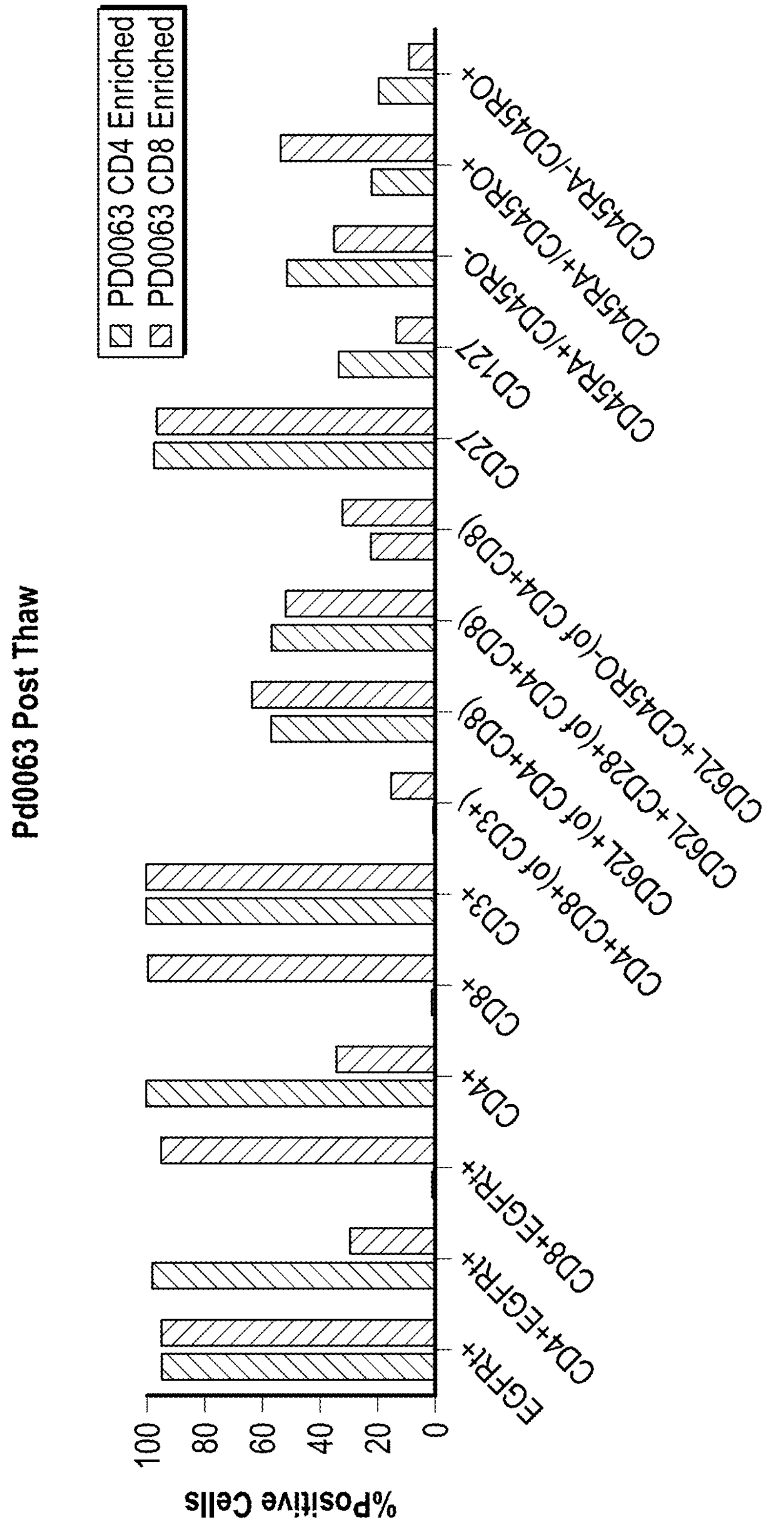

Shown in FIGS. 30A-30C are the growth curve for PD0063. Growth curves show TNC from both V-197 bags of cells together. Bead removal and EGFRt enrichment then occurred D+14 for CD4's and D+15 for CD8's are shown. CD8+ cells were grown in IL-2 (50 U/mL)/IL-15 (0.5 ng/mL) and CD4+ cells were grown in IL-7 (5 ng/mL)/IL-15 (0.5 ng/mL). Bead removal and EGFRt enrichment then occurred.

Shown in FIGS. 31A-B, is the expansion of cells from bulk PBMC cultures when grown in the presence of cytokines. As shown, CD4+ cells (●) were grown in the presence of IL2 and IL15. CD8+ cells (■) were grown in in the presence of IL7 and IL15. The lower panel, (phenotypic comparison) of FIGS. 31A and 31B, shows percentage of total cells expressing the indicated markers on their surfaces following incubation with the different conditions, each of which resulted in cells expressing markers of engraftment fitness, e.g., CD62L, CD28, CD27, CD45RA. Growing CD8− enriched cultures in IL-2/IL-15 and CD4− enriched cultures in IL-7/IL-15 yielded robust expansion of both cultures and strong expression of memory phenotype.

Shown in FIGS. 32A-B, are the expansion of enriched CD8+ and CD4+ cells in cytokine mixtures. As shown in sample PD0044, enriched CD8+ T-cells were expanded in the presence of IL2 and IL15 (top panel). In sample PD0044, enriched CD4+ T-cells were expanded in the presence of IL7 and IL15 for over 20 days. As shown, the pooled CD4+ and CD8+ T-cells expressed CD3, CD4, CD8, CD62L, CD28, CD27, CD45RA and CD45RO. Also tested was sample 14602-S14 (See FIG. 32B). As shown, growing CD8+ enriched cultures in IL-2/IL-15 and CD4+ enriched cultures in IL-7/IL-15 yielded robust expansion of both cultures and strong expression of memory phenotype. Importantly, from the data generated and shown in FIGS. 31A-B and 32A-B, CD4+ T-cells and CD8+ T-cells grew optimally with different cytokine combinations such that CD4+ T-cells performed best in these studies with IL7 and IL15, while CD8+ T-cells grew best in these studies with the cytokines IL2 and IL15. Growth with their respective optimal cytokine combinations led to cells that had a phenotype following cell expansion in which the cells expressed the surface markers CD45RA, CD62L, CD28, and CD27, which indicate a high or improved or enhanced engraftment fitness upon adoptive transfer.

Figure 33A:
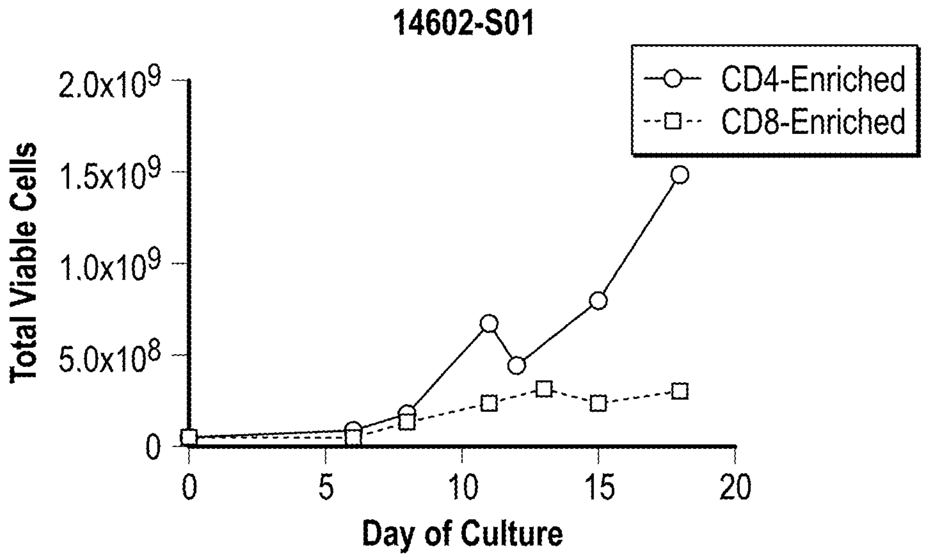
FIGS. 33A-C show expansion of enriched CD4+ and CD8+ expressing T-cells using an earlier methodology as shown in the flow chart of FIGS. 18A-B. Shown are experiments of cells in sample 14602-S01, 14602-S02, and 14602-S03/14602-S03-02.
Figure 33B:
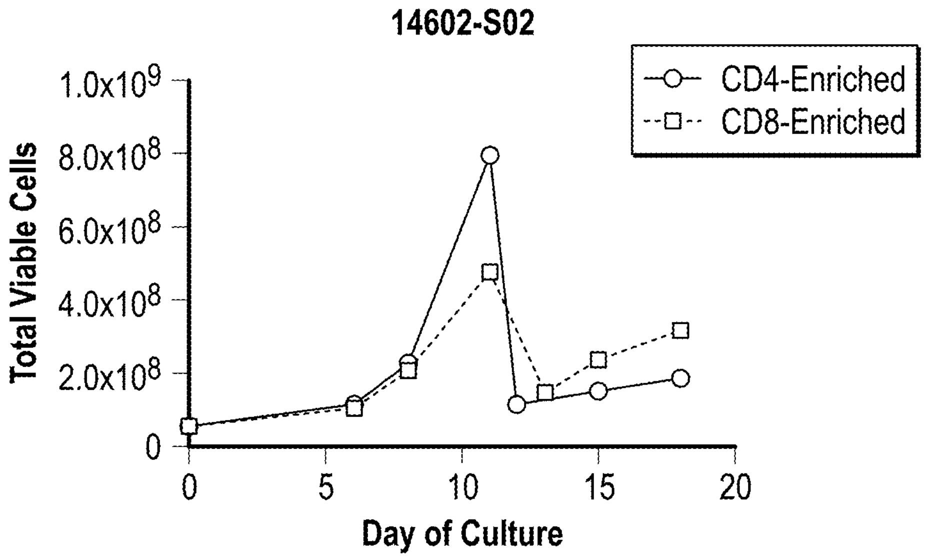
Figure 33C:
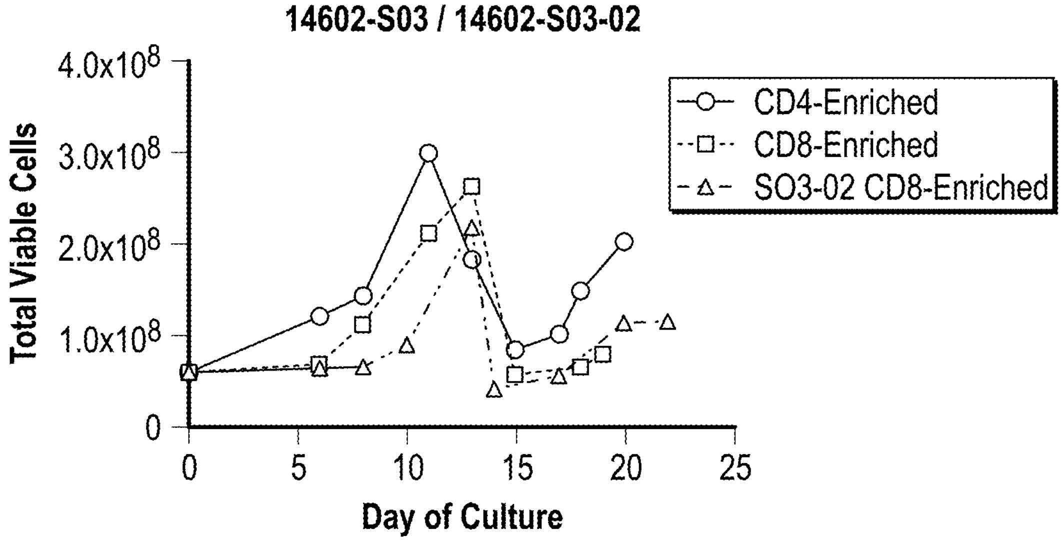

Shown in FIGS. 33A-C, are samples from 14602-S01 through 14602-SO6 using the original PLAT-02 (Phase I and Phase II of clinical trials) methodology of cell expansion. The cells were positive for EGFRt prior to cyropreservation. The cells were tested for viability. As shown in the bottom table, the cells 14602-SO3 CD8+ and 14602-SO3-CD8+ cells did not express CD3, CD62L, CD27, CD127, CD45RA/CD45RO− or CD45RA.

Figure 34A:
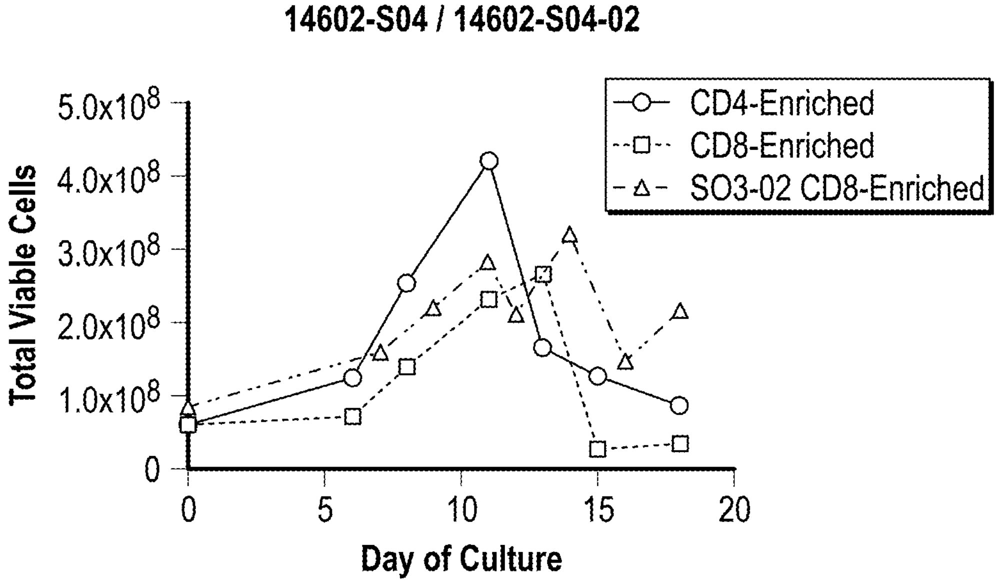
Figure 34B:
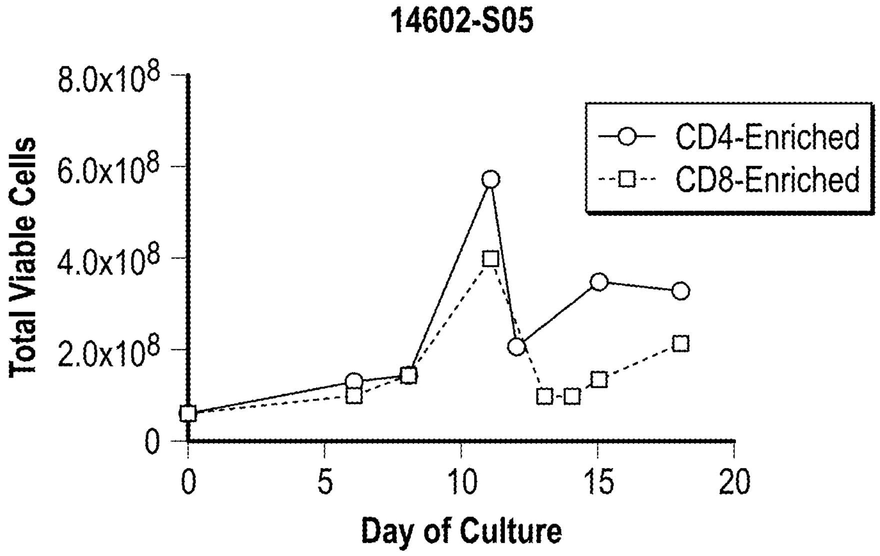

Shown in FIGS. 34A-C, are tests on the cell product 14602-SO4 and 14602-SO4-02 which have both CD4+ and CD8+ T-cells. The cells were grown in cultures using the "early expansion" methodology. The cells were tested positive for EGFRt expression prior to cryopreservation.

Figure 35A:
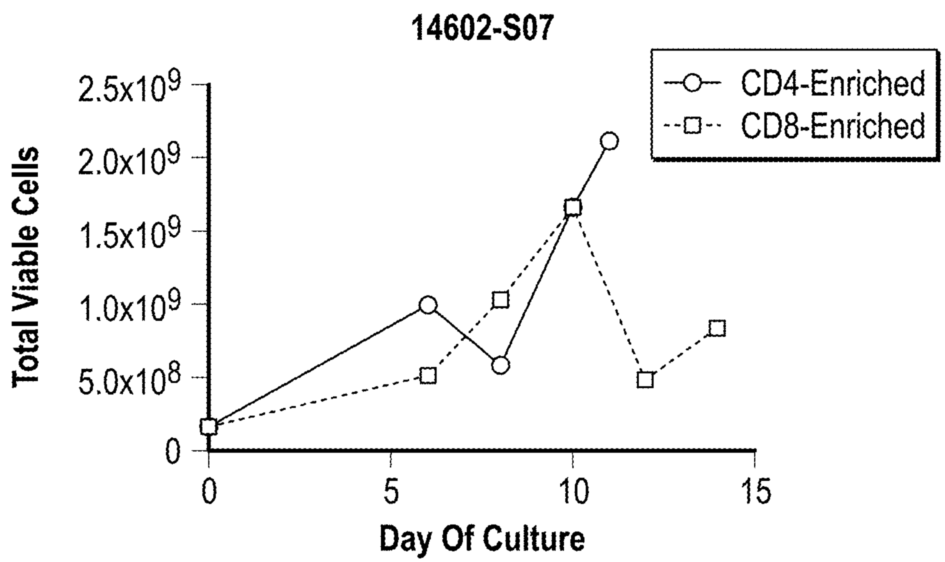
FIGS. 35A-C show the expansion of enriched CD4+ and CD8+ expressing T-cells using the "Early Expansion methodology as shown in the flow chart of FIGS. 18A-B. Shown are experiments of cells in sample 14602-S07, 14602-S08, and 14602-S09.
Figure 35B:
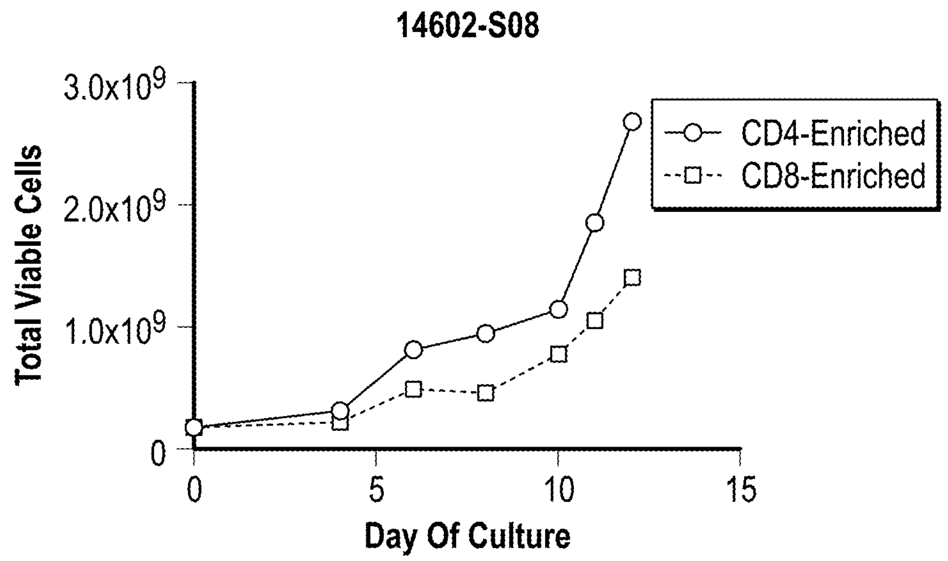
Figure 35C:
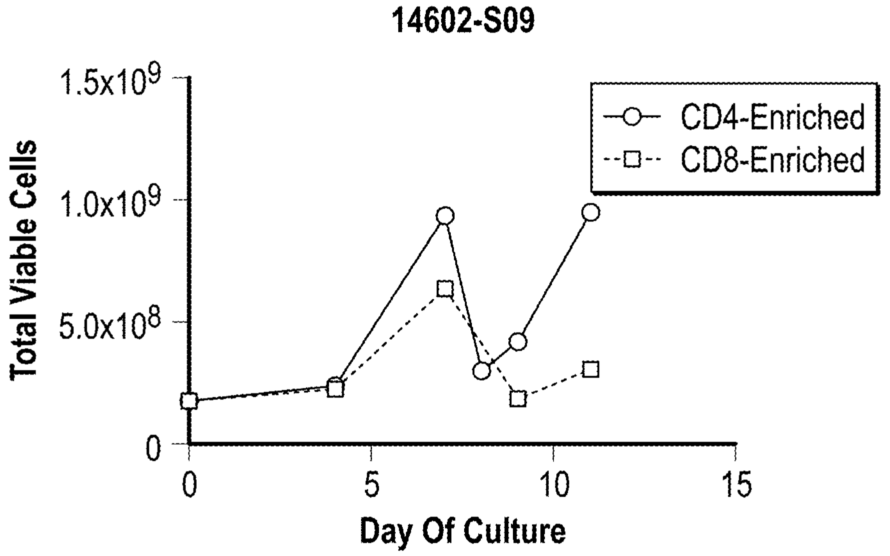
Figure 36A:
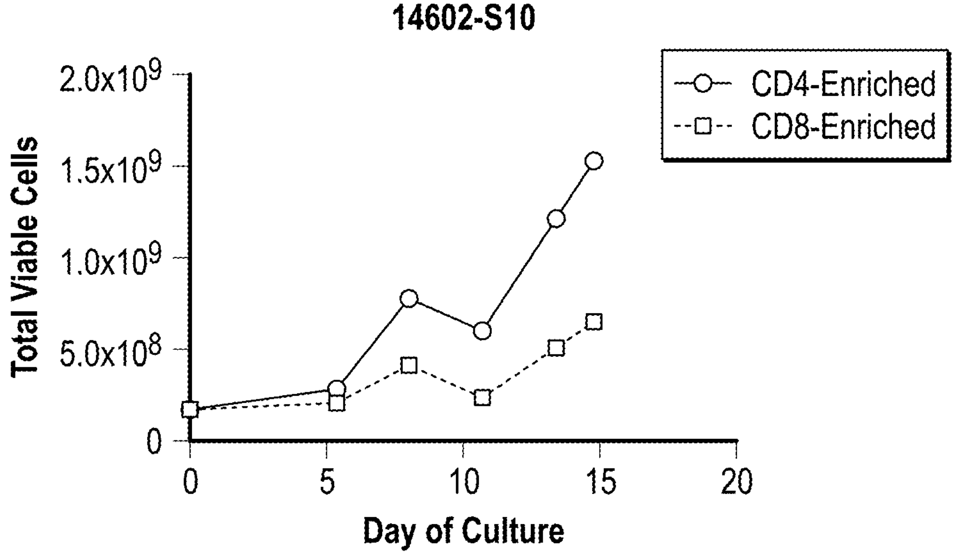
FIGS. 36A-D show the expansion of cells in samples 14602-S10, 14602-S11, 14602-S12, and 14602-S13.
Figure 36B:
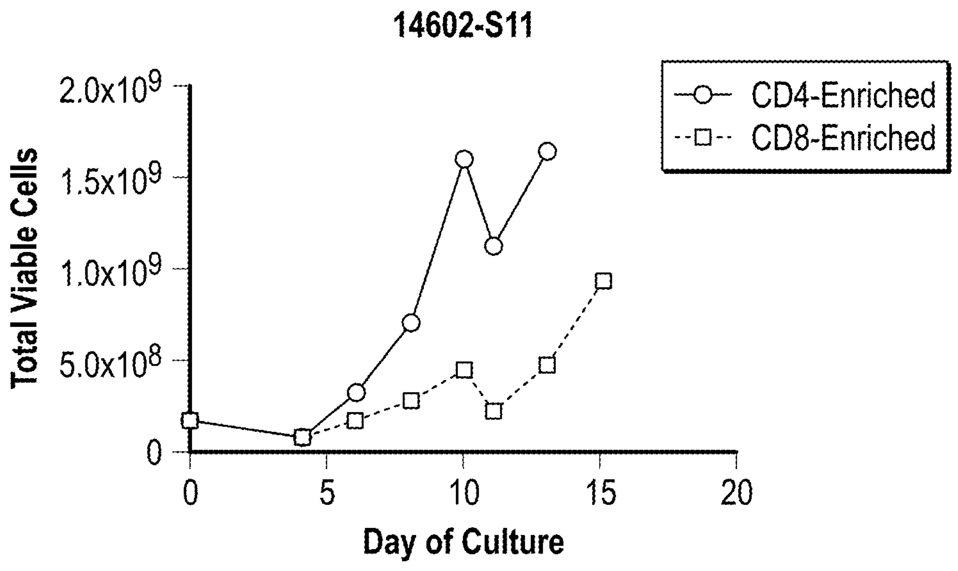
Figure 36C:
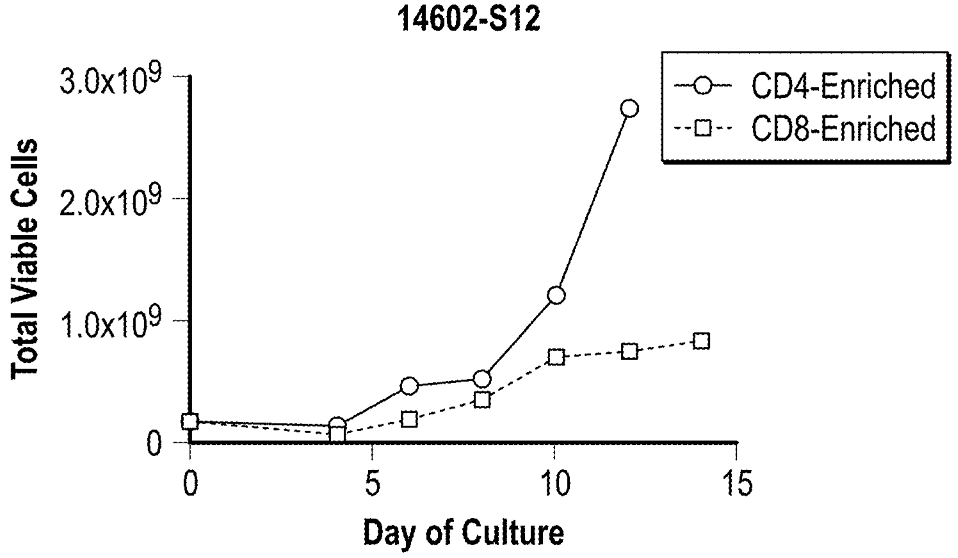
Figure 36D:
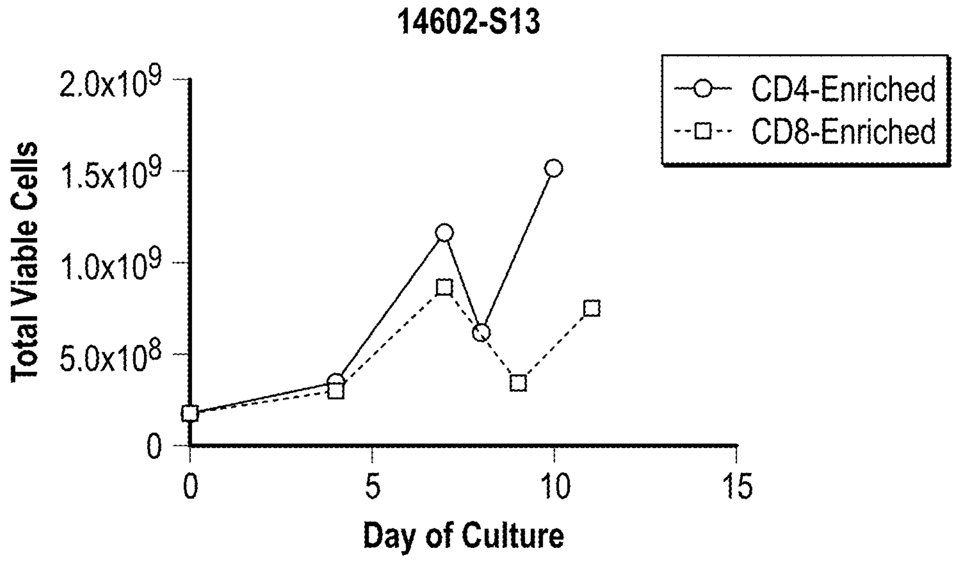

Shown in FIGS. 35A-C, are the cells from samples 14602-SO7, 14602-SO8, and 14602-SO9. The CD4+ and CD8+ cells were expanded using the early expansion methodology. In the top panel, as shown in the table for 14602-SO7 CD4+, cells and 14602-SO7 CD8+ cells, shows percentage of cells expressing various markers including CD3, CD62L, CD27, CD27, CD127, and CD45RA+ at various times. In the bottom panel for sample 14602-SO8, CD4+ and CD8+ enriched T-cells remained viable after 10 days in culture.

Shown in FIGS. 36A-D, are the cells tested for viability from the batch samples of 14602-S10, 14602-S11, 14602-S12 and 14602-S13. As shown in the accompanying tables, the cells all expressed EGFRt prior to cryopreservation. The cells were tested for viability in cell culture for at least 12 days.

Figure 37A:
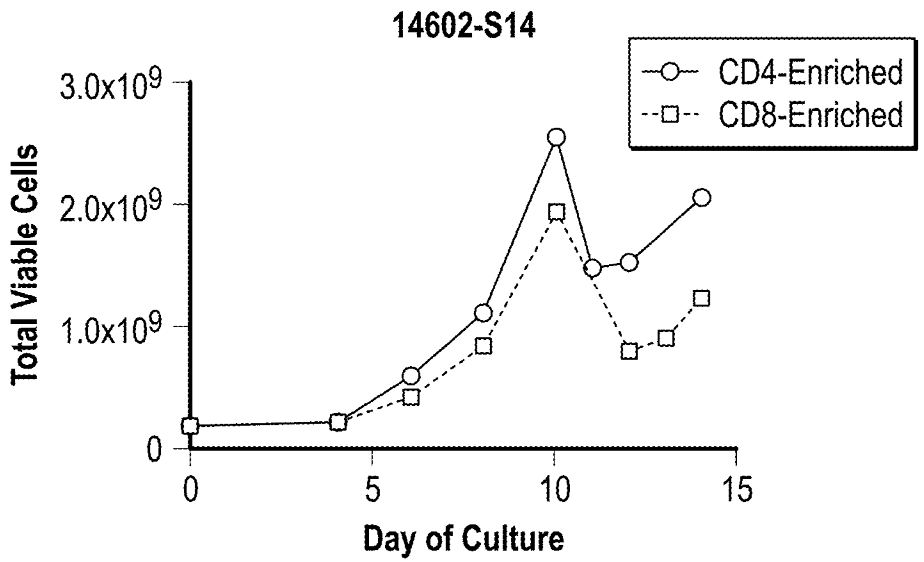
FIGS. 37A-C show the expansions of cells in samples 14602-S14, 14602-S15, and 14602-S16.
Figure 37B:
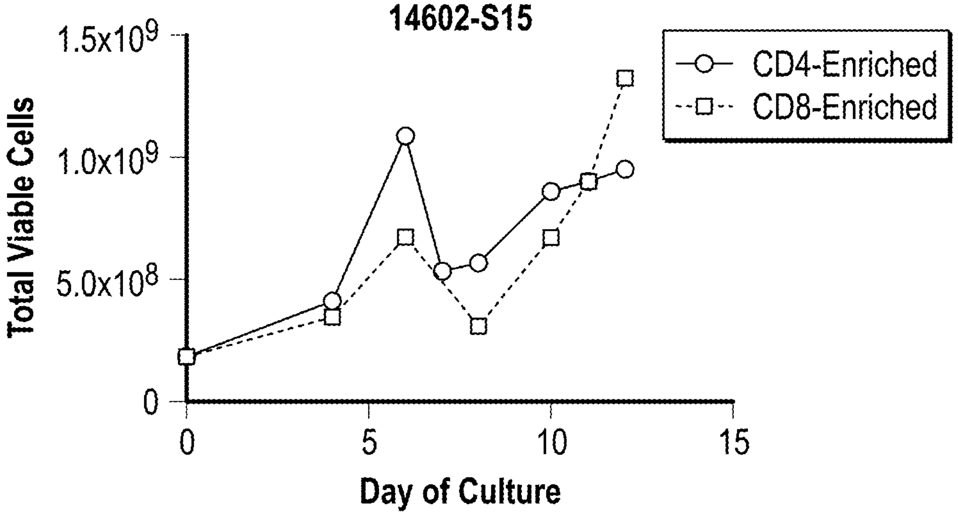
Figure 37C:
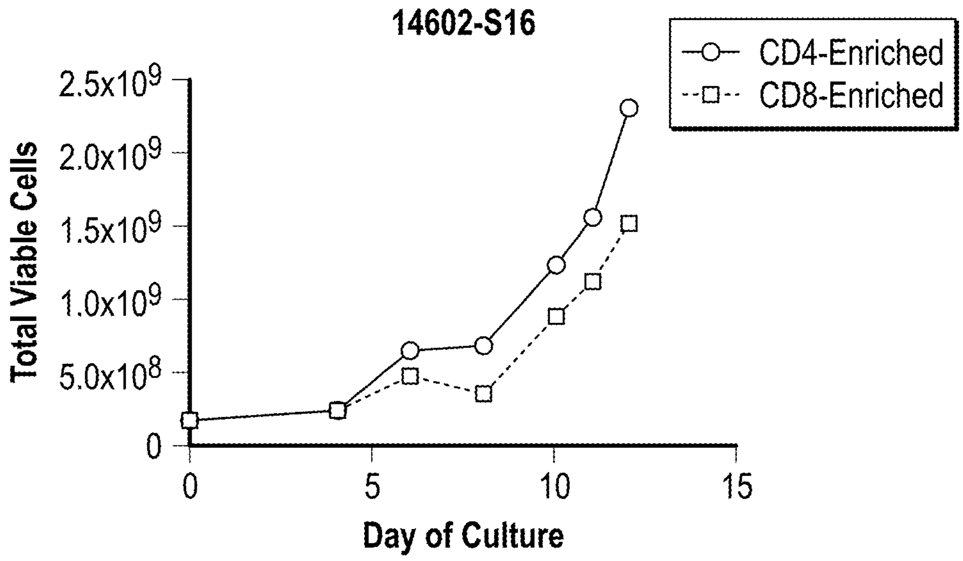

Shown in FIGS. 37A-C, are the cells tested for viability from the batch samples of 14602-514, 14602-515 and 14602-S16. As shown in the accompanying tables, the cells all expressed EGFRt prior to cryopreservation. The cells were tested for viability in cell culture for at least 12 days.

Figure 38A:
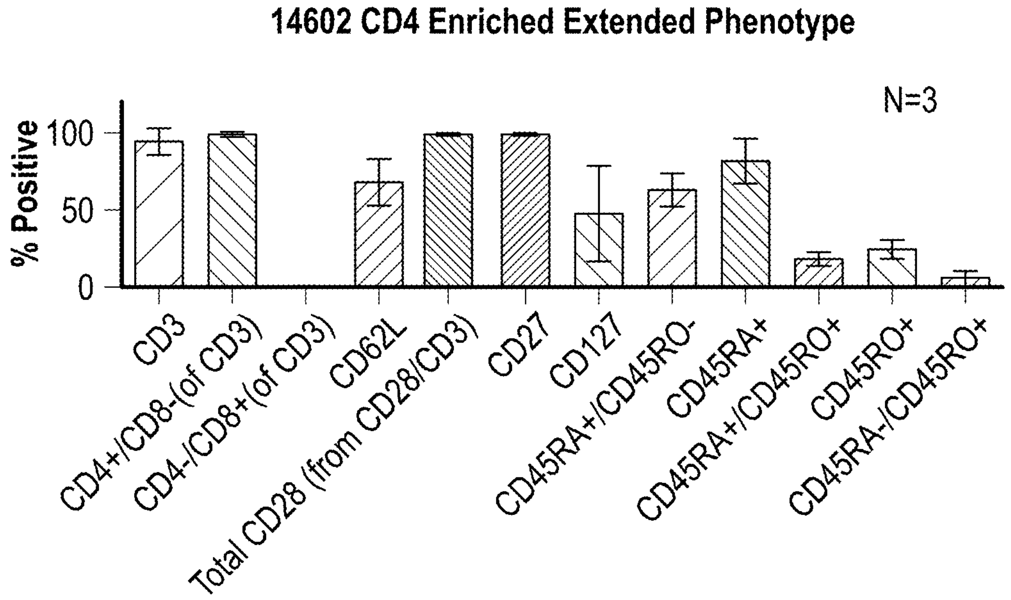
FIGS. 38A-B show the enriched CD4+ and CD8+ expressing T-cells extended phenotypes after cell expansion.
Figure 38B:
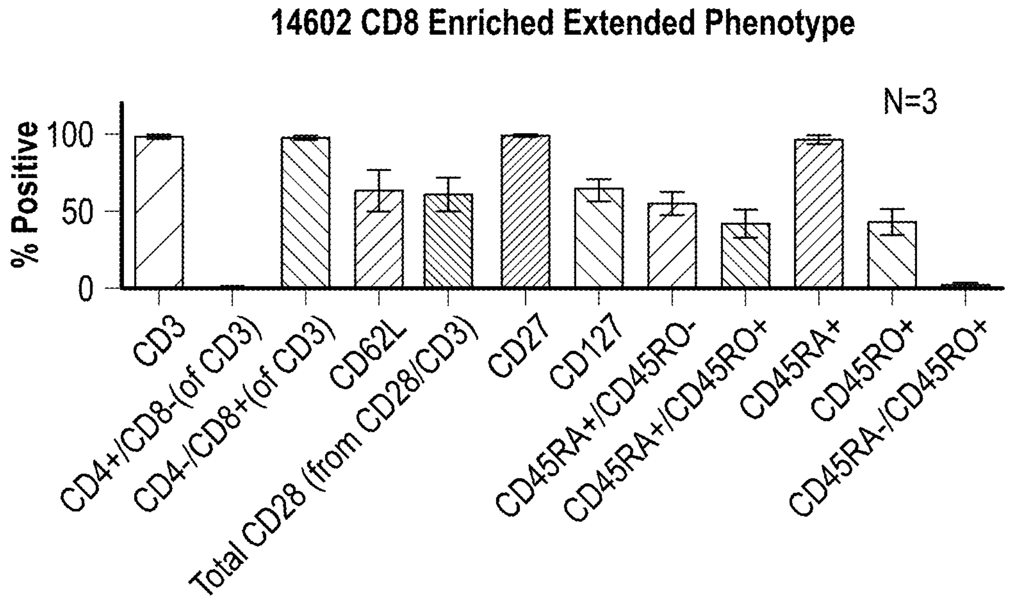

As shown in FIGS. 38A-B, the cells from the sample of 14602, which CD4+ and CD8+ T-cells were enriched from, were positive for CD3, CD62L, CD28, CD127, CD45RA+/CD45RO−, CD45RA and CD45RO. These are specific markers which to indicate that both CD4+ and CD8+ cells had a high level of engraftment fitness following the treatment with their specific cytokine combinations.

Figure 39A:
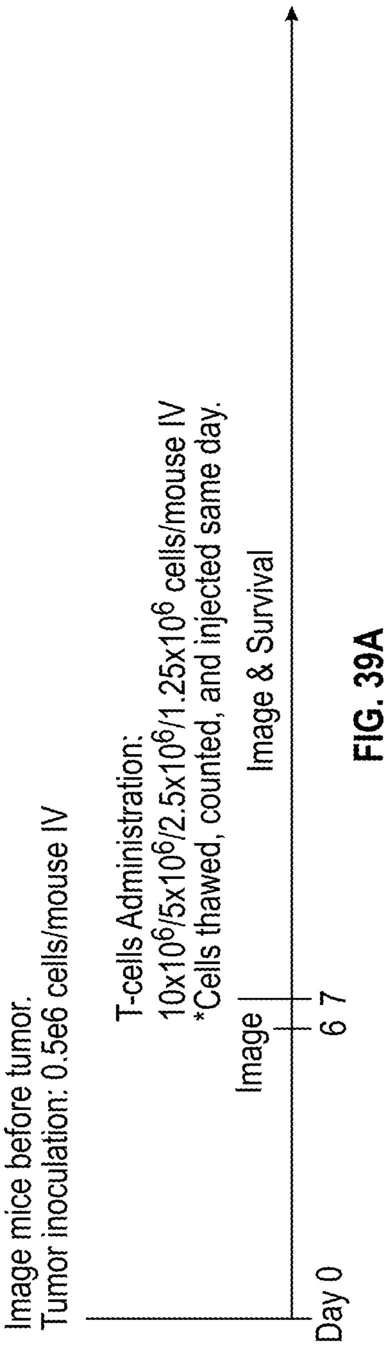
Figure 40A:
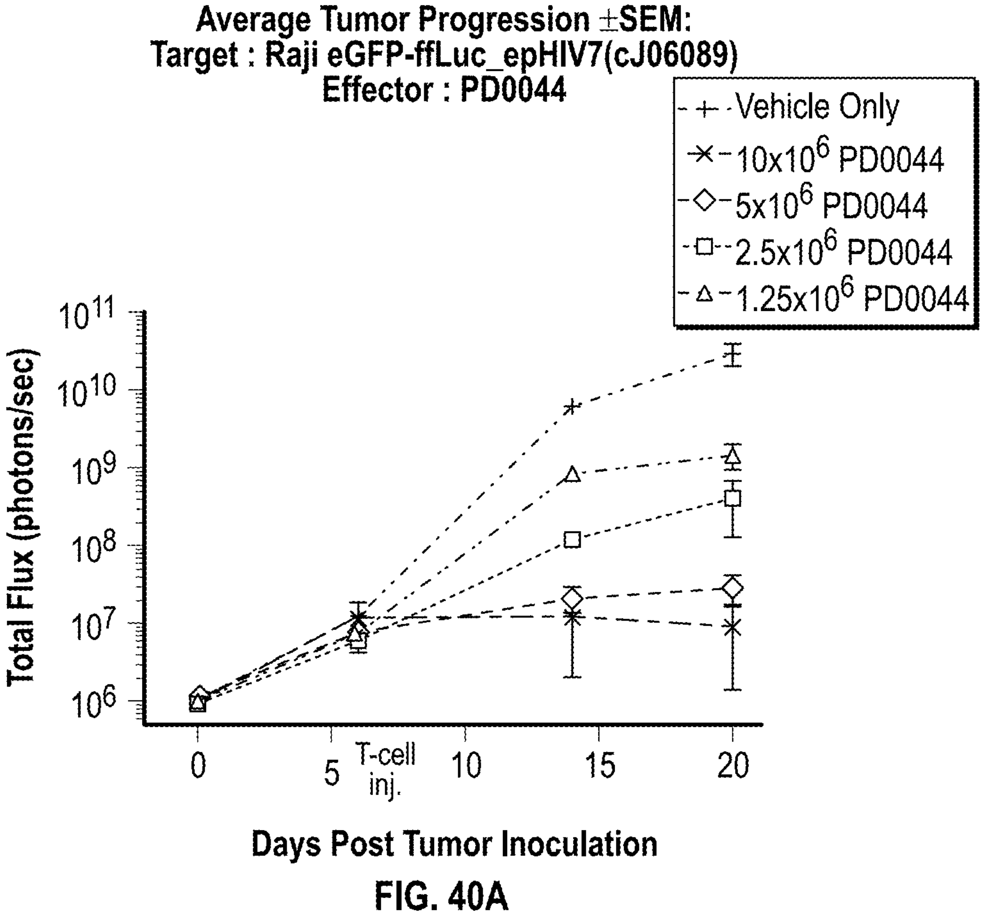
FIGS. 40A-D show the average tumor progression in mice treated with cells from the PD0044 and PD0046 cell batches.
Figure 40B:
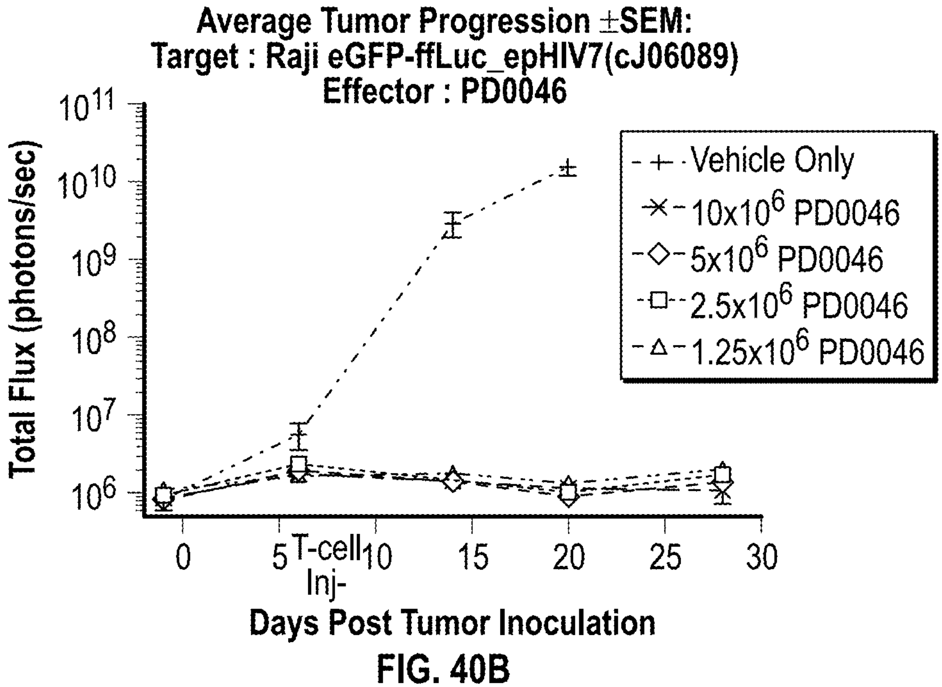
Figure 40C:
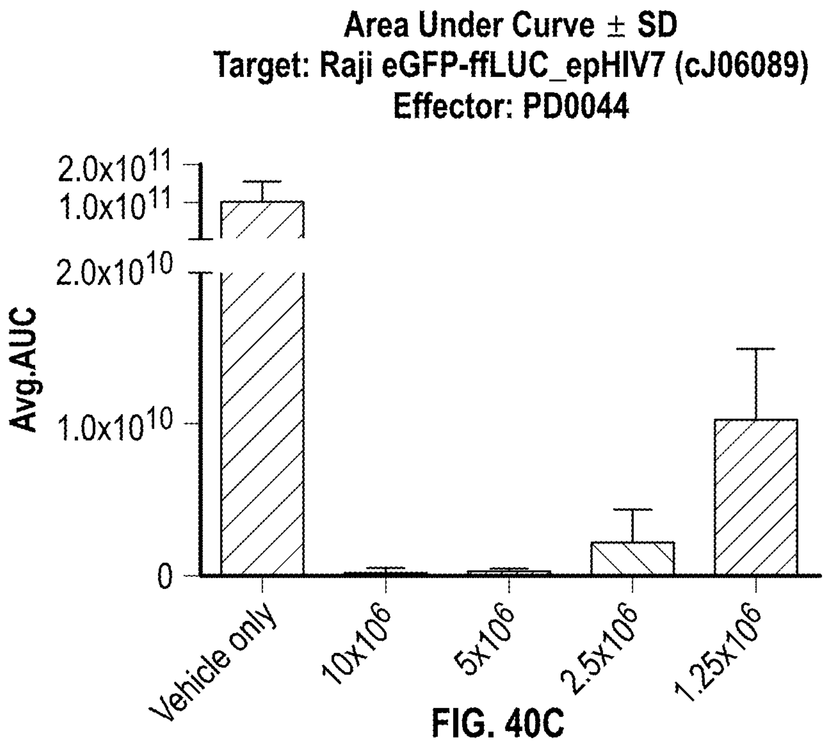
Figure 40D:
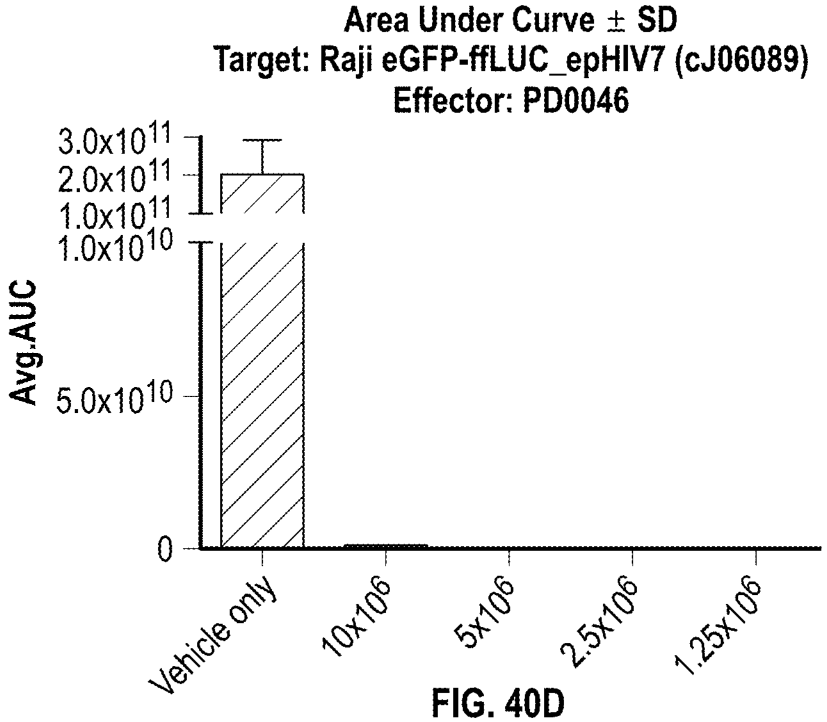
Figure 42A:
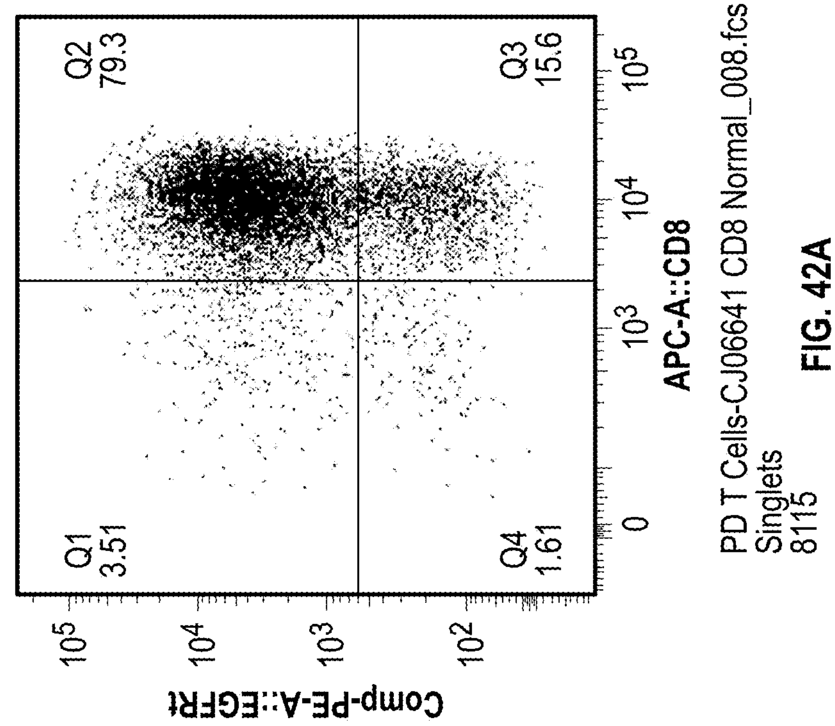
Figure 42B:
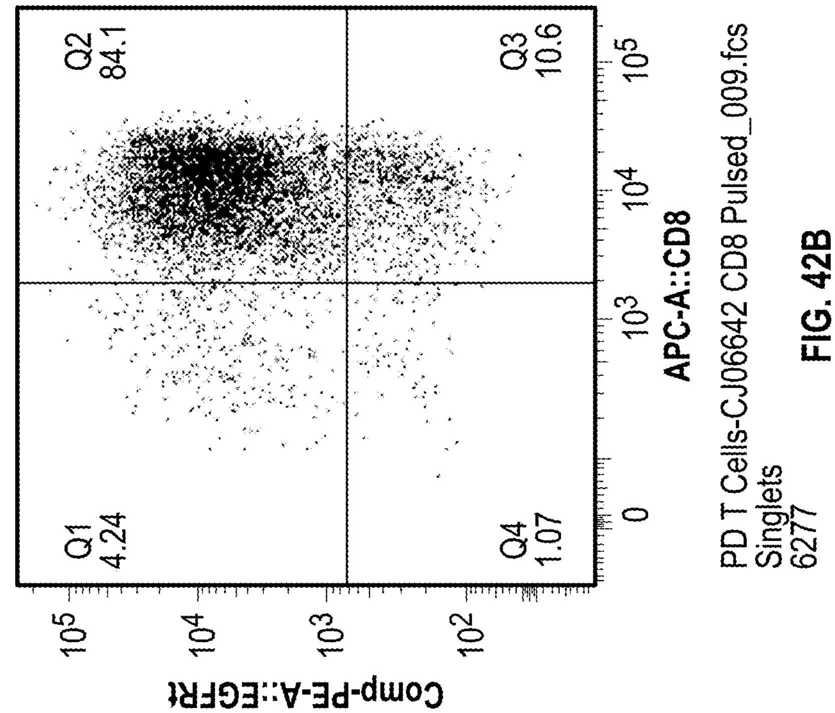
Figure 42C:
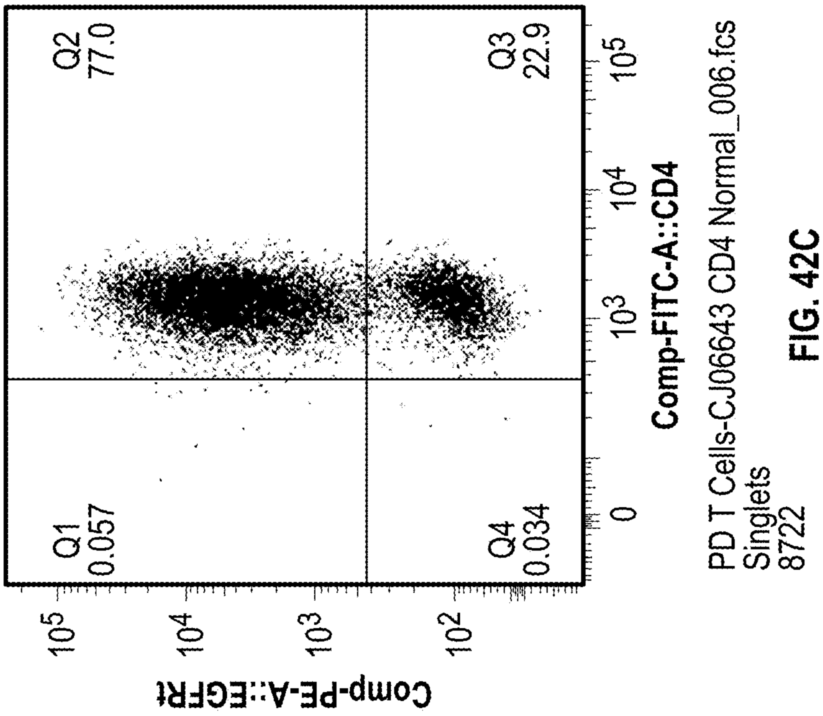
Figure 42D:
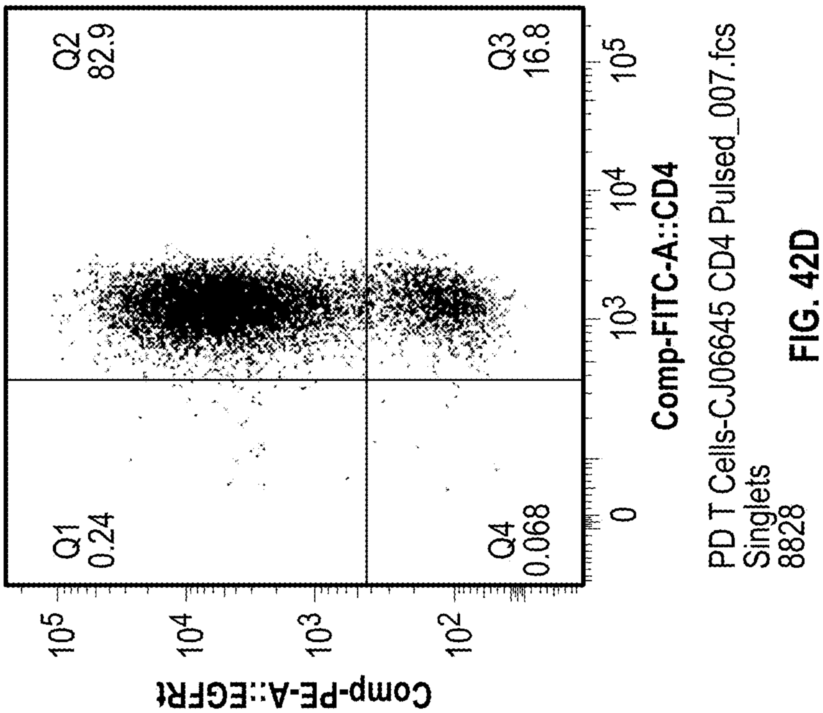

Shown in FIGS. 39A-B, are the results for a mouse after T-cell administration after tumor inoculation (survival, tumor progression). As shown, the mouse injected with the cells from the sample PD0046 indicated that the cells had a high, improved, or enhanced engraftment fitness due to the survival of the mouse after 80 days of administration using multiple concentrations of cells. The sample PD00044 did not have a high, improved, or enhanced engraftment fitness as the percent survival dropped at day 40 (FIG. 39B).

As shown in FIGS. 40A-D is the average tumor progression in mice treated with cells from the PD0044 and PD0046 cell batches. As shown in the graphs, the tumor progression in the mouse decreased if they were administered the CD8+ and CD4+ T-cells from the PD0046 batch, in which the cells were originally grown in the appropriate cytokine mixtures for CD4+ and CD8+ T-cells (IL7/IL15 for CD4+ T-cells and IL2/IL15 for CD8+ T-cells). As a control, the vehicle cells did not halt tumor progression in either study with PD0044 and PD0046. As shown in the bottom panels, tumor progression increased in mice treated with cells from the PD0044 sample, and in particular increased substantially when treated with the least concentration of T-cells. Tumor progression decreased in comparison to the vehicle control.

As a further test, three groups of mice were tested in which each group had a total number of 5 mice per group. For Group A, the mice were treated with a placebo of phosphate buffered saline (PBS). Group B utilized cells from "normal" expansion" which had a 1:1 EGFRt+CD4:CD8 transduced with Zrx-014. The cells used were from group PD0055 #1 (Donor PD0038 CD4 with 5 ng/ml IL7 & 0.5 ng/ml IL15, S1D14 at 75.9% EGFRt+) and group PD0051 #1 (Donor PD0038 CD8 with 50 U/ml IL2 & 0.5 ng/ml IL15, S1D21 @ 76.8% EGFRt+) Group C utilized cells that were "pulsed" with cytokine treatments which comprised 1:1 EGFRt+CD4:CD8 transduced with Zrx-014 PD0055 #2 (Donor PD0038 CD4 with 50 U/ml IL2 pulse 5 days, then 5 ng/ml IL7 & 5 ng/ml IL21, S1D11 at 81.2% EGFRt+) PD0051 #2 (Donor PD0038 CD8 with 50 U/ml IL2 pulse 5 days, then 5 ng/ml IL7 & 5 ng/ml IL21, S1D21 at 89.5% EGFRt+).

As shown in FIGS. 42A-E, are the FACS analysis on cells post thaw that were used for injection into mice in JME13-25 (PD0051 and PD00055 cells). As shown both samples of cells had CD8+ and CD4+ T-cells that expressed EGFRt.

Figure 43A:
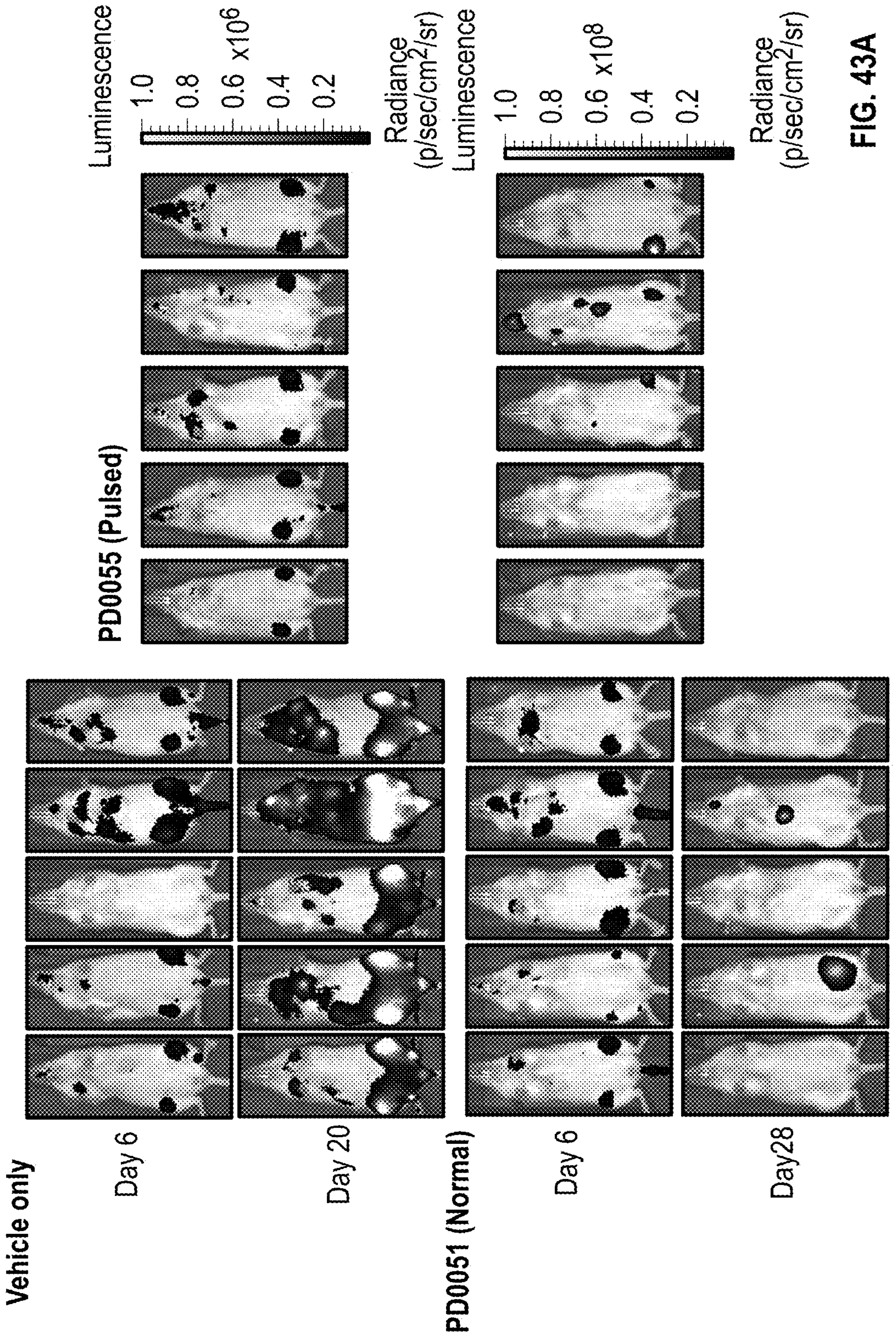
FIGS. 43A-C show a comparison of the three groups of mice that were treated with PBS, PD0051 (normal expansion cells) and PD00055 (cells expanded in the presence of cytokine combinations)
Figure 43B:
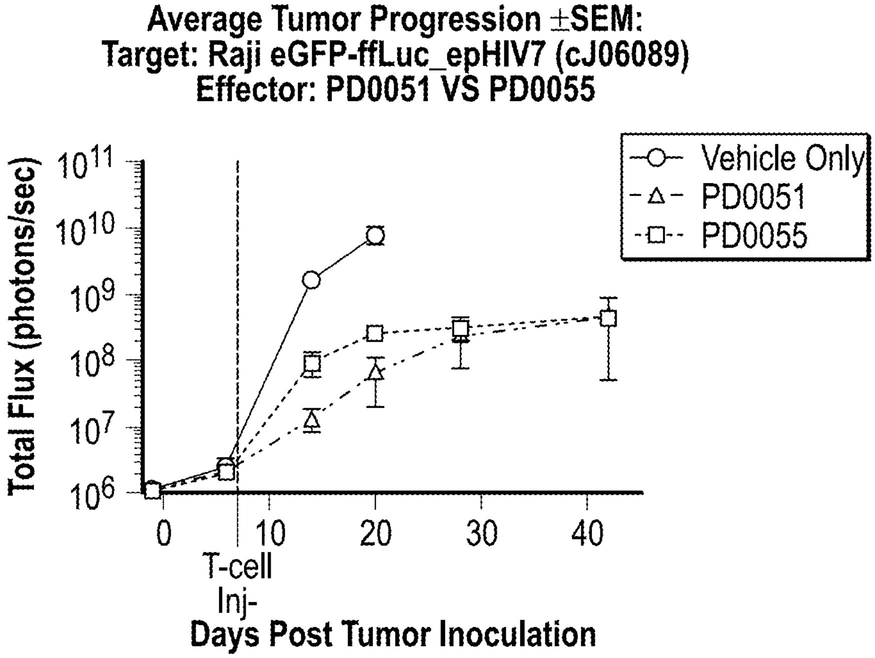
Figure 43C:
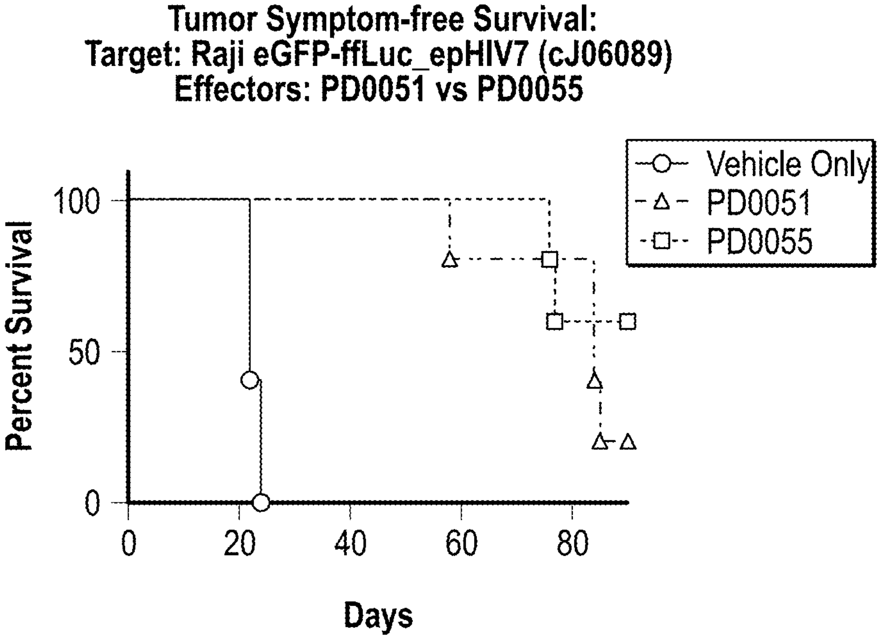

As shown in FIGS. 43A-C, are the three groups of mice from groups A, B, and C that were treated with placebo PBS (group A), group B (PD00051 "normal expansion cells") and group C (PD00055, cells pulsed with cytokine combinations). As shown, mice that were treated with the placebo in Group A had tumor progression that is visibly seen at day 20. For the Group B mice treated with PD0051 (normal expansion cells), the mice, it is shown that tumor progression increases in two mice substantially. In the Group C, mice, the mice treated with PD00055 show only a small amount of tumor progression, therefore indicating the cells treated with the cytokine mixture prior to use in treatment had a higher engraftment fitness.

Figure 44A:
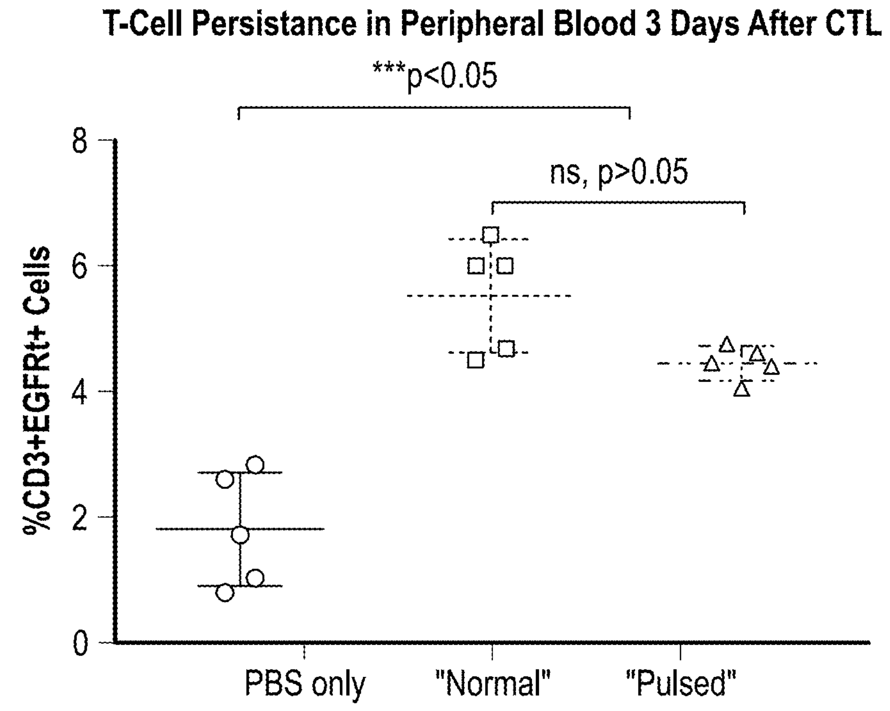
FIGS. 44A-C show the T-cell persistence in peripheral blood of the mice by detection of the EGFRt CAR marker.
Figure 44B:
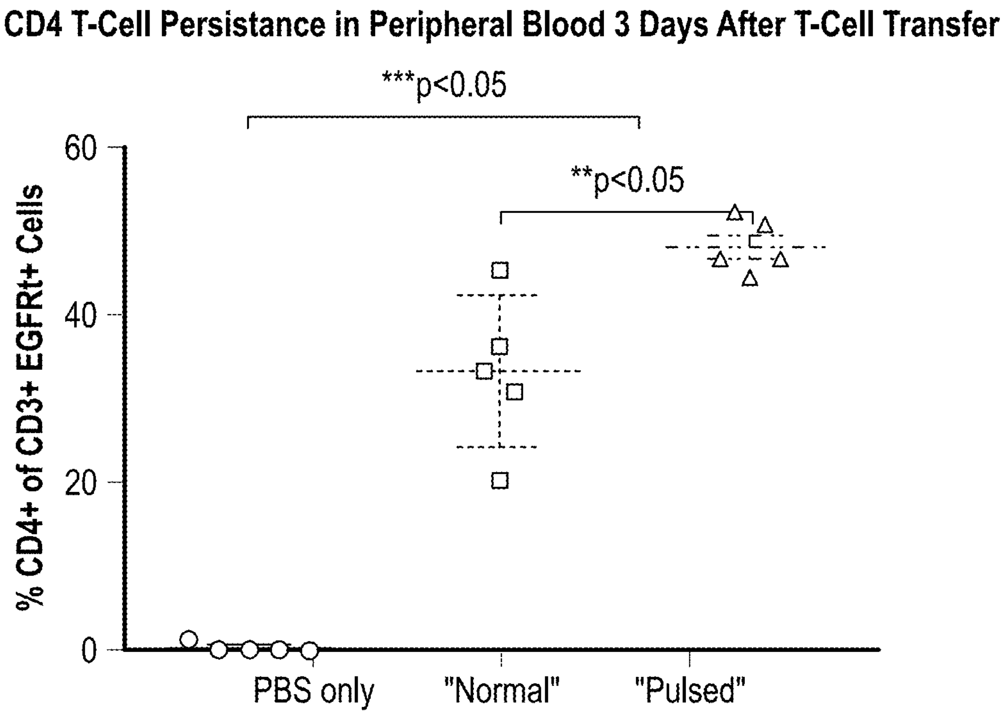
Figure 44C:
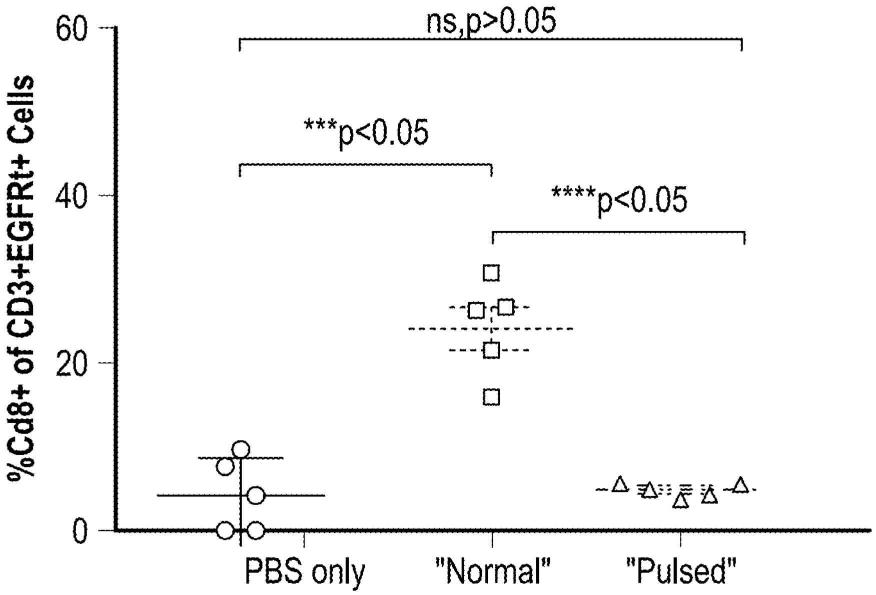

As shown in FIGS. 44A-C, is the persistence of the CAR expressing T-cells in the mice after three days of administration. As indicated, the CD4+ T-cells expressing the CARs had a higher persistence compared to the cells of normal expansion as well as the CD8+ T-cells.

Following experiments examining tumor progression after T-cell treatments with CAR expressing T-cells, experiments were performed to determine if there is an in vivo difference in killing ability between cells that have been grown in various cytokine conditions in vitro with repeat antigen encounters (FIG. 45). For the experiment 3 groups of mice were used in which the groups utilized 3 mice each. For Group A, the mice were treated with a placebo (PBS). Group B were treated with cells that were expanded by the "normal expansion method" ("Normal" 1:1 EGFRt+CD4:CD8 transduced with Zrx-014 PD0055 #1 (Donor PD0038 CD4 with 5 ng/ml IL7 & 0.5 ng/ml IL15, S1D14 @ 75.9% EGFRt+) PD0051 #1 (Donor PD0038 CD8 with 50 U/ml IL2 & 0.5 ng/ml IL15, S1D21 @ 76.8% EGFRt+) (FIGS. 18A-B). Group C were treated with cells pulsed with cytokines during expansion ("Pulsed" 1:1 EGFRt+CD4:CD8 transduced with Zrx-014 PD0055 #2 (Donor PD0038 CD4 with 50 U/ml IL2 pulse 5 days, then 5 ng/ml IL7 & 5 ng/ml IL21, S1D11 at 81.2% EGFRt+) PD0051 #2 (Donor PD0038 CD8 with 50 U/ml IL2 pulse 5 days, then 5 ng/ml IL7 & 5 ng/ml IL21, S1D21 at 89.5% EGFRt+).

Figure 46A:
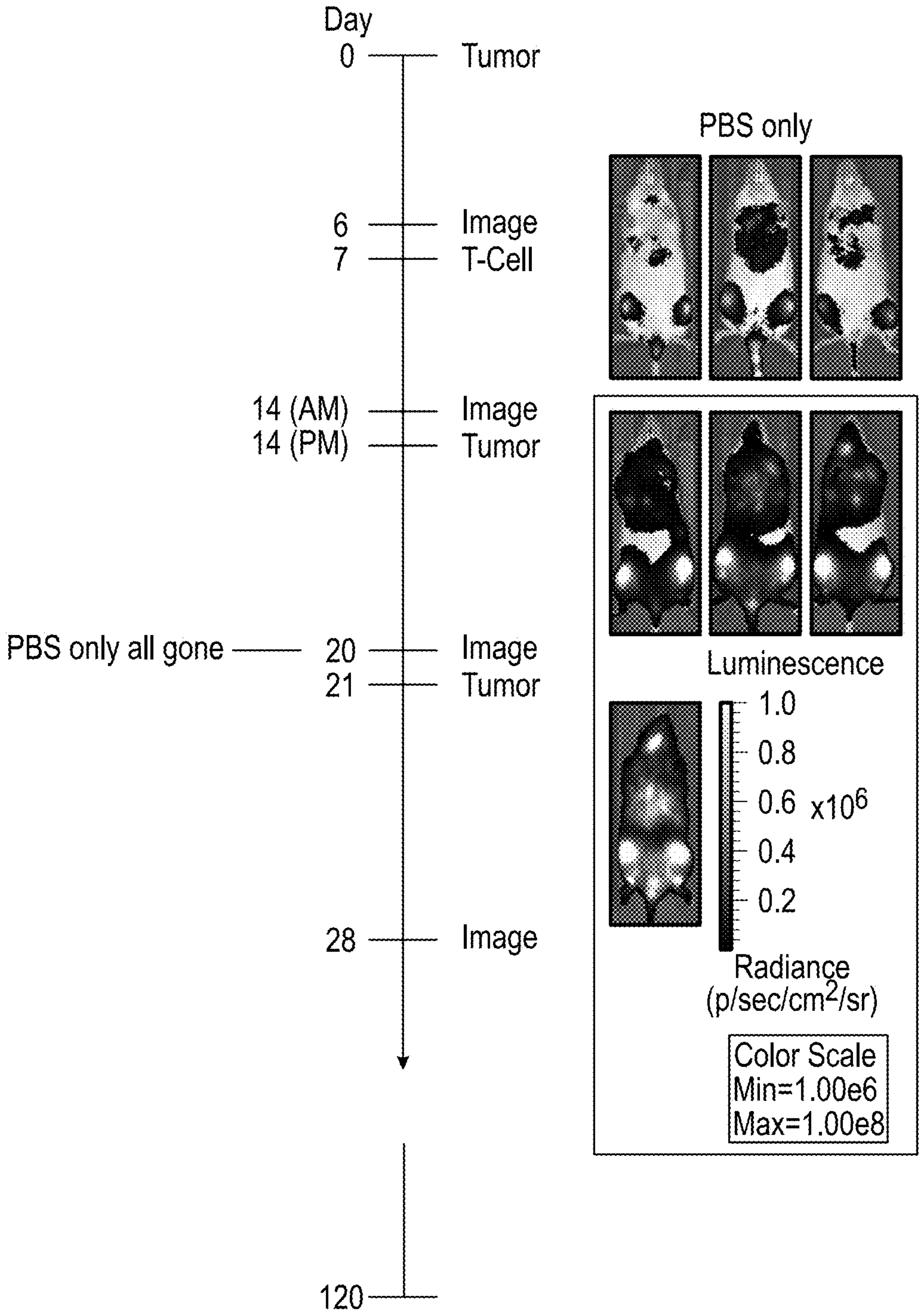
FIGS. 46A-B show the tumor progression of PD0051 and PD0055 treated mice following treatment from day 0 to day 120.
Figure 46B:
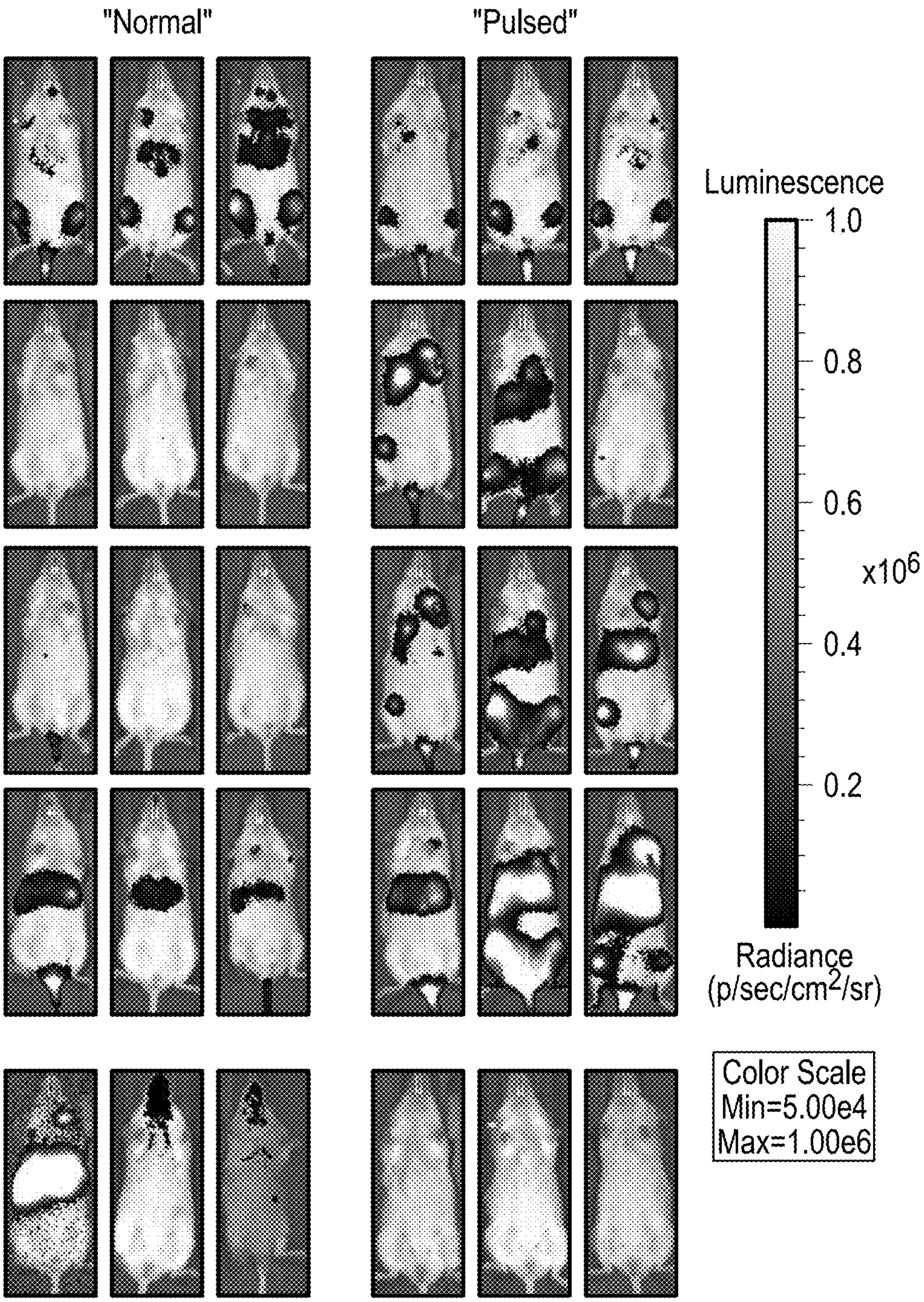

As shown in FIGS. 46A-B, group A mice died by day 20 following injection with PBS. Group B mice treated with cells that were expanded by the "normal expansion method" had tumor progression in one mouse by day 120. However, for mice treated with the cells that were expanded in cytokines, the mice were tumor free by day 120. As such the data indicate that the cells treated in the cytokine mixtures specific for CD4+ and CD8+ led to a higher engraftment rate and increased survival in the mice. Additionally, the cells were more efficient in preventing tumor progression.

Figure 47A:
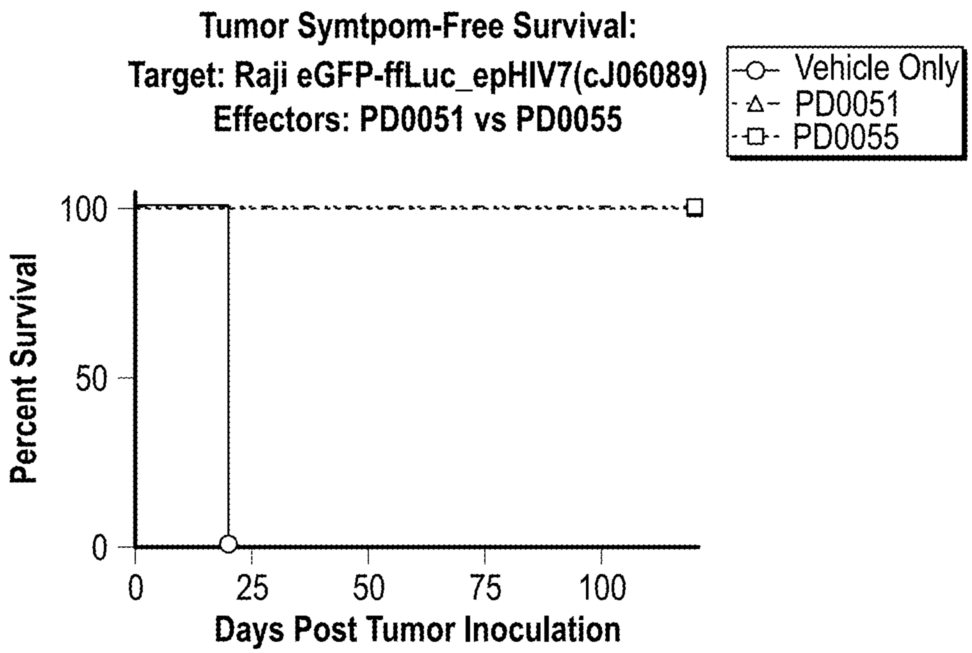
FIGS. 47A-C show PD0051 and PD0055 cells challenged with repeat antigen exposure.
Figure 47B:
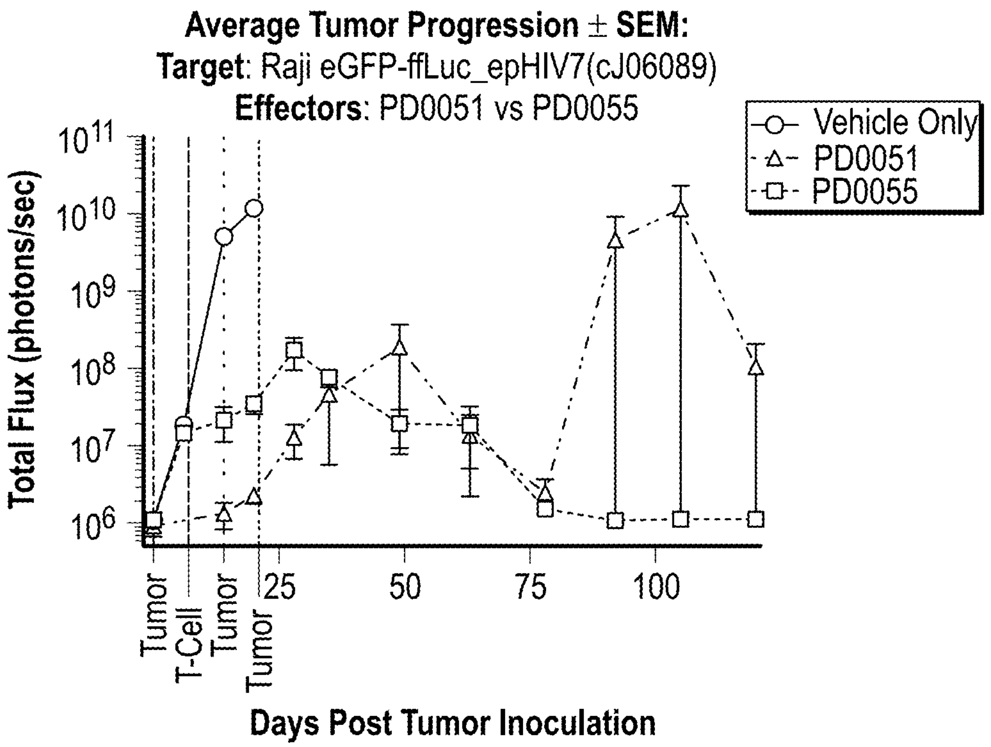
Figure 47C:
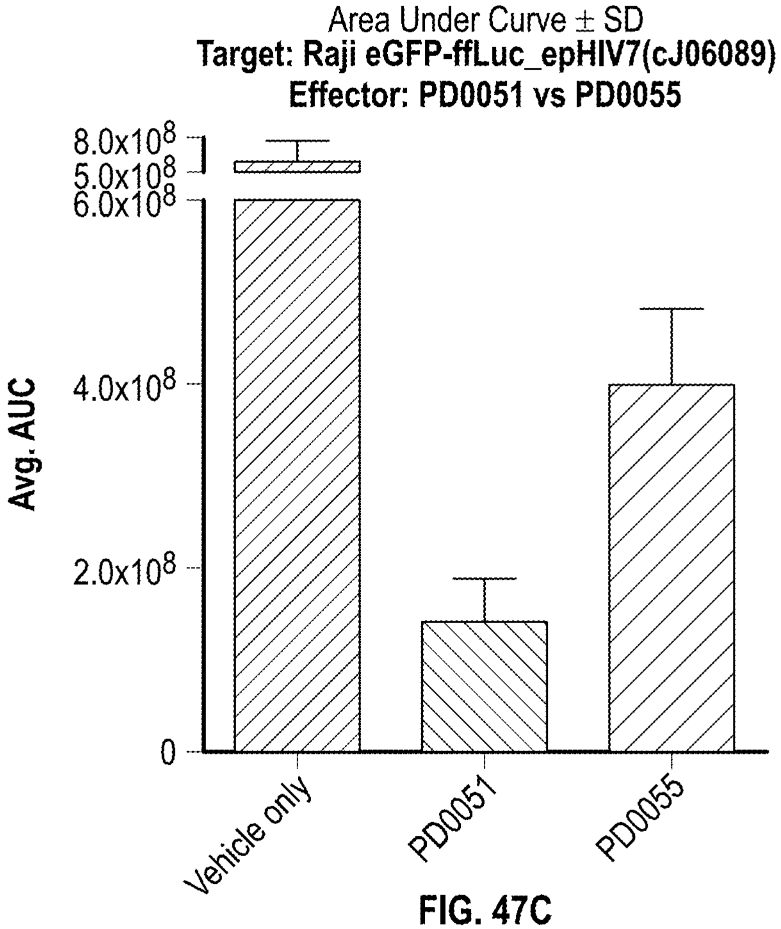
Figure 48A:
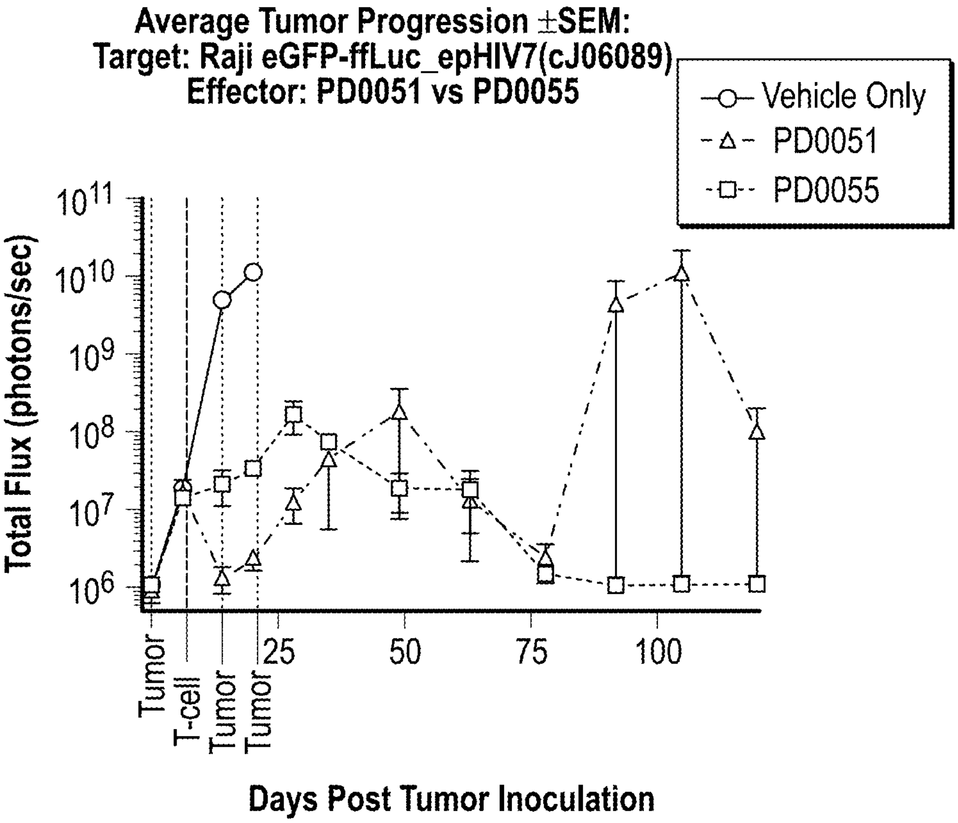
FIGS. 48A-D show JME13-29 repeated Raji Tumor challenge of "normal expansion cells" versus T-cells pulsed with cytokine combinations.
Figure 48B:
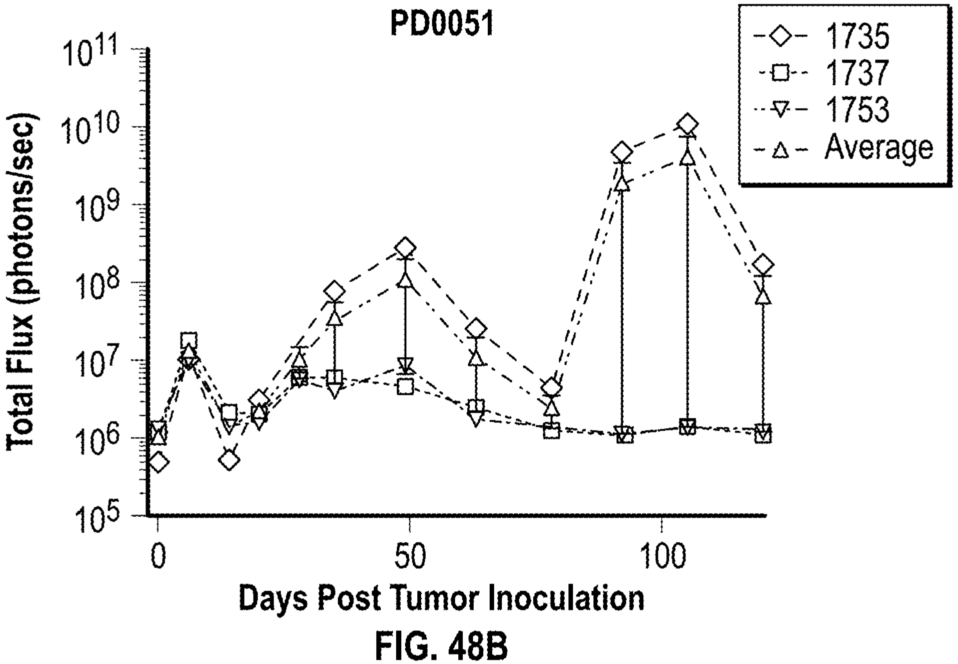
Figures 48C, 48D:
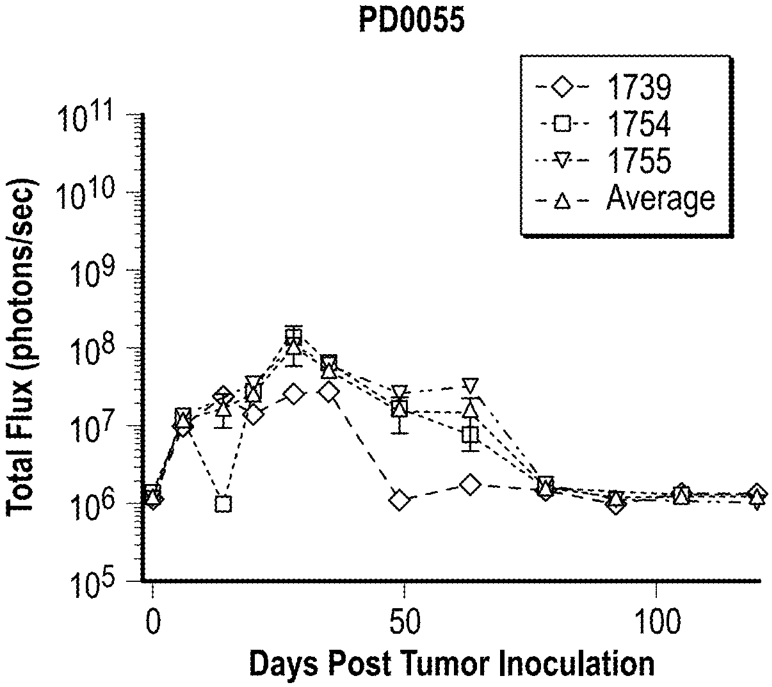
Figure 51A:
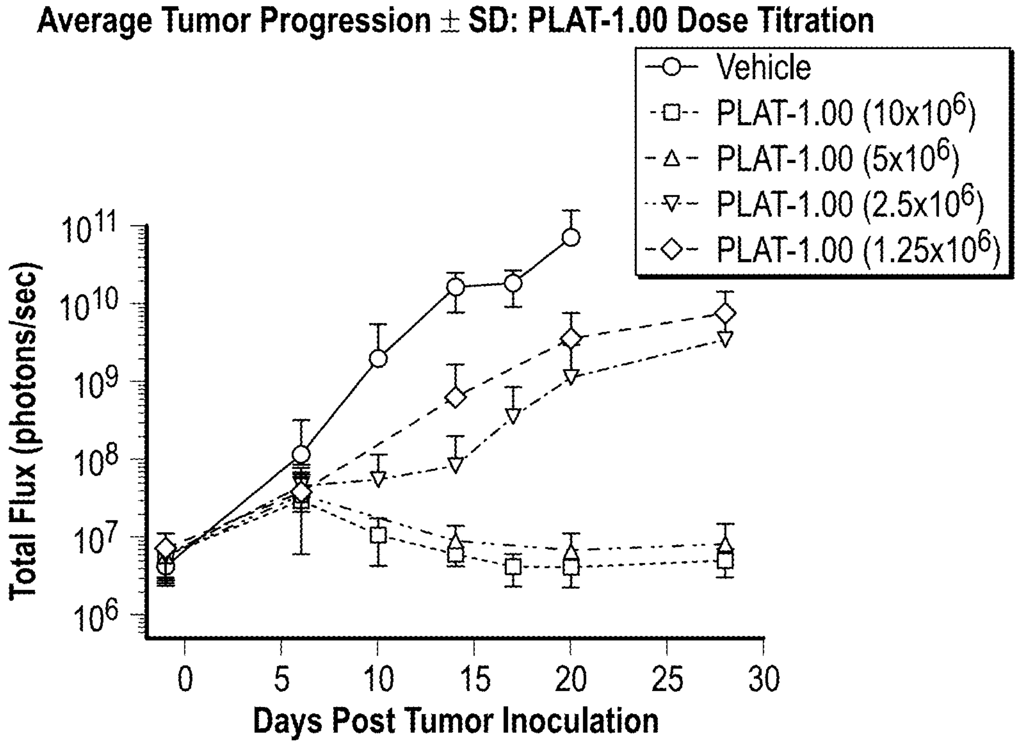
FIGS. 51A-D show the average tumor progression after treatment with T-cells at specific dose titrations.
Figure 51B:
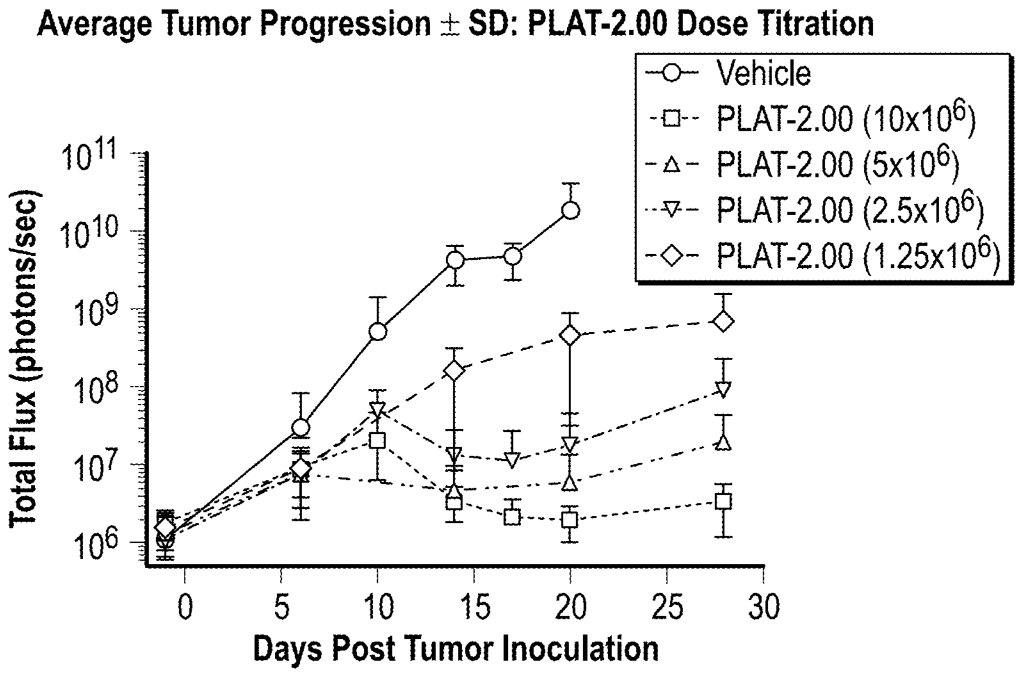
Figure 51C:
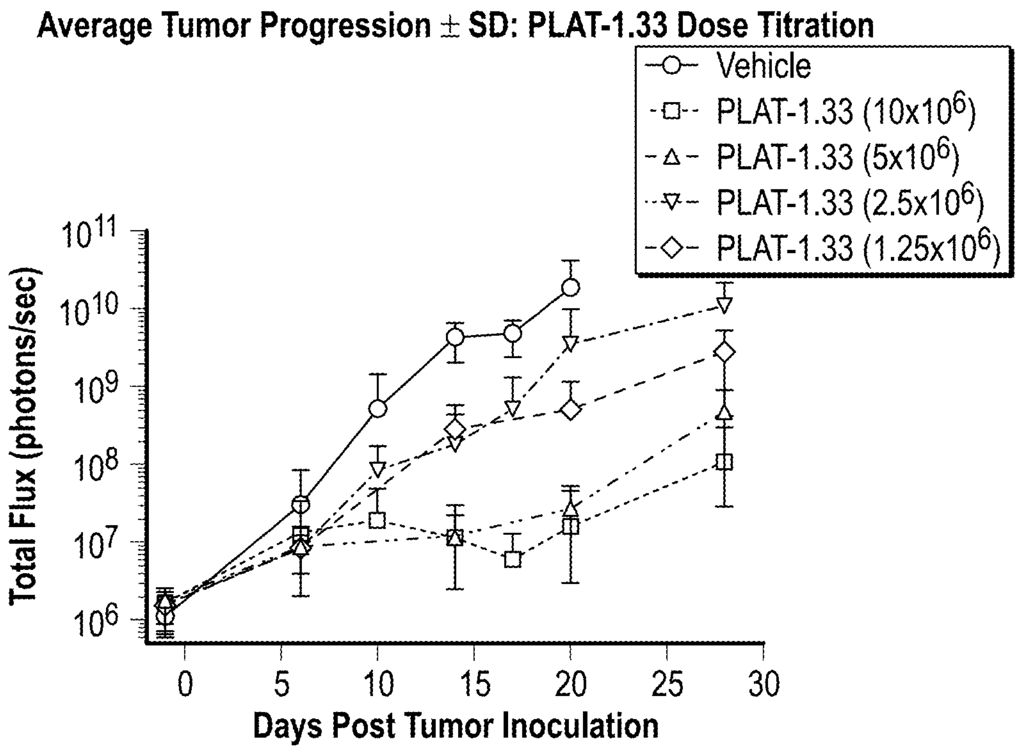
Figure 51D:
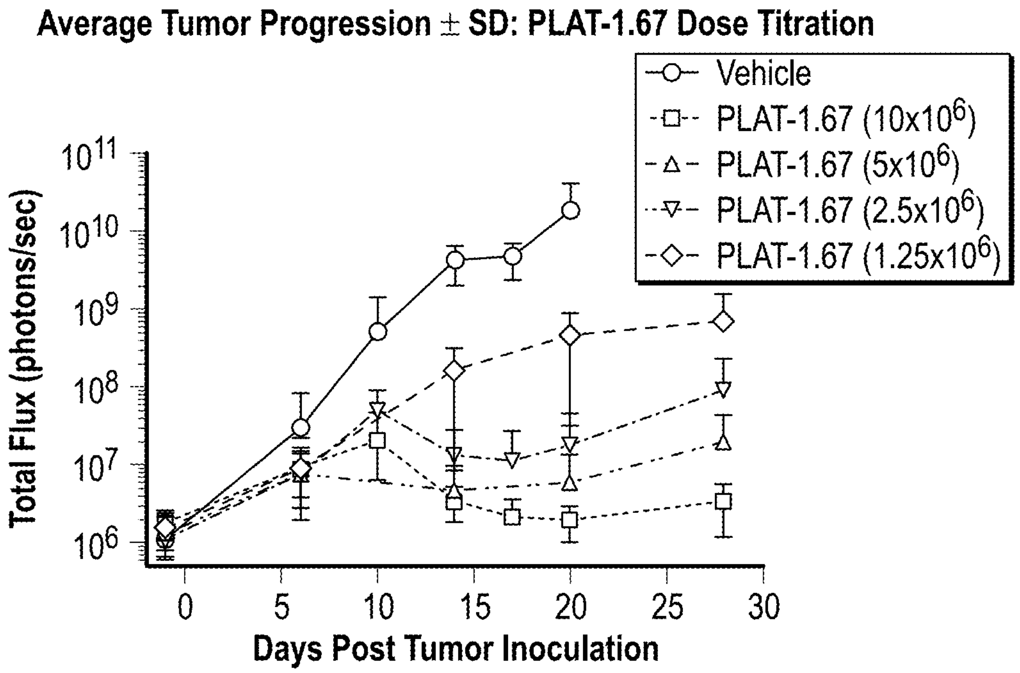
Figure 52A:
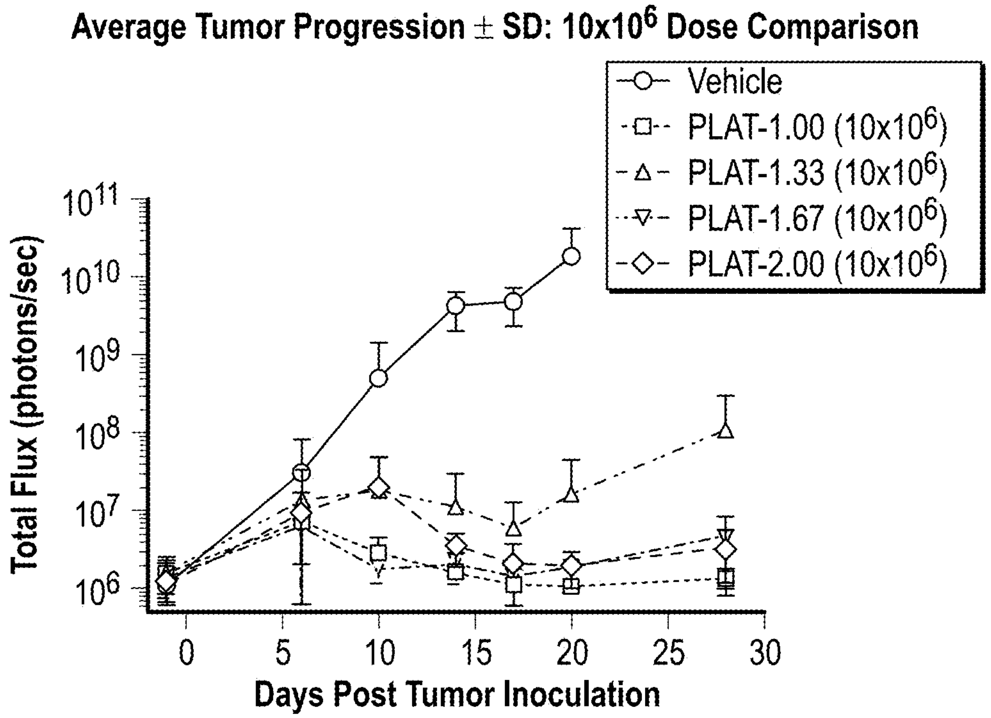
FIGS. 52A-D show the PLAT comparisons within dosing groups of T-cell treatments.
Figure 52B:
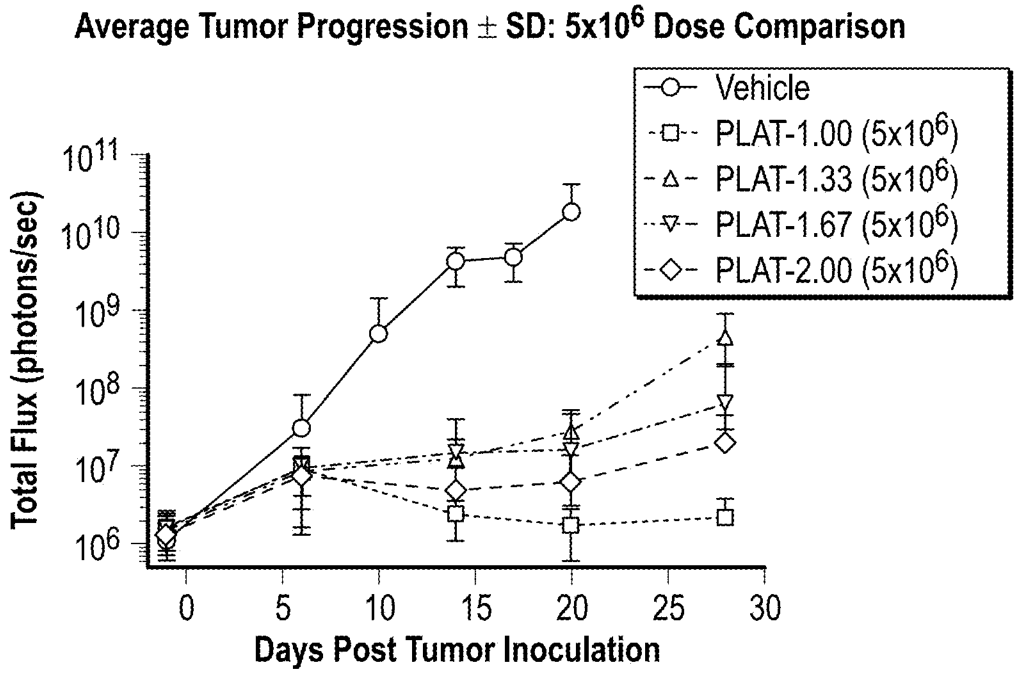
Figure 52C:
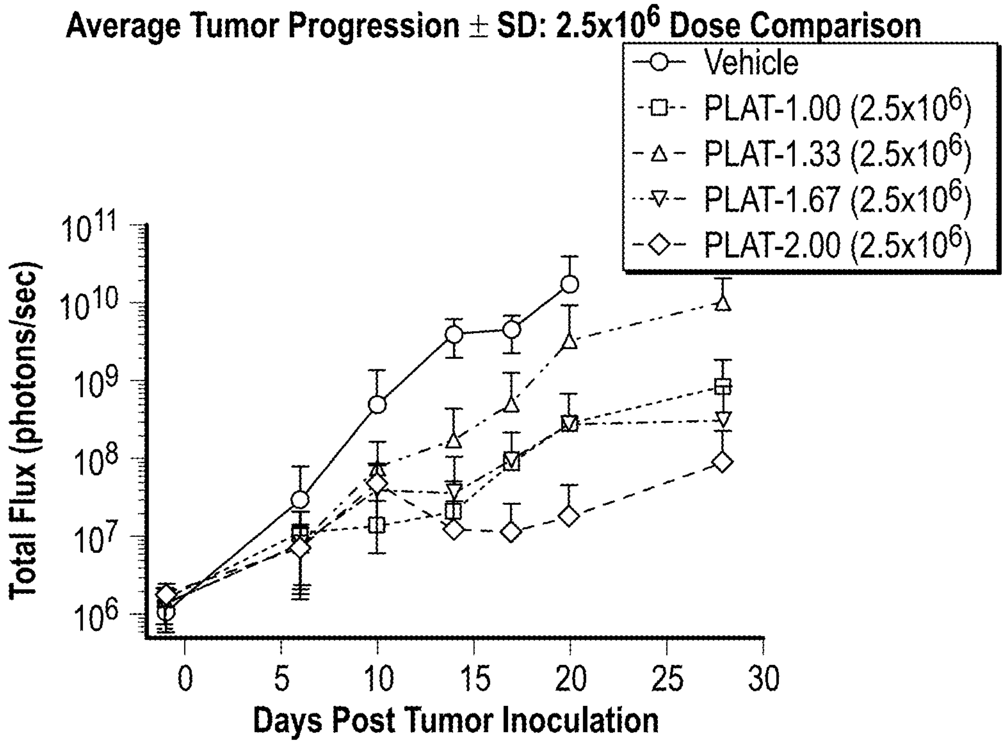
Figure 52D:
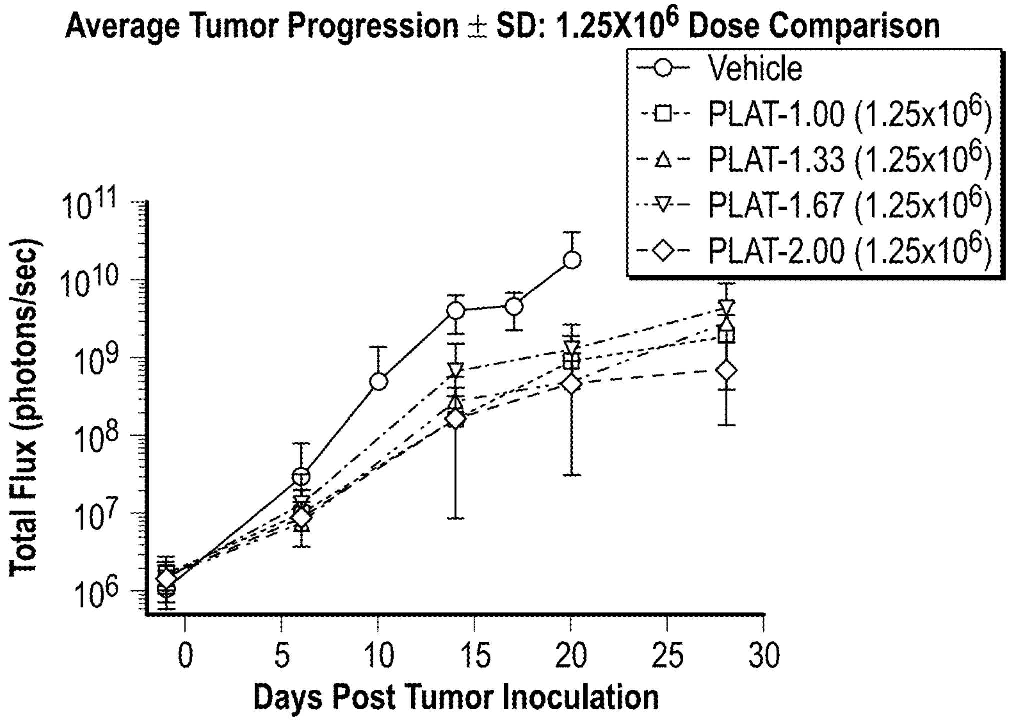
Figure 54A:
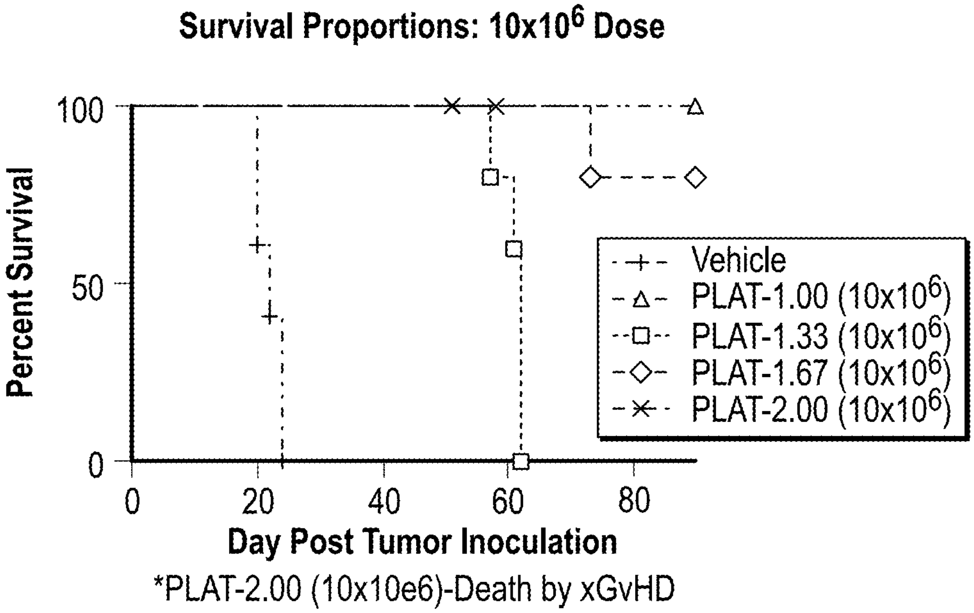
FIGS. 54A-D show the dose titration survival of mice treated with T-cells from the products of PLAT-1.00, PLAT-1.33, PLAT-1.67 and PLAT-2.00. The figures illustrate the PLAT comparison within dosing groups of cell treatments.
Figure 54B:
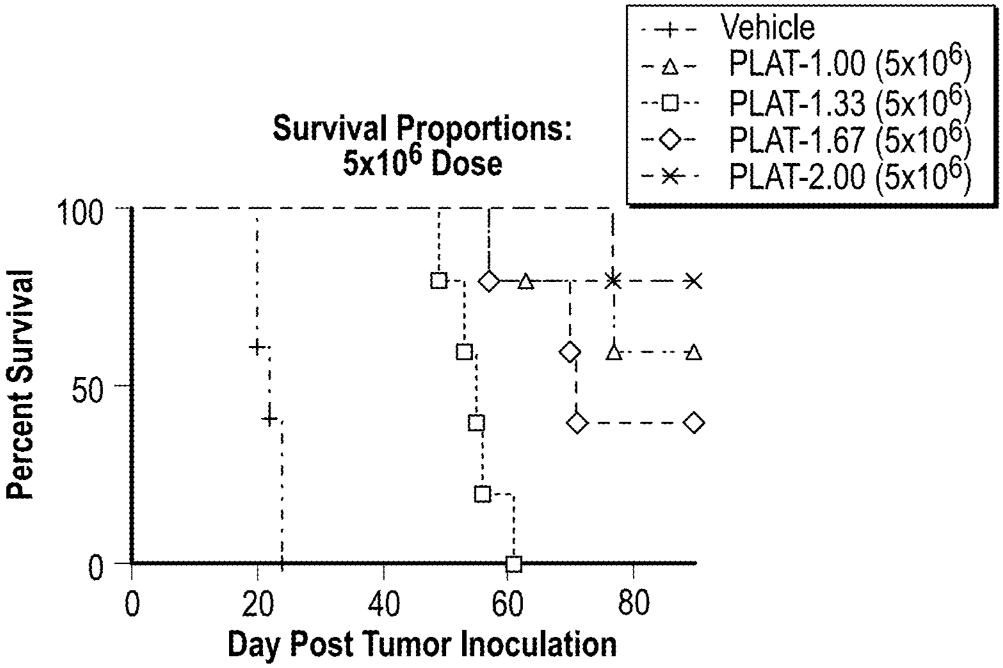
Figure 54C:
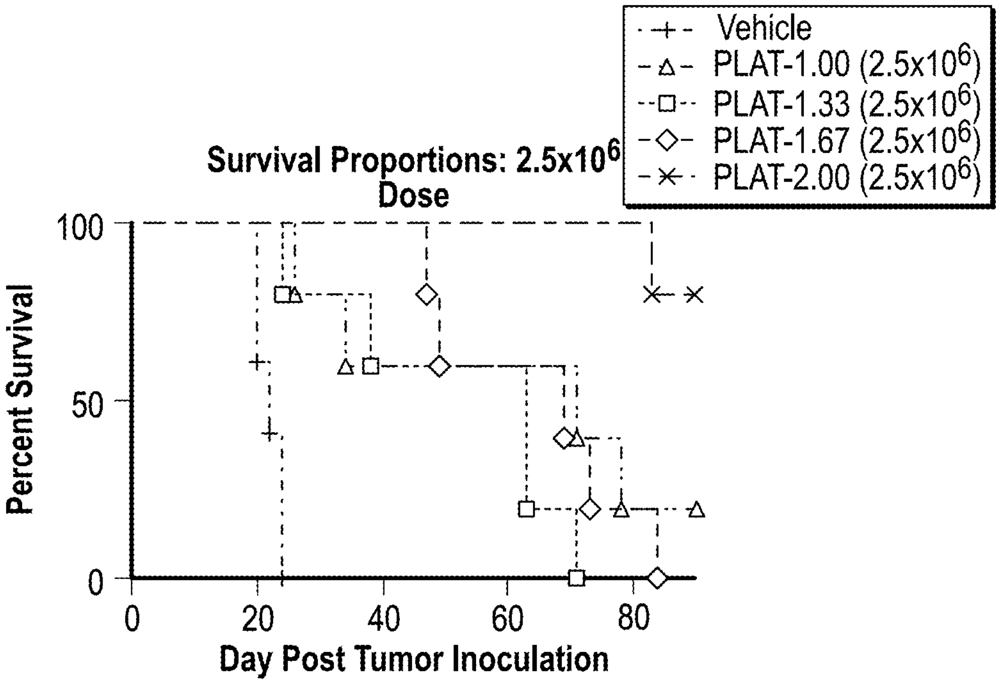
Figure 54D:
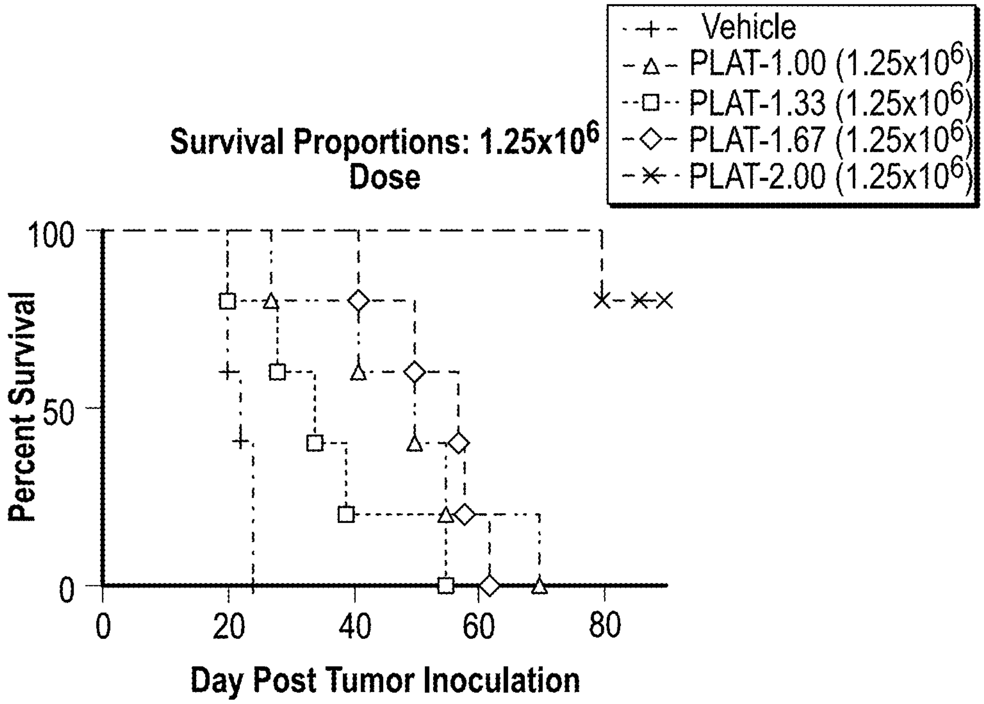
Figure 55A:
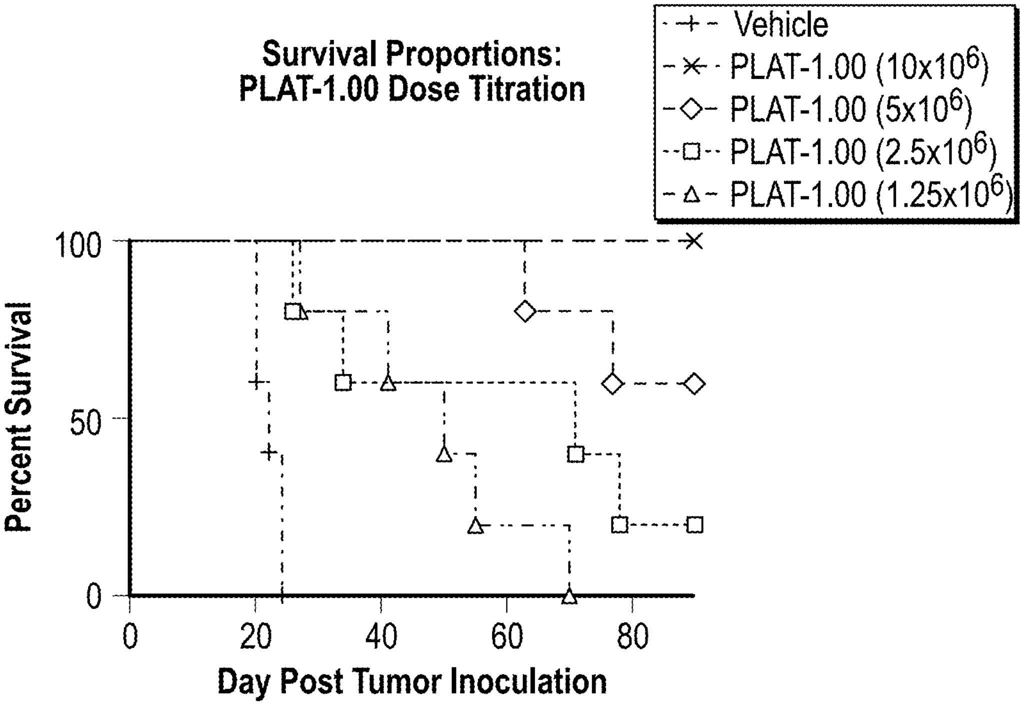
FIGS. 55A-D show the PLAT comparison of survival curves. The figures illustrate the average tumor progression after treatment with T-cells at specific doses.
Figure 55B:
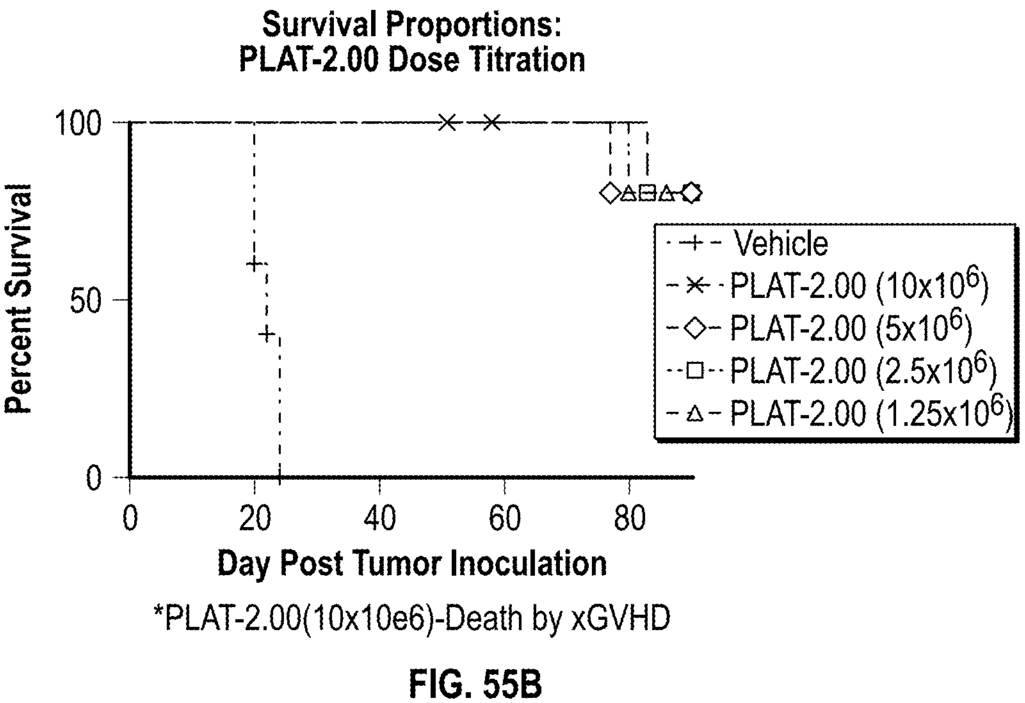
Figure 55C:
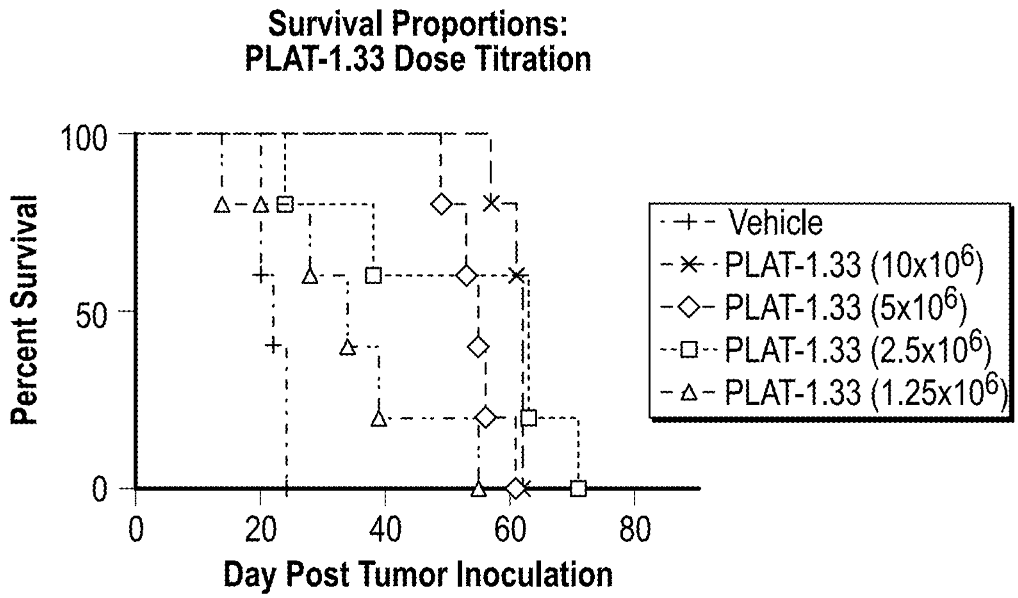
Figure 55D:
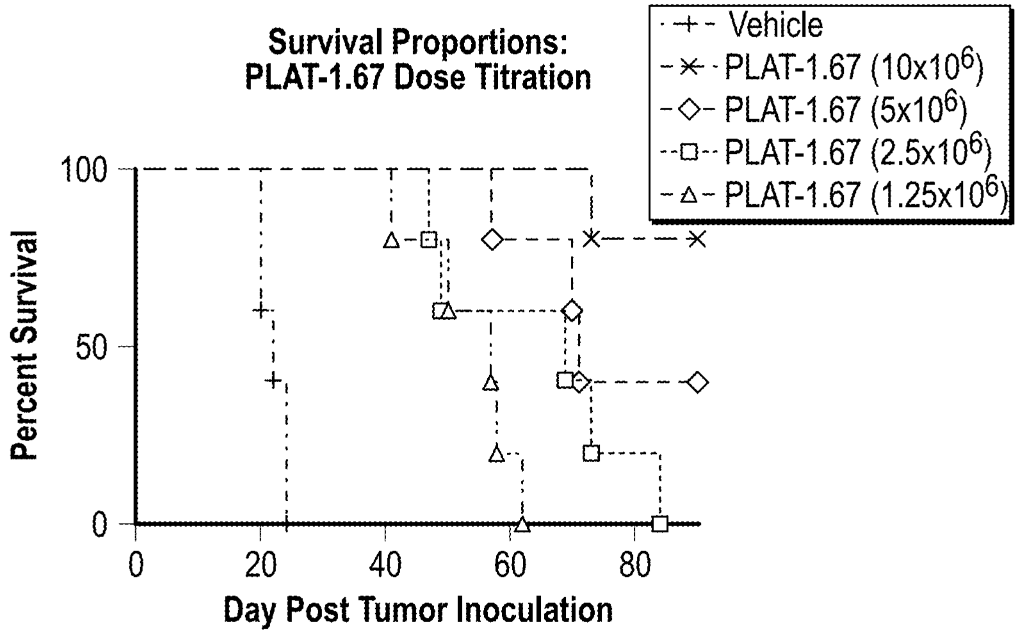
Figure 56A:
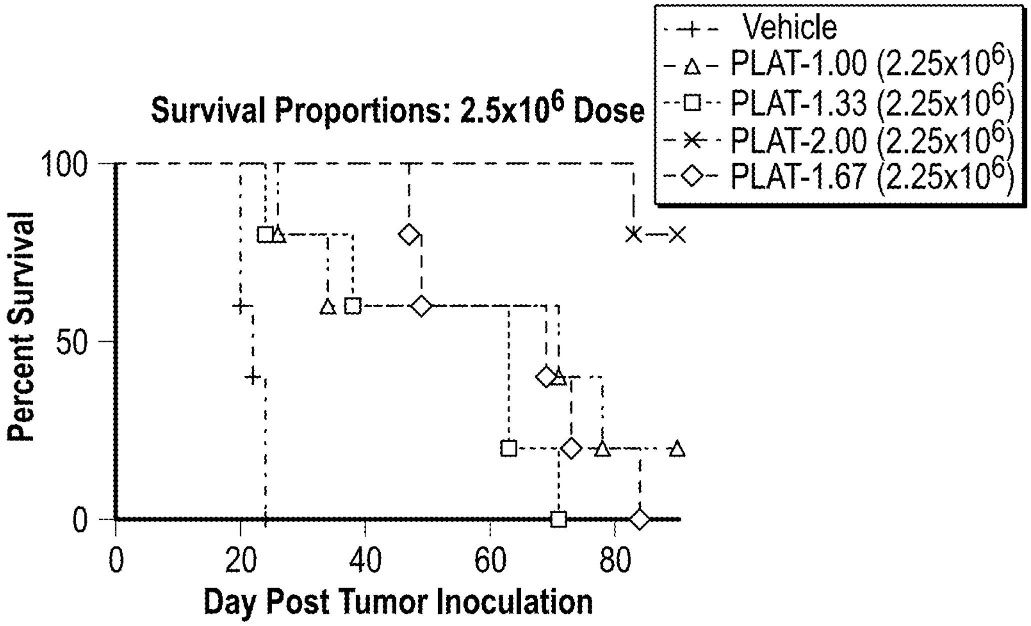
FIGS. 56A-D show the survival of the mice in response to T-cell treatment in which the T-cells were grown in normal expansion methods or grown in the presence of cytokines. The figures also show if the mice developed xenoGraft Host disease after T-cell treatment
Figure 56B:
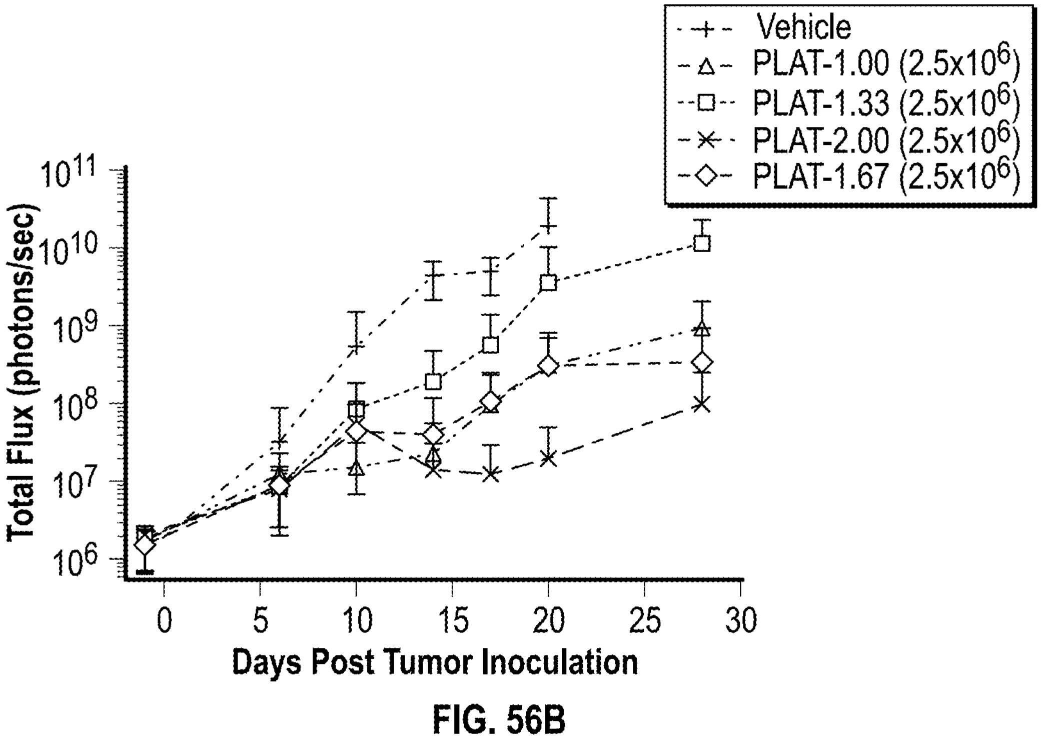
Figure 56C:
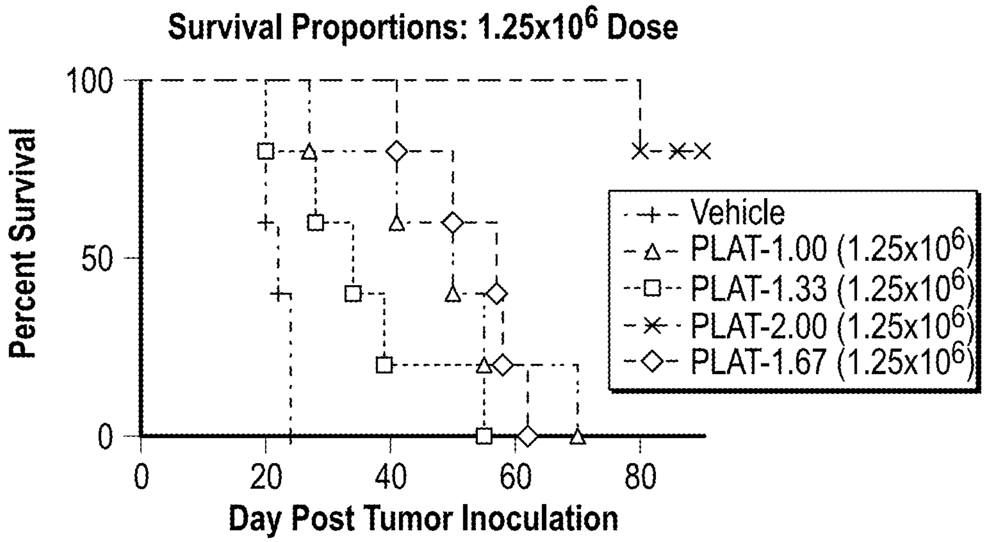
Figure 56D:
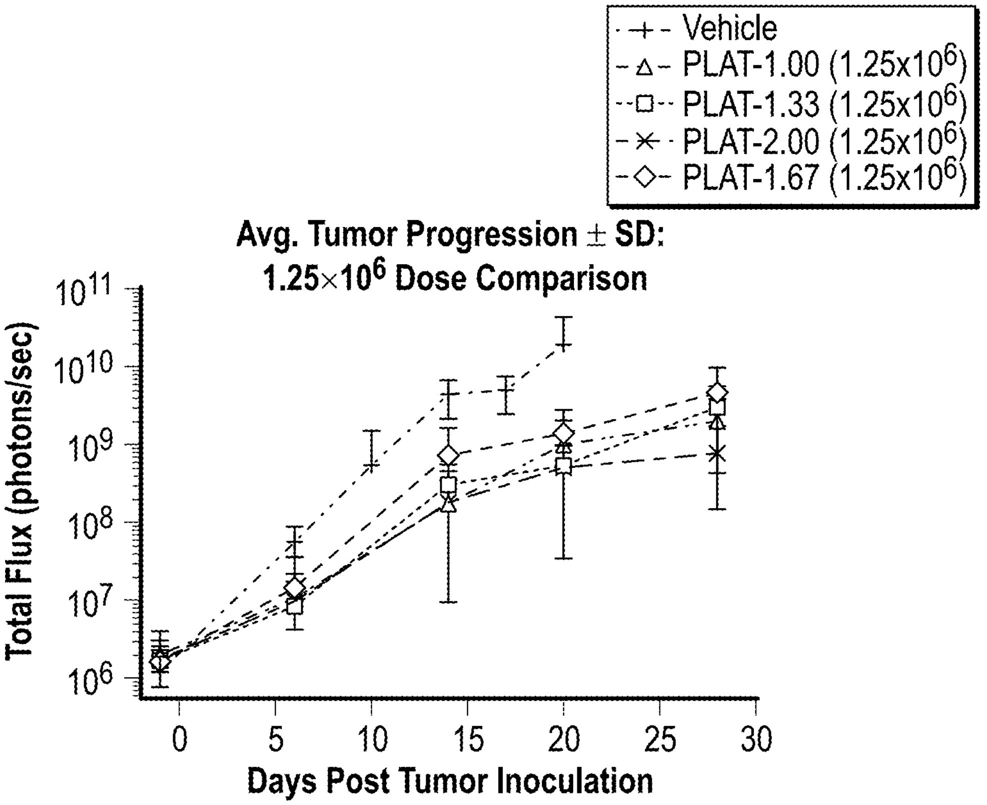
Figures 57A, 57B:
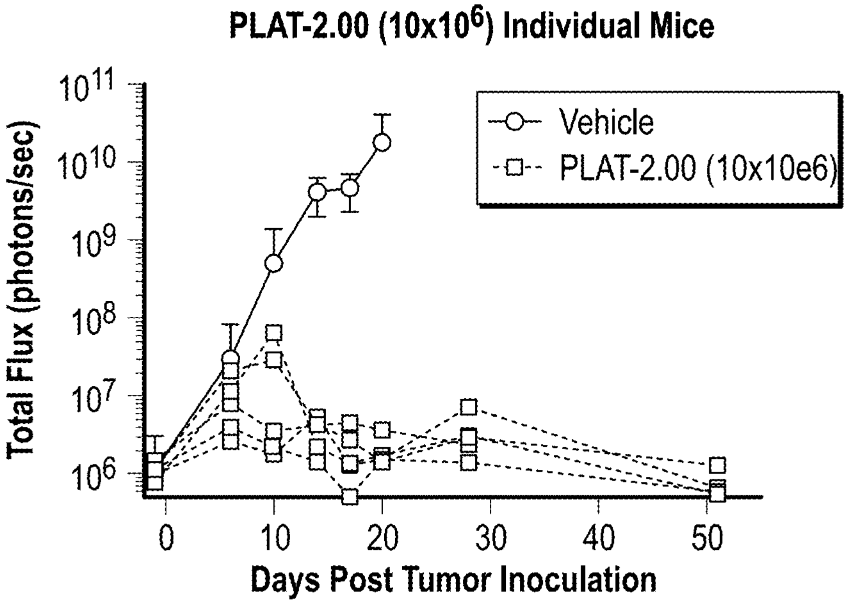
FIGS. 57A-C show the survival of the mice in response to T-cell treatment in which the T-cells were grown in normal expansion methods or grown in the presence of cytokines. The figures also show if the mice developed xenoGraft Host disease after T-cell treatment
Figure 57C:
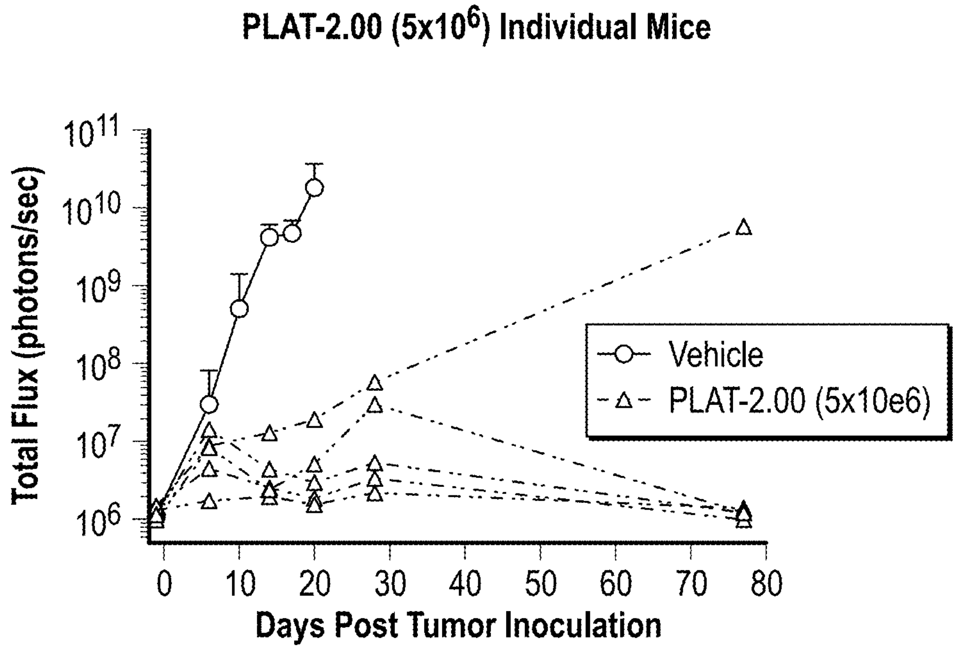
Figure 59A:
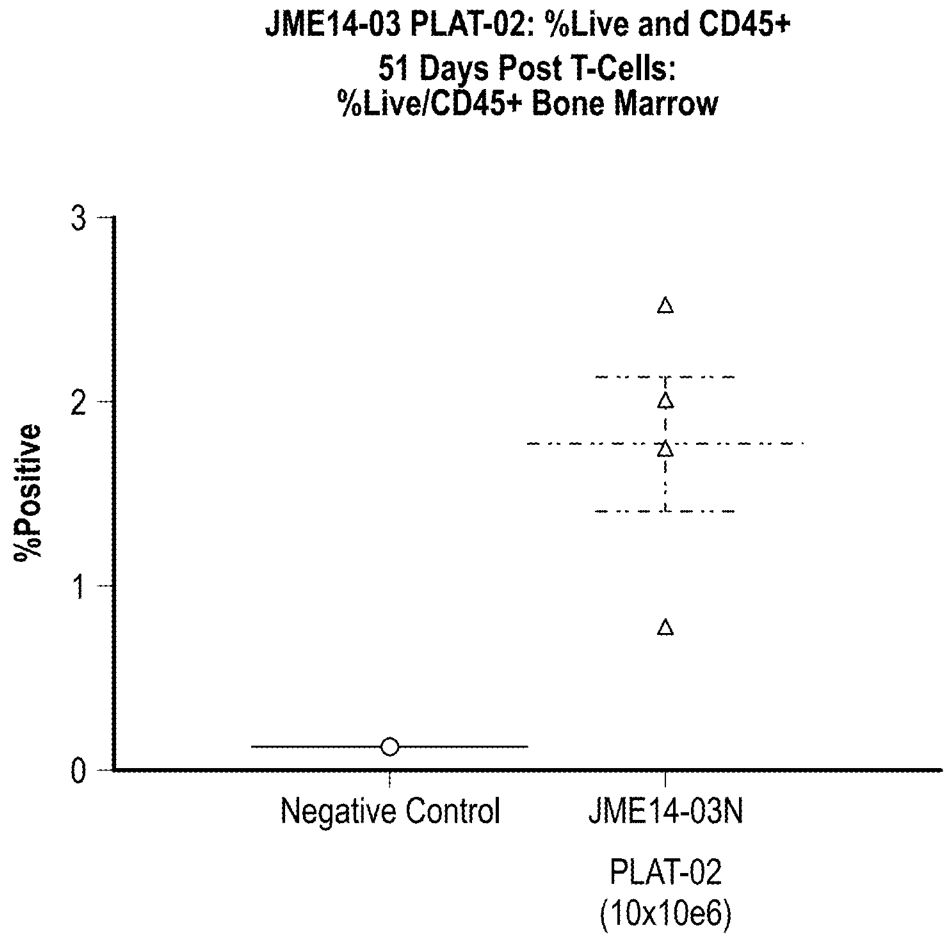
Figure 59C:
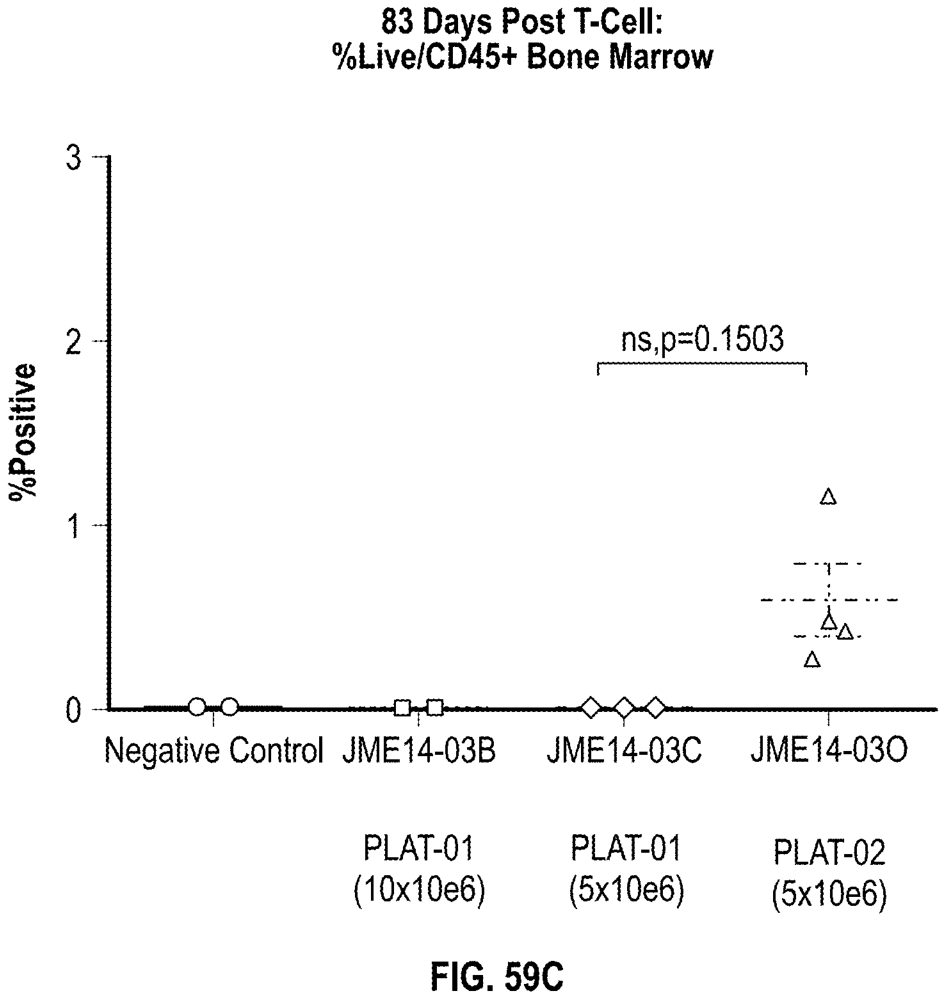
Figure 59E:
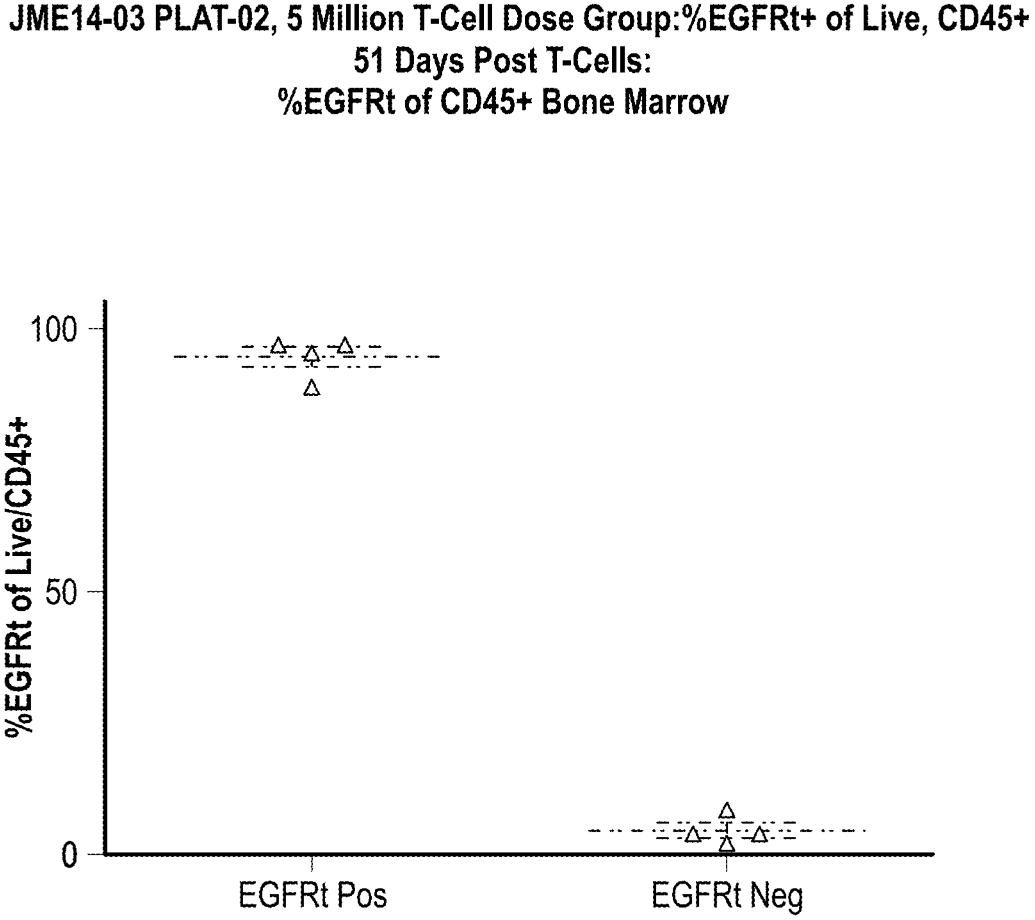
Figure 59G:
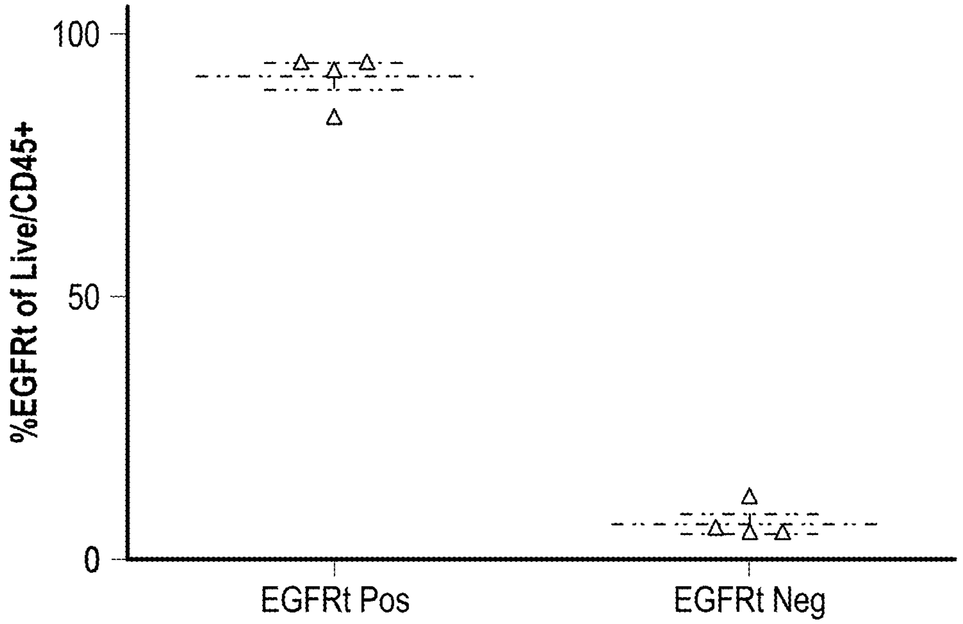
Figure 60A:
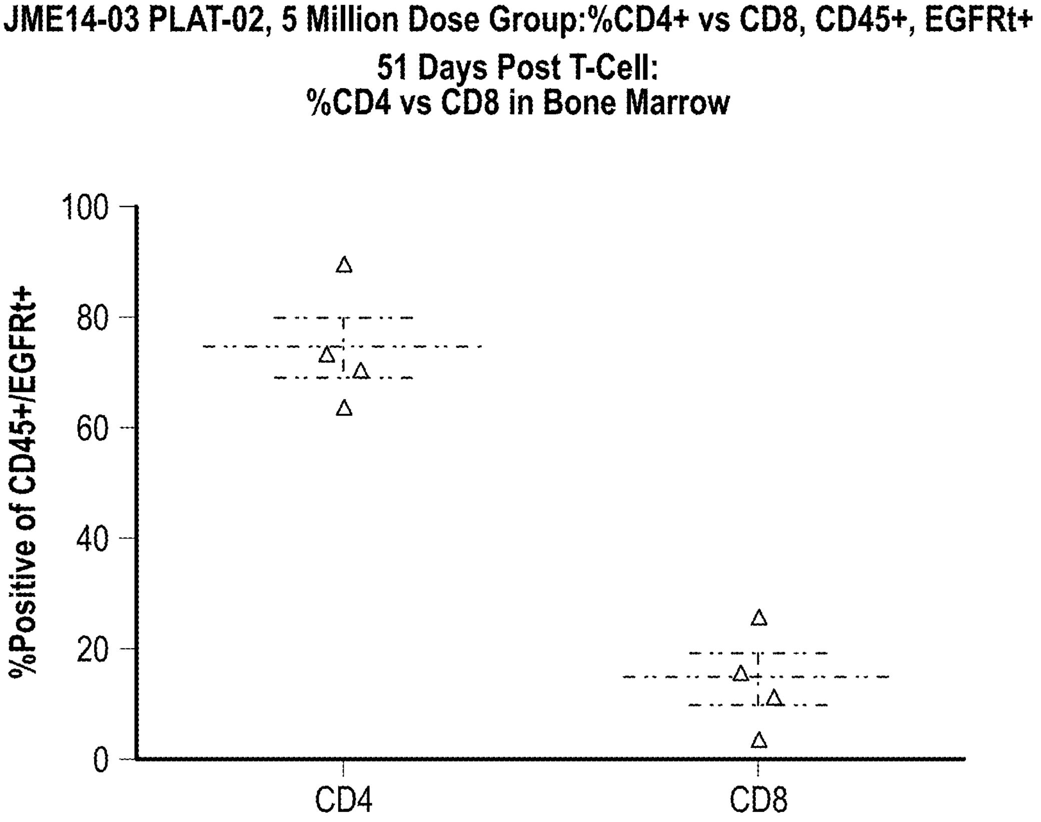
Figure 60C:
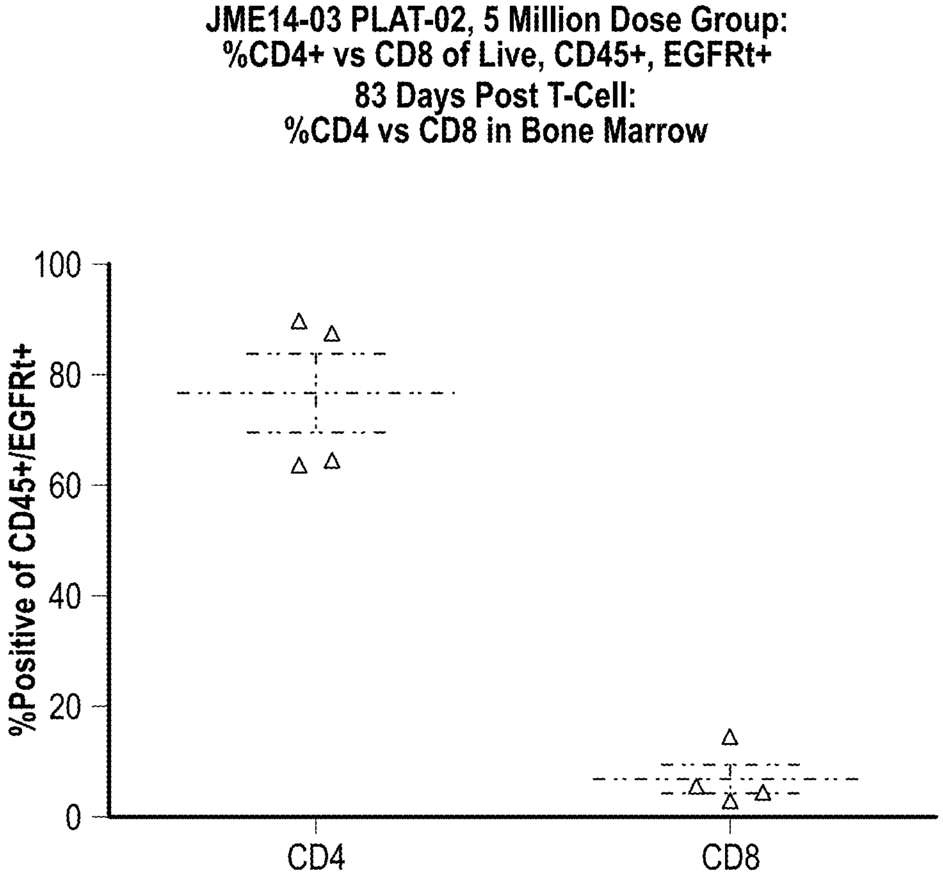

As shown in FIGS. 47A-C, the mice had a 100% survival rate when treated with PD0051 and PD0055 cells post tumor inoculation. However, the tumor progression was shown to decrease with the treatment using PD0055 cells.

As shown in FIGS. 48A-D, the average tumor progression was examined in mice treated with placebo, T-cells grown under "normal expansion" methods, and T-cells that were pulsed with cytokine combinations. For the experiment at day 0, mice were tumor inoculated and imaged for tumors at day 6. At day 7, T-cells or a placebo was then administered. Tumor inoculation was then repeated at day 14 and day 21.

The mice were examined for tumor progression at day 28, 35, 49, 63, 78, 92, 105 and 120, in which images of the tumors were taken. As shown in the groups of mice, tumor progression decreased in the mice treated with the cells that were pulsed with cytokines thus indicating that the cells pulsed with cytokines had a higher, improved, or enhanced engraftment fitness than the cells that were expanded under normal conditions without cytokines.

As shown in FIG. 49, experiments were set up to determine if there is an in vivo difference in killing ability between cells that have been grown under the same conditions as PLAT-01 and PLAT-02 as well as "in between" protocols. For the experiment 17 groups of 5 mice were used test the cells in the treatment of mice after tumor inoculation. The groups were given a dose of cells ($1.25\times10^6$, $2.5\times10^6$, $5\times10^6$, $10\times10^6$) per product condition as indicated on the Table of FIG. 49. The cells were thawed, counted and injected into the mice on the same day. As shown in FIG. 50, are the amounts of CD4+ and CD8+ cells in the different cell products from the two expansion methods and their amounts of EGFRt in the cells.

As shown in FIGS. 51A-D, the 17 groups of mice were tumor inoculated then treated with dose titrations with T-cells that were expanded under normal expansion methods or pulsed with cytokine combinations. As seen in the graphs, mice that were dosed with PLAT-1.00 cells at the higher concentrations had a decrease in tumor progression. Mice that were dosed with PLAT-2.00 also saw a decrease in tumor progression after 25 days of administration at a higher concentration of cells. However, for mice dosed with PLAT-1.33, the mice saw an increase in tumor progression regardless of cell concentration indicating a low or reduced engraftment fitness for these cells. For mice that were given cells from PLAT-1.67, the mice had a decrease in tumor progression when treated with the highest concentration of cells in the administration. However as noted in FIG. 50, the cells of PLAT-1.33 also had a low EGFRt count which could also indicate a decreased amount of CAR on the cell surface.

Shown in the FIGS. 51A-D, is the initiation comparisons between the PD104 and the PD116 cell product. For the PD0104 produce, PD0063 CD8+ and CD4+ enriched cells were used to repeat experiment to test the expansion of cells on Tx day to $0.7\times10^6$ cell/mL ("early expansion"). For normal PLAT-02 culture conditions, IL-2 (50 U/ml)+IL-15 (0.5 ng/mL) for CD8+ cells and IL-7 (5 ng/mL)+IL-15 (0.5 ng/mL) for CD4+ T cells were used. Growth and viability were increased dramatically. These curves mimic what was seen in clinical products as far as timing of growth/bead removal/selection/cryo.

As shown in FIGS. 52A-D, mice were treated with dose titrations of cell products of PLAT-1.00, PLAT-1.33, PLAT-1.67 and PLAT-2.00. As shown in all graphs, the lowest concentration of cells was least effective in the treatment of tumor progression. However, the cells that showed the most engraftment fitness were the PLAT-1.00 and the PLAT-2.00 at higher concentration.

As shown in FIGS. 53A-E, all the cells were least effective at concentration $1.25\times10^6$. The cells from PLAT-1.00 showed to be the most effective at inhibiting tumor progression indicating that the engraftment fitness of the cells were superior or improved, or enhanced as compared to the other groups and indicated that the treatment with cytokines also promoted, improved, or enhanced engraftment fitness for the cells. As shown at a concentration of $5\times10^6$, the tumor progression was halted at 25 days in comparison to the other groups of cells used to treat the mice.

As shown in FIGS. 54A-D, the mice had a higher rate of survival if treated with a dose of cells between $2.5\times10^6$ and $10\times10^6$ cells per dose. However, the mice treated with the cells from the PLAT-1.00 product had a longer survival rate indicating that the T-cells from this group were more robust and exhibited a higher, improved, or enhanced engraftment fitness.

As shown in FIGS. 55A-D, the survival of the mice was dependent on the dose concentration of the cells. For all cells, the survival of the mice decreased with the lowest dose of T-cell treatments. However, as previously shown the mice treated with the cells from the PLAT-1.00 product had a longer survival rate indicating that the T-cells from this group were more robust and had an improved engraftment fitness.

Additional Alternatives

In some alternatives, a method of making genetically modified T-cells, which have a chimeric antigen receptor is provided, wherein the method comprises separating, isolating, or enriching a CD8+ population of T-cells and/or a CD4+ population of T-cells from a mixed population of T-cells, such as T-cells that are derived from thymocytes or T-cells that are derived from engineered precursors, desirably iPS cells, so as to generate an isolated population of T-cells, stimulating the obtained population of T-cells so as to generate a stimulated population of CD8+ T-cells and/or CD4+ T-cells, transducing the stimulated population of CD8+ T-cells and/or CD4+ T-cells with a vector, wherein the vector encodes a chimeric antigen receptor and a marker sequence, wherein said marker sequence encodes a cell surface selectable marker, so as to generate a transduced population of CD8+ T-cells and/or CD4+ T-cells, contacting the transduced population of CD8+ T-cells and/or CD4+ T-cells with at least one cytokine so as to generate a transduced, cytokine-stimulated population of CD8+ T-cells and/or CD4+ T-cells, enriching the transduced, cytokine-stimulated population of CD8+ T-cells and/or CD4+ T-cells by selection of the marker sequence so as to generate an enriched population of transduced, cytokine-stimulated CD8+ T-cells and/or CD4+ T-cells and propagating the enriched population of transduced, cytokine-stimulated CD8+ T-cells and/or CD4+ T-cells for at least one day so as to obtain said genetically modified T-cells, which have a chimeric antigen receptor.

In some alternatives, the separating of the CD8+ population of T-cells and/or a CD4+ population of T-cells from a mixed population of T-cells is performed by affinity selection for T-cells having an epitope present on CD8 and/or CD4. In some alternatives, the separating of the CD8+ population of T-cells and/or a CD4+ population of T-cells from a mixed population of T-cells is performed by flow cytometry. In some alternatives, the separating of the CD8+ population of T-cells and/or a CD4+ population of T-cells from a mixed population of T-cells is performed by immunomagnetic selection. In some alternatives, the genetically modified CD8+ T-cells and/or CD4+ T-cells comprise at least one receptor that promotes engraftment fitness. In some alternatives, the at least one receptor is CD45 RA, CD45 RO, CCR7, CD25, CD127, CD57, CD137, CD27, CD28 and/or CD62L. In some alternatives, the at least one receptor is CD27, CD28 and/or CD62L. In some alternatives, the stimulating of the isolated population of T-cells is performed by contacting the CD8+ and/or CD4+ T-cells with an antibody-bound support, such as a bead or particle. In some alternatives, the antibody-bound support comprises anti-TCR, anti-CD2, anti-CD3, anti-CD4 and/or anti-CD28 antibodies. In some alternatives, the antibody-bound support comprises anti-CD3 and/or anti-CD28 antibodies. In some alternatives, the vector further comprises a first sequence encoding a leader sequence, a second sequence encoding a ligand binding domain, a third sequence encoding a signaling domain and a fourth sequence encoding a selectable marker sequence. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the marker sequence encodes a truncated epidermal growth factor receptor (EGFRt). In some alternatives, the at least one cytokine comprises GM-CSF, IL-7, IL-12, IL-15, IL-18, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives, the contacting is performed for 2, 3, 4, 5, 6, 7, 8, 9, 10, 11, 12, 13, 14, 15, 16, 17, 18, 19, or 20 days or a period of time within a range defined by any two of these values. In some alternatives, the method is performed with isolated CD4+ cells in the absence of CD8+ cells. In some alternatives, the method is performed with isolated CD8+ in the absence of or enriched over CD4+ cells. In some alternatives, the CD4+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or for a period that is within a range defined by any two of the aforementioned time periods. In some alternatives, the CD8+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or fora period that is within a range defined by any two of the aforementioned time periods. In some alternatives, the method further comprises removing the antibody-bound support, such as beads or particles. In some alternatives, the ligand binding domain of the chimeric antigen receptor comprises an antibody, or a binding portion thereof. In some alternatives, the ligand binding domain of the chimeric antigen receptor comprises a single chain variable fragment (scFv), or a binding portion thereof. In some alternatives, the ligand binding domain of the chimeric antigen receptor comprises FMC63, or a binding portion thereof. In some alternatives, the ligand binding domain of the chimeric antigen receptor is specific for CD19. In some alternatives, the method further comprises cryopreserving the genetically modified CD8+ and/or CD4+ T-cells.

In some alternatives, a population of genetically modified T-cells is provided wherein the population of genetically modified T-cells comprises a plurality of affinity selected CD8+ and/or CD4+ T-cells, in the absence of, enriched over, or isolated from CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ T-cells have been re-stimulated with at least one cytokine. In some alternatives, the at least one cytokine comprises GM-CSF, IL-7, IL-12, IL-18, IL-15, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives, the said plurality of affinity selected CD8+ and/or CD4+ T-cells further comprise at least one receptor that promotes, induces, contribute to or enhances engraftment fitness. In some alternatives, the at least one receptor that promotes, induces, contribute to or enhances engraftment fitness is CD45 RA, CD45 RO, CCR7, CD25, CD127, CD57, CD137, CD27, CD28 and/or CD62L. In some alternatives, the at least one receptor that promotes, induces, contribute to or enhances engraftment fitness is CD27, CD28 and/or CD62L. In some alternatives, the plurality of affinity selected CD8+ and/or CD4+ T-cells further comprises a vector having a first sequence encoding a leader sequence, a second sequence encoding a ligand binding domain, a third sequence encoding a signaling domain and a fourth sequence encoding a selectable marker sequence. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the cell surface selectable marker encodes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof. In some alternatives, the ligand binding domain is specific for CD19. In some alternatives, the population comprises isolated CD4+ T-cells in the absence of or enriched over CD8+ T-cells. In some alternatives, the population comprises isolated CD8+ T-cells in the absence of or enriched over CD4+ T-cells.

In some alternatives, a composition or product combination for human therapy is provided, wherein the composition or product combination comprises a pharmaceutical excipient and at least one population of genetically modified T-cells. In some alternatives, the at least one population of genetically modified T-cells comprises a plurality of affinity selected CD8+ and/or CD4+ T-cells, in the absence of, enriched over, or isolated from CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ T-cells have been re-stimulated with at least one cytokine. In some alternatives, the at least one cytokine comprises GM-CSF, IL-7, IL-12, IL-15, IL-18, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives, the said plurality of affinity selected CD8+ and/or CD4+ T-cells further comprise at least one receptor that promotes, induces, contribute to or enhances engraftment fitness. In some alternatives, the at least one receptor that promotes, induces, contribute to or enhances engraftment fitness is CD45 RA, CD45 RO, CCR7, CD25, CD127, CD57, CD137, CD27, CD28 and/or CD62L. In some alternatives, the at least one receptor that promotes, induces, contribute to or enhances engraftment fitness is CD27, CD28 and/or CD62L. In some alternatives, the plurality of affinity selected CD8+ and/or CD4+ T-cells further comprises a vector having a first sequence encoding a leader sequence, a second sequence encoding a ligand binding domain, a third sequence encoding a signaling domain and a fourth sequence encoding a selectable marker sequence. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the cell surface selectable marker encodes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof. In some alternatives, the ligand binding domain is specific for CD19. In some alternatives, at least one population comprises isolated CD4+ T-cells in the absence of or enriched over CD8+ T-cells. In some alternatives, at least one population comprises isolated CD8+ T-cells in the absence of or enriched over CD4+ T-cells. In some alternatives, the composition or product combination comprises the population of genetically modified T-cells, wherein the population of genetically modified T-cells comprises isolated CD8+ T-cells in the absence of or enriched over CD4+ T-cells. In some alternatives, the composition or product combination comprises the population of genetically modified T-cells, wherein the population of genetically modified T-cells comprises isolated CD4+ T-cells in the absence of or enriched over CD8+ T-cells. In some alternatives, the population comprises isolated CD8+ T-cells in the absence of or enriched over CD4+ T-cells and isolated CD4+ T-cells in the absence of or enriched over CD8+ T-cells mixed or co-administered in a 1:1 ratio.

In some alternatives, a method of treating, inhibiting, or ameliorating a disease in a subject in need thereof is provided, wherein the method comprises administering to the subject at least one composition or product combination. In some alternatives, the at least one composition or product combination comprises a pharmaceutical excipient and at least one population of genetically modified T-cells. In some alternatives, the at least one population of genetically modified T-cells comprises a plurality of affinity selected CD8+ and/or CD4+ T-cells, in the absence of, enriched over or isolated from CD8− and/or CD4− T-cells, wherein said plurality of affinity selected CD8+ and/or CD4+ T-cells have stimulated CD2, CD3, CD4 and/or CD28 receptors, wherein said plurality of affinity selected CD8+ and/or CD4+ T-cells further comprise a gene encoding a chimeric antigen receptor and a cell surface selectable marker and, wherein said plurality of affinity selected CD8+ and/or CD4+ T-cells have been re-stimulated with at least one cytokine. In some alternatives, the at least one cytokine comprises GM-CSF, IL-7, IL-12, IL-15, IL-18, IL-2, and/or IL-21. In some alternatives, the at least one cytokine comprises IL/7, IL-15 and/or IL-21. In some alternatives, the at least one cytokine comprises IL-2, IL-15 and/or IL-21. In some alternatives, the said plurality of affinity selected CD8+ and/or CD4+ T-cells further comprise at least one receptor that promotes engraftment fitness In some alternatives, the at least one receptor that promotes, induces, contribute to or enhances engraftment fitness is CD45 RA, CD45 RO, CCR7, CD25, CD127, CD57, CD137, CD27, CD28 and/or CD62L. In some alternatives, the at least one receptor that promotes, induces, contribute to or enhances engraftment fitness is CD27, CD28 and/or CD62L. In some alternatives, the plurality of affinity selected CD8+ and/or CD4+ T-cells further comprises a vector having a first sequence encoding a leader sequence, a second sequence encoding a ligand binding domain, a third sequence encoding a signaling domain and a fourth sequence encoding a selectable marker sequence. In some alternatives, the vector further comprises a sequence encoding a spacer. In some alternatives, the spacer comprises an IgG4 hinge. In some alternatives, the vector is a viral vector. In some alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. In some alternatives, the viral vector is a lentivirus vector. In some alternatives, the cell surface selectable marker encodes for a truncated epidermal growth factor receptor (EGFRt). In some alternatives, the ligand binding domain comprises an antibody, or a binding portion thereof. In some alternatives, the ligand binding domain comprises a single chain variable fragment (scFv), or a binding portion thereof. In some alternatives, the ligand binding domain comprises FMC63, or a binding portion thereof. In some alternatives, the ligand binding domain is specific for CD19. In some alternatives, at least one population comprises isolated CD4+ T-cells in the absence of or enriched over CD8+ T-cells. In some alternatives, at least one population comprises isolated CD8+ T-cells in the absence of or enriched over CD4+ T-cells. In some alternatives, the composition or product combination comprises the population of genetically modified T-cells, wherein the population of genetically modified T-cells comprises isolated CD8+ T-cells in the absence of or enriched over CD4+ T-cells. In some alternatives, the composition or product combination comprises the population of genetically modified T-cells, wherein the population of genetically modified T-cells comprises isolated CD4+ T-cells in the absence of or enriched over CD8+ T-cells. In some alternatives, the population comprises isolated CD8+ T-cells in the absence of or enriched over CD4+ T-cells and isolated CD4+ T-cells in the absence of or enriched over CD8+ T-cells mixed or co-administered in a 1:1 ratio. In some alternatives, the method comprises administering the composition or product combination, wherein the composition or product combination comprises at least one population, wherein the at least one population comprises isolated CD4+ T-cells in the absence of or enriched over CD8+ T-cells. In some alternatives, the method comprises administering the composition or product combination, wherein the composition or product combination comprises at least one population, wherein the at least one population comprises isolated CD8+ T-cells in the absence of or enriched over CD4+ T-cells. In some alternatives, the method comprises administering the composition or product combination, wherein the composition or product combination comprises at least one population, wherein the at least one population comprises isolated CD4+ T-cells in the absence of or enriched over CD8+ T-cells and isolated CD8+ T-cells in the absence of or enriched over CD4+ T-cells mixed or co-administered in a 1:1 ratio. In some alternatives, the method further comprises administering the composition or product combination, wherein the composition or product combination comprises at least one population, wherein the at least one population comprises isolated CD8+ T-cells in the absence of or enriched over CD4+ T-cells. In some alternatives, the method further comprises administering the composition or product combination, wherein the composition or product combination comprises at least one population, wherein the at least one population comprises isolated CD4+ T-cells in the absence of or enriched over CD8+ T-cells. In some alternatives, the subject is identified or selected to receive an anti-cancer therapy. In some alternatives, the method further comprises measuring or evaluating an inhibition of a disease. In some alternatives, the method further comprises providing said subject an additional anti-cancer therapy before, during, or after administration of the composition or product combination. In some alternatives, the composition or product combinations are administered to said subject by adoptive cell transfer. In some alternatives, the composition or product combinations are administered to said subject after said subject has received another form of anti-cancer therapy. In some alternatives, the composition or product combinations are administered to said subject after said subject has received another form of anti-cancer therapy. In some alternatives, the subject is suffering from leukemia. In some alternatives, the subject has recurrent and/or chemotherapy refractory CD19+ childhood acute lymphoblastic leukemia (ALL). In some alternatives, the subject has recurrent and/or chemotherapy refractory CD19+ acute lymphoblastic leukemia (ALL). In some alternatives, the subject is suffering from an autoimmune disease. In some alternatives, the subject is suffering from a post-HSCT relapse.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

More Alternatives

In some alternatives, the separating, enriching, or isolating of the CD8+ expressing population of T-cells and/or a CD4+ expressing population of T-cells, such as T-cells that are derived from thymocytes or T-cells that are derived from engineered precursors, desirably iPS cells, from a mixed population of T-cells is performed by affinity selection for T-cells having an epitope present on CD8 and/or CD4. In some alternatives, the separating, enriching, or isolating of the CD8+ expressing population of T-cells and/or a CD4+ expressing population of T-cells from a mixed population of T-cells is performed by flow cytometry. In some alternatives, the separating, enriching, or isolating of the CD8+ expressing population of T-cells and/or a CD4+ expressing population of T-cells from a mixed population of T-cells is performed by immuno-magnetic selection. In some alternatives, the genetically modified CD8+ expressing T-cells and/or CD4+ expressing T-cells comprise at least one receptor that promotes, induces, or contributes to engraftment fitness. In some alternatives, the at least one receptor that promotes, induces, or contributes to engraftment fitness is CD45 RA, CD45 RO, CCR7, CD25, CD127, CD57, CD137, CD27, CD28 and/or CD62L. In preferred alternatives, the at least one receptor that promotes, induces, or contributes to engraftment fitness is CD27, CD28 and/or CD62L. In some alternatives, the stimulating of the isolated, enriched, or separated population of T-cells is performed by contacting the CD8+ and/or CD4+ expressing T-cells with an antibody-bound support, such as a bead or particle. In some of these alternatives, the antibody-bound support comprises anti-TCR, anti-CD2, anti-CD3, anti-CD4 and/or anti-CD28 antibodies. In preferred alternatives, the antibody-bound support comprises anti-CD3 and/or anti-CD28 antibodies.

In many of the aforementioned alternatives, the vector further comprises a first sequence encoding a leader sequence, a second sequence encoding a ligand binding domain, a third sequence encoding a signaling domain and a fourth sequence encoding a selectable marker sequence. In some of these alternatives, the vector further comprises a sequence encoding a spacer, which in some alternatives may comprise an IgG4 hinge. In many of the aforementioned alternatives, the vector is a viral vector or a mini-circle.

In many of the aforementioned alternatives, the viral vector is derived from simian virus 40, adenoviruses, adeno-associated virus (AAV), lentivirus, or retroviruses. In some alternatives, the viral vector is a recombinant adenovirus, adeno-associated virus, lentivirus or retrovirus vector. Preferably, the viral vector is a lentivirus vector. In many of the aforementioned alternatives, the marker sequence encodes a truncated epidermal growth factor receptor (EGFRt). In many of the aforementioned alternatives, the at least one cytokine that is utilized comprises GM-CSF, IL-7, IL-12, IL-15, IL-18, IL-15, IL-2, and/or IL-21 and said cytokine is provided exogenously to the T-cells e.g., in addition to any cytokine that may be produced by the cells or present in media.

In desirable alternatives, the at least one cytokine comprises IL-7, IL-15 and/or IL-21. In many of the aforementioned alternatives, the at least one cytokine comprises IL-2, IL-15 and/or IL-21. In desirable alternatives, the at least one cytokine comprises IL-21 and another cytokine, and/or comprises IL-7 and at least one other cytokine, and/or comprises IL-15 and at least one other cytokine, such as comprising IL-21 and IL-15, comprising IL-21 and IL-7, or comprising IL-15 and IL-7, or comprising IL-2 and IL-15, or comprising IL-7 and IL-15. In preferred alternatives, the contacting period is performed for at least 1, 2, 3, 4, 5, 6, 7, 8, 9, 10, 11, 12, 13, 14, 15, 16, 17, 18, 19, or 20 days or a period of time within a range defined by any two of these time points. In many of the aforementioned alternatives, the methods are performed with isolated, separated, or enriched populations of CD4+ expressing T-cells, such as T-cells that are derived from thymocytes or T-cells that are derived from engineered precursors, desirably iPS cells, in the absence of or having a reduced amount CD8+ expressing T-cells, as compared to a native population of unseparated, non-enriched, or non-isolated population of T-cells. In many of the aforementioned alternatives, these methods are performed with isolated, separated, or enriched populations of CD8+ expressing T-cells, such as T-cells that are derived from thymocytes or T-cells that are derived from engineered precursors, desirably iPS cells, in the absence of or having a reduced amount of CD4+ expressing T-cells, as compared to a native population of unseparated, non-enriched, or non-isolated population of T-cells. In many of the aforementioned alternatives, the CD4+ expressing T-cells are propagated for at least 1 day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points. In many of the aforementioned alternatives, the CD8+ expressing T-cells are propagated for at least 1 day, such as 1, 2, 3, 4, 5, 6, 7, 8, 9, 10, 11, 12, 13, 14, 15, 16, 17, 18, 19, or 20 days or any time that is within a range of times defined by any two of the aforementioned time points.

In some alternatives, a method of making genetically modified T-cells, which have a chimeric antigen receptor is provided, wherein the method comprises separating or enriching a CD8+ expressing population of T-cells and/or a CD4+ expressing population of T-cells, such as T-cells that are derived from thymocytes or T-cells that are derived from engineered precursors, wherein the precursors are optionally iPS cells, from a mixed population of T-cells, so as to generate a separated or enriched population of T-cells, stimulating the separated or enriched population of T-cells so as to generate a stimulated population of CD8+ T-cells and/or CD4+ T-cells, transducing the stimulated population of CD8+ T-cells and/or CD4+ T-cells with a vector, wherein the vector encodes a chimeric antigen receptor so as to generate a transduced population of CD8+ T-cells and/or CD4+ T-cells, contacting the transduced population of CD8+ T-cells and/or CD4+ T-cells with at least one cytokine, provided exogenously, for 1, 2, 3, 4, 5, 6, 7, 8, 9, 10, 11, 12, 13, 14, 15, 16, 17, 18, 19, or 20 days, or for a period that is within a range defined by any two of the aforementioned time periods, so as to generate a transduced, cytokine-stimulated population of CD8+ T-cells and/or CD4+ T-cells, wherein the method thereby obtains said genetically modified T-cells, which have a chimeric antigen receptor. In some alternatives, the method further comprises enriching the transduced, cytokine-stimulated population of CD8+ T-cells and/or CD4+ T-cells by selection of a marker, so as to generate an enriched population of transduced, cytokine-stimulated CD8+ T-cells and/or CD4+ T-cells. In some alternatives, the marker is encoded by the vector and optionally is a cell surface marker. In some alternatives, the method further comprises further comprising propagating the enriched population of transduced, cytokine-stimulated CD8+ T-cells and/or CD4+ T-cells for at least one day, such as 1, 2, 3, 4, 5, 6, 7, 8, 9, 10, 11, 12, 13, 14, 15, 16, 17, 18, 19, or 20 days or fora period that is within a range defined by any two of the aforementioned time periods.

In some alternatives, a method of producing genetically modified T cells is provided, wherein the method comprises introducing a vector encoding a recombinant protein into cells of a CD4+-enriched T cell composition, and incubating cells of the CD4+ enriched T cell composition with a combination of cytokines comprising IL-7 and IL-15, and/or introducing a vector encoding a recombinant protein into cells of a CD8+ enriched T cell composition and incubating cells of the CD8+ enriched T cell composition with a combination of cytokines comprising IL-2 and IL-15, wherein the method thereby generates a transduced CD4+ enriched population and/or a transduced CD8+ enriched population. In some alternatives, the transduced CD4+ enriched population has a higher level of surface expression of CD62L, CD27, and/or CD28, as compared to a reference enriched population of transduced CD4+ cells, and/or has an increased indicator of engraftment fitness and/or expansion, and/or persistence, upon administration to a subject as compared to the reference enriched population of transduced CD4+ cells, wherein the reference population is a CD4+-enriched population prepared by another method, which is identical to the method, except that the IL-2 alone is used in place of the combination of cytokines. In some alternatives, the transduced CD8+ enriched population has a higher level of surface expression of CD62L, CD27, and/or CD28, as compared to a reference enriched population of transduced CD8+ cells, and/or has an increased indicator of engraftment fitness and/or expansion, and/or persistence, upon administration to a subject as compared to the reference enriched population of transduced CD8+ cells, wherein the reference population is a population of CD8+-enriched cells prepared by another method that is identical to the method, except that the IL-2 alone is used in place of the combination of cytokines.

In some alternatives, a method of producing genetically modified T cells is provided, wherein the method comprises introducing a vector encoding a recombinant protein into cells of a CD4+ enriched T cell composition and incubating cells of the CD4+ enriched T cell composition with a first combination of cytokines and introducing a vector encoding a recombinant protein into cells of a CD8+ enriched T cell composition and incubating cells of the CD8+ enriched T cell composition with a second combination of cytokines which is distinct from the first combination of cytokines, wherein the method thereby generates a transduced CD4+ enriched population and a transduced CD8+ enriched population. In some alternatives, the transduced CD4+ enriched population has a higher level of surface expression of CD62L, CD27, and/or CD28, as compared to a reference enriched population of transduced CD4+ cells prepared by another method that is identical to the method, except that the first and second combination of cytokines are identical, and/or has an increased indicator of engraftment fitness and/or expansion, and/or persistence, upon administration to a subject as compared to the reference enriched population of transduced CD4+ cells. In some alternatives, the transduced CD8+ enriched population has a higher level of surface expression of CD62L, CD27, and/or CD28, as compared to a reference enriched population of transduced CD8+ cells prepared by another method that is identical to the method, except that the first and second combination of cytokines are identical, and/or has an increased indicator of engraftment fitness and/or expansion, and/or persistence, upon administration to a subject as compared to the reference enriched population of transduced CD8+ cells. In some alternatives, the first combination comprises IL-7 and IL-15 and the second combination comprises IL-2 and IL-15. In some alternatives, the cytokine combination(s) is added subsequently to transduction initiation, and optionally on the same day as transduction initiation. In some alternatives, the concentration of IL-2 is at or about 50 U/mL, where applicable, the concentration of IL-15 is at or about 0.5 ng/mL, where applicable, and/or the concentration of IL-7 is at or about 5 ng/mL, where applicable. In some alternatives, the addition of the combination of cytokines to the CD4+-enriched and/or to the CD8+-enriched composition comprises increasing the volume of the composition in which the cells are incubated, thereby decreasing cell density. In some alternatives, the indicator of engraftment fitness comprises a percentage of cells in the composition or total surface expression levels for the population of a cell surface marker selected from the group consisting of CD62L, CD27, and/or CD28. In some alternatives, the indicator of engraftment fitness comprises persistence in a subject upon administration. In some alternatives, the cells are derived from the subject. In some alternatives, transduced CD8+ and/or CD4+ cells persist upon administration to a subject from which the cells were derived, for at least at or about 30 or 60 days post injection of the cells into the subject. In some alternatives, the recombinant protein is a chimeric antigen receptor. In some alternatives, the method further comprises prior to the transduction, enriching a T cell composition for cells expressing CD4, thereby generating the enriched CD4+ enriched T cell composition so-transduced, and/or, prior to the transduction, enriching a T cell composition for cells expressing CD8, thereby generating the enriched CD8+ enriched T cell composition so-transduced. In some alternatives, the method further comprises cryopreserving the engineered cells. In some alternatives, the method further comprises administering the engineered cells to a subject, and optionally further comprising pooling the transduced CD4+ enriched and the transduced CD8+ enriched compositions prior to said administering.

In some alternatives, a cell or composition is produced by any of the alternatives of the methods listed in the previous paragraphs of this section of more alternatives. In some alternatives, a method of administering the cell produced by any of the alternatives of the method or the alternatives of the compositions listed in the previous paragraphs is contemplated. In some alternatives, the cell or composition is administered to a subject. In some alternatives, the administration is to a subject from which the cells were derived.

In some alternatives, a method of adoptive cell therapy is provided, wherein the method comprises (a) incubating a CD4+-enriched T cell composition under stimulating conditions and in the presence of IL-15 and IL-7, thereby generating an expanded CD4+ composition, (b) separately incubating a CD8+-enriched T cell composition under stimulating conditions and in the presence of IL-15 and IL-2, thereby generating an expanded CD8+ composition, and (c) administering the expanded CD4+ and expanded CD8+ populations to a subject, optionally simultaneously. In some alternatives, the CD4+ and CD8+ populations are obtained from the subject. In some alternatives, the one or more of the recited cytokines or combinations of cytokines further comprises CD21. In some alternatives, the CD4+-enriched population or the total number of T cells therein comprises at least 70, 80, 90, 95, 96, 97, 98, or 99% CD4+ cells, and/or the C8+-enriched population or the total number of T cells therein comprises at least 70, 80, 90, 95, 96, 97, 98, or 99% CD8+ cells.

In addition, where features or aspects of the disclosure are described in terms of Markush groups, those skilled in the art will recognize that the disclosure is also thereby described in terms of any individual member or subgroup of members of the Markush group.

What is claimed is:

1. A method of preparing an isolated population of genetically modified T-cells having an improved engraftment fitness, comprising:

(a) obtaining an isolated population of T-cells comprising a chimeric antigen receptor (CAR), wherein the isolated population of T-cells comprises CD4+ T-cells or CD8+ T-cells;

(b) contacting the isolated population of T-cells with exogenous IL-2 to obtain an IL-2 stimulated population of T-cells; and (c) contacting the IL-2 stimulated population of T-cells with an exogenous combination of IL-7 and IL-21, wherein step (b) is performed before step (c), so as to obtain said genetically modified T-cells having an improved engraftment fitness.

2. The method of claim 1, wherein step (a) comprises enriching for a CD8+ population of T-cells or a CD4+ population of T-cells from a mixed population of T-cells by affinity selection for T-cells having an epitope present on CD8 or CD4 to obtain the isolated population of T-cells.

3. The method of claim 2, wherein the enriching is performed by flow cytometry.

4. The method of claim 2, wherein the enriching is performed by immuno-magnetic selection.

5. The method of claim 1, wherein step (a) further comprises stimulating the population of T-cells by contacting the population of T-cells with an antibody-bound support.

6. The method of claim 5, wherein the antibody-bound support comprises an anti-TCR antibody, an anti-CD2 antibody, an anti-CD3 antibody, an anti-CD4 antibody, an anti-CD28 antibody, or an antigen binding fragment thereof.

7. The method of claim 1, wherein step (a) comprises transducing a population of T-cells with a vector encoding the CAR to obtain the isolated population of T-cells comprising a CAR.

8. The method of claim 7, wherein the vector is a viral vector.

9. The method of claim 8, wherein the viral vector is selected from an adenovirus vector, an adeno-associated virus vector, a lentivirus vector, or a retrovirus vector.

10. The method of claim 1, wherein the IL-2, the IL-7 or the IL-21 are recombinant cytokines.

11. The method of claim 1, wherein the IL-2, the IL-7, or the IL-21 is provided within a range from 0.1 ng/ml to 1.0 ng/ml, or within a range from 10 U/mL to 100 U/mL.

12. The method of claim 1, wherein step (b) comprises contacting the population of T-cells with exogenous IL-2 for a period of about 5 days.

13. The method of claim 1, wherein steps (b) and (c) together are performed for a period within a range from 1 day to 20 days.

14. The method of claim 1, further comprising cryopreserving the genetically modified T-cells.

15. The method of claim 1, wherein the method is performed with isolated, purified, or separated CD4+ T-cells in the absence of or substantially depleted of CD8+ T-cells.

16. The method of claim 1, wherein the method is performed with isolated, purified, or separated CD8+ T-cells in the absence of or substantially depleted of CD4+ T-cells.

17. The method of claim 1, wherein the population of T-cells comprises a precursor T cell or a hematopoietic stem cell.

18. The method of claim 1, further comprising administering the population of genetically modified T-cells to a subject having a hematopoietic cancer, wherein the CAR specifically binds CD19, and wherein the method comprises (i) selecting for CD4+ T cells and CD8+ T cells from a population of T cells to obtain the isolated population of T-cells, and (ii) performing steps (b) and (c) for a period of about 5 days to obtain the population of genetically modified T-cells.

19. An in vitro method of making an isolated population of genetically modified T-cells having an improved engraftment fitness, comprising:

(a) isolating a CD8+ expressing population of T-cells or a CD4+ expressing population of T-cells from a mixed population of isolated T-cells so as to generate an isolated population of T-cells;

(b) stimulating the isolated population of T-cells so as to generate a stimulated population of T-cells;

(c) transducing the stimulated population of T-cells with a vector encoding a chimeric antigen receptor (CAR), so as to generate a transduced population of T-cells;

(d) contacting the transduced population of T-cells with exogenous IL-2 to obtain an IL-2 stimulated population of T-cells; and (e) contacting the IL-2 stimulated population of T-cells with an exogenous combination of IL-7 and IL-21, wherein step (e) is performed subsequent to step (d).

20. The method of claim 19, wherein the transduced population of T-cells is contacted with the exogenous IL-2 for a period of about 5 days.

* * * * *